(12) United States Patent
Schlicker et al.

(10) Patent No.: US 7,696,748 B2
(45) Date of Patent: Apr. 13, 2010

(54) ABSOLUTE PROPERTY MEASUREMENTS USING ELECTROMAGNETIC SENSORS

(75) Inventors: Darrell E. Schlicker, Watertown, MA (US); Neil J. Goldfine, Newton, MA (US); David C. Grundy, Reading, MA (US); Robert J. Lyons, Boston, MA (US); Vladimir A. Zilberstein, Chestnut Hill, MA (US); Andrew P. Washabaugh, Chula Vista, CA (US); Vladimir Tsukernik, West Roxbury, MA (US); Mark D. Windoloski, Burlington, MA (US); Ian C. Shay, Waltham, MA (US)

(73) Assignee: Jentek Sensors, Inc., Waltham, MA (US)

( * ) Notice: Subject to any disclaimer, the term of this patent is extended or adjusted under 35 U.S.C. 154(b) by 763 days.

(21) Appl. No.: 10/963,482

(22) Filed: Oct. 12, 2004

(65) Prior Publication Data

US 2005/0127908 A1      Jun. 16, 2005

Related U.S. Application Data

(60) Provisional application No. 60/510,668, filed on Oct. 10, 2003, provisional application No. 60/616,963, filed on Oct. 8, 2004.

(51) Int. Cl.
  *G01N 27/82*  (2006.01)
  *G01R 33/12*  (2006.01)
  *G01B 7/24*  (2006.01)
(52) U.S. Cl. .................. 324/240; 324/262; 324/202
(58) Field of Classification Search ................ 324/202, 324/228–243, 262, 260
  See application file for complete search history.

(56) References Cited

U.S. PATENT DOCUMENTS

| | | | |
|---|---|---|---|
| 4,814,690 A | 3/1989 | Melcher et al. | |
| 5,015,951 A | 5/1991 | Melcher | |
| 5,453,689 A | 9/1995 | Goldfine et al. | |
| 5,629,621 A | 5/1997 | Goldfine et al. | |
| 5,793,206 A | 8/1998 | Goldfine et al. | |
| RE36,986 E | 12/2000 | Melcher | |
| 6,188,218 B1 | 2/2001 | Goldfine et al. | |
| 6,380,747 B1 | 4/2002 | Goldfine et al. | |
| 6,486,673 B1 | 11/2002 | Goldfine et al. | |
| 6,532,791 B2 * | 3/2003 | Schmid et al. | ................ 73/1.79 |
| 6,657,429 B1 | 12/2003 | Goldfine et al. | |
| 6,734,670 B2 * | 5/2004 | Crouzen | ..................... 324/240 |
| 6,781,387 B2 | 8/2004 | Goldfine et al. | |
| 6,784,662 B2 | 8/2004 | Schlicker et al. | |
| 6,798,198 B2 | 9/2004 | Tsukernik et al. | |

(Continued)

*Primary Examiner*—Reena Aurora
(74) *Attorney, Agent, or Firm*—Hamilton, Brook, Smith & Reynolds, P.C.

(57) ABSTRACT

Methods and apparatus are described for absolute electrical property measurement of materials. This is accomplished with magnetic and electric field based sensors and sensor array geometries that can be modeled accurately and with impedance instrumentation that permits accurate measurements of the in-phase and quadrature phase signal components. A dithering calibration method is also described which allows the measurement to account for background material noise variations. Methods are also described for accounting for noise factors in sensor design and selection of the optimal operating conditions which can minimize the error bounds for material property estimates. Example application of these methods to automated engine disk slot inspection and assessment of the mechanical condition of dielectric materials are presented.

18 Claims, 28 Drawing Sheets

U.S. PATENT DOCUMENTS

2002/0075006 A1 6/2002 Goldfine et al.
2002/0105325 A1* 8/2002 Goldfine et al. ............. 324/242
2002/0158626 A1 10/2002 Shay et al.
2002/0163333 A1 11/2002 Schlicker et al.
2004/0004475 A1 1/2004 Goldfine et al.

* cited by examiner

ABSOLUTE PROPERTY MEASUREMENTS USING ELECTROMAGNETIC SENSORS

RELATED APPLICATIONS

This application claims the benefit of U.S. Provisional Application No. 60/510,668 filed Oct. 10, 2003, and claims the benefit of U.S. Provisional Application No. 60/616,963, filed on Oct. 8, 2004. The entire teachings of the above applications are incorporated herein by reference.

BACKGROUND OF THE INVENTION

The technical field of this invention is that of nondestructive materials characterization. This includes inspection of materials for hidden objects and characterization of surface, near-surface, and bulk material condition for flat and curved parts or components using magnetic field based or eddy-current sensors or electric field based or capacitive sensors. These nondestructive evaluation (NDE) techniques are applied across a wide variety of applications, ranging from manufacturing quality control to the detection of buried objects. Interrogation using electromagnetic fields is one technique that often proves to be of great use since it is sensitive to both geometric and electrical properties of materials. Additionally, many other non-electrical properties of interest can affect the measured electrical properties, such as cure state, fatigue, cracking, and temperature, which further the use of electromagnetic methods.

Although the full electromagnetic spectrum can be considered useful to some degree for NDE, here the focus is on fields that are sufficiently low in frequency to be considered quasi-static. A common magnetoquasistatic (MQS) measurement device used in NDE is the eddy-current sensor. Conventional eddy-current sensing involves the excitation of a conducting winding, the primary, with an electric current source of prescribed frequency. This produces a time-varying magnetic field, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. Traditionally, scanning of eddy-current sensors across the material surface is then used to detect flaws, such as cracks. Similarly, a common electroquasistatic (EQS) measurement technique uses capacitive sensors. This involves placing parallel plates on either side of a relatively insulating material, forming a capacitor, for which the admittance is dependent on the properties of the material.

Advances in these techniques have resulted in sensors which utilize spatially-periodic planar windings (MQS) or electrodes (EQS) which can be fabricated accurately using micro-fabrication, flex-circuit, or wire winding techniques depending on the sensor's size. Representative sensor geometries are described in U.S. Pat. Nos. 4,814,690 and 5,015,951. The periodic and planar nature of these sensors has allowed their terminal response to be modeled for layered materials, using semi-analytic methods. Their periodic nature also allows a means for affecting the cumulative depth to which a material is interrogated.

SUMMARY OF THE INVENTION

Aspects of the methods described herein involve nondestructive evaluation of material condition using electric and magnetic field sensors and sensor arrays. The material condition is assessed through variation in electrical properties, such as the magnetic permeability, electrical conductivity and dielectric permittivity, or geometric properties such as layer thicknesses or sensor lift-off. Absolute properties can be obtained when the sensor responses can be modeled accurately, the impedance measurement instrumentation is accurate, and the calibration method is robust.

In one embodiment of the invention, a multiple layered quasi-analytical model is used to account for the effect of finite conductor thicknesses in sensor electrodes or windings. This improves the accuracy of these computationally rapid models and can provide absolute measurements of material properties. The sensor is assumed to have at least one source conductor that can create an interrogating field and terminals for connecting to electrical measurement instrumentation. The quasi-analytical model uses mathematical expressions to represent the physical behavior and material interaction with the interrogating field in each layer, and numerically computes a self-consistent source distribution on the drive conductor. This source distribution is then related to the terminal values for comparison measurable values. In one embodiment of the invention, the sensor is an electromagnetic sensor. In some embodiments of the invention, the interrogating field is a predominantly magnetic or electric field. In other embodiments of the invention, the source is an electrical current or an electrical voltage. In a further embodiment of the invention, additional conductors, separate from the drive conductors, are used to sense the interrogating field. These sense conductors may be in the same or different planes as the drive or source conductors.

One aspect of this invention also relates to a method for measuring the electrical impedance, particularly for sensors. A signal generator controlled by a master microcontrollers is used to create an excitation signal having a specific frequency, amplitude, and phase that is passed into a test circuit. A reference signal is also created that has the same frequency as the excitation signal. A signal from the test circuit is then combined with the reference signal using a microcontroller based data acquisition channel to create measurement data that can be transmitted to and then stored and processed on a host computer. In one embodiment of the invention, the phase of the reference signal relative to the excitation signal is switched between zero and 90 degrees so that the in-phase and quadrature phase components of the test signal can be determined. Alternatively, instead of switching the phase, extra circuitry can be added by adding a second reference signal that is 90 degrees out of phase with the first reference signal so that the switching and time delays associated with the switching can be eliminated. Furthermore, by adding data acquisition channels both the in-phase and quadrature phase signals can be measured in parallel, which can improve the data acquisition rate.

In another aspect of the invention, calibration of the sensor involves measuring the sensor response as the sensor is moved over a reference material surface. This provides a reference measurement for the calibration that better represents test measurement conditions and reduces sensitivity to locally different material properties. In some embodiments of the invention, the sensor is a magnetic field or an electric field sensor. In other embodiments of the invention, the motion is constant in a single direction or back-and-forth in a dithering motion. In one embodiment of the invention the sensor has a linear array of sense elements. Furthermore, the motion can be in a direction parallel to the linear array of sense elements, which even permits each sense element to be over the same test material location for the calibration. These reference measurements can be performed with and without shims to perturb the sensor lift-off and can be performed at multiple excitation frequencies. The motion direction can be translation, rotation, or some combination of the two.

In yet another aspect of the invention, the mechanical condition of a dielectric material is determined from measurements of the dielectric properties of the material and correlations between these measured properties and the mechanical condition. In one embodiment of the invention, the sensor has an array of elements to permit measurements over larger areas or to provide a higher spatial resolution. In some embodiments of the invention, the mechanical condition is stress or strain. In another embodiment of the invention, a dielectric coating is applied to the test material to improve the measurement response, with the applied coating having a greater change in dielectric properties than the test material for a given change in test material mechanical condition. In some embodiments of the invention, the test material can be an automotive component or can be a representative material from an impact test.

For many materials, such as engine disk slots, inspections for damage can require the detection of cracks in regions with or without fretting. In one embodiment of the invention, this inspection is accomplished by scanning a flexible eddy current sensor array, which conforms to the surface of the test material, along the slot surface. The array can be held in place by a shuttle that contains a pressurizable balloon that can be inflated once the sensor array is positioned within the slot. With the disk placed on a turntable, after scanning each slot, the disk is rotated to the next slot position using a single motor that also translates the shuttle through the slot. The measurement data is then processed in effective property measurements as the material electrical conductivity or sensor lift-off. In some embodiments of the invention, the property data is displayed as an image or as a plot. In a further embodiment of the invention, a sacrificial coating is placed between the sensor and the disk slot material surface. Variations in the lift-off data can then be used a diagnostic to indicate wear of the coating and a need to replace the coating. In some embodiments of the invention, the sensor array is calibrated in air or on a reference material, or the response is normalized by measured properties near the center region of the slot.

In another aspect of the invention, the noise levels obtained from the various components of the measurement system are incorporated into the design of the sensor to improve the response for a measurement application. In this case, a model for the sensor response is used to calculate the sensor response for both reference (nominal) and perturbation material conditions. The difference in the signal levels between the reference and perturbation conditions are compared to the signal noise and the geometry of the sensor is modified, possibly iteratively, until an optimal response is obtained. This can be applied to electromagnetic, magnetic, and electric field based sensors. In a particular embodiment of the invention, for a magnetic field sensor having a primary winding, the spacing between the winding components in opposite directions can be adjusted based on the skin depth into the test material. In another embodiment of the invention, the signal noise level represents the instrument, sensor, and probe instrumentation noise.

In yet another aspect of the invention, methods are described for rapidly estimating measurement errors for the material properties. These error estimates are then used in optimizing sensor designs and selecting optimal test parameters. In one embodiment of the invention, this is accomplished by forming a relationship between measurable sensor responses and the material properties, linearizing this relationship around a nominal values for the material properties to create a matrix expression that can be inverted, and then calculating the measurement errors based on known sensors response errors. The relationship preferably comes from a model from the sensor response, but empirical methods can also be employed. Preferably, the model uses relatively rapid quasi-analytical techniques, but generic numerical methods such as finite or boundary element methods can also be used. In one embodiment of the invention, the linearization uses partial derivatives of the sensor response with respect to the material properties, as in a Jacobian. This linearization can also be accomplished numerically by calculating the sensor response variations for the perturbations in the material properties.

Inputs for estimating these measurement errors are known sensor response errors. These sensor response errors can be assumed but are preferably based on some empirical data. They may be systematic or bias errors associated with deterministic sources. They may also be probabilistic or stochastic, such that they can be estimated from Monte Carlo-type simulations or even non-log-normal probability density functions. For example, the probability density function could be obtained empirically and then, using latin hypercubes, translated into sensor impedance noise. Furthermore, if some of the material properties are not being measured, any variations in the non-measured properties can be included as sensor response errors. In some embodiments of the invention, the sensor uses magnetic or electric fields. In another embodiment of the invention, the sensor response is an impedance. The sensor response may be measured at multiple frequencies, at multiple locations on the material, or may use multiple sense elements as in an array.

In one embodiment of the invention, a material property for the measurement errors is an electrical property. In some embodiments of the invention, this electrical property is an electrical conductivity, magnetic permeability, or a dielectric permittivity. In another embodiment of the invention, the measured material property characterizes a spatial distribution or variation of an electrical property with depth into the material. In yet another embodiment of the invention, the material and model have multiple layers, so that a measured material property is a layer thickness. In a particular embodiment of the invention, this layer thickness is the sensor proximity or lift-off. Alternatively, a material property could be a geometric dimension associated with a discrete feature in the material, such as the length, width, or depth of one or more cracks.

In a further embodiment of the invention, the method for estimating measurement errors can be extended to optimize sensor designs. This involves defining sensor design parameters that can be adjusted, such as the primary to secondary winding gap for a magnetic field sensor, determining the measurement errors for each design parameter, and then adjusting the design parameters until the measurement error is minimized. In a particular embodiment of the invention, a sensor dimension is adjusted, such as the primary winding width or the primary to secondary gap. In one embodiment of the invention, the measurement errors are determined over a range of values for each design parameter and the optimization is based on the minimum error over the range. Alternatively, the design parameters can be adjusted iteratively to converge on optimal values. In one embodiment of the invention, the sensor has multiple sense elements, which may be a different distances to a drive conductor to provide measurement sensitivity to multiple field penetration depths.

In an alternative embodiment of the invention, the method for estimating measurement errors can be extended to optimize test parameters for a measurement. This involves defining at least one test parameter that can be adjusted, such as the excitation frequency, determining the measurement errors for each test parameter, and then adjusting the test parameters until the measurement error is minimized. In a particular embodiment of the invention, the test parameters include multiple excitation frequencies and the errors can indicate desirable combinations of frequencies to be used for multiple property measurements. In another embodiment of the invention, a test parameter is sensor lift-off or even multiple lift-offs. In yet another embodiment of the invention, the test parameters include multiple sensor locations.

One embodiment of the invention for determining stochastic or probabilistic noise source parameters uses measurements of sensor response errors under multiple test conditions and a model that relates the sensor response to the noise source parameters throughout a measurement system, such as an instrument, probe, and sensor. The noise source parameters are then determined by fitting the model to the measured errors so that the model errors and measured errors are in close agreement. In one embodiment of the invention, the model can use other system parameters, such as gain settings at different stages of the instrumentation. The model may also only be used to determine some of the noise source parameters, such as the ratio of the voltage to a current, rather than for each independently. This can also provide an indirect measurement of the noise source parameters.

Another aspect of the invention is a method for estimating bias or systematic error bounds in the sensor response. In this case, the sensor response is measured over a range of frequencies on a reference material, which is then used to estimate a material property at each frequency, a parametric model is created for a calculating error bounds over the frequency range, and then the bias error bounds are determined by comparing measurement and calculated errors for the material properties. In one embodiment of the invention, the calculated response can use the linearization method as described above where the known sensor response errors are obtained from the parametric model. In one embodiment of the invention, the reference material has uniform electrical properties. In another embodiment of the invention, the parametric model uses knowledge of the operation of the impedance instrumentation and probe so that the error bounds are set to a constant fraction of a full scale response.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENTS

A description of preferred embodiments of the invention follows.

This invention is directed toward the use of single and multiple sensing elements into quasistatic sensors for the characterization of materials. These sensors are typically flexible so that the sensor windings or electrodes conform to the test material surface and the material surface remains essentially planar over the footprint of the sensor. These sensors, along with electromagnetic modeling techniques, instrumentation, and inversion methods provide improved robustness of the measurement system, and the capability for the estimation of absolute electrical and geometric properties. This is accomplished by maintaining sufficient accuracy in modeling and inversion techniques, while reducing and accounting for unmodeled affects in the physically realized system.

An important aspect of this invention is that the sensor geometry and the interaction of the interrogating fields from the sensor with the test material need to be modeled accurately. One such sensor geometry is the conformable eddy-current sensor of the Meandering Winding Magnetometer (MWM®), described in U.S. Pat. Nos. 5,015,951, 5,453,689, and 5,793,206. The MWM is a "planar," conformable eddy-current sensor that was designed to support quantitative and autonomous data interpretation methods. These methods, called grid measurement methods, permit crack detection on curved surfaces without the use of crack standards, and provide quantitative images of absolute electrical properties (conductivity and permeability) and coating thickness without requiring field reference standards (i.e., calibration is performed in "air," away from conducting surfaces). MWM sensors and MWM-Arrays can be used for a number of applications, including fatigue monitoring and inspection of structural components for detection of flaws, degradation and microstructural variations as well as for characterization of coatings and process-induced surface layers. Characteristics of these sensors and sensor arrays include directional multi-frequency magnetic permeability or electrical conductivity measurements over a wide range of frequencies, e.g., from 250 Hz to 40 MHz with the same MWM sensor or MWM-Array, high-resolution imaging of measured permeability or conductivity, rapid permeability or conductivity measurements with or without a contact with the surface, and a measurement capability on complex surfaces with a hand-held probe or with an automated scanner.

Figure 1:
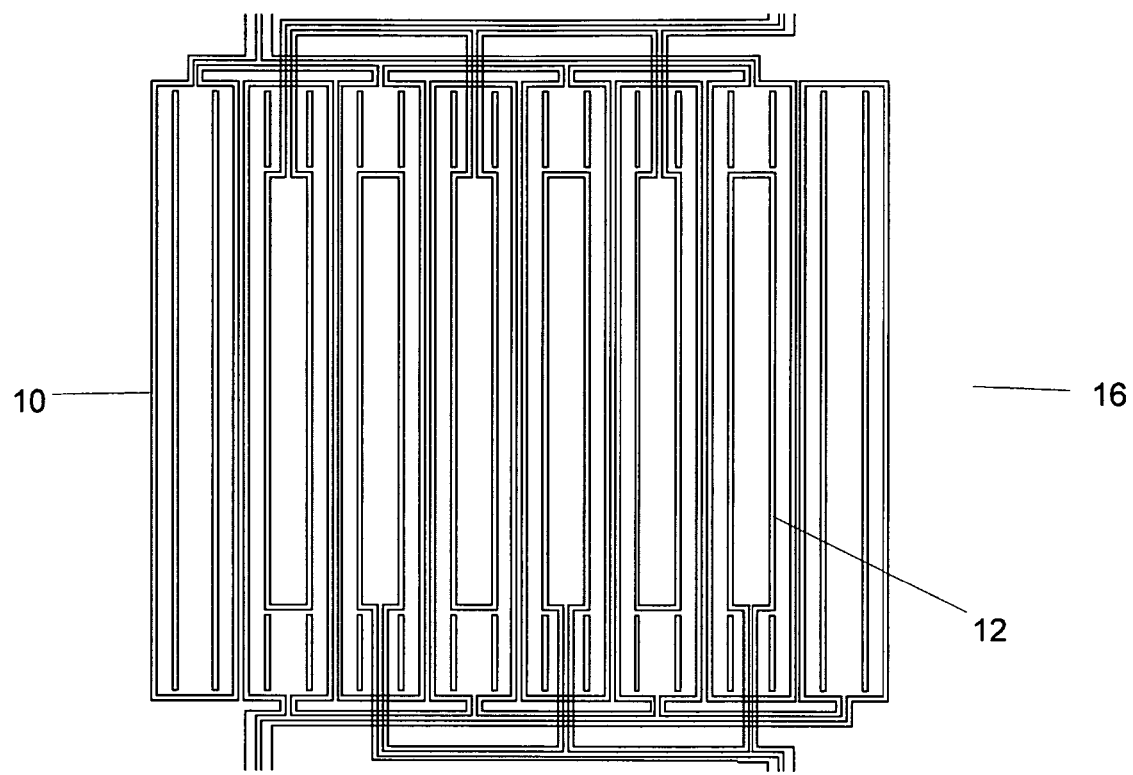
FIG. 1 is a drawing of a spatially periodic field eddy-current sensor.

FIG. 1 illustrates the basic geometry of an the MWM sensor 16, a detailed description of which is given in U.S. Pat. Nos. 5,453,689, 5,793,206, and 6,188,218 and U.S. patent application Ser. Nos. 09/666,879 and 09/666,524, both filed on Sep. 20, 2000, the entire teachings of which are incorporated herein by reference. The sensor includes a primary winding 10 having extended portions for creating the magnetic field and secondary windings 12 within the primary winding for sensing the response. The primary winding is fabricated in a spatially periodic pattern with the dimension of the spatial periodicity termed the spatial wavelength λ. A current is applied to the primary winding to create a magnetic field and the response of the material under test (MUT) to the magnetic field is determined through the voltage measured at the terminals of the secondary windings. This geometry creates a magnetic field distribution similar to that of a single meandering primary winding. A single element sensor has all of the sensing elements connected together. The net magnetic vector potential produced by the current in the primary can be accurately modeled as a Fourier series summation of spatial sinusoids, with the dominant mode having the spatial wavelength λ. For an MWM-Array, the responses from individual or combinations of the secondary windings can be used to provide a plurality of sense signals for a single primary winding construct as described in U.S. Pat. No. 5,793,206 and Re. 36,986.

Figure 2:
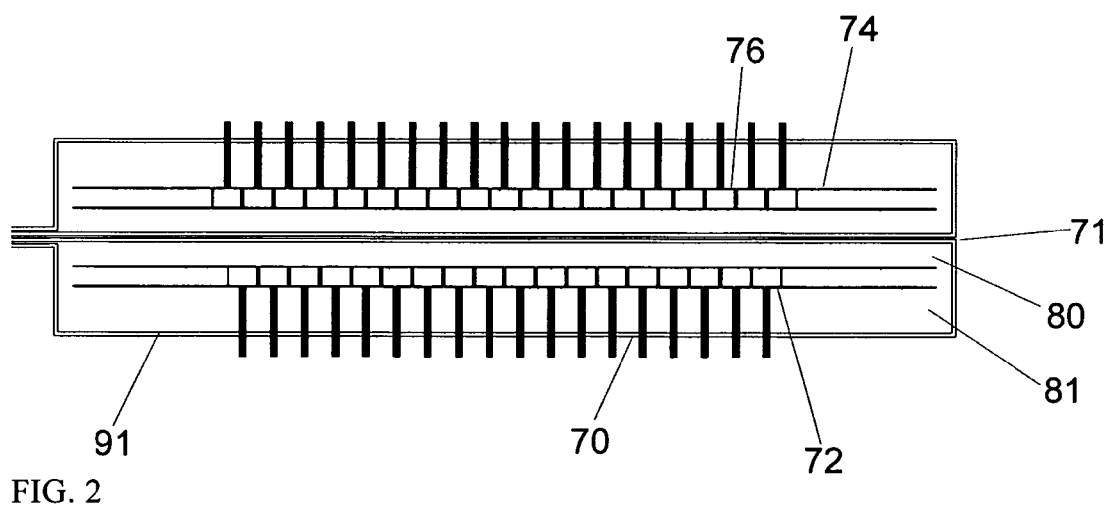
FIG. 2 is an expanded view of the drive and sense elements for an eddy-current array having offset rows of sensing elements.
Figure 3:
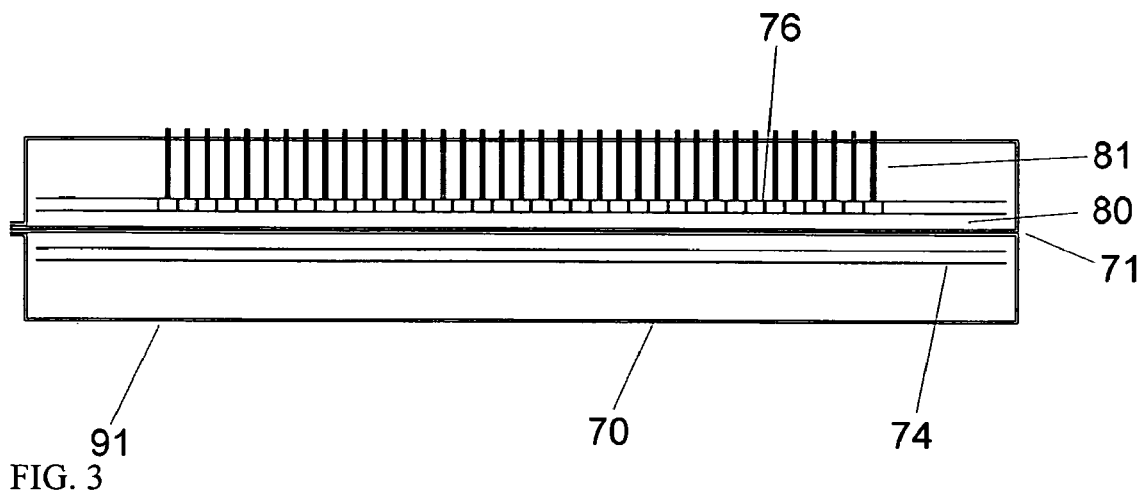
FIG. 3 is an expanded view of the drive and sense elements for an eddy-current array having a single row of sensing elements.
Figure 4:
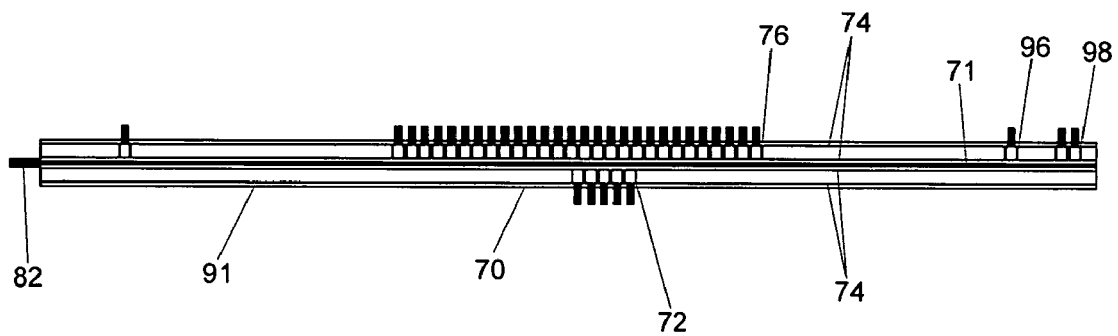
FIG. 4 is an expanded view of an eddy-current array where the locations of the sensing elements along the array are staggered.

The MWM-Arrays typically have one or more drive windings, possibly a single rectangle, and multiple sensing elements for inspecting the test material. Some of the motivation for the use of multiple sensing elements is to increase the spatial resolution of the material being characterized without loss of coverage, to add additional information for use in the estimation of multiple unknown material properties, and to cover large inspection areas in a faster time. Example sensor arrays are shown in FIG. 2 through FIG. 4 some embodiments of which are described in detail in U.S. patent application Ser. Nos. 10/102,620, filed Mar. 19, 2002, and Ser. No. 10/010, 062, filed Mar. 13, 2001, the entire teachings of which are incorporated herein by reference. These arrays include a primary winding 70 having extended portions for creating the magnetic field and a plurality of secondary elements 76 within the primary winding for sensing the response to the MUT. The secondary elements are pulled back from the connecting portions of the primary winding to minimize end effect coupling of the magnetic field. Dummy elements 74 can be placed between the meanders of the primary to maintain the symmetry of the magnetic field, as described in U.S. Pat. No. 6,188,218, incorporated herein by reference in its entirety.

When the sensor is scanned across a part or when a crack propagates across the sensor, perpendicular to the extended portions of the primary winding, secondary elements 72 in a primary winding loop adjacent to the first array of sense elements 76 provide a complementary measurement of the part properties. These arrays of secondary elements 72 can be aligned with the first array of elements 76 so that images of the material properties will be duplicated by the second array (improving signal-to-noise through combining the responses or providing sensitivity on opposite sides of a feature such as a fastener as described in-U.S. patent application Ser. Nos. 10/102,620 and 10/010,062. Alternatively, to provide complete coverage when the sensor is scanned across a part the sensing elements, can be offset along the length of the primary loop or when a crack propagates across the sensor, perpendicular to the extended portions of the primary winding, as illustrated in FIG. 2.

The dimensions for the sensor array geometry and the placement of the sensing elements can be adjusted to improve sensitivity for a specific inspection. For example, the effective spatial wavelength or four times the distance 80 between the central conductors 71 and the sensing elements 72 can be altered to adjust the sensitivity of a measurement for a particular inspection. For the sensor array of FIG. 2, the distance 80 between the secondary elements 72 and the central conductors 71 is smaller than the distance 81 between the sensing elements 72 and the return conductor 91. An optimum response can be determined with models, empirically, or with some combination of the two. An example of a modified sensor design is shown FIG. 3. In this sensor array, all of the sensing elements 76 are on one side of the central drive windings 71. The size of the sensing elements and the gap distance 80 to the central drive windings 71 are the same as in the sensor array of FIG. 2. However, the distance 81 to the return of the drive winding has been increased, as has the drive winding width to accommodate the additional elements in the single row of elements. Increasing the distance to the return reduces the size of the response when the return crosses a feature of interest such as a crack. Another example of a modified design is shown in FIG. 4. Here, most of the sensing elements 76 are located in a single row to provide the basic image of the material properties. A small number of sensing elements 72 are offset from this row to create a higher image resolution in a specific location.

Figure 5:
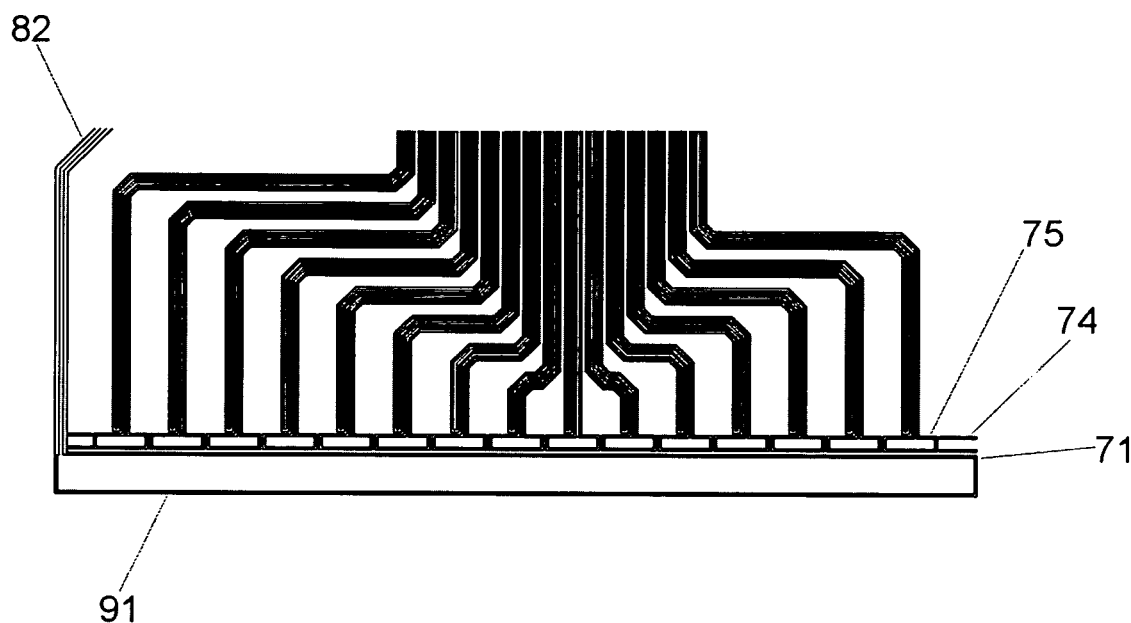
FIG. 5 is an expanded view of an eddy current array with a single rectangular loop drive winding and a linear row of sense elements on the outside of the extended portion of the loop.

The number of conductors used in the primary winding can be reduced further so that a single rectangular drive is used. As shown in FIG. 5, a single loop having extended portions is used for the primary winding. A row of sensing elements 75 is placed on the outside of one of the extended portions. This is similar to designs described in U.S. Pat. No. 5,453,689 where the effective wavelength of the dominant spatial field mode is related to the spacing between the drive winding and sensing elements. This spacing can be varied to change the depth of sensitivity to properties and defects. This distance can be optimized using models to maximize sensitivity to a feature of interest such as a buried crack or stress at a specific depth. Advantages of the design in FIG. 5 include a narrow drive and sense structure that allows measurements close to material edges and non-crossing conductor pathways so that a single layer design can be used with all of the conductors in the sensing region in the same plane. The width of the conductor 91 farthest from the sensing elements can be made wider in order to reduce any ohmic heating from large currents being driven through the drive winding.

The MWM sensor and sensor array structure can be produced using micro-fabrication techniques typically employed in integrated circuit and flexible circuit manufacture. This results in highly reliable and highly repeatable (i.e., essentially identical) sensors, which has inherent advantages over the coils used in conventional eddy-current sensors. The lack of reproducibility with conventional coils introduces severe requirements for calibration of the sensors (e.g., matched sensor/calibration block sets). In contrast, duplicate MWM sensor tips have nearly identical magnetic field distributions around the windings as standard micro-fabrication (etching) techniques have both high spatial reproducibility and resolution. As the sensor was also designed to produce a spatially periodic magnetic field in the MUT, the sensor response can be accurately modeled which dramatically reduces calibration requirements. For example, calibration in air can be used to measure an absolute electrical conductivity without calibration standards, which makes the sensor geometry well-suited to surface mounted or embedded applications where calibration requirements will be necessarily relaxed.

For measuring the response of the individual sensing elements in an array, multiplexing between the elements can be performed. However, this can significantly reduce the data acquisition rate so a more preferably approach is to use an impedance measurement architecture that effectively allows the acquisition of data from all of the sense elements in parallel. Furthermore, ability to measure the MUT properties at multiple frequencies extends the capability of the inspection to better characterize the material and/or geometric properties under investigation. This type of instrument is described in detail in U.S. patent application Ser. No. 10/155,887, filed May 23, 2002, the entire teachings of which are incorporated herein by reference. The use of multiple sensing elements with one meandering drive and parallel architecture measurement instrumentation then permits high image resolution in real-time and sensitivity with relatively deep penetration of fields into MUT.

An efficient method for converting the response of the MWM sensor into material or geometric properties is to use grid measurement methods. These methods map two known values, such as the magnitude and phase or real and imaginary parts of the sensor impedance, into the properties to be determined and provide for a real-time measurement capability. The measurement grids are two-dimensional databases that can be visualized as "grids" that relate two measured parameters to two unknowns, such as the magnetic permeability (or electrical conductivity) and lift-off (where lift-off is defined as the proximity of the MUT to the plane of the MWM windings). For the characterization of coatings or surface layer properties, three- (or more)-dimensional versions of the measurement grids called lattices and hypercubes, respectively, can be used. Alternatively, the surface layer parameters can be determined from numerical algorithms that minimize the least-squares error between the measurements and the predicted responses from the sensor, or by intelligent interpolation search methods within the grids, lattices or hypercubes.

An advantage of the measurement grid method is that it allows for real-time measurements of the absolute electrical properties of the material and geometric parameters of interest. The database of the sensor responses can be generated prior to the data acquisition on the part itself, so that only table lookup and interpolation operations, which are relatively fast, needs to be performed after measurement data is acquired. Furthermore, grids can be generated for the individual elements in an array so that each individual element can be lift-off compensated to provide absolute property measurements, such as the electrical conductivity. This again reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations using standards and instrument preparation.

Figure 6:
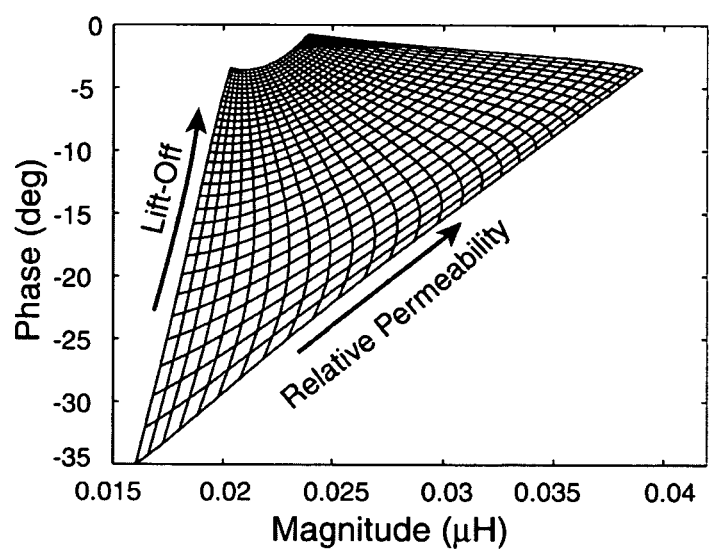
FIG. 6 shows a representative measurement grid relating the magnitude and phase of the sensor terminal impedance to the lift-off and magnetic permeability.
Figure 7:
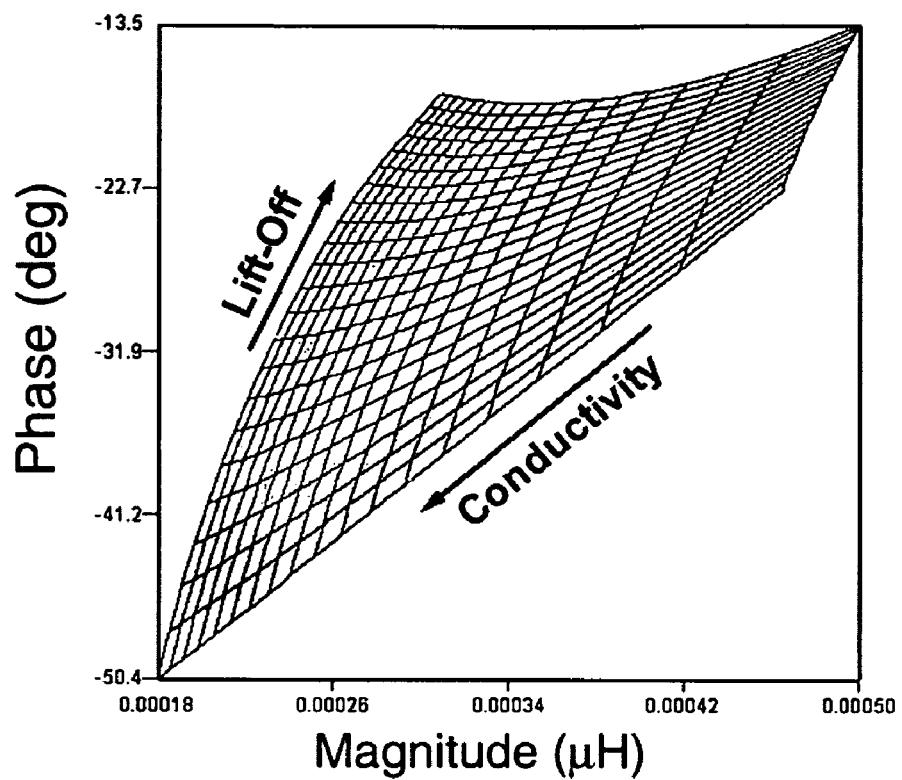
FIG. 7 shows a representative measurement grid relating the magnitude and phase of the sensor terminal impedance to the lift-off and electrical conductivity.

For ferromagnetic materials, such as most steels, a measurement grid can provide a conversion of raw data to magnetic permeability and lift-off. A representative measurement grid for ferromagnetic materials is illustrated in FIG. 6. A representative measurement grid for a low-conductivity nonmagnetic alloy (e.g., titanium alloys, some superalloys, and austenitic stainless steels) is illustrated in FIG. 7. For coated materials, such as cadmium and cadmium alloys on steels, the properties of the coatings can be incorporated into the model response for the sensor so that the measurement grid accurately reflects, for example, the permeability variations of substrate material with stress and the lift-off. Lattices and hypercubes can be used to include variations in coating properties (thickness, conductivity, permeability), over the imaging region of interest. The variation in the coating can be corrected at each point in the image to improve the measurement of permeability in the substrate for the purpose of imaging stresses.

In addition to inductive coils, other types of sensing elements, such as Hall effect sensors, magnetoresistive sensors, SQUIDS, and giant magnetoresistive (GMR) devices, can also be used for the measurements. The use of GMR sensors for characterization of materials is described in more detail in U.S. patent application Ser. No. 10/045,650, filed Nov. 8, 2001, the entire teachings of which are incorporated herein by reference. Conventional eddy-current sensors are effective at examining near surface properties of materials but have a limited capability to examine deep material property variations. GMR sensors respond to magnetic fields directly, rather than through an induced response on sensing coils, which permits operation at low frequencies, even DC, and deeper penetration of the magnetic fields into the test material. The GMR sensors can be used in place of sensing coils, conventional eddy-current drive coils, or sensor arrays. Thus, the GMR-based sensors can be considered an extension of conventional eddy-current technology that provides a greater depth of sensitivity to hidden features and are not deleteriously affected by the presence of hidden air gaps or delaminations.

Figure 8:
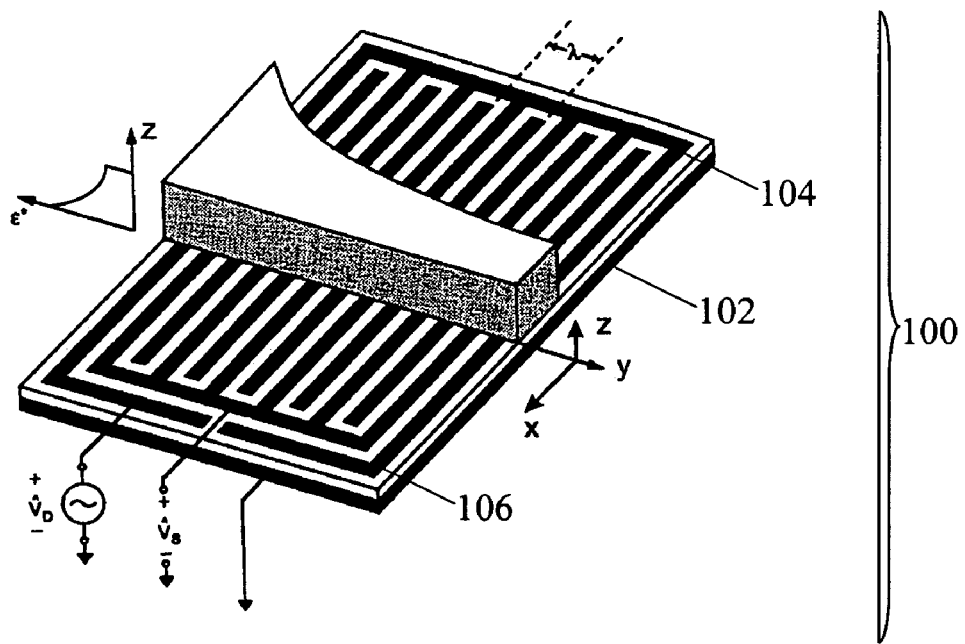
FIG. 8 shows a representative single wavelength interdigitated electrode dielectrometer with spatially periodic driven and sensing electrodes of wavelength $\lambda$ that can measure dielectric properties of the adjacent material for remotely monitoring the temperature of a plate.

For insulating or weakly conducting materials such as fiberglass composites, capacitive or dielectric sensors can be used. The sensors are the electromagnetic dual to the inductive sensors, with electric fields taking the place of magnetic fields for inspecting the materials and can be used to monitor stress or temperature, moisture content or contamination or overload of fatigue in adhesives, epoxies, glass, oil, plastics and in single or multiple layered media. Here the conductivity and dielectric constant or complex permittivity and layer thicknesses are measured using the same methods as for magnetic field sensing. In one such electric field method multiple layers of material are added to a base material with each layer sensitive to different chemicals or biological materials. A representative single sided sensor geometry is shown in FIG. 8 The application of a sinusoidally time varying potential of angular frequency $\omega=2\pi f$ results in the flow of a terminal current, whose magnitude and phase is dependent on the complex permittivity of the material. The capacitive sensor 100 has interdigitated electrodes as presented in U.S. Pat. Nos. 4,814,690, 6,380,747, and 6,486,673 and in U.S. patent application Ser. Nos. 10/040,797, filed Jan. 7, 2002, and Ser. No. 10/225,406, filed Aug. 20, 2002, the entire teachings of which are hereby incorporated by reference. This sensor 102 utilizes a pair of interdigitated electrodes 104 and 106 to produce a spatially periodic electric field. The electrodes are adjacent to the material of interest with an insulating substrate and a ground plane on the other side of the substrate. One of the two electrodes, 104, is driven with a sinusoidally varying voltage $v_D$ while the other, 106, is connected to a high-impedance buffer used to measure the magnitude and phase of the floating potential $v_S$ or to a virtually grounded amplifier to measure the magnitude and phase of the terminal current I. The periodicity of the electrode structure is denoted by the spatial wavelength $\lambda=2\pi r/k$, where k is the wavenumber.

The ability to develop accurate models for the sensor response permits the recovery of electrical and geometric material properties from measured data with minimal calibration. Without the ability to simulate sensor-material interaction, one is left to optimize sensor performance and gain intuition only through trial and error with physically realized sensors. The ability to predict sensor responses theoretically and observe practical deviations provides indications of unmodeled effects allowing further improvements in sensors and instrumentation. Solving the inverse problem of determining material properties from measured sensor response would be much more difficult if done using purely empirical methods. Accurate empirical sensor characterization would require a significant number of well-defined measurement specimens and the ability to independently measure all measurement dependent parameters, such as the sensor lift-off.

One popular option for modeling electromagnetic systems is the use of finite element methods (FEM), which are some of the most generic in terms of applicable geometries and property distributions. They are, however, generally inferior in speed and accuracy when solutions are available through analytic or semi-analytic methods. It is important that the models utilized be computationally efficient, especially if they are to be applied to near real-time inversion where either repeated solutions or large tables are required. The drawback of the analytic and semi-analytic methods is that they are most often limited to a given geometry or class of geometries. Planar MQS sensor quasi-analytical models have been developed, for example as described in U.S. Pat. No. 5,629,621, but these models are limited to periodic winding designs which have odd half-wave symmetry. The windings are also considered thin compared to all other geometric dimensions and the drive and sense windings are confined to a single plane. These quasi-analytical models are not directly applicable to the sensor geometries of FIGS. 1 through 5.

Figure 9:
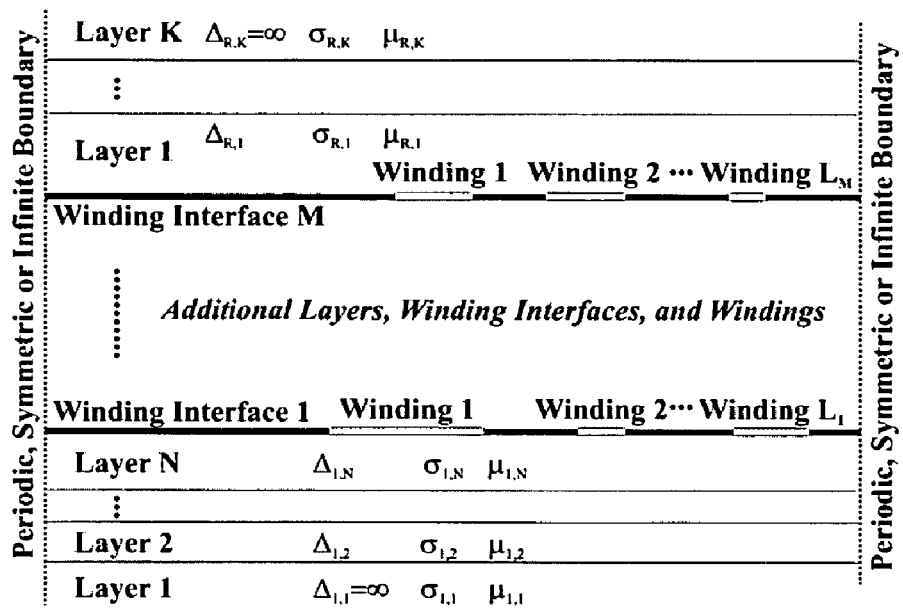
FIG. 9 shows a generic MQS sensor and MUT structure.
Figure 9:
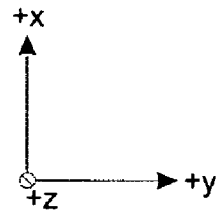

FIG. 9 shows a schematic view of a generic MQS sensor and MUT structure indicating the various possible boundary conditions and composed of multiple material layers, winding interfaces, and windings. The cross-sectional structure consists of one or more homogenous material layers which are characterized by their properties: permeability $\mu$, conductivity $\sigma$ and thickness $\Delta$. The planar boundaries separating each layer are all parallel to one another and the layers extend to infinity in the y and z directions. The outermost layers (topmost and bottommost) of the structure are assumed to have an infinite thickness such that there is no interaction between the system, consisting of the sensor and MUT, and the surroundings. The system is excited by any number of windings placed between the layers. These windings are assumed to be infinitely long in the z direction and infinitely thin in the x direction, such that the currents can be modeled as surface currents which flow in the z direction only. The surface conductivity of these windings can be defined such that only the net current of the winding needs to be specified, in which case diffusion effects within the windings are accounted for by the model. Additional windings defined with zero net current can also be located at interfaces and are typically used to represent secondary windings for which an induced potential is sought; the specification of a surface conductivity again allows diffusion effects to be included. The left and right planar boundaries can impose several symmetries including periodic, even, odd, and half-wave. For the case when the structure is aperiodic, these boundaries are essentially located at an infinite distance from the windings of the structure.

Figure 10:
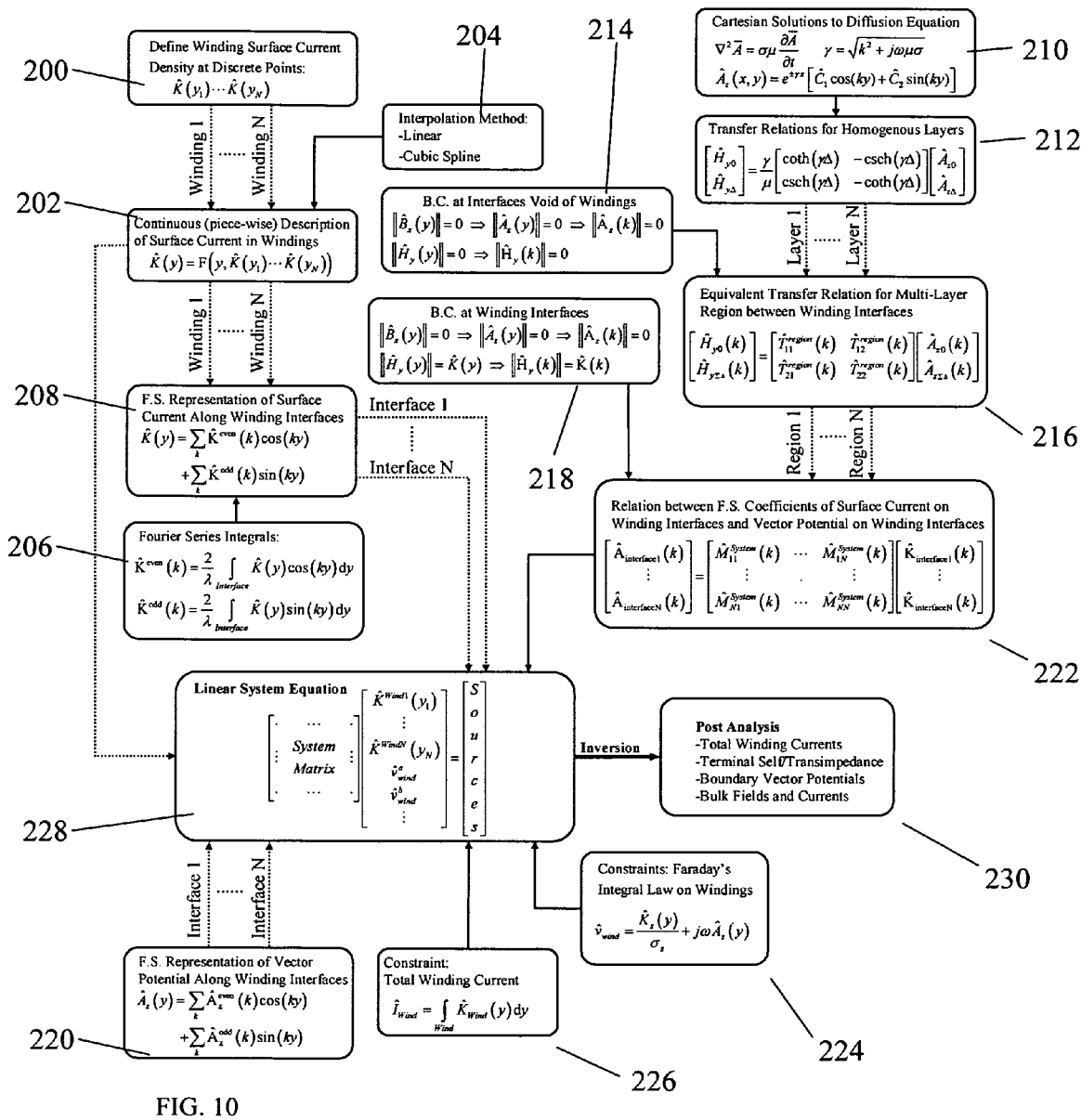
FIG. 10 shows a schematic overview of the MQS layered model.

FIG. 10 shows a schematic outline for the flow of information for an MQS model, showing how the equations, boundary conditions, function parameterization, Fourier representation, geometry and constraints are combined to produce a linear system equation. The details of the approach are shown later, where analytical solutions to Maxwell's equations in the form of transfer relations and boundary conditions relating layer solutions and winding constraints are joined with numerical techniques and linear algebra methods.

The modeling approach requires expressing unknown electromagnetic quantities at the interfaces containing windings in terms of functions contained in a finite dimensional function space or equivalently functions which are described by a finite number of parameters. At any of these interfaces there are two independent choices of quantities which may be parameterized, either the surface current density or the vector potential. Here, the surface current density will be parameterized. By making this choice, it is easier to choose the parameterization of the functions which result in a reduction in the number of function parameters because the surface current density is zero in the gaps separating windings. Fewer parameters lead to a smaller number of unknowns and ideally to a faster solution. Additional possible benefits lie in numerical issues associated with imposing boundary conditions near the edges of windings and in allowing for efficient methods for dealing with thin span-wise skin depths which exist in the windings at high temporal frequencies. The following outline of the methodology is therefore based on the parameterization of surface current density:

1. Since the actual surface current densities within the windings are unknown at the outset, they are defined by parameterized functions (202). These parameterized functions consist of defined values at discrete points along the windings in terms of unknown current densities (200). The current density between discrete points is then assigned by interpolation functions based on the values at the discrete points. The use of linear interpolations (204) produces a piece-wise linear description of the current density. It is however desirable to use smooth functions (i.e. continuous derivatives) such as splines, since the current distributions will actually be smoothly varying. Fourier methods are utilized in the solution and smooth functions also provide more rapidly convergent Fourier representations. The piece-wise description of the current density, utilizing either linear or spline interpolation, results in functions which are linear in terms of the unknown current densities at the discrete points, which will ultimately become important if linear algebra techniques are to be applied.

2. With a functional form for the surface current distributions, the Fourier series coefficients describing the spatial Fourier expansion of the surface current density along each interface containing windings can be found in terms of the unknown current densities at the discrete points (206 and 208).

3. Relationships in the form of a single transfer relation per spatial mode can be developed for each region between interfaces containing windings or between interfaces containing windings and the upper or lower extremes of the structure (210 and 212). This is accomplished by combining two adjacent layers within each region, by applying the relevant boundary conditions (214), to form a new effective layer described by a single transfer relation. By repeating this process between the effective layer and its adjacent layer repeatedly all of the layers within a region can be reduced. The process can be repeated for each region within a structure until a single transfer relation per is computed for each region. The resulting relationships relate the coefficients of complex exponentials of the spatial modes of the tangential magnetic field with those of the vector potential for adjacent boundaries containing windings. The details of the layer structure in these regions are therefore absorbed into the final transfer relation for the region (216).

4. At the interfaces containing windings, the MQS boundary conditions (218) require the normal component of the magnetic flux density to be continuous along the whole boundary, which further requires that the vector potential also be continuous and therefore be represented by a single function on the boundary. For each interface containing windings, the function representing the vector potential will be expressed in terms of its Fourier series and associated coefficients (220). The jump condition on tangential magnetic field at each interface, containing windings, also requires the jump in the coefficient for each mode of the tangential magnetic field to be equal to the corresponding coefficient of the current density. This boundary condition, in combination with single transfer relation for each region, allows the formulation of a matrix equation relating the coefficient of a specific mode of the current on each interface to the coefficients of the corresponding mode of the vector potential on each interface (222).

5. Additional constraint equations can then be generated for each winding. These include the constraints associated with Faraday's integral law which require the voltage induced on each winding to be constant within the winding (224). The winding constraints specifying the net current into each winding also provide necessary equations (226).

6. The resulting system of equations is then solved for the unknown current densities at discrete points and winding voltages (228). Once the discrete current densities are determined, total winding currents, terminal impedances, bulk/boundary vector potential, interpolated winding current distributions and internal fields can be evaluated (230).

The analytical portion of the sensor model relies upon solutions to the fundamental physical equations as building block for the total field solution for layered materials. These solutions lend themselves to being formulated as algebraic relations between spatial harmonics of electromagnetic quantities at a layer's interfaces and are described as transfer relations in the text "Continuum Electromechanics," by J. R. Melcher, MIT Press, Cambridge, Mass., 1981, the entire contents of which are incorporated herein by reference. This allows a system that would normally be described by a complex differential equation to be reduced to set of algebraic equations.

To obtain these building block transfer relations, in the MQS system the relevant Maxwell's equations are approximated by:

$$\nabla \times \vec{H} = \vec{J} \quad (1)$$

$$\nabla \cdot \vec{B} = 0 \quad (2)$$

$$\nabla \times \vec{E} = -\frac{\partial \vec{B}}{\partial t} \quad (3)$$

Since the magnetic flux density $\vec{B}$ is solenoidal it can be represented as the curl of the vector potential as:

$$\vec{B} = \nabla \times \vec{A} \quad (4)$$

The divergence of the vector potential must be specified in order for the vector potential to be unique and therefore the Coulomb gauge is chosen, requiring that $\nabla \cdot \vec{A} = 0$. Ohmic conduction is assumed for the material such that $\vec{J} = \sigma \vec{E}$, where $\sigma$ is the electrical conductivity and the material is assumed linear such that $\vec{B} = \mu \vec{H}$, where $\mu$ is the magnetic permeability. Using these constitutive relations then allows the governing equation for the vector potential to be expressed as a diffusion equation as:

$$\nabla^2 \vec{A} + \mu\sigma \frac{\partial \vec{A}}{\partial t} = 0 \quad (5)$$

For the sinusoidal steady state response, using the convention that $\vec{A}(\vec{r},t) = \vec{A}(\vec{r})e^{j\omega t}$, the time-harmonic form of (5) becomes:

$$\nabla^2 \vec{\bar{A}} + j\omega\mu\sigma \vec{\bar{A}} = 0 \quad (6)$$

Figure 11:
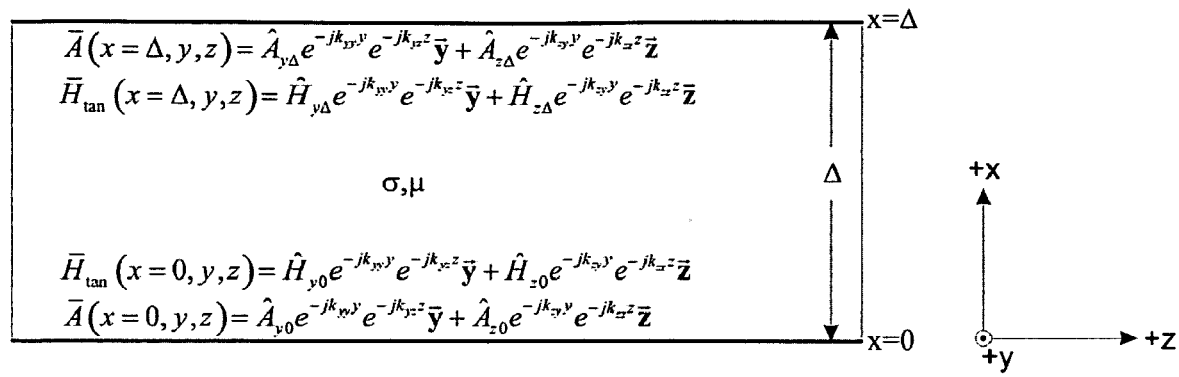
FIG. 11 shows a homogenous material layer for the MQS system with the dependence of the vector potential and the tangential magnetic field indicated at interfaces.

Next consider the homogeneous layer geometry of FIG. 11, which shows the vector potential and tangential magnetic field at each interface. These field quantities are related by transfer relations, which are the coefficients of the complex exponential terms and are dependent on the electrical and geometric properties in addition to the k parameters. The layer in FIG. 11 is assumed to be homogenous within the region bounded by the planes located at x=0 and x=Δ and orthogonal to the x-axis. This layer is excited by a planar winding structure with currents flowing only in the y-z plane and therefore it is expected that currents in the layer will also flow only in the y-z plane. Since the constitutive relation between the current and the electric field requires the electric field to be in the same direction as the current, the vector potential will also contain only y and z components. In order to find solutions to (6) a product solution having only these components is assumed:

$$\vec{\bar{A}}(x,y,z) = \hat{A}_{yx}(x)\hat{A}_{yy}(y)\hat{A}_{yz}(z)\vec{y} + \hat{A}_{zx}(x)\hat{A}_{zy}(y)\hat{A}_{zz}(z)\vec{z} \quad (7)$$

where the first subscript of $\hat{A}$ indicates the vector component and the second subscript indicates the Cartesian coordinate on which it is dependent. The method of separation of variables can then be applied by substituting this expression into (6) which then results in two independent partial differential equations. The equation resulting from the y component of the vector potential is:

$$\left[\frac{\hat{A}''_{yx}(x)}{\hat{A}_{yx}(x)}\right] + \left[\frac{\hat{A}''_{yy}(y)}{\hat{A}_{yy}(y)}\right] + \left[\frac{\hat{A}''_{yz}(z)}{\hat{A}_{yz}(z)}\right] = j\omega\mu\sigma \quad (8)$$

with a similar expression for the z component of the vector potential. Since each term is only dependent on a single coordinate, each term must be a constant for the preceding equations to be satisfied. The constant terms in the above equations can then be replaced with constant parameters. The relation resulting from the y component of the vector potential is:

$$\hat{\gamma}_{yx}^2 - k_{yy}^2 - k_{yz}^2 = j\omega\mu\sigma \quad (9)$$

with a similar relation for the z component.

Ordinary differential equations are produced when the terms in these equations are equated with their corresponding terms in the partial differential equations. By forcing the k parameters to be real, the associated differential equations are forced to have solutions consisting of complex exponentials with purely imaginary exponents. These solutions are desired for the associated products of the product solution because they are dependent on the coordinates along the layer's interfaces and will allow Fourier methods to be utilized later. The remaining parameter $\hat{\gamma}$ must then be complex which results in exponential solutions, whose coefficients must be determined according to boundary conditions at the layer's interfaces. It should be noted that in the case when both k terms for a given vector component of $\vec{\bar{A}}$ are zero in addition to the conductivity being zero, the parameter $\hat{\gamma}$ becomes zero and the ordinary differential equation on $\hat{A}(x)$ will no longer have exponential solutions.

Although the solutions to all of the ordinary differential equations could be substituted back into (7), which could then be equated to the boundary conditions, a more elegant approach exists. The y and z components of the vector potential at the layer's interfaces must have a complex exponential dependence equivalent to that dictated by the solutions to the differential equations produced by the k parameters. These solutions have undetermined coefficients which can be rearranged in the product solutions such that they are lumped with $\hat{A}_{yx}(x)$ and $\hat{A}_{zx}(x)$. At the interfaces there is no x dependence of the vector potential and therefore $\hat{A}_{yx}(x)$ and $\hat{A}_{zx}(x)$ must be equal to the coefficients of the y and z dependent complex exponentials as shown in FIG. 11. The coefficients on the exponential solutions required to produce this result must be determined; however, a linear combination of the exponentials can first be taken to produce hyperbolic sine functions. A linear combination of these hyperbolic functions with proper normalizations and translations produces the following result:

$$\hat{A}_x(x) = \hat{A}_\Delta \frac{\sinh(\hat{\gamma}x)}{\sinh(\hat{\gamma}\Delta)} - \hat{A}_0 \frac{\sinh(\hat{\gamma}(x-\Delta))}{\sinh(\hat{\gamma}\Delta)} \quad \text{for } \hat{\gamma} \neq 0 \qquad (10)$$

where again a portion of each subscript has been dropped due to the similarity between the analysis between y and z components of the vector potential. The complete solution for the vector potential is now obtained by substituting each component of the product solution into (7), leading to:

$$\bar{A}(x,y,z) = \qquad (11)$$

$$\begin{cases} \left[\hat{A}_{y\Delta} \frac{\sinh(\hat{\gamma}_{yx}x)}{\sinh(\hat{\gamma}_{yx}\Delta)} - \hat{A}_{y0} \frac{\sinh(\hat{\gamma}_{yx}(x-\Delta))}{\sinh(\hat{\gamma}_{yx}\Delta)}\right] e^{-jk_{yy}y} e^{-jk_{yz}z} \vec{y} + \\ \left[\hat{A}_{z\Delta} \frac{\sinh(\hat{\gamma}_{zx}x)}{\sinh(\hat{\gamma}_{zx}\Delta)} - \hat{A}_{z0} \frac{\sinh(\hat{\gamma}_{zx}(x-\Delta))}{\sinh(\hat{\gamma}_{zx}\Delta)}\right] e^{-jk_{zy}y} e^{-jk_{zz}z} \vec{z} \end{cases}$$

$$\text{for } \hat{\gamma}_{yx}, \hat{\gamma}_{zx} \neq 0$$

where:

$$\hat{\gamma}_{yx} = \sqrt{k_{yy}^2 + k_{yz}^2 + j\omega\mu\sigma} \qquad (12)$$

$$\hat{\gamma}_{zx} = \sqrt{k_{zy}^2 + k_{zz}^2 + j\omega\mu\sigma} \qquad (13)$$

The magnetic flux density can be evaluated from the vector potential as:

$$\bar{B}(x,y,z) = \qquad (14)$$

$$\begin{cases} \left[jk_{yz}\left[\hat{A}_{y\Delta}\frac{\sinh(\hat{\gamma}_{yx}x)}{\sinh(\hat{\gamma}_{yx}\Delta)} - \hat{A}_{y0}\frac{\sinh(\hat{\gamma}_{yx}(x-\Delta))}{\sinh(\hat{\gamma}_{yx}\Delta)}\right]e^{-jk_{yy}y}e^{-jk_{yz}z} - \\ jk_{zy}\left[\hat{A}_{z\Delta}\frac{\sinh(\hat{\gamma}_{zx}x)}{\sinh(\hat{\gamma}_{zx}\Delta)} - \hat{A}_{z0}\frac{\sinh(\hat{\gamma}_{zx}(x-\Delta))}{\sinh(\hat{\gamma}_{zx}\Delta)}\right]e^{-jk_{zy}y}e^{-jk_{zz}z}\right]\vec{x} - \\ \hat{\gamma}_{zx}\left[\hat{A}_{z\Delta}\frac{\cosh(\hat{\gamma}_{zx}x)}{\sinh(\hat{\gamma}_{zx}\Delta)} - \hat{A}_{z0}\frac{\cosh(\hat{\gamma}_{zx}(x-\Delta))}{\sinh(\hat{\gamma}_{zx}\Delta)}\right]e^{-jk_{xy}y}e^{-jk_{zz}z}\vec{y} \\ \hat{\gamma}_{yx}\left[\hat{A}_{y\Delta}\frac{\cosh(\hat{\gamma}_{yx}x)}{\sinh(\hat{\gamma}_{yx}\Delta)} - \hat{A}_{y0}\frac{\cosh(\hat{\gamma}_{yx}(x-\Delta))}{\sinh(\hat{\gamma}_{yx}\Delta)}\right]e^{-jk_{yy}y}e^{-jk_{yz}z}\vec{z} \end{cases}$$

$$\text{for } \hat{\gamma}_{yx}, \hat{\gamma}_{zx} \neq 0$$

A set of transfer relations which relates the coefficients of the complex exponential dependence of the tangential magnetic field to the coefficients of the complex exponential dependence of the vector potential on the layer's interfaces can now be constructed. Evaluating the z component of (14) at x=0 and x=Δ, followed by using the constitutive relation between the magnetic field and magnetic flux density, results in two equations which can be put into matrix form as follows:

$$\begin{bmatrix} \hat{H}_{z0} \\ \hat{H}_{z\Delta} \end{bmatrix} = \frac{\hat{\gamma}_{yx}}{\mu} \begin{bmatrix} -\coth(\hat{\gamma}_{yx}\Delta) & \operatorname{csch}(\hat{\gamma}_{yx}\Delta) \\ -\operatorname{csch}(\hat{\gamma}_{yx}\Delta) & \coth(\hat{\gamma}_{yx}\Delta) \end{bmatrix} \begin{bmatrix} \hat{A}_{y0} \\ \hat{A}_{y\Delta} \end{bmatrix} \quad \text{for } \hat{\gamma}_{yx} \neq 0 \qquad (15)$$

The contribution to the normal component of the magnetic flux density from the y component of the vector potential can also be evaluated and put into matrix form:

$$\begin{bmatrix} \hat{B}_{x0} \\ \hat{B}_{x\Delta} \end{bmatrix} = jk_{yz} \begin{bmatrix} \hat{A}_{y0} \\ \hat{A}_{y\Delta} \end{bmatrix} \qquad (16)$$

The electric field can be determined from the vector potential as:

$$\begin{bmatrix} \hat{E}_{y0} \\ \hat{E}_{y\Delta} \end{bmatrix} = -j\omega \begin{bmatrix} \hat{A}_{y0} \\ \hat{A}_{y\Delta} \end{bmatrix} \quad \text{for } \hat{\gamma}_{yx} \neq 0 \qquad (17)$$

The preceding methodology can be repeated for the y component of the tangential field and for the contribution to the normal flux density due to the z component of the vector potential to produce:

$$\begin{bmatrix} \hat{H}_{y0} \\ \hat{H}_{y\Delta} \end{bmatrix} = \frac{\hat{\gamma}_{zx}}{\mu} \begin{bmatrix} \coth(\hat{\gamma}_{zx}\Delta) & -\operatorname{csch}(\hat{\gamma}_{zx}\Delta) \\ \operatorname{csch}(\hat{\gamma}_{zx}\Delta) & -\coth(\hat{\gamma}_{zx}\Delta) \end{bmatrix} \begin{bmatrix} \hat{A}_{z0} \\ \hat{A}_{z\Delta} \end{bmatrix} \quad \text{for } \hat{\gamma}_{zx} \neq 0 \qquad (18)$$

$$\begin{bmatrix} \hat{B}_{x0} \\ \hat{B}_{x\Delta} \end{bmatrix} = -jk_{zy} \begin{bmatrix} \hat{A}_{z0} \\ \hat{A}_{z\Delta} \end{bmatrix} \qquad (19)$$

$$\begin{bmatrix} \hat{E}_{z0} \\ \hat{E}_{z\Delta} \end{bmatrix} = -j\omega \begin{bmatrix} \hat{A}_{z0} \\ \hat{A}_{z\Delta} \end{bmatrix} \quad \text{for } \hat{\gamma}_{zx} \neq 0 \qquad (20)$$

Although the case, in which σ≠0 and each term k associated with a specific component of $\bar{A}$ is zero, falls into the development of the previous relations, some nuances exist. An arbitrary periodic vector potential at a layer interface can be expressed in terms of a one or two dimensional Fourier series (assuming the potential is sufficiently well-behaved). The functions composing these series are mutually orthogonal and therefore a unique coefficient for the constant term is produced. In the development of the diffusion equation it was indicated that an arbitrary constant may be added to the vector potential without violation. This constant has the correct dependence at the interfaces to be included with the product solutions which result when both k terms are zero; however, in the general product solution no constant solution was included. Adding this arbitrary term results in a third unknown coefficient, which must be determined. However, the Fourier series representation of the potential only results in one equation for the coefficient of the constant term per layer interface. Specification of the interfacial potential is then insufficient to determine these coefficients uniquely. A second byproduct of allowing this term to be nonzero is that the relation between the vector potential and the electric field now includes a constant term (only in the case when both k terms are zero). Therefore, by specifying the electric field at one interface in addition to the potential at both interfaces this constant term can be determined and related back to the constant term in the vector potential; this allows the two coefficients of the remaining product solution to be evaluated. The transfer relations developed can therefore be directly applied if this constant term is either zero or if it can be determined and first removed from the constant part of the interfacial potentials. In practice, this constant term will only need to be considered and can be dealt with without its specific evaluation.

The boundary conditions generally require the tangential electric field and the vector potential to be continuous at interfaces. Since the electric field is directly related to the potential, this will require that the constant term be identical between neighboring layers. In handling the case when both k terms are zero, only the difference in potential usually needs to be considered and therefore calculation of this constant will be unnecessary. In the special cases where the boundary condition on the tangential field is not appropriate, the evaluation of these constants can still be avoided by special handling of the multilayered region.

In the special case when both the k terms associated with a specific vector potential component are zero and the conductivity is zero, the solutions to the ordinary differential equations containing the components of the product solution are altered. With the $\hat{\gamma}$ parameter now equal to zero, the solutions to the ordinary differential equation are of the form $$\hat{A}_x(x) = \hat{A}_\Delta \frac{x}{\Delta} + \hat{A}_0\left(1 - \frac{x}{\Delta}\right) \quad \text{for } \hat{\gamma} = 0 \tag{21}$$

where the coefficients can be determined by matching the vector potential at the layer interfaces. This result can be used for both the y and z components of $\overline{A}$ from which the flux density can then be determined:

$$\overline{B}(x, y, z) = \begin{cases} -\frac{1}{\Delta}[\hat{A}_{z\Delta} - \hat{A}_{z0}]\vec{y} \\ +\frac{1}{\Delta}[\hat{A}_{y\Delta} - \hat{A}_{y0}]\vec{z} \end{cases} \quad \text{for } \hat{\gamma}_{yx}, \hat{\gamma}_{zx} = 0 \tag{22}$$

It can be seen that the magnetic flux density has no normal component for the case when $\hat{\gamma}=0$. The tangential magnetic field is still present and can be related to the vector potential in the form of a transfer relation. The y component of the vector potential produces the relation:

$$\begin{bmatrix} \hat{H}_{z0} \\ \hat{H}_{z\Delta} \end{bmatrix} = \frac{1}{\mu\Delta}\begin{bmatrix} -1 & 1 \\ -1 & 1 \end{bmatrix}\begin{bmatrix} \hat{A}_{y0} \\ \hat{A}_{y\Delta} \end{bmatrix} \quad \text{for } \hat{\gamma}_{yx} = 0 \tag{23}$$

Although this form will be useful when handling regions composed of both conducting and nonconducting layers, the following more simplistic relationship is possible since the tangential field is identical on either boundary and only dependent on the difference of the potential:

$$\hat{H}_{z0} = \hat{H}_{z\Delta} = -\frac{1}{\mu\Delta}(\hat{A}_{y0} - \hat{A}_{y\Delta}) \quad \text{for } \hat{\gamma}_{yx} = 0 \tag{24}$$

Similar relationships can be developed for the z component of the vector potential:

$$\begin{bmatrix} \hat{H}_{y0} \\ \hat{H}_{y\Delta} \end{bmatrix} = \frac{1}{\mu\Delta}\begin{bmatrix} 1 & -1 \\ 1 & -1 \end{bmatrix}\begin{bmatrix} \hat{A}_{z0} \\ \hat{A}_{z\Delta} \end{bmatrix} \quad \text{for } \hat{\gamma}_{zx} = 0 \tag{25}$$

$$\hat{H}_{y0} = \hat{H}_{y\Delta} = \frac{1}{\mu\Delta}(\hat{A}_{z0} - \hat{A}_{z\Delta}) \quad \text{for } \hat{\gamma}_{zx} = 0 \tag{26}$$

In some cases there are advantages to utilize an approximation for the coefficients of the transfer relations resulting from limiting behavior. In particular, the effects of the layer thickness and of the wave number k becoming large are of interest. In both cases, the behavior of the transfer relations is dependent only on the hyperbolic functions for the relations of (15) and (18). Since $\hat{\gamma}$ will always have a real part and may have an imaginary part the limit of the terms containing the hyperbolic cosecant terms go to zero and the hyperbolic cotangent terms go to one. This is a good approximation when $$\Delta \gg \frac{1}{\gamma_r},$$

where the subscript r denotes the real part. Substituting these approximations into the transfer relations of (15) and (18) results in the following approximate transfer relations:

$$\begin{bmatrix} \hat{H}_{z0} \\ \hat{H}_{z\Delta} \end{bmatrix} = \frac{\hat{\gamma}_{yx}}{\mu}\begin{bmatrix} -1 & 0 \\ 0 & 1 \end{bmatrix}\begin{bmatrix} \hat{A}_{y0} \\ \hat{A}_{y\Delta} \end{bmatrix} \quad \text{for } \hat{\gamma}_{yx} \neq 0, \Delta \gg \frac{1}{\mathcal{R}\{\hat{\gamma}_{yx}\}} \tag{27}$$

$$\begin{bmatrix} \hat{H}_{y0} \\ \hat{H}_{y\Delta} \end{bmatrix} = \frac{\hat{\gamma}_{zx}}{\mu}\begin{bmatrix} 1 & 0 \\ 0 & -1 \end{bmatrix}\begin{bmatrix} \hat{A}_{z0} \\ \hat{A}_{z\Delta} \end{bmatrix} \quad \text{for } \hat{\gamma}_{zx} \neq 0, \Delta \gg \frac{1}{\mathcal{R}\{\hat{\gamma}_{zx}\}} \tag{28}$$

These relations show that the electromagnetic quantities on a given interface of a layer are independent of the electromagnetic quantities on the opposite interface. This is useful for the layers bounding the modeled structure, which are assumed to be infinitely thick and therefore satisfy the requirements for using the approximation. The electromagnetic quantities at the layer's interface, located at infinity, then have no influence and the quantities at the opposite interface are directly related.

The Fourier series representation of interface quantities will generally require an infinite number of terms to be exact. Since the series involves terms with increasing values of k, a value of k will be reached for each of the structure's layer where the layer is considered infinitely thick. The structure is essentially broken into multiple structures for which there is no direct interaction between solution components with values of k equal to or larger than that at which the approximation became valid. Groups of layers which become isolated from interfaces containing windings by layers using the approximation then have solutions with no components corresponding to these k values. The result is that for larger values of k fewer of the structure's layers generally need to be considered. At some value of k all of the layers will allow the approximations to be used and only layers adjacent to interfaces containing windings need to be considered; this behavior will be useful in reducing excess computations in later discussion of the model development and implementation.

The approximate transfer relations in (27) and (28) are used to replace the regular relations for the case when $\hat{\gamma} \neq 0$ and therefore separate approximations for the case when $\hat{\gamma}=0$ are now investigated. The requirement that $\hat{\gamma}=0$ for the relations of (23) and (25), makes an approximation for the case when $k \to \infty$ immediately meaningless. In the case when $\Delta \to \infty$ the relations force the tangential magnetic field to zero for any finite potential. Therefore the k=0 component of the tangential magnetic field will generally be zero at the interface of the infinitely thick layers bounding the structure and no approximation relation is necessary. However, the vector potential is only finite when there is no net current being returned at infinity. Since there is no net current in these infinitely thick layers, the magnetic field at these interfaces is directly dependent on the current at infinity. Approximations associated with these layers being infinitely thick will then enter through the imposed boundary conditions involving the tangential magnetic field.

Traditionally inhomogeneous material layers have been successfully dealt with by discretizing the material into numerous homogenous sub-layers in order to approximate the inhomogeneous property distribution. Although this technique is effective, when a closed form method is available, it is generally provides faster and more accurate computations. Therefore closed form solutions are specifically investigated for layers in which the conductivity is non-homogenous. In this case, the focus is on layers for which the conductivity is only dependent on the x coordinate and the permeability is constant. It follows that the time-harmonic form the diffusion equation then becomes:

$$\nabla^2 \overline{A} = \sigma(x) j \omega \mu \overline{A} \qquad (29)$$

The product solution of (7) can be substituted into (29) after which the method of separation of variables can again be used. Equating each constant term of these equations with the corresponding term in the partial differential equations results in a set of ordinary differential equations. The term $-j\omega\mu\sigma(x)$ is grouped with the x dependent components of the produce solution, such that the the ordinary differential equations associated with the y and z dependent terms result in complex exponential solutions with purely imaginary exponents. This will again allow Fourier methods to be applied in matching solutions to the boundary conditions. In order for the $\hat{A}(x)$ components of the product solution to be explicitly evaluated, the exact form of the conductivity variation must now be specified.

A linear dependence was choosen due to its relative simplicity and its general applicability. A linear conductivity distribution is valuable for both modeling corresponding physical distributions and as a piece of a piecewise linear approximation of more complex property distributions. In both cases the use of a linear distribution will generally provide a better approximation with fewer pieces than a piecewise constant representation using homogenous layers. The linear conductivity variation is expressed as:

$$\sigma(x) = \sigma_0 + \frac{\sigma_\Delta - \sigma_0}{\Delta} x \qquad (30)$$

The ordinary differential equations associated with the constant $\alpha$ parameters are now expressed as:

$$\hat{A}_x''(x) - \hat{A}_x(x)\left(j\omega\mu\frac{\sigma_\Delta - \sigma_0}{\Delta}x + j\omega\mu\sigma_0 + \alpha\right) = 0 \qquad (31)$$

where the first subscript on $\hat{A}(x)$ and $\hat{\alpha}$ have been temporarily dropped due to the identical analysis for each vector component equation. The complete solution for the vector potential in the layer can be expressed as:

$$\overline{A}(x,y,z) = \begin{cases} [\hat{c}_y \hat{a}_y(x) + \hat{d}_y \hat{b}_y(x)] e^{-jk_{yy}y} e^{-jk_{yz}z} \vec{y} + \\ [\hat{c}_z \hat{a}_z(x) + \hat{d}_z \hat{b}_z(x)] e^{-jk_{zy}y} e^{-jk_{zz}z} \vec{z} \end{cases} \qquad (32)$$

where:

$$\hat{a}(x) = Ai(\hat{\beta}^{-2/3}(\hat{\beta}x + \hat{\chi})) \qquad (33)$$

$$\hat{b}(x) = Bi(\hat{\beta}^{-2/3}(\hat{\beta}x + \hat{\chi})) \qquad (34)$$

$$\hat{\beta} = j\omega\mu\frac{\sigma_\Delta - \sigma_0}{\Delta} \qquad (35)$$

$$\hat{\chi} = \omega\mu\sigma_0 + \alpha \qquad (36)$$

The functions $Ai(\hat{z})$ and $Bi(\hat{z})$ are the Airy functions of the first and second kind respecively, while $\hat{c}$ and $\hat{d}$ are coefficients which must be determined by the layer boundaries. The unknown coefficients can now be choosen such that the previous expression matches the vector potential at the layer interfaces:

$$\overline{A}(x=0,y,z) = \hat{A}_{y,0} e^{-jk_{yy}y} e^{-jk_{yz}z} \vec{y} + \hat{A}_{z,0} e^{-jk_{zy}y} e^{-jk_{zz}z} \vec{z} \qquad (37)$$

$$\overline{A}(x=\Delta,y,z) = \hat{A}_{y,\Delta} e^{-jk_{yy}y} e^{-jk_{yz}z} \vec{y} + \hat{A}_{z,\Delta} e^{-jk_{zy}y} e^{-jk_{zz}z} \vec{z} \qquad (38)$$

to give:

$$\hat{c} = \frac{\hat{A}_0 \hat{b}(\Delta) - \hat{A}_\Delta \hat{b}(0)}{\hat{a}(0)\hat{b}(\Delta) - \hat{a}(\Delta)\hat{b}(0)} \qquad (39)$$

$$\hat{d} = \frac{\hat{A}_0 \hat{a}(\Delta) - \hat{A}_\Delta \hat{a}(0)}{\hat{a}(0)\hat{b}(\Delta) - \hat{a}(\Delta)\hat{b}(0)} \qquad (40)$$

The corresponding magnetic flux density can now be evaluated from the vector potential:

$$\overline{B}(x,y,z) = \begin{cases} [[\hat{c}_y \hat{a}_y(x) + \hat{d}_y \hat{b}_y(x)]jk_{yz} e^{-jk_{yy}y} e^{-jk_{yz}z}] - \\ [\hat{c}_z \hat{a}_z(x) + \hat{d}_z \hat{b}_z(x)]jk_{zy} e^{-jk_{zy}y} e^{-jk_{zz}z}]\vec{x} - \\ [\hat{c}_z \hat{a}_z'(x) + \hat{d}_z \hat{b}_z'(x)] e^{-jk_{zy}y} e^{-jk_{zz}z}\vec{y} + \\ [\hat{c}_y \hat{a}_y'(x) + \hat{d}_y \hat{b}_y'(x)] e^{-jk_{yy}y} e^{-jk_{yz}z}\vec{z} \end{cases} \qquad (41)$$

where:

$$\hat{a}'(x) = \hat{\beta}^{1/3} Ai'(\hat{\beta}^{-2/3}(\hat{\beta}x + \hat{\chi})) \qquad (42)$$

$$\hat{b}'(x) = \hat{\beta}^{1/3} Bi'(\hat{\beta}^{-2/3}(\hat{\beta}x + \hat{\chi})) \qquad (43)$$

The y and z components of the tangential magnetic field can be evaluated at the layer interfaces using (41). The resulting expressions can then be used to relate the coefficients of the complex exponentials which describe the vector potential and tangential magnetic field. The transfer relation associated with the y component of the vector potential is:

$$\begin{bmatrix} \hat{H}_{z0} \\ \hat{H}_{z\Delta} \end{bmatrix} = \frac{1}{\mu} \begin{bmatrix} \hat{f}_y(0, \Delta) & \hat{g}_y(\Delta, 0) \\ \hat{g}_y(0, \Delta) & \hat{f}_y(\Delta, 0) \end{bmatrix} \begin{bmatrix} \hat{A}_{y0} \\ \hat{A}_{y\Delta} \end{bmatrix} \quad (44)$$

where:

$$\hat{f}(\rho, \tau) = \frac{\hat{a}'(\rho)\hat{b}(\tau) - \hat{a}(\tau)\hat{b}'(\rho)}{\hat{a}(\rho)\hat{b}(\tau) - \hat{a}(\tau)\hat{b}(\rho)} \quad (45)$$

$$\hat{g}(\rho, \tau) = \frac{\hat{a}'(\tau)\hat{b}(\tau) - \hat{a}(\tau)\hat{b}'(\tau)}{\hat{a}(\rho)\hat{b}(\tau) - \hat{a}(\tau)\hat{b}(\rho)} \quad (46)$$

The relations between the coefficients of the normal flux density or the coefficients of the electric field and the vector potential are identical to those of (16) and (17) for the uniform layer. A similar relation holds for the z component of the vector potential.

For layers with linear variation, there is no special case equivalent to the $\hat{\gamma}=0$ case of the uniform layer. However, the behavior of the transfer relation as $k\to\infty$ may be of interest. Although not specifically evaluated it is expected that the off-diagonal terms of the transfer relations will approach zero as $k\to\infty$, since this behavior would obviously be present if the layer was approximated with one or more uniform layers. As an estimate as to when the diagonal terms can be taken as zero, the uniform layer requirement that $\Delta\Re\{\hat{\gamma}\}>>1$ can be used by choosing σ to be the smallest conductivity value present in the linear variation of the layer. This should be conservative since it underestimates the shielding between the layer's interfaces. From the approximate relations for the uniform layer, it can be shown that the influence of the conductivity diminishes as $k\to\infty$, since $\hat{\gamma}\to k$. Therefore, the approximation that $\hat{\gamma}=k$ can be used when $\omega\mu\sigma<<k^2$. By choosing σ to be the largest value in the linear variation, a conservative estimate as to when the conductivity can be neglected is made. In the case when both of the aforementioned requirements are met, the approximations of (27) and (28) for the uniform layer can be invoked for the linear layer by setting σ=0.

While the preceding discussion developed sets of solutions for regions consisting of a single layer with uniform electrical properties or linear spatial variations in conductivity, these solutions are typically applied to each layer of a multilayer structure to form the total solution. In order for this total solution to be self-consistent with Maxwell's equations, the proper boundary conditions must be applied at each layer interface such that the correct boundary values for each component of the solution can be determined.

The interfaces separating layers within the modeled structure can be divided into one of two possible categories. Some of the interfaces contain the windings which excite the system and are assumed to be infinitely thin; these windings reside at the interfaces corresponding to the winding position. The remaining interfaces are void of windings; the associated boundary conditions are described first.

The first boundary condition is produced by the considering continuity of the magnetic flux and requires that the normal component of the magnetic flux density be continuous at layer interfaces:

$$\vec{x} \cdot [\vec{B}(x=a^+,y,z) - \vec{B}(x=a^-,y,z)] = \hat{B}_x(x=a^+,y,z) - \hat{B}_x(x=a^-,y,z) = 0 \quad (48)$$

where the interface is located at x=a and the positive and negative superscripts indicate that the flux density is evaluated by the limit as x→a from either the positive or negative side of the interface. In terms of the solutions for each layer, this simply indicates that the flux density at $x=a^+$ is evaluated using the solution for the layer on the positive side of the interface at x=a and similarly the flux density at $x=a^-$ is evaluated using the solution for the layer on the negative side of the interface.

The second boundary condition results from the expression of the flux density in terms of the vector potential of (4). Taking the integral of this relation and applying Stokes' theorem yields $$\vec{A}(x=a^+,y,z) - \vec{A}(x=a^-,y,z) = 0 \quad (49)$$

since there is no surface flux at the interface. The vector potential must also be continuous at the interfaces between layers. The relationships in (16) and (19) between the coefficients of the normal flux density and the coefficients the vector potential also shows that they are related in a way that is independent of layer properties and only dependent on k. Therefore, for a specific value of k the continuity of the vector potential automatically guarantees that the normal flux will be continuous.

An additional boundary condition results from the integral form of Faraday's law, which in the absence of a surface flux density requires:

$$\vec{x} \times [\vec{E}(x=a^+,y,z) - \vec{E}(x=a^-,y,z)] = \hat{E}_{y,z}(x=a^+,y,z) - \hat{E}_{y,z}(x=a^-,y,z) = 0 \quad (50)$$

In other words the tangential electric field must be continuous at the interface. The relations in (17) and (19) between the coefficients of the tangential electric field and the vector potential imply that if the vector potential is continuous then the tangential electric field will also be continuous. For the layer interfaces of the structure which do not coincide with interfaces containing the sensor's windings, no surface current density is expected. Ampere's integral law then requires that the tangential magnetic field is continuous at these interfaces:

$$\vec{x} \times [\vec{H}(x=a^+,y,z) - \vec{H}(x=a^-,y,z)] = \hat{H}_{y,z}(x=a^+,y,z) - \hat{H}_{y,z}(x=a^+y,z) = 0 \quad (51)$$

The four preceding boundary conditions originate either directly from Maxwell's equations or from defining relations and are all exact. However, special consideration needs to be given in applying these boundary conditions to layer solutions with k=0. From the relations between the normal magnetic flux density and the vector potential of (16) and (19) it can be seen that there is no normal flux density when k=0 and σ≠0. Likewise from (22) it can be observed that when k=0 and σ=0 there is also no normal flux density. Therefore when k=0, the boundary condition on the normal component of the flux density no longer needs to be imposed. A tangential component of the magnetic field is maintained in both instances and requires the associated boundary condition.

In the case of two adjacent conducting layers (k=0 solutions), the electric field at the interface due to either layer is still expressed in terms of vector potential by (17) and (19) (assuming no constants are added to the vector potential) and therefore continuity of one quantity implies the continuity of the other. The solutions for the nonconducting layers with $k=0$ and $\hat{\gamma}=0$ did not include any relationships between the electric field and the vector potential due to the lack of uniqueness of the electric field. This results from the use of the MQS approximation of Maxwell's equations and the lack of coupling between the current density and the electric field in Ohm's law when $\sigma=0$. Therefore only the curl of the electric field appears in the governing equations and a unique solution for the electric field is not implied. The boundary condition on the electric field then provides no immediately useful information at an interface involving a nonconducting layer. For the case of two adjacent nonconducting layers ($k=0$ solution), the remaining boundary conditions on the continuity of the vector potential and the continuity of the tangential magnetic field are sufficient to constrain the solution coefficients.

Figure 12:
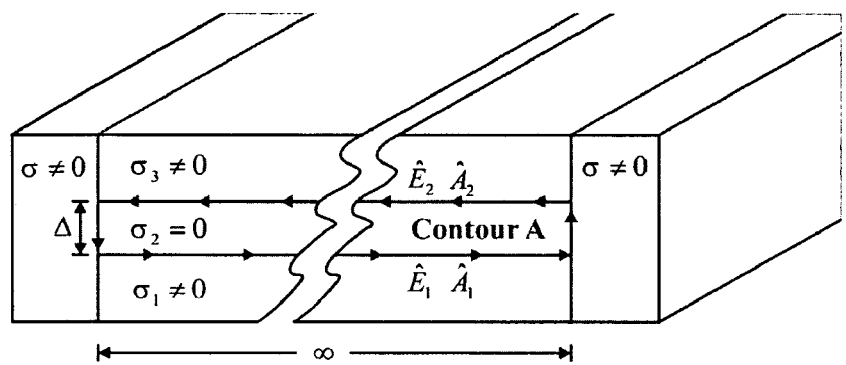
FIG. 12 shows a cross-section view of conducting layers separated by an insulating layer with a conduction path at infinity.
Figure 13:
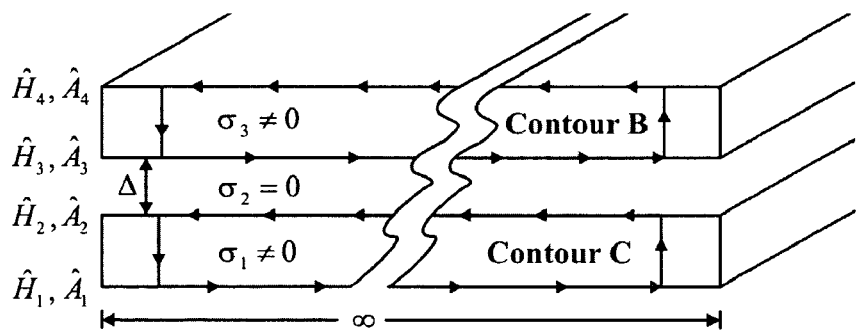
FIG. 13 shows a cross-section view of conducting layers separated by an insulating layer without a conducting path between the conducting layers.

When a conducting layer ($k=0$ solution) is adjacent to a nonconducting layer ($k=0$ solution) imposing the continuity of the vector potential and the tangential field carry certain implications about the layer interactions. In order to demonstrate this, two possible scenarios for the interaction between layers in a three layer system composed of an insulating layer placed between two conducting layers are shown in FIGS. 12 and 13. In FIG. 12 the two conducting layers are connected at the infinite extents of the layers such that there is a conducting path for current to flow between these layers. The flux density in the integral form of Faraday's law can be related to the vector potential as:

$$\oint_C \bar{E} \cdot d\bar{s} = -j\omega \oint_C \bar{A} \cdot d\bar{s} \tag{52}$$

Note that, for this to be consistent, the vector potential must be continuous. This relation can be applied to contour A, which follows a path that lies an incremental distance from the interface inside the conducting media. Since the $k=0$ solutions are being considered, both the tangential electric field and the vector potential are constant along the interfaces. The portions of the contour path at the infinite extent of the layers and normal to the layer interfaces have thicknesses equal to the insulating layer thickness, which is much smaller than the infinite path length parallel to the interface. The current density in the conducting material will be finite as will the vector potential and therefore in the limit where these layers have infinite extent, the smaller path portions of length $\Delta$ will make no contribution to the total contour integral. The contour integral along the designated path then requires:

$$\hat{E}_1 - \hat{E}_2 = -j\omega \hat{A}_1 + j\omega \hat{A}_2 \tag{53}$$

However, the electric field at the interfaces of the conducting layers can be related to the vector potential using the relations of (17) and (19), which can then be substituted into the previous result. This produces an expression of self-consistency with:

$$\hat{E}_1 - \hat{E}_2 = \hat{E}_1 - \hat{E}_2 \tag{54}$$

It is important to note that although the freedom existed to add different constants to the vector potential solutions for $k=0$ and $\sigma \ne 0$, this would have resulted in different relations (17) and (19) for each conducting layer. The self-consistency observed would then have been lost. Therefore by choosing not to add a constant term to the product solution for conducting layers and imposing continuity of the vector potential and continuity of the tangential magnetic field, the layer interactions of FIG. 12 are imposed.

In FIG. 13, the flow of current between the two conducting layers is restricted. Attempting to apply (52) to a contour path similar to the one used previously is no longer convenient since the electric field is not uniquely defined in the insulating layer. Instead Ampere's integral law now becomes valuable:

$$\oint_C \bar{H} \cdot d\bar{s} = \int_S \bar{J} \cdot d\bar{a} \tag{55}$$

Since current is no longer transferred between the layers, the integral of the current density over the surface defined by contours B and C must be zero. For the $k=0$ solutions, the tangential magnetic field is again constant along the interfaces. The portion of the path with length $\Delta$ makes no contribution do to the lack of a magnetic field component in the direction normal to the layer surfaces and therefore applying (55) to each contour results in $\hat{H}_1 = \hat{H}_2$ and $\hat{H}_3 = \hat{H}_4$. The magnetic field for insulating layers is independent of position within the layer and therefore $\hat{H}_2 = \hat{H}_3$. With the tangential magnetic field now known to be equivalent at each interface, the vector potential at interfaces can be determined. The relationships between the tangential field and the vector potential of (15) and (18) can be used for the conducting layers. However, the matrix relation needs to be inverted so that the vector potential is expressed in terms of the magnetic field, which is identical at each interface. The relationships of (24) and (26) can be used for the insulating layer and only constrains the difference in the vector potential at each layer interface. It should now become apparent that since the tangential magnetic field $\hat{H}_1 = \hat{H}_2 = \hat{H}_3 = \hat{H}_4$ imposes the vector potential $\hat{A}_2$ and $\hat{A}_3$ through the conducting layer relations and the vector potential must be continuous at interfaces, that the difference $\hat{A}_2 - \hat{A}_3$ dictated by the insulting layer relation will not be self-consistent.

This inconsistency can be resolved by the addition of the allowed free constant term in the product solution of the vector potential for the conducting layers. In order for a unique vector potential solution to be determined, the vector potential at one interface must be defined as a reference value. The correct constants which must be added to the conducting layer solutions can then be determined using the reference value, the interface values without constants, and the required difference $\hat{A}_2 - \hat{A}_3$. This then provides a total solution in which no current is transferred between layers, and both the tangential magnetic field and vector potential are continuous at interfaces. However, as will be shown later, the regions composed of multiple layers between interfaces containing the windings only need to be described by expressions consisting of the identical magnetic field at the interfaces bounding the multilayered region and the difference in vector potential between these interfaces. Since the constant terms make no contribution to the difference in the vector potential between the interfaces of each layer, the difference in the vector potential between the interfaces of group of layers can be determined as the sum of the differences for each layer, which avoids the determination of these constants.

Other interfaces contain the windings which excite the interrogating fields. The windings which excite the system are assumed to be infinitely thin and are therefore modeled as residing at interfaces between layers rather than occupying a finite volume. The windings do not usually occupy the complete length of the interface and therefore the finite thickness gaps separating one or more windings are also modeled as infinitely thin. Since in actuality the physical windings and gaps have finite dimensions, the assumptions made in order to model each winding as infinitely thin will be briefly discussed. However, determining the accuracy of simulation quantities resulting from these approximations a priori is generally not possible. After simulation an estimate of the errors in relevant quantities is most easily obtained by comparison with an alternate accurate solution method, although it is expected that other methods of bounding the error may be devised. One alternate solution method which always exists and allows a more accurate simulation is based on approximating the finite thickness winding using multiple infinitely thin windings and the modeling techniques described in this chapter (this method is discussed in more detail elsewhere).

Determining actual errors may present some difficulty, but general trends associated with the magnitude of certain errors can be stated. The fields resulting from current sources such as the windings have a nature in which they become more diffuse and smoothly varying with distance from the source. Therefore, as the distance from the winding becomes much larger than its thickness, the errors introduced in the fields decrease. Errors in other quantities such as self-inductance are dependent on fields both near and far from the winding and do not lend themselves to this simple reasoning.

The first assumption required by the infinitely thin approximation relates to the normal magnetic flux entering and exiting the interfaces of thin layer containing the finite windings and gaps. The flux density is assumed to be identically distributed along these interfaces. Ideally, this requires that none of the flux entering or exiting at these interfaces is redirected tangentially within the thin layer of the gaps and windings, while as an approximation this implies that normal flux directed tangentially is a relatively small portion of the normal flux. The goal is to replace the bulk behavior of the winding with relations that only involve electromagnetic quantities at the planar interfaces of the thin layer and net winding properties over the thickness. This assumption then implies that the normal flux density is continuous at interfaces on which windings are placed and produces a boundary condition identical to (48).

The second assumption is that the vector potential is identical between interfaces of the thin layer. An integral relating the vector potential to the flux density was previously applied to the interfaces not containing windings and the continuity of the vector potential was reasoned by the lack of a surface flux tangential to the interface. Due to the finite thickness of the thin layer containing the gaps and windings, any tangential flux within the layer requires a mismatch in the vector potential between layer interfaces. Assuming that the potential is identical between interfaces implies that affects of this flux are negligible. The boundary condition for the continuity of the vector potential of (49) then applies to the winding interface. A similar argument of an absence of surface flux was used in the development of the boundary condition on the tangential electric field for layers not containing windings. Therefore, ignoring the tangential flux density in the thin layer also implies the continuity of the tangential electric field described by the boundary condition of (50). Since the interfaces of the thin layer being approximated are adjacent to normal material layers, the vector potential on an interface is directly related to both the normal flux density and the tangential electric field on the same interface, independent of material properties. By making any of the preceding assumptions the others must also follow for the boundary conditions of the regular material layers to be simultaneously met.

The last boundary condition replacing the thin layer is produced by Ampere's integral law (55) applied to a contour through the thin layer with a path similar to contour B in FIG. 13. If the length of the long side of this path is shrunk to a differential size, the surface integral over the current density can be expressed in terms of the product of a differential length and a surface current density $\overline{K}$ which is dependent on the position along the interface. The contour on the left side of Ampere's law involves four linear segments, two with length equal to the thickness of the layer, and two of the differential length. If the magnetic field in the normal direction is assumed to be sufficiently constant, an assumption that is consistent with the assumption of the continuity of the normal flux, then the paths of length equal to the thickness make no contribution to the contour integral. The result can then be expressed in terms of an additional boundary condition replacing the thin layer as:

$$\vec{x} \times [\overline{H}(x=a^+,y,z) - \overline{H}(x=a^-,y,z)] = \overline{K}(x=a,y,z) \tag{56}$$

Since the thin layer is composed of both windings and gaps, the surface current density will be exactly zero in locations along the interface corresponding to the gaps, while for locations along the windings the surface current density must be determined.

Figure 14:
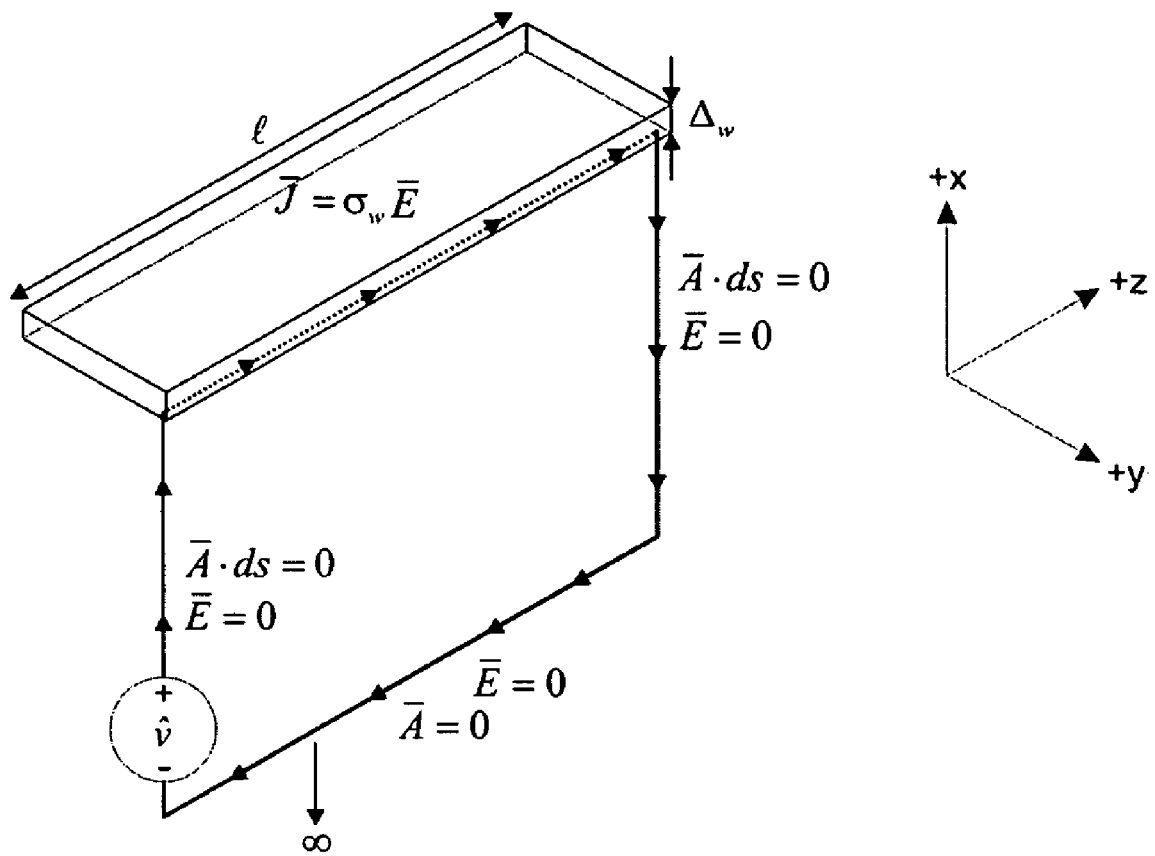
FIG. 14 shows a contour path for applying Faraday's integral law to a winding in order to generate constraint equations.

In order to constrain the current density in the locations corresponding to the windings, Faraday's law in integral form (52) is applied to the contour path shown in FIG. 14. The path passes through an arbitrary location on the windings and then is connected to a voltage source using perfectly conducting wires such the electric field is zero except in the winding. Though the winding will be approximated as infinitely thin, it has the physical thickness $\Delta_w$ and bulk conductivity $\sigma_w$. It is assumed that the currents and fields are identical to those for windings of infinite length in the z direction such there is no z dependence due to symmetry. However, the z directed portion of the contour path is applied over a finite length l, which is equal to that of the physical winding; this effectively ignores the edge effects of the finite length windings. The contour path passes through the winding where the electric field and the current density are related by Ohm's law. Since the winding is approximated as infinitely thin, only the surface current density is specified rather than the current density. The average current density is therefore determined as the z directed surface current density divided by the winding thickness. The electric field is then related to the surfaces current density by:

$$\hat{E}_z(y) = \frac{1}{\sigma_s} \hat{K}_z(y) \tag{57}$$

where the surface conductivity is defined as $\sigma_s \equiv \sigma_w \Delta_w$ and where $\sigma_w$ is the bulk conductivity of the winding. Due to the symmetry and the assumptions for modeling the winding as infinitely thin, the vector potential inside the winding only has a z component and is dependent only on the position along the winding in the y direction; it is therefore expressed as $\hat{A}_z(y)$. The symmetry also forces the vector potential to have only a z component throughout the remaining volume of the modeled structure and therefore the x oriented portions of the path do not contribute to the contour integral of the vector potential. The vector potential at the leg opposite the winding leg and at infinity is assumed to be far from the structure where the vector potential can be taken as zero.

The electric field along the path excluding the winding is zero except at the location corresponding to the voltage source, for which the contour integral is simply evaluated as the voltage $-\hat{v}$. The electric field is zero at these indicated locations by using the abstraction that the windings are connected to the voltage source with perfectly conducting wires. This is an abstraction in the sense that it does not represent a practical method of connecting the winding due to the infinite path lengths in reaching the leg of the path opposite the winding. Additionally the wires are assumed not to influence the fields except for imposing the electric field to be zero. However, this representation is useful since most often more than one winding will be connected in a way such there interconnection is through a short segment, which is highly conducting such that the electric field can be approximated as zero. The voltage of interest is then located at the winding ends opposite to the short interconnect. Applying Faraday's law to this new path of finite length through each winding and the interconnect results in a voltage which is equivalent to the difference of the voltages produced by using the path of FIG. 14 for each winding. Since the exact value of the voltage is normally not imposed, this technique allows the connections between winding segments to be ignored until a solution for the voltage of each winding is calculated. The voltage for a specific connection scheme can then be simply determined.

Applying the Faraday's law to the path of FIG. 14 and utilizing the electric field, voltage, and vector potential discussed results in the following relation:

$$\tilde{\hat{v}} = \frac{\hat{K}_z(y)}{\sigma_s} + j\omega \hat{A}_z(y) \tag{58}$$

where the voltage have been normalized by the winding. The constraint of (58) is valid for any arbitrary y coordinate within the winding, where the voltage $\hat{v}$ is a winding specific constant. The requirement that the voltage is constant can be seen by choosing a contour which passes through the winding at one location and connects to a returning path within the same windings at another location using the highly conducting winding material at one edge. A voltage developed at the edge opposite to this connection would result in a y directed electric field within the conductor with currents in the same direction; this is not allowed by the symmetry and therefore the voltage must be zero. Since this zero voltage can be calculated as the difference of the voltages using the path of FIG. 14 for each leg within the winding, the voltages calculated for each path must be identical.

Equation (58) constrains the distribution of the surface current subject to the vector potential and the winding voltage. The vector potential and the surface current density are related by the bulk relations leading to the transfer relations equations. The voltage is often not constrained other than being constant for a specific winding since the net current through a specific winding is generally imposed in order to excite the system. The net current through a winding is simply calculated as the integral of the surface current density distribution along the winding. The current is then constrained by the relation:

$$\int_{wind} \hat{K}_z(y) dy = \hat{i} \tag{59}$$

where $\hat{i}$ is the current through the specific winding.

The preceding algorithm is a generic formulation, which allows for multiple winding interfaces containing an arbitrary number of windings at arbitrary positions and can therefore accommodates a variety of sensor constructs. The important governing equations, solutions for individual layers, relevant boundary conditions, and winding constraints were presented for the MQS system along with an overview of how these items are interconnected in arriving at an overall solution. A common exhaustive development of the equations of the final system for both MQS and EQS systems described later draws on these specific results for the MQS system as needed. Methods of utilizing the symmetry present in the modeled structure in addition to dealing with aperiodic structures are also discussed later.

In a similar fashion, quasianalytical models and transfer relations can be developed for EQS sensors. This model permits aperiodic electrode pattern, a variety of symmetries and electrode configurations in order to accommodate multiple sensing elements, and placement of electrodes on multiple layers in order to accommodate finite thickness approximations using multiple electrodes.

FIG. 9 presents a schematic view that can represent a generic EQS sensor and MUT configuration, with the "windings" taken as "electrodes" and the magnetic permeability $\mu$ replaced by the dielectric permittivity $\in$. The cross-sectional structure consists of any number of homogenous layers of material which are characterized by their properties: electrical permittivity $\in$, conductivity $\sigma$ and thickness $\Delta$. The planar boundaries separating each layer are all parallel to one another and the layers extend infinitely in the y and z directions. The outermost interfaces of the structure, consisting of planes normal to the x direction, can be constrained with a zero potential (i.e., ground plane) or the outermost layers can be assumed to have an infinite thickness. In either case the structure has no interaction with the surroundings beyond the constrained interface or infinitely thick layer. The system is excited by any number of electrodes which have an imposed voltage and are placed between the layers. These electrodes are assumed to be infinitely thin such that the charge on the surfaces of each electrode can be modeled as surface charge in a single plane. The boundaries described by planes normal to the y coordinate can impose several symmetries including periodic, even, odd, and half-wave. In the case of an aperiodic structure, these boundaries are located far from the electrodes of interest and the periodic model is adapted to approximate the aperiodic structures.

The development of the EQS model has focused on sets of solutions for layers of uniform electrical properties, which have been expressed in terms of relations between the complex current density and the potential at their interfaces. Additionally, the proper boundary conditions to relate these quantities at interface containing electrodes and void of electrodes have been developed. These results were based on analytic solutions to the governing EQS equations and from the application of these governing equations to interfaces with the only assumptions involving the handling of the electrode thickness. In order to produce a solution to the modeled structure, the preceding results must now be combined with numerical techniques. Additionally, symmetry requiring that the electromagnetic quantities are independent of the z coordinate will now be imposed, although the preceding development of the model has generally not made this restriction. This symmetry forces the electrodes to be infinitely long in the z direction; however, the results will generally be a good approximation to the finite structure of interest as long as the length of the electrodes are sufficiently large compared to the electrode widths.

Similar to the MQS model, this modeling technique requires expressing undetermined electromagnetic quantities at the electrode interfaces in terms of parameterized functions. At any electrode interface there are two choices of quantities which may be parameterized: the surface current density, which is the current introduced by the electrode into the interface per unit area, or the electric potential. The potential is a natural choice since it is constant at individual electrodes and therefore this information can be incorporated exactly. The potential between electrodes must still be handled by parameterized functions. For structures in which the area composing electrode interfaces is mostly void of electrodes this can be a disadvantages; this is due to the number of unknowns and constraint equations which must be introduced. Aperiodic sensors are an example of these types of structures where electrodes generally make up a relatively small area of the electrode interface. A second issue with parameterizing the potential is related to applying boundary constraints to Fourier series reconstructions of the surface current density near electrode edges where transitions from zero current density to very large densities (impulse like) are observed. These large discontinuities result in a slowly convergent Fourier series and generally require special treatment using fast converging series and special considerations when imposing constraints on the surface current density in the vicinity of the electrode edges.

By parameterizing the surface current density some of these issues may be better dealt with. In sections along the electrode interfaces void of electrodes the surface current density is zero and therefore requires no parameterized functions. It is also not necessary to impose constraints on the value of the potential in these sections; constraints on the potential are only required at electrodes. The issues associated with constraining the surface current density near electrodes edges are also diminished. This is due to the constraints now being imposed on the potential which has a smoother behavior. An additional advantage of parameterizing the surface current density is special functions such as impulses can explicitly be added to the representation which may result in improved numerical performance. Due to some numerical behavior observed, the anticipated advantages, and the similarity of the formulation of the model with the MQS model (based on the MQS parameterization choice of surface current density), the parameterization of the surface current is used here.

Figure 15:
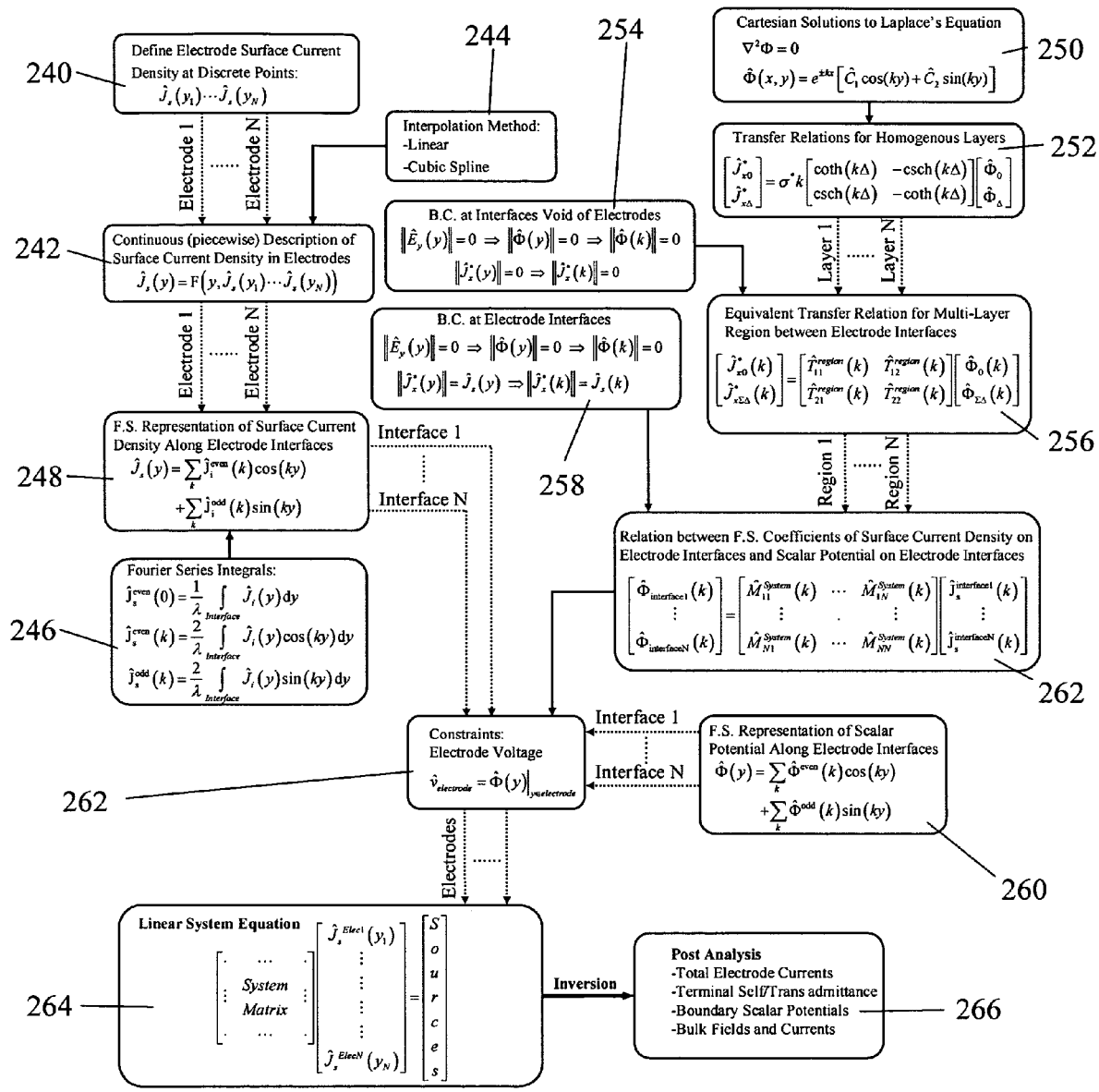
FIG. 15 shows a schematic overview of the EQS layered model.

FIG. 15 shows a schematic outline for the flow of information for the EQS model, showing how the equations, boundary conditions, surface current density parameterization, Fourier representation, geometry and constraints are combined to produce a linear system equation. The details of the approach are shown later, where analytical solutions to Maxwell's equations in the form of transfer relations and boundary conditions relating layer solutions and winding constraints are joined with numerical techniques and linear algebra methods.

1. The surface current density is exactly zero at sections of interfaces void of electrodes. The distribution of the surface current density on the electrodes is unknown at the outset. These distributions are therefore defined by functions described by a finite number of parameters (240). The function parameters having yet unknown values specify the function value at discrete points along the electrode. The values between the discrete points are then assigned by interpolation functions based on the values at the discrete points (242). The use of linear interpolations produces a piece-wise linear description of the current density. It is however desirable to use smooth functions (i.e., continuous derivatives) such as splines, since in reality the current distributions will be smooth, except at electrode edges (244). Fourier methods are utilized in the solution and smooth functions provide more rapidly convergent Fourier representations. Furthermore, significantly fewer splines can often provide a better fit than linear pieces and therefore there use is investigated. Impulses in the current density located at electrode edges and defined in terms of unknowns can also be added to the piecewise description, but handled separately to improve efficiency of subsequent calculations. The piece-wise description of the current density, utilizing either linear or spline interpolation and possibly including impulses, results in functions which are linear in terms of the unknown current densities at the discrete points, which will ultimately become important when linear algebra techniques are later applied.

2. With an expression for the functions describing the surface current density distributions, the Fourier series coefficients of the Fourier expansion of the surface current density at interfaces containing electrodes can be found as linear functions of the unknowns (246, 248).

3. Relationships in the form of a single transfer relation per spatial mode can be developed for each region between interfaces containing electrodes and for each region between interfaces containing electrodes and the upper or lower extremes of the structure (250, 252). This is accomplished by combining two adjacent layers within each region by applying the boundary conditions (continuous potential and zero surface current density) at their shared interface to form a new effective layer described by a new transfer relation (254). By applying this procedure between the new effective layer and an adjacent layer repeatedly, the behavior of all the layers within a region can be reduced to a single relation between the Fourier coefficients of the complex current density and the potential at the region interfaces. The process can be repeated for each region within a structure until a single transfer relation is computed for each region (256).

4. At the interfaces containing electrodes, approximate boundary conditions were developed including the condition that the scalar potential is continuous (258). The scalar potential is therefore represented by a single function on the interface and will be expressed in terms of its Fourier series expansion (260). Due to the orthogonality of the modes of the Fourier series, the jump condition $\|\hat{J}_x^*(y)\|=\hat{J}_s$ (y) at the interfaces containing electrodes also requires an equivalent condition on the coefficients such that $\|\hat{J}_x^*(k)\|=\hat{J}_s(k)$. This boundary condition, in combination with the single transfer relations for each region, allows the formulation of a matrix equation for each value of k which relates the Fourier coefficients of the surface current density on each interface containing electrodes to the coefficients of the scalar potential on these interfaces (260).

5. Equations specifying the terminal constraints for each electrode are imposed and require the electrode's voltage to be a constant value throughout the electrode (262). The electrode voltage at a specific location can be evaluated through the Fourier series expansion of the potential at the interface of the electrode. The coefficients of this expansion can be expressed in terms of matrix relations and the expressions for the Fourier series coefficients of the current density which are further expressed in terms of the unknown parameters. The method of imposing this constraint for each electrode results in a system of equations in terms of unknown current density parameters (264).

6. The system of equations generated is then solved for the surface current density parameters. Once these parameters are determined, the total electrode current, terminal admittances, interpolated surface current density distributions, boundary potentials, and internal fields can further be evaluated (266).

The existence of analytical solutions to the EQS approximation of Maxwell's equations for layers of uniform electrical properties is again the enabling factor in the modeling technique being described. However, the arrangement of these solutions in the form of transfer relations having a similar form to those of the MQS system allows a systematic approach for dealing with multi-layer structures. The use of transfer relations also simplifies the development of common equations for both EQS and MQS systems. The development of the solutions and their formulation into transfer relation serve as the starting point of the analysis for the EQS system. The relevant equations for the EQS approximation of Maxwell's equations are:

$$\nabla \cdot \in \vec{E} = \rho \tag{60}$$

$$\nabla \cdot \vec{J} = -\frac{\partial \rho}{\partial t} \tag{61}$$

$$\nabla \times \vec{E} = 0 \tag{62}$$

where ohmic conduction is assumed in the layers composed of uniform electrical properties such that the constitutive relation between the current and the electric field is $\vec{J} = \sigma \vec{E}$. This can be used to derive an equation for charge relaxation in the layer. Since in the regions of uniform properties the charge can only decay from its initial value, it is assumed that the charge in these regions is completely relaxed and therefore there is no volume charge to consider. Since Faraday's law requires that the curl of the electric field is zero, it can be represented as the gradient of the scalar potential:

$$\vec{E} = -\nabla \Phi \tag{63}$$

Assuming a time-harmonic form for the scalar potential with the convention that $\omega(\vec{r}, t) = \hat{\Phi}(\vec{r})e^{j\omega t}$ results in the following time-harmonic form of Laplace's equation as the governing equation for the potential in the layer:

$$\nabla^2 \hat{\Phi} = 0 \tag{64}$$

Solutions to this equation can then be determined by first assuming a product solution in Cartesian coordinates with the form:

$$\hat{\Phi}(x,y,z) = \hat{\Phi}_x(x)\hat{\Phi}_y(y)\hat{\Phi}_z(z) \tag{65}$$

Substituting this solution into Laplace's equation and using the method of separation of variables produces the partial differential equation:

$$\left[\frac{\hat{\Phi}_x''(x)}{\hat{\Phi}_x(x)}\right] = \left[-\frac{\hat{\Phi}_y''(y)}{\hat{\Phi}_y(y)}\right] + \left[-\frac{\hat{\Phi}_z''(z)}{\hat{\Phi}_z(z)}\right] \tag{66}$$

Since each term is only dependent on a single coordinate, the components of the product solution must be chosen such that each term in (66) is a constant. Replacement of each term with a constant parameter results in the following relation among parameters:

$$k_x^2 = k_y^2 + k_z^2 \tag{67}$$

Figure 16:
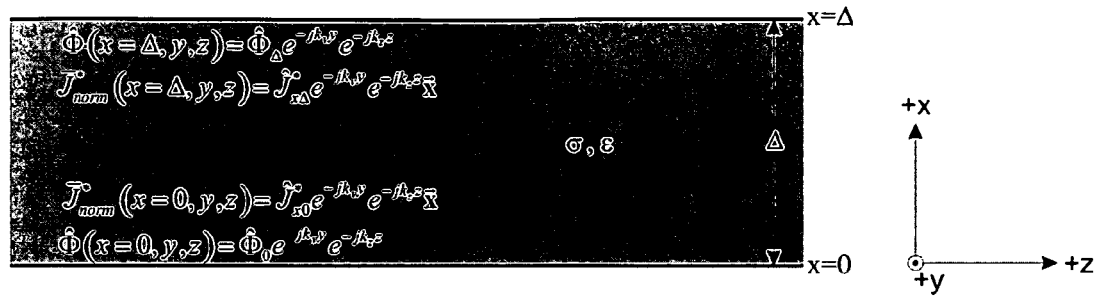
FIG. 16 shows a homogenous material layer for the EQS system with the dependence of the scalar potential and the normal complex current density indicated at interfaces.

Equating each term in (66) to each term in (67) produces a set of three ordinary differential equations. The signs of the terms associated with the parameters $k_y$ and $k_z$ have been chosen such that solutions to corresponding ordinary differential equations have the form $e^{\pm jk_y y}$ and $e^{\pm jk_z z}$ in anticipation of applying Fourier series methods for the variations in these coordinate directions. In order to match the potential at the layer boundaries as shown in FIG. 16, these solutions can be formulated in terms of hyperbolic functions. The total product solution has the form:

$$\hat{\Phi}(x, y, z) = \left[\hat{\Phi}_\Delta \frac{\sinh(k_x x)}{\sinh(k_x \Delta)} - \hat{\Phi}_0 \frac{\sinh(k_x(x-\Delta))}{\sinh(k_x \Delta)}\right] e^{-jk_y y} e^{-jk_z z} \tag{68}$$

for $k_x \neq 0$

The electric field inside the layer can then be evaluated from the potential as:

$$\bar{E}(x, y, z) = \tag{69}$$

$$\begin{cases} -k_x \left[\hat{\Phi}_\Delta \frac{\cosh(k_x x)}{\sinh(k_x \Delta)} - \hat{\Phi}_0 \frac{\cosh(k_x(x-\Delta))}{\sinh(k_x \Delta)}\right] e^{-jk_y y} e^{-jk_z z} \overline{x} \\ +jk_y \left[\hat{\Phi}_\Delta \frac{\sinh(k_x x)}{\sinh(k_x \Delta)} - \hat{\Phi}_0 \frac{\sinh(k_x(x-\Delta))}{\sinh(k_x \Delta)}\right] e^{-jk_y y} e^{-jk_z z} \overline{y} \\ +jk_z \left[\hat{\Phi}_\Delta \frac{\sinh(k_x x)}{\sinh(k_x \Delta)} - \hat{\Phi}_0 \frac{\sinh(k_x(x-\Delta))}{\sinh(k_x \Delta)}\right] e^{-jk_y y} e^{-jk_z z} \overline{z} \end{cases}$$

for $k_x \neq 0$

However, due to the boundary conditions which must later be imposed at interfaces of adjacent layers, it will be more useful to utilize a complex current density rather than the electric field. The complex current density is expressed in terms of the electric field such that:

$$\vec{J}^* = \sigma^* \vec{E} \tag{70}$$

where the complex conductivity $\sigma^*$ is defined in terms of the electrical properties of the layer:

$$\sigma^* \equiv \sigma + j\omega \in \tag{71}$$

By evaluating the normal component of the complex current density at $x=0$ and $x=\Delta$, a set of transfer relations relating the coefficients of the complex exponential dependence of the current density to the coefficients of the potential at the layer interfaces can be developed in matrix form:

$$\begin{bmatrix} \hat{J}_{x0}^* \\ \hat{J}_{x\Delta}^* \end{bmatrix} = k_x \sigma^* \begin{bmatrix} \coth(k_x \Delta) & -\operatorname{csch}(k_x \Delta) \\ \operatorname{csch}(k_x \Delta) & -\coth(k_x \Delta) \end{bmatrix} \begin{bmatrix} \hat{\Phi}_0 \\ \hat{\Phi}_\Delta \end{bmatrix} \text{ for } k_x \neq 0 \tag{72}$$

The special case of $k_x = 0$ must be considered separately, as the solution to the ordinary differential equation produced by the x dependent component of the product solution required that $k_x \neq 0$. For $k_x$ to equal zero, both $k_y$ and $k_z$ must also be zero in which case the y and z dependent components of the product solution become constant. The potential then varies linearly across the layer and the potential in the layer can be expressed in terms of the potentials at the $x=0$ and $x=\Delta$ interfaces as:

$$\hat{\Phi}(x, y, z) = \hat{\Phi}_\Delta \frac{x}{\Delta} - \hat{\Phi}_0 \frac{x-\Delta}{\Delta} \text{ for } k_x = 0 \quad (73)$$

The electric field is then:

$$\bar{E}(x, y, z) = \frac{1}{\Delta}\left[-\hat{\Phi}_\Delta + \hat{\Phi}_0\right]\bar{x} \text{ for } k_x = 0 \quad (74)$$

From this relation it can be seen that the electric field is constant within the layer and has only a single vector component normal to the layer's interfaces. A matrix relationship is therefore unnecessary and (70) can be used to relate the normal complex current density to the vector potential at the layer's interfaces:

$$\hat{j}_{0x}^* = \hat{j}_{\Delta x}^* = \frac{\sigma^*}{\Delta}\left[-\hat{\Phi}_\Delta + \hat{\Phi}_0\right] \text{ for } k_x = 0 \quad (75)$$

Certain limiting behavior of the transfer relations developed will be useful for imposing boundary conditions in addition to enhancing computational efficiency in the implementation of the model. Three types of limiting cases are of interest and include: the case of an infinitely thick layer, the case of large $k_x$ values, and the case where one interface of a layer is constrained to zero potential. Since the cases of an infinitely thick layer and large values of $k_x$ result in similar transfer relation behavior they are illustrated first.

The two outermost layers of the structure being modeled each allow for one of two options in the boundary condition applied to the outermost interface. One of these options consists of the boundary being located at infinitely or equivalently that the corresponding layer is infinitely thick. Although in the actual structure no layer can be truly infinitely thick, determining the limit of the transfer relations as $\Delta \to \infty$ can result in a useful approximation. The matrix elements of the transfer relations in (72) have two distinct forms and are dependent on the layer thickness $\Delta$ such that the limits are easily evaluated. In this limit, the hyperbolic cotangent goes to one and the hyperbolic cosecant goes to zero. This is a good approximation when $k_x \Delta \gg 1$.

Since the thickness of a layer for a given simulation is a constant, the validity of the approximation must be determined by the smallest nonzero value of $k_x$ which will be used. From (67) it is seen that $k_x$ is directly dependent on $k_y$ and $k_z$. The modeling of the structure will employ Fourier series methods and therefore the smallest nonzero values $k_y$ and $k_z$ can be related to the periodicity of the structure, such that the smallest nonzero value of $k_x$ is determined by:

$$2\pi\sqrt{\frac{1}{\lambda_y^2} + \frac{1}{\lambda_z^2}} \quad (.77)$$

The upcoming modeling techniques will assume no z dependence in which case the associated term in the expression above can be taken as zero.

In the case of large values of $k_x$, the limiting behavior of the transfer relations as $k_x \to \infty$ is of interest. The matrix elements of (72) are again involved and the resulting limits are identical to those above. The situation differs from that involving a layer being approximated as infinitely thick in which case the limiting values are either a good approximation for the layer or not. Since the Fourier series techniques will involve many $k_x$ values, a layer of finite thickness may allow the limiting values to be used for larger values of $k_x$, while requiring the full evaluation of matrix terms for the smaller values. The limiting form of the transfer relation of (72) results in:

$$\begin{bmatrix} \hat{j}_{x0}^* \\ \hat{j}_{x\Delta}^* \end{bmatrix} = k_x \sigma^* \begin{bmatrix} 1 & 0 \\ 0 & -1 \end{bmatrix} \begin{bmatrix} \hat{\Phi}_0 \\ \hat{\Phi}_\Delta \end{bmatrix} \quad (78)$$

for $k_x \ne 0, k_x \Delta \gg 1$ or $k_x \ne 0, \frac{2\pi}{\lambda}\Delta \gg 1$ From this result it can be seen that if the transfer relations can be approximated in this way, then there is no interaction between each layer interface; the current density at an interface is then only dependent on the potential associated with that interface. The transfer relation can then be simplified to two linear relationships between the complex current density and the potential at each the interface. Often only one of these relationships is of significance, since the behavior at the other interface is either known to be zero, or of no interest.

The preceding results have focused on the limiting behavior for the transfer relation associated with $k_x \ne 0$. The case of $k_x = 0$ is contradictory to $k_x \to \infty$ and therefore only the behavior as $\Delta \to \infty$ is considered. The potential at infinity is assumed to be finite and therefore the relation for the current density in (75) becomes independent of the potential. The current density at either interface is then:

$$\hat{j}_{0x}^* = \hat{j}_{\Delta x}^* = 0 \text{ for } k_x = 0, \Delta \to \infty \quad (79)$$

In this case the result and the condition for its validity are essentially one in the same. In other words, if the current density associated with $k_x = 0$ within a layer is sufficiently small due to the layers thickness and bounding interfacial potentials, then the current density can be considered zero.

The last case of interest involves the constraining of the potential on an interface to zero. This is a physical situation that often occurs when a ground plane is used at an outermost extreme interface. From the transfer relation of (72) and the relation of (75), it can be seen that by setting the potential of one interface to zero, the current density and potential at the opposite interface become linearly related. This behavior will become useful in later model development because the linear form is identical to that observed for the cases when $\Delta$ or $k_x$ were sufficiently large. It is also worth noting that the approximate relation of (78) in the case of large $k_x$ values can also be applied to layers with a constrained interface, when the criteria $k_x \Delta \gg 1$ is met. In order to link these transfer relation solutions for each layer together, the appropriate boundary conditions are needed for both interfaces containing electrodes and those void of electrodes. Addition constraints will also become necessary in order to impose the desired excitation and constrain the solution to that matching the configuration of the modeled structure.

Adjacent layers composing the modeled structure share an interface which either contains no electrodes, or which is assumed to contain an infinitely thin approximation to the physical electrodes. In the case when the interface contains no electrodes, the boundary conditions follow directly from the EQS form of Maxwell's equations and the defining relation for the electric field in terms of the potential in order to provide a self consistent solution for the complete structure.

The electric field at the interface between two layers is expected to be finite. Since the electric field is defined in term of the gradient of the scalar potential, this requires that the potential is continuous at the interface such that:

$$\hat{\Phi}(x=a^+,y,z)=\hat{\Phi}(x=a^-,y,z) \quad (80)$$

where the planar interface is located at x=a and the superscripts indicate that the potential is evaluated as the limit approached from the corresponding side of the interface. The evaluation of the potential can also be interpreted as choosing the layer solution from the corresponding side of the interface and evaluating it at x=a. This also guarantees that the tangential portion of the electric field is continuous. The charge conservation law of (61) can be written in time-harmonic integral form, for Ohmic conduction as:

$$\oint_S (\sigma + j\omega\varepsilon)\vec{E} \cdot d\vec{a} = 0 \quad (81)$$

so that the divergence of the complex current density is zero. Applying this integral to a close incremental surface around the interface results in the following boundary condition requiring the continuity of the normal complex current density:

$$\vec{x} \cdot [\vec{J}^*(x=a^+,y,z) - \vec{J}^*(x=a^-,y,z)] = \hat{J}_x^*(x=a^+,y,z) - \hat{J}_x^*(x=a^-,y,z) = 0 \quad (82)$$

The boundary conditions of (80) and (82) are then sufficient to mathematically connect the transfer relations of two adjacent layers.

The interfaces containing the infinitely thin electrodes in the modeled structure have the purpose of approximating the behavior of the finite thickness electrodes and gaps of the physical structure. The goal is to forego the distribution of the electromagnetic quantities in the volume of the thin layer containing the windings and gaps in lieu of expressions which simply relate the electromagnetic quantities at the interfaces of this thin layer to each other and to other mean layer quantities. These relationships can then be used as boundary conditions for adjacent layers sharing the interfaces which coincide with the interfaces of the thin layer and allowing the existence of this thin layer to be ignored in other respects. This simplification does not come for free since several assumptions must be made and some degree of error is introduced into the final solution.

The first assumption in developing the boundary conditions requires the potential at each of the thin layer's interfaces to be identical. For the regions of the thin layer in which the electrodes are present this is accurate since these electrodes are highly conducting and represent equipotential regions. The gaps between the electrodes do not physically represent equipotential regions and therefore this assumption forces the normal component of the electric field in the gap to be zero. The normal electric field is expected to be finite in the physical problem, which in the case of a sufficiently thin layer results in a minimal jump in the potential between interfaces. One of the boundary condition replacing the thin layer of electrodes and gaps is then equivalent to (80).

Figure 17:
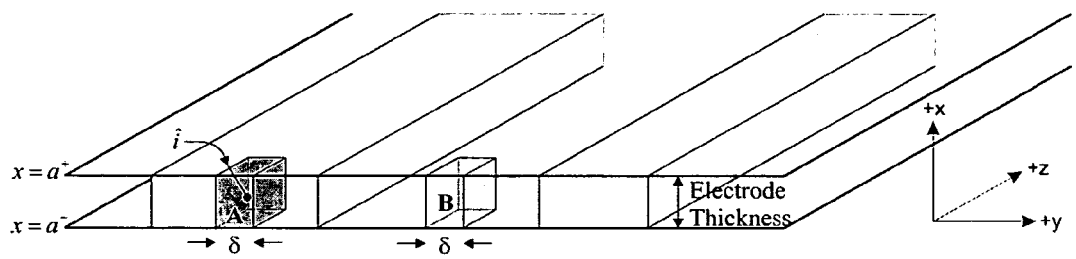
FIG. 17 shows an application of the charge conservation intergral to the thin finite thickness layer containing electrodes in order to replace the layer by approximate boundary conditions.

The next boundary condition results from applying the charge conservation law to the thin layer. The same reasoning used to arrive at (81) from the charge conservation integral is again employed. This integral can then be applied to the surface labeled "A" enclosing the electrode which is shown in FIG. 17. Since the electrode is highly conducting ($\sigma\to\infty$), the electric field inside is assumed to be zero. However, a current density may be present in the electrode which contributes to the four surfaces of integration normal to the layer interfaces. The net contribution to the integral due to this current density is expressed in terms of the current î. The surface integral then becomes:

$$\oint_S \vec{J}^* \cdot d\vec{a} = \hat{i} \quad (83)$$

By taking the limit as the surfaces coincident with the layer interfaces become incremental, the following relation results:

$$\vec{x} \cdot [\vec{J}^*(x=a^+,y,z) - \vec{J}^*(x=a^-,y,z)] = \hat{J}_x^*(x=a^+,y,z) - \hat{J}_x^*(x=a^-,y,z) = \hat{J}_s(y,z) \quad (84)$$

where $\hat{J}_s$ represents the current per unit area that is supplied through the electrode to the electrode surfaces and the surrounding material. As long as the y and z coordinates correspond to a location within the electrode and non-inclusive of the electrode edge (84) does not involve any assumptions about the electrode thickness. However, at an electrode edge the surface of integration now includes a surface on the gap side of the electrode, where the electric field is not necessarily zero. The assumption must then be made that the electrode is sufficiently thin that the contribution of this surface can be neglected such that (84) can still be used. A similar integration surface can be applied to the gaps between electrodes and is labeled "B" in FIG. 17. In this case there is no additional source of current and î=0. The tangentially oriented electric field is not necessarily zero and it must again be assumed that the surfaces normal to the layer interfaces make no contribution to the surface integral. The boundary condition of (84) can then be used in the gaps between electrodes with $\hat{J}_s(y,z)=0$.

The boundary conditions of (80) and (84) are sufficient to mathematically connect the transfer relations of two adjacent layers sharing an interface on which electrodes are approximated as infinitely thin. However, the surface current density $\hat{J}_s$ is not imposed and therefore additional constraints are required such that a unique solution to the system can be obtained.

In the development of continuity of potential boundary condition the electrode was considered an equipotential region and therefore no assumptions were necessary at the electrode for this condition. The equipotential nature of the electrode also requires the potential to be continuous along the boundary in addition to being continuous across the boundary. This produces the additional constraint that:

$$\hat{\Phi}(x=a,y,z)=\hat{v} \quad (85)$$

at an interface located at x=a which contains an electrode and where the y and z coordinate are located within the electrode. The voltage $\hat{v}$ is the imposed voltage for the specific electrode and is independent of the position within the electrode. This constraint imposes the electrode voltages which result in the excitation of the modeled structure.

With respect to the electrodes, one additional equation is of value, since the terminal behavior of the modeled structure is often of interest. Since the electrode voltage is imposed and therefore known, the electrode current is then required for computations such as the self-admittance and the transadmittance. Once the solution for the system is obtained, the current density $\hat{J}_s$ will be known in some form for each electrode. The total current flowing into the terminal of each electrode is then simply determined as the integral over the surface of the electrode as:

$$\hat{i}_e = \int_{elect} \hat{J}_s da \qquad (86)$$

When symmetry is assumed such that there is no z dependence to any electromagnetic quantity, the current is normalized to the length l of the structure in the z direction and the integral in only needs to be evaluated over the width of the winding such that (86) becomes:

$$\tilde{i} = \int_{elect} \hat{J}_s dy \qquad (87)$$

Due to the duality of the EQS and MQS systems and the associated choice of electromagnetic quantity which is parameterized in each, the majority of the equations involved in the model formulations have identical forms. To avoid the independent development of each, it has been chosen to follow through the development using generic symbols, which are then defined for the specific system by Table 1. In a few instances certain terms in equations are only applicable only to the EQS or MQS system and are indicated as such. The term "conductor" has been used to replace the term "winding" in the MQS case and "electrode" in the EQS case. For completeness, the development of the models also include parameterization of quantities in terms of both piecewise linear and cubic spline functions.

TABLE 1

Relation of the symbols used in the general model equations to the equivalent MQS or EQS system symbols.

| Symbol | MQS | EQS |
|---|---|---|
| P | $A_z$, z component of vector potential | $\Phi$, Electric potential |
| K | $K_z$, winding surface current density in the z direction | $J_s$, surface current density introduced by the electrode |
| $\hat{Q}$ | $\hat{H}_y$, y component of magnetic field tangential to MUT surfaces | $\hat{J}_x^* = \hat{\sigma}^* \hat{E}_x$, x component of complex current density |
| $\hat{v}_p$ | voltage on the pth winding | voltage on the pth electrode |
| $\hat{i}_p$ | net current into the pth winding | net current into the pth electrode |

For each sensor conductor for which the distribution of current density is not explicitly defined, the distribution must be represented in terms of a parameterized function for which the parameters are currently undetermined. There are an essentially unlimited number of choices for this function; however a good choice will allow the current distribution to match the physical distribution as closely as possible. Since the solution method is numerical, the number of unknown parameters describing the current distribution must be finite and preferably as small as possible. In order for this criterion to be met, the solutions for the current distribution which these parameters allow should ideally cover only the function space in the neighborhood of true solutions. These solutions include those encountered for various frequencies of operation and material configurations. For example, these solutions will have the form of a constant value over the winding in the low frequency limit of the MQS problem. In the high frequency limit, a large current density is expected at the edges of windings as compared to the center of the winding due to magnetic diffusion.

Since the geometry between edges of each conductor does not meet with any discontinuities, it is expected that the current density distribution be continuous within the conductor and also smooth to infinite degree (continuous derivatives). The approach is to parameterize the functional description of the current density by values of the current density at discrete points along the conductor, which must be equivalent to the continuous function description. As mentioned in earlier discussion, one method of obtaining the continuous description from these values, which has been utilized in other work, is to interpolate between these points using linear functions. Continuity of the function is then automatically imposed, putting a significant constraint on the allowed function space. The use of a piecewise description such as this has the additional property in that each function only has local support (values for a specific function piece are zero outside the interval of the piece), which results in a set of mutually orthogonal functions. This part of the criterion on functions forming a basis helps to promote numerical stability. However, the piecewise linear functions do not posses a continuous first derivatives at interval boundaries. Additional derivates are continuous, but only as a result of the limitation that they must be zero. The limitation in the function space of allowed solution that this creates is in general overly restrictive, but is typically dealt with by the intelligent concentration of interpolation intervals.

The limitations of the linear method are in the inclusion of the non-physical function space having discontinuities in derivatives, and the exclusion of function spaces involving non-linear changes within the interpolation interval. To improve upon this the models will also be developed using a cubic spline method. This has the advantage in that continuity of up to a second derivative can be imposed in addition to allowing more complex function variation within intervals. This should lead to a reduction in the number of unknowns due to a reduction in the number of intervals required to achieve a comparable match with the piecewise linear description at the additional expense of complexity in calculations. However, a study of the appearance of these additional terms in computation will reveal that for a given sensor geometry they need only be computed once. As compared to number of unknowns, which must always be determined, this will always yield a benefit when doing modeling of a single sensor geometry for a variety of MUT configurations, as is often the case.

Figure 18:
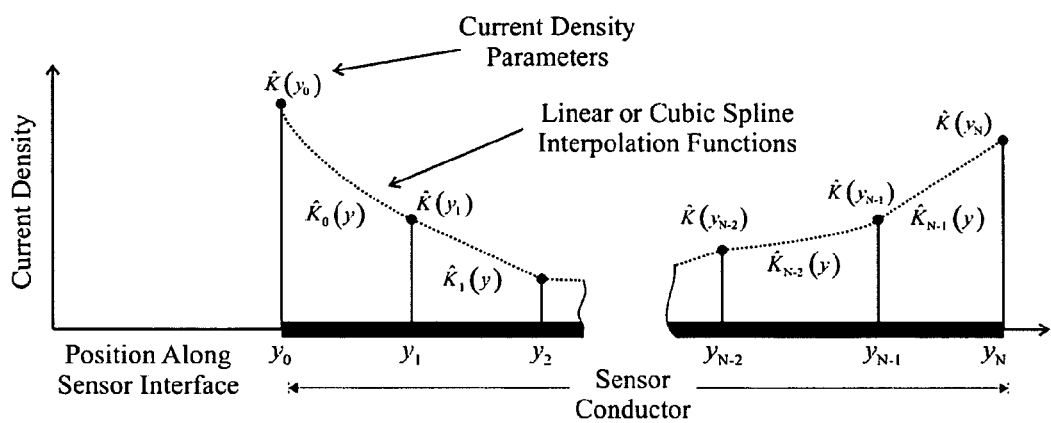
FIG. 18 shows the interpolation of current density along sensor conductors using piecewise linear or cubic spline functions.

The parameterization and description of the surface current density by interpolation functions is shown in FIG. 18. The parameters are the undetermined current density values at location $y_0$ through $y_N$ denoted by $\hat{K}(y_0)$ through $\hat{K}(y_N)$ respectively. The interpolation functions are defined by the current density parameters at the edge of each interpolation interval. The interpolation functions now need to be described in terms of these parameters.

The piecewise linear current density is described by the sum over each linear interpolation function as:

$$\hat{K}(y) = \sum_{n=0}^{N-1} \hat{K}_n(y) \qquad (88)$$

where the interpolation functions have the form:

$$\hat{K}_n(y) = \begin{cases} \hat{C}_n(y - y_n) + \hat{D}_n & \text{for } y_n \leq y \leq y_{n+1} \\ 0 & \text{for } y < y_n, y > y_{n+1} \end{cases} \qquad (89)$$

and N is the number of intervals covering the sensor conductor. The coefficients $\hat{C}_n$ and $\hat{D}_n$ are directly evaluated from the values of each function at $y=y_n$ and $y=y_{n+1}$. Substituting back into (89) produces the following expression for the linear interpolation functions in terms of the current density parameters:

$$\hat{K}_n(y) = \begin{cases} \dfrac{\hat{K}(y_{n+1}) - \hat{K}(y_n)}{h_n}(y - y_n) + \hat{K}(y_n) & \text{for } y_n \leq y \leq y_{n+1} \\ 0 & \text{for } y < y_n, y > y_{n+1} \end{cases} \quad (90)$$

where $h_n = (y_{n+1} - y_n)$.

The cubic spline representation of the current density replaces the summation of linear functions found in (88) by the cubic functions:

$$\hat{K}_n(y) = \qquad (91)$$
$$\begin{cases} \hat{A}_n(y-y_n)^3 + \hat{B}_n(y-y_n)^2 + \hat{C}_n(y-y_n) + \hat{D}_n & \text{for } y_n \leq y \leq y_{n+1} \\ 0 & \text{for } y < y_n, y > y_{n+1} \end{cases}$$

Each of these cubic polynomials must match the current density specified at $y=y_n$ and $y=y_{n+1}$ such that:

$$\hat{D}_n = \hat{K}(y_n) \text{ for } n=0 \ldots (N-1) \qquad (92)$$

$$\hat{A}_n h_n^3 + \hat{B}_n h_n^2 + \hat{C}_n h_n + \hat{D}_n = \hat{K}(y_{n+1}) \text{ for } n=0 \ldots (N-1) \qquad (93)$$

where $h_n = (y_{n+1} - y_n)$. Continuity of the first and second derivatives of neighboring requires:

$$3\hat{A}_n h_n^2 + 2\hat{B}_n h_n + \hat{C}_n - \hat{C}_{n+1} 0 \text{ for } n=0 \ldots (N-2) \qquad (94)$$

$$3\hat{A}_n h_n + \hat{B}_n - \hat{B}_{n+1} = 0 \text{ for } n=0 \ldots (N-2) \qquad (95)$$

Equations (92) and (93) result in a total of 2N equations on the cubic coefficients, while (94) and (95) result in a total of 2(N−1) equations. Therefore there are a total of 4N−2 equations for the 4N unknown cubic coefficients. The additional two equations required to fully define the solution are typically obtained by specifying the first derivative or by setting the second derivative to zero at $y=y_0$ and $y=y_N$. The first constraint is typically called the clamped boundary condition while the latter is referred to as the natural boundary condition. It is possible to introduce two new unknowns, one for the derivative of the surface current density at each of these boundaries, and add these to the set of unknown parameters. However, since a discontinuity will be present at these identical locations due to the zero current density off of the conductor, these slopes will play a lesser role in the solution. This is due to the spectral relationship between the potential along the boundary and the current density along the boundary. Since the size of the step discontinuity at these locations will produce a more dramatic effect on spectral content than a change in slope, the inclusion of the slopes as parameters is avoided. The natural boundary condition is chosen since it does not introduce additional unknowns and does not overly constrain the solution. It is imposed by the following constraints on cubic coefficients for the first and last interpolation interval:

$$\hat{B}_0 = 0 \qquad (96)$$

$$3\hat{A}_{N-1} h_{N-1} + \hat{B}_{N-1} = 0 \qquad (97)$$

Spline interpolation is typically applied when the values of the function being interpolated are known numerical at the points $y_n$. In the purely numeric case the previous equations, constraining the cubic coefficients, can be arranged in a banded diagonal linear system which allows for rapid solution. In the current problem the values of the current density at the points $y_n$ will only be determined from additional constraints formulated in terms of the cubic polynomials that the unknowns define and therefore computation of a matrix inverse is required. The equations constraining the spline coefficients can now be expressed in the following matrix equation:

$$Ws = g \qquad (98)$$

The column vector s contains the coefficients of the cubic polynomials, defined as:

$$s = [\hat{A}_0 \hat{B}_0 \hat{C}_0 \ldots \hat{A}_{N-1} \hat{B}_{N-1} \hat{C}_{N-1} \hat{D}_{N-1}]^T \qquad (99)$$

and the elements of W are defined as:

$$W_{l,m} = \begin{cases} 1 & \text{for } l=1, m=2 \\ 1 & \text{for } l=2,6,10 \ldots (4(N-2)+2), m=l+2 \\ h_{(l-3)/4}^2 & \text{for } l=3,7,11 \ldots (4(N-2)+3), m=l-2 \\ 2h_{(l-3)/4}, & m=l-1 \\ 1, & m=l \\ -1, & m=l+4 \\ 3h_{(l-4)/4} & \text{for } l=4,8,12 \ldots (4(N-2)+4), m=l-3 \\ 1, & m=l-2 \\ -1, & m=l+2 \\ h_{(l-5)/4}^3 & \text{for } l=5,9,13 \ldots (4(N-2)+5), m=l-4 \\ h_{(l-5)/4}^2, & m=l-3 \\ h_{(l-5)/4}, & m=l-2 \\ 1, & m=l-1 \\ 1 & \text{for } l=4(N-2)+6, m=l+2 \\ h_{N-1}^3 & \text{for } l=4(N-2)+7, m=l-2 \\ h_{N-1}^2, & m=l-1 \\ h_{N-1}, & m=l \\ 1, & m=l+1 \\ 3h_{N-1} & \text{for } l=4(N-2)+8, m=l-3 \\ 1, & m=l-2 \\ 0 & \text{for all other } l,m \end{cases} \qquad (100)$$

The column vector g has the form:

$$g = [0|\hat{K}(y_0) 0\, 0\, \hat{K}(y_1) \ldots \hat{K}(y_{N-2}) 0\, 0\, \hat{K}(y_{N-1})|\hat{K}(y_{N-1})\; \hat{K}(y_N) 0]^T \qquad (101)$$

The goal is to obtain the inverse of the matrix W such that:

$$s = W^{-1} g \qquad (102)$$

However, it is desired to obtain the cubic coefficients in terms of a column vector containing a simple list of the undetermined surface current densities. From (101) it can be seen that g contains many zeros in addition to the unknown current densities being repeated. In order to allow g to be replaced by the simple list of unknown parameters, the inverse matrix $W^{-1}$ must be modified. The multiplication of $W^{-1} g$ shows that many of the columns of $W^{-1}$ are not required since they are always multiplied by the associated zero elements of g. It is also possible to add the columns of $W^{-1}$ which multiply the same $\hat{K}(y_n)$ in g, and thereby eliminating duplicate $\hat{K}(y_n)$ elements in g. These modifications could be carried out on $W^{-1}$ to produce a new matrix U such that:

$$s = UK \tag{103}$$

$$K = [\hat{K}(y_0) \ldots \hat{K}(y_N)]^T \tag{104}$$

Roughly half of the columns of $W^{-1}$ need not be computed due to the zeros in g, while the direct calculation of combined columns can also reduce computation. One method of obtaining the inverse of $W^{-1}$ is by solving $WW^{-1}=I$ for one column of $W^{-1}$ at a time. From this it can be seen that by removing the columns from I corresponding to the unneeded columns of $W^{-1}$ the extra computations are avoided. Also, this is a linear system and therefore $W^{-1}[a_1 + a_1] = b_1 + b_2$. This property implies that adding columns of I, before solving for $W^{-1}$, will result in the addition of corresponding columns of $W^{-1}$. Therefore U can most directly be obtained by solving:

$$WU = \Theta \tag{105}$$

One column at a time, where the $4N \times (N+1)$ matrix $\Theta$ is defined as:

$$\Theta = [I_2 | (I_5 + I_6) \ldots (I_{4l-3} + I_{4l-2}) \ldots (I_{4N-3} + I_{4N-2}) | I_{4N-1}] \tag{106}$$

where the subscript l corresponds to the column index within $\Theta$, and $I_a$ represents the ath column of the $4N \times 4N$ identity matrix I.

The current density can now be interpolated between the discrete set of points at which its value has been defined using either the piecewise linear or piecewise cubic functions. This continuous representation allows the Fourier series coefficients to be calculated from the interpolation functions. The integrals used to determine the contribution to the Fourier coefficients, describing the surface current density at a single interface due to a single conductor of the sensor, are:

$$\hat{K}^{even}[\tilde{k}] = \frac{1}{\lambda} \int_{y_0}^{y_N} \hat{K}(y) \, dy \tag{107}$$

$$= \frac{1}{\lambda} \sum_{n=0}^{N-1} \int_{y_n}^{y_{n+1}} \hat{K}_n(y) \, dy \quad \text{for } \tilde{k} = 0$$

$$\hat{K}^{even}[\tilde{k}] = \frac{2}{\lambda} \int_{y_0}^{y_N} \hat{K}(y) \cos(ky) \, dy \tag{108}$$

$$= \frac{2}{\lambda} \sum_{n=0}^{N-1} \int_{y_n}^{y_{n+1}} \hat{K}_n(y) \cos(ky) \, dy \quad \text{for } \tilde{k} = 1, 2,$$

$$\hat{K}^{odd}[\tilde{k}] = \frac{2}{\lambda} \int_{y_0}^{y_N} \hat{K}(y) \sin(ky) \, dy \tag{109}$$

$$= \frac{2}{\lambda} \sum_{n=0}^{N-1} \int_{y_n}^{y_{n+1}} \hat{K}_n(y) \sin(ky) \, dy \quad \text{for } \tilde{k} = 1, 2,$$

where $\hat{K}^{even}[\tilde{k}]$ and $\hat{K}^{odd}[\tilde{k}]$ are the coefficients of the even and odd modes in the Fourier series expansion of the surface current density $\hat{K}(y)$, $$k \equiv \frac{2\pi}{\lambda} \tilde{k}$$

is the wave number of the Fourier mode, $\tilde{k}$ an integer indicating the mode number, and $\lambda$ is the periodicity of the modeled structure. Since the function $\hat{K}(y)$ is described in a piecewise fashion, these integrals are also expressed in terms of a sum of integrals over each piece of the piecewise function. The specific piecewise functions (linear or cubic) can then be inserted and the integration carried out.

Substitution of the linear interpolation functions of (90) into the Fourier series integrals produces:

$$\hat{K}^{even}[\tilde{k}] = \frac{1}{2\lambda} \sum_{n=0}^{N-1} h_n \left( \hat{K}(y_n) + \hat{K}(y_{n+1}) \right) \quad \text{for } \tilde{k} = 0 \tag{111}$$

$$\hat{K}^{even}[\tilde{k}] = \frac{2}{\lambda} \sum_{n=0}^{N-1} \left\{ \begin{array}{l} \frac{1}{k} \left[ \hat{K}(y_{n+1}) \sin(ky_{n+1}) - \hat{K}(y_n) \sin(ky_n) \right] + \\ \frac{1}{k^2} \frac{\hat{K}(y_{n+1}) - \hat{K}(y_n)}{h_n} [\cos(ky_{n+1}) - \cos(ky_n)] \end{array} \right. \quad \text{for } \tilde{k} = 1, 2, \tag{112}$$

$$\hat{K}^{odd}[\tilde{k}] = \frac{2}{\lambda} \sum_{n=0}^{N-1} \left\{ \begin{array}{l} \frac{1}{k} \left[ -\hat{K}(y_{n+1}) \cos(ky_{n+1}) - \hat{K}(y_n) \cos(ky_n) \right] + \\ \frac{1}{k^2} \frac{\hat{K}(y_{n+1}) - \hat{K}(y_n)}{h_n} [\sin(ky_{n+1}) - \sin(ky_n)] \end{array} \right. \quad \text{for } \tilde{k} = 1, 2, \tag{113}$$

The terms in these summations contain both factors of $\hat{K}(y_n)$ and $\hat{K}(y_{n+1})$; in preparation for arrangement as matrix equations, neighboring terms in the summation series are arranged to produce summations containing only terms with factors of $\hat{K}(y_n)$. These expressions can be further simplified by normalizing the dimensions, such that $$\tilde{y}_n = \frac{2\pi}{\lambda} y_n$$

and $\tilde{h}_n = (\tilde{y}_{n+1} - \tilde{y}_n)$, which results in:

$$\hat{K}^{even}[\tilde{k}] = \sum_{n=0}^{N} \hat{F}_n^{even}[\tilde{k}] \hat{K}(\tilde{y}_n) \tag{114}$$

$$\hat{K}^{odd}[\tilde{k}] = \sum_{n=0}^{N} \hat{F}_n^{odd}[\tilde{k}] \hat{K}(\tilde{y}_n) \tag{115}$$

where:

$$\hat{F}_n^{even}[\tilde{k}=0] = \begin{cases} \frac{1}{4\pi}\tilde{h}_0 & \text{for } n=0 \\ \frac{1}{4\pi}(\tilde{h}_n + \tilde{h}_{n-1}) & \text{for } 1 \leq n < N \\ \frac{1}{4\pi}\tilde{h}_{N-1} & \text{for } n=N \end{cases} \quad (116)$$

$$\hat{F}_n^{even}[\tilde{k} \neq 0] = \begin{cases} -\frac{1}{\pi}\left[\frac{\sin(\tilde{k}\tilde{y}_0)}{\tilde{k}} + \frac{\cos(\tilde{k}\tilde{y}_1) - \cos(\tilde{k}\tilde{y}_0)}{\tilde{k}^2 \tilde{h}_0}\right] & \text{for } n=0 \\ \frac{1}{\pi}\frac{1}{\tilde{k}^2}\left[\frac{\cos(\tilde{k}\tilde{y}_n) - \cos(\tilde{k}\tilde{y}_{n-1})}{\tilde{h}_{n-1}} - \frac{\cos(\tilde{k}\tilde{y}_{n+1}) - \cos(\tilde{k}\tilde{y}_n)}{\tilde{h}_n}\right] & \text{for } 1 \leq n < N \\ \frac{1}{\pi}\left[\frac{\sin(\tilde{k}\tilde{y}_N)}{\tilde{k}} + \frac{\cos(\tilde{k}\tilde{y}_N) - \cos(\tilde{k}\tilde{y}_{N-1})}{\tilde{k}^2 \tilde{h}_{N-1}}\right] & \text{for } n=N \end{cases} \quad (117)$$

$$\hat{F}_n^{odd}[\tilde{k} \neq 0] = \begin{cases} \frac{1}{\pi}\left[\frac{\cos(\tilde{k}\tilde{y}_0)}{\tilde{k}} + \frac{\sin(\tilde{k}\tilde{y}_1) - \sin(\tilde{k}\tilde{y}_0)}{\tilde{k}^2 \tilde{h}_0}\right] & \text{for } n=0 \\ \frac{1}{\pi}\frac{1}{\tilde{k}^2}\left[\frac{\sin(\tilde{k}\tilde{y}_n) - \sin(\tilde{k}\tilde{y}_{n-1})}{\tilde{h}_{n-1}} - \frac{\sin(\tilde{k}\tilde{y}_{n+1}) - \sin(\tilde{k}\tilde{y}_n)}{\tilde{h}_n}\right] & \text{for } 1 \leq n < N \\ \frac{1}{\pi}\left[-\frac{\cos(\tilde{k}\tilde{y}_N)}{\tilde{k}} + \frac{\sin(\tilde{k}\tilde{y}_N) - \sin(\tilde{k}\tilde{y}_{N-1})}{\tilde{k}^2 \tilde{h}_{N-1}}\right] & \text{for } n=N \end{cases} \quad (118)$$

Substitution of the spline interpolation functions of (91) into the Fourier series integrals produces:

$$\hat{K}^{even}[\tilde{k}] = \frac{1}{\lambda}\sum_{n=0}^{N-1}\frac{1}{4}\hat{A}_n h_n^4 + \frac{1}{3}\hat{B}_n h_n^3 + \frac{1}{2}\hat{C}_n h_n^2 + \hat{D}_n h_n \quad \text{for } \tilde{k}=0 \quad (119)$$

$$\hat{K}^{even}[\tilde{k}] = \frac{2}{\lambda}\sum_{n=0}^{N-1}\begin{cases} \frac{1}{k}\left[[\hat{A}_n h_n^3 + \hat{B}_n h_n^2 + \hat{C}_n h_n + \hat{D}_n]\sin(ky_{n+1}) - \hat{D}_n\sin(ky_n)\right] + \\ \frac{1}{k^2}\left[[3\hat{A}_n h_n^2 + 2\hat{B}_n h_n + \hat{C}_n]\cos(ky_{n+1}) - \hat{C}_n\cos(ky_n)\right] - \\ \frac{1}{k^3}\left[[6\hat{A}_n h_n + 2\hat{B}_n]\sin(ky_{n+1}) - 2\hat{B}_n\sin(ky_n)\right] \\ -\frac{1}{k^4}\left[6\hat{A}_n\cos(ky_{n+1}) - 6\hat{A}_n\cos(ky_n)\right] \end{cases} \quad \text{for } \tilde{k}=1, 2, \quad (120)$$

$$\hat{K}^{odd}[\tilde{k}] = \frac{2}{\lambda}\sum_{n=0}^{N-1}\begin{cases} -\frac{1}{k}\left[[\hat{A}_n h_n^3 + \hat{B}_n h_n^2 + \hat{C}_n h_n + \hat{D}_n]\cos(ky_{n+1}) - \hat{D}_n\cos(ky_n)\right] + \\ \frac{1}{k^2}\left[[3\hat{A}_n h_n^2 + 2\hat{B}_n h_n + \hat{C}_n]\sin(ky_{n+1}) - \hat{C}_n\sin(ky_n)\right] - \\ \frac{1}{k^3}\left[[6\hat{A}_n h_n + 2\hat{B}_n]\cos(ky_{n+1}) - 2\hat{B}_n\cos(ky_n)\right] \\ -\frac{1}{k^4}\left[6\hat{A}_n\sin(ky_{n+1}) - 6\hat{A}_n\sin(ky_n)\right] \end{cases} \quad \text{for } \tilde{k}=1, 2, \quad (121)$$

Each term in these sums depend only on coefficients from a single cubic, which will allow it to be readily arranged in matrix form, although the existence of simplifications can be seen by observing the Fourier series coefficient's decay with mode number.

The rate of decay of Fourier series coefficients with increasing wave number k is directly related to the smoothness of the function being expanded and its derivatives, such that the slowest decay rate is proportional to $1/k^\alpha$. Here $\alpha$ represents the number of derivative of the function being expanded before a delta function is observed. In the present case the of the cubic splines with continuous second derivative, the slowest decay rate should be related to $1/k^4$, however the terms contain powers of $1/k$ ranging from the first to the fourth. This motivates the search for simplifications which would eliminate terms of slower decay, except for those due to the cubic functions at the extremes of the piecewise representation, where continuity is not imposed. By using the relationships of (92) through (95), which define the continuity of the spline interpolation and derivatives, parts of neighboring terms in the previous sums can be canceled. Additional terms are eliminated by using the natural boundary condition of equations (96) and (97). As with the linear case, these expressions can also be simplified by normalizing the dimensions, such that $$\tilde{y}_n = \frac{2\pi}{\lambda} y_n$$

and $\tilde{h}_n = (\tilde{y}_{n+1} - \tilde{y}_n)$. The normalized cubic coefficients in the following expressions are related to the current density parameters by utilizing the normalized quantities $\tilde{h}_n$ in place of the unnormalized quantities $h_n$ in building the W matrix, which is used for evaluating U. The resulting expressions for the coefficients are:

$$\hat{K}^{even}[\tilde{k}] = \frac{1}{2\pi} \sum_{n=0}^{N-1} \frac{1}{4}\tilde{A}_n \tilde{h}_n^4 + \frac{1}{3}\tilde{B}_n \tilde{h}_n^3 + \frac{1}{2}\tilde{C}_n \tilde{h}_n^2 + \tilde{D}_n \tilde{h}_n \quad \text{for } \tilde{k} = 0 \tag{122}$$

$$\hat{K}^{even}[\tilde{k}] = \sum_{n=0}^{N-1} \begin{cases} -\frac{1}{\tilde{k}^4}\frac{6}{\pi}[\cos(\tilde{k}\tilde{y}_1) - \cos(\tilde{k}\tilde{y}_0)]\tilde{A}_0 - \\ \frac{1}{\tilde{k}^2}\frac{1}{\pi}\cos(\tilde{k}\tilde{y}_0)\tilde{C}_0 - \frac{1}{\tilde{k}}\frac{1}{\pi}\sin(\tilde{k}\tilde{y}_0)\tilde{D}_0 + \\ \frac{6}{\pi}\sum_{n=1}^{N-2}\frac{1}{\tilde{k}^4}[-\cos(\tilde{k}\tilde{y}_{n+1}) + \cos(\tilde{k}\tilde{y}_n)]\tilde{A}_n + \\ \frac{1}{\pi}\left[\frac{1}{\tilde{k}}\tilde{h}_{N-1}^3 \sin(\tilde{k}\tilde{y}_N) + \frac{3}{\tilde{k}^2}\tilde{h}_{N-1}^2 \cos(\tilde{k}\tilde{y}_N) - \right. \\ \left. \frac{6}{\tilde{k}^4}[\cos(\tilde{k}\tilde{y}_N) - \cos(\tilde{k}\tilde{y}_{N-1})]\right]\tilde{A}_{N-1} + \\ \frac{1}{\pi}\left[\frac{1}{\tilde{k}}\tilde{h}_{N-1}^2 \sin(\tilde{k}\tilde{y}_N) + \frac{2}{\tilde{k}^2}\tilde{h}_{N-1}\cos(\tilde{k}\tilde{y}_N)\right]\tilde{B}_{N-1} + \\ \frac{1}{\pi}\left[\frac{1}{\tilde{k}}\tilde{h}_{N-1}\sin(\tilde{k}\tilde{y}_N) + \frac{1}{\tilde{k}^2}\cos(\tilde{k}\tilde{y}_N)\right]\tilde{C}_{N-1} + \\ \frac{1}{\pi}\frac{1}{\tilde{k}}\sin(\tilde{k}\tilde{y}_N)\tilde{D}_{N-1} \end{cases} \quad \text{for } \tilde{k} = 1, 2, \tag{123}$$

$$\hat{K}^{odd}[\tilde{k}] = \begin{cases} -\frac{1}{\tilde{k}^4}\frac{6}{\pi}[\sin(\tilde{k}\tilde{y}_1) - \sin(\tilde{k}\tilde{y}_0)]\tilde{A}_0 - \\ \frac{1}{\tilde{k}^2}\frac{1}{\pi}\sin(\tilde{k}\tilde{y}_0)\tilde{C}_0 + \frac{1}{\tilde{k}}\frac{1}{\pi}\cos(\tilde{k}\tilde{y}_0)\tilde{D}_0 + \\ \frac{6}{\pi}\sum_{n=1}^{N-2}\frac{1}{\tilde{k}^4}[-\sin(\tilde{k}\tilde{y}_{n+1}) + \sin(\tilde{k}\tilde{y}_n)]\tilde{A}_n + \\ \frac{1}{\pi}\left[-\frac{1}{\tilde{k}}\tilde{h}_{N-1}^3 \cos(\tilde{k}\tilde{y}_N) + \frac{3}{\tilde{k}^2}\tilde{h}_{N-1}^2 \sin(\tilde{k}\tilde{y}_N) - \right. \\ \left. \frac{6}{\tilde{k}^4}[\sin(\tilde{k}\tilde{y}_N) - \sin(\tilde{k}\tilde{y}_{N-1})]\right]\tilde{A}_{N-1} + \\ \frac{1}{\pi}\left[-\frac{1}{\tilde{k}}\tilde{h}_{N-1}^2 \cos(\tilde{k}\tilde{y}_N) + \frac{2}{\tilde{k}^2}\tilde{h}_{N-1}\sin(\tilde{k}\tilde{y}_N)\right]\tilde{B}_{N-1} + \\ \frac{1}{\pi}\left[-\frac{1}{\tilde{k}}\tilde{h}_{N-1}\cos(\tilde{k}\tilde{y}_N) + \frac{1}{\tilde{k}^2}\sin(\tilde{k}\tilde{y}_N)\right]\tilde{C}_{N-1} - \\ \frac{1}{\pi}\frac{1}{\tilde{k}}\cos(\tilde{k}\tilde{y}_N)\tilde{D}_{N-1} \end{cases} \quad \text{for } \tilde{k} = 1, 2, \tag{124}$$

The preceding relations for the even and odd Fourier series coefficients have been expressed in terms of the coefficients of the cubic interpolation functions. However, summations in the form of (114) and (115), involving the current density parameters, is desired. The matrix U in (103) relates the surface current density parameters for a conductor to the cubic coefficients of that conductor. Each column of U corresponds to a surface current density parameter and represents the parameter's contribution to each of the cubic coefficients. Therefore, the required expressions for the contribution to the even and odd Fourier series coefficients by a surface current density parameter are obtained by substituting each element of the corresponding column of U for the corresponding cubic coefficients in (122), (123), and (124). The terms for the desired summation form can then be represented as:

(MQS) at the bounding surfaces. The regions separating the interfaces which contain the sensor's conductors are composed of one or more layers of material. The interfaces between these layers are assumed to have no surface conductors, so that the current density K(y) is zero there. In the case when any one of the aforementioned regions is composed of more than one material layer, it becomes possible to simplify the problem by reducing the multiple transfer relations corresponding to each layer of the region into a single relation for the region. To facilitate the reduction to a single relation, the transfer relations for two adjacent layers are first examined, as:

$$\hat{F}_n^{even}[\tilde{k} \neq 0] = \begin{cases} -\frac{1}{\tilde{k}^4}\frac{6}{\pi}[\cos(\tilde{k}\tilde{y}_1) - \cos(\tilde{k}\tilde{y}_0)]U_{1,n+1} - \\ \frac{1}{\tilde{k}^2}\frac{1}{\pi}\sin(\tilde{k}\tilde{y}_0)U_{3,n+1} + \frac{1}{\tilde{k}}\frac{1}{\pi}\cos(\tilde{k}\tilde{y}_0)U_{4,n+1} + \\ \frac{6}{\pi}\sum_{n=1}^{N-2}\frac{1}{\tilde{k}^4}[-\cos(\tilde{k}\tilde{y}_{n+1}) + \cos(\tilde{k}\tilde{y}_n)]U_{4n+1,n+1} + \\ \frac{1}{\pi}\left[\frac{1}{\tilde{k}}\tilde{h}_{N-1}^3\sin(\tilde{k}\tilde{y}_N) + \frac{3}{\tilde{k}^2}\tilde{h}_{N-1}^2\cos(\tilde{k}\tilde{y}_N) - \right. \\ \left. \frac{6}{\tilde{k}^4}[\cos(\tilde{k}\tilde{y}_N) - \cos(\tilde{k}\tilde{y}_{N-1})]\right]U_{4N-3,n+1} + \\ \frac{1}{\pi}\left[\frac{1}{\tilde{k}}\tilde{h}_{N-1}^2\sin(\tilde{k}\tilde{y}_N) + \frac{2}{\tilde{k}^2}\tilde{h}_{N-1}\cos(\tilde{k}\tilde{y}_N)\right]U_{4N-2,n+1} + \\ \frac{1}{\pi}\left[\frac{1}{\tilde{k}}\tilde{h}_{N-1}\sin(\tilde{k}\tilde{y}_N) + \frac{1}{\tilde{k}^2}\cos(\tilde{k}\tilde{y}_N)\right]U_{4N-1,n+1} + \\ \frac{1}{\pi}\frac{1}{\tilde{k}}\sin(\tilde{k}\tilde{y}_N)U_{4N,n+1} \end{cases} \quad (125)$$

$$\hat{F}_n^{odd}[\tilde{k} \neq 0] = \begin{cases} -\frac{1}{\tilde{k}^4}\frac{6}{\pi}[\sin(\tilde{k}\tilde{y}_1) - \sin(\tilde{k}\tilde{y}_0)]U_{1,n+1} - \\ \frac{1}{\tilde{k}^2}\frac{1}{\pi}\sin(\tilde{k}\tilde{y}_0)U_{4,n+1} - \frac{1}{\tilde{k}}\frac{1}{\pi}\cos(\tilde{k}\tilde{y}_0)U_{4,n+1} + \\ \frac{6}{\pi}\sum_{n=1}^{N-2}\frac{1}{\tilde{k}^4}[-\sin(\tilde{k}\tilde{y}_{n+1}) + \sin(\tilde{k}\tilde{y}_n)]U_{4n+1,n+1} + \\ \frac{1}{\pi}\left[-\frac{1}{\tilde{k}}\tilde{h}_{N-1}^3\cos(\tilde{k}\tilde{y}_N) + \frac{3}{\tilde{k}^2}\tilde{h}_{N-1}^2\sin(\tilde{k}\tilde{y}_N) - \right. \\ \left. \frac{6}{\tilde{k}^4}[\sin(\tilde{k}\tilde{y}_N) - \sin(\tilde{k}\tilde{y}_{N-1})]\right]U_{4N-3,n+1} + \\ \frac{1}{\pi}\left[-\frac{1}{\tilde{k}}\tilde{h}_{N-1}\cos(\tilde{k}\tilde{y}_N) + \frac{2}{\tilde{k}^2}\tilde{h}_{N-1}\sin(\tilde{k}\tilde{y}_N)\right]U_{4N-2,n+1} + \\ \frac{1}{\pi}\left[-\frac{1}{\tilde{k}}\tilde{h}_{N-1}\cos(\tilde{k}\tilde{y}_N) + \frac{1}{\tilde{k}^2}\sin(\tilde{k}\tilde{y}_N)\right]U_{4N-1,n+1} - \\ \frac{1}{\pi}\frac{1}{\tilde{k}}\cos(\tilde{k}\tilde{y}_N)U_{4N,n+1} \end{cases} \quad (126)$$

$$\hat{F}_n^{even}[\tilde{k} = 0] = \frac{1}{2\pi}\sum_{n=0}^{N-1}\frac{1}{4}\tilde{h}_n^4 U_{4n+1,n+1} + \frac{1}{3}\tilde{h}_n^3 U_{4n+2,n+1} + \frac{1}{2}\tilde{h}_n^2 U_{4n+3,n+1} + \tilde{h}_n U_{4n+4,n+1} \quad (127)$$

where the subscript of U indicates the row and column of the desired element of the matrix.

In the preceding discussion, transfer relations have been shown for each system which can relate the Fourier coefficients of the potential at the bounding surfaces of a material layer to the complex amplitudes of either the normal complex current density $\hat{J}_x^*$ (EQS) or the tangential magnetic field $\hat{H}_y$ $$\begin{bmatrix} \hat{Q}_m^+[\tilde{k}] \\ \hat{Q}_{m+1}^-[\tilde{k}] \end{bmatrix} = \begin{bmatrix} \hat{M}_{11}^m[\tilde{k}] & \hat{M}_{12}^m[\tilde{k}] \\ \hat{M}_{21}^m[\tilde{k}] & \hat{M}_{22}^m[\tilde{k}] \end{bmatrix} \begin{bmatrix} \hat{P}_m^+[\tilde{k}] \\ \hat{P}_{m+1}^-[\tilde{k}] \end{bmatrix} \quad (128)$$

Figure 19:
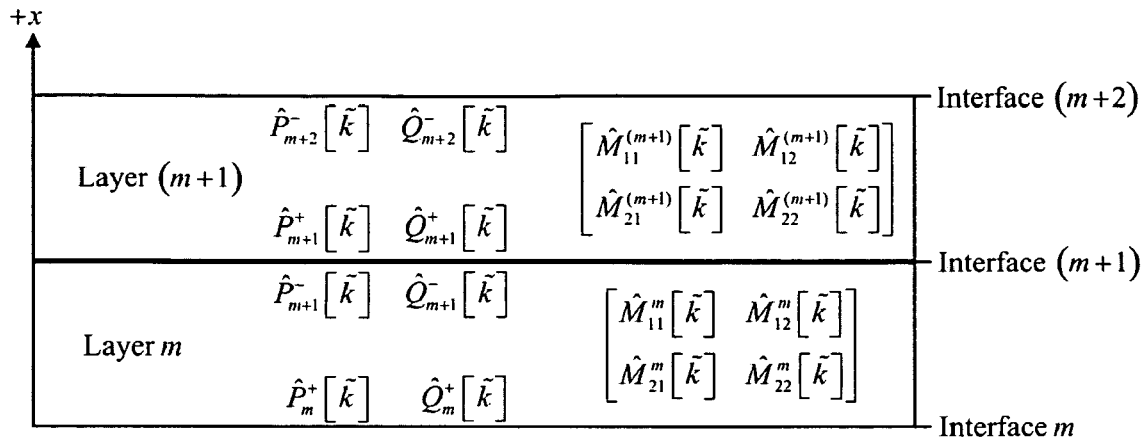
FIG. 19 shows adjacent material layers to be represented by a single transfer relation.

-continued $$\begin{bmatrix} \hat{Q}^+_{m+1}[\tilde{k}] \\ \hat{Q}^-_{m+2}[\tilde{k}] \end{bmatrix} = \begin{bmatrix} \hat{M}^{(m+1)}_{11}[\tilde{k}] & \hat{M}^{(m+1)}_{12}[\tilde{k}] \\ \hat{M}^{(m+1)}_{21}[\tilde{k}] & \hat{M}^{(m+1)}_{22}[\tilde{k}] \end{bmatrix} \begin{bmatrix} \hat{P}^+_{m+1}[\tilde{k}] \\ \hat{P}^-_{m+2}[\tilde{k}] \end{bmatrix} \quad (129)$$

where the subscripts on the quantities P and Q indicate the layer interface number within the region, the "+" or "−" superscripts indicate the upper or low side of the interface respectively, and the superscripts on the matrix elements $\hat{M}$ indicate the layer index of the transfer relations elements to which they are equal. FIG. 19 shows the physical association of the quantities to the two layer structure.

The boundary conditions at the (m+1) interface, from (51) for MQS system and (82) for the EQS systems, require $\hat{Q}_{(n+1)}^- = \hat{Q}_{(n+1)}^+$ since there is no current density K(y) at these interfaces. The boundary condition of (49) for the MQS system and (80) for the EQS system requires that the potential at all interfaces is continuous such that $\hat{P}_{(n+1)}^- = \hat{P}_{(n+1)}^+$. By applying these conditions to the transfer relations of (128) and (129) yields:

$$\begin{bmatrix} \hat{Q}^+_{m}[\tilde{k}] \\ \hat{Q}^-_{m+2}[\tilde{k}] \end{bmatrix} = \begin{bmatrix} \hat{M}^{m:(m+1)}_{11}[\tilde{k}] & \hat{M}^{m:(m+1)}_{12}[\tilde{k}] \\ \hat{M}^{m:(m+1)}_{21}[\tilde{k}] & \hat{M}^{m:(m+1)}_{22}[\tilde{k}] \end{bmatrix} \begin{bmatrix} \hat{P}^+_{m}[\tilde{k}] \\ \hat{P}^-_{m+2}[\tilde{k}] \end{bmatrix} \quad (130)$$

$$\hat{M}^{m:(m+1)}_{11}[\tilde{k}] = \hat{M}^m_{11}[\tilde{k}] - \frac{\hat{M}^m_{12}[\tilde{k}]\hat{M}^m_{21}[\tilde{k}]}{\hat{M}^m_{22}[\tilde{k}] - \hat{M}^{(m+1)}_{11}[\tilde{k}]} \quad (131)$$

$$\hat{M}^{m:(m+1)}_{12}[\tilde{k}] = \frac{\hat{M}^m_{12}[\tilde{k}]\hat{M}^{(m+1)}_{12}[\tilde{k}]}{\hat{M}^m_{22}[\tilde{k}] - \hat{M}^{(m+1)}_{11}[\tilde{k}]} \quad (132)$$

$$\hat{M}^{m:(m+1)}_{21}[\tilde{k}] = -\frac{\hat{M}^m_{21}[\tilde{k}]\hat{M}^{(m+1)}_{21}[\tilde{k}]}{\hat{M}^m_{22}[\tilde{k}] - \hat{M}^{(m+1)}_{11}[\tilde{k}]} \quad (133)$$

$$\hat{M}^{m:(m+1)}_{22}[\tilde{k}] = \hat{M}^{(m+1)}_{22}[\tilde{k}] - \frac{\hat{M}^{(m+1)}_{12}[\tilde{k}]\hat{M}^{(m+1)}_{21}[\tilde{k}]}{\hat{M}^m_{22}[\tilde{k}] - \hat{M}^{(m+1)}_{11}[\tilde{k}]} \quad (134)$$

where the notation of m: (m+1) indicates that the matrix element is for the single transfer relation produced from reducing layers m through (m+1).

Figure 20:
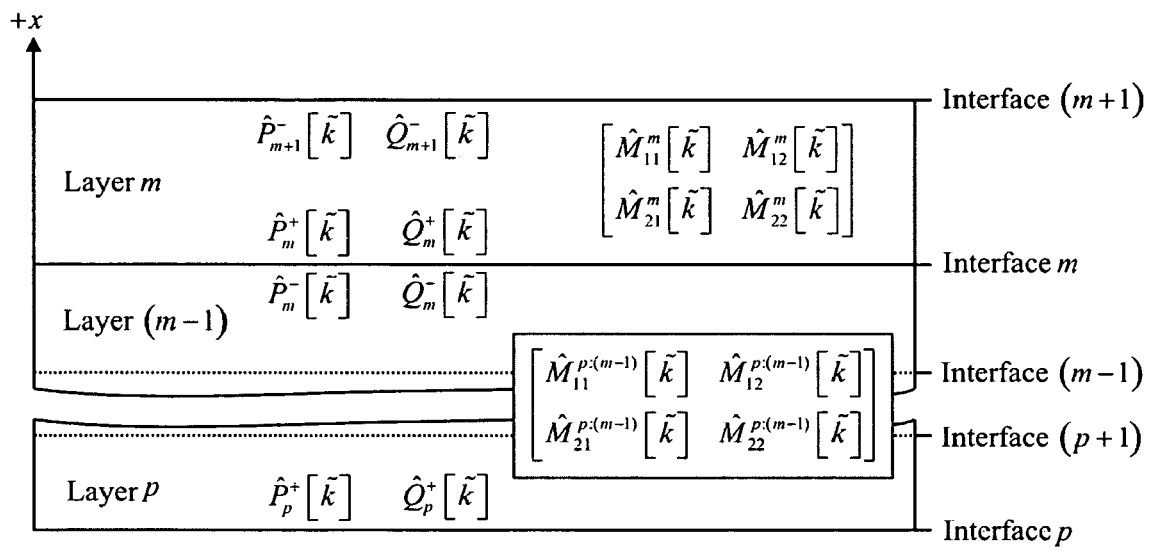
FIG. 20 shows one iterative step in the reduction of adjacent materials layers to a single transfer relation representation.

The transfer relation of (130) is the reduction of the two transfer relations of the two layers to a single relation for the region composed of those two layers. Since this transfer relation has the same form of the original two adjacent layers found in (128) and (129), this reduction process can be continued in an iterative manner. This is accomplished by repeating the previous process for the two adjacent layers, with the exception that the transfer relation describing one of the layers is replaced by that describing the region of previously reduced layers. The situation of a reduced region of layers being combined with an adjacent layer is shown in FIG. 20. The transfer relation for the upper layer can be combined with the equivalent relation for the lower region of layers to produce a single transfer relation for layers p through m. This process is repeated to produce single relations for regions separated by interfaces containing sensor conductors.

The expressions for the elements of the combined transfer relation can be simplified by observing the symmetry present in the transfer relations for a single layer. In both the MQS and EQS expressions for the transfer relation of single layer, it can be seen that the matrix elements are related such that: $\hat{M}_{12}[\tilde{k}] = -\hat{M}_{21}[\tilde{k}]$. If this relationship is used in the expressions for elements of the combined transfer relation, then it can be shown that the elements of the new transfer relation will exhibit the same $\hat{M}_{12}[\tilde{k}] = -\hat{M}_{21}[\tilde{k}]$ relation. Therefore continued iteration will continue this relation in the reduced transfer relation of the region and will reduce computation. For the iterative step, as shown in FIG. 20, where layers p to m−1 have been reduced to a single relation which is being combined with layer index m above, the new reduced relation is described by:

$$\begin{bmatrix} \hat{Q}^+_{p}[\tilde{k}] \\ \hat{Q}^-_{m+1}[\tilde{k}] \end{bmatrix} = \begin{bmatrix} \hat{M}^{p:m}_{11}[\tilde{k}] & \hat{M}^{p:m}_{12}[\tilde{k}] \\ \hat{M}^{p:m}_{21}[\tilde{k}] & \hat{M}^{p:m}_{22}[\tilde{k}] \end{bmatrix} \begin{bmatrix} \hat{P}^+_{p}[\tilde{k}] \\ \hat{P}^-_{m+1}[\tilde{k}] \end{bmatrix} \quad (135)$$

$$\hat{M}^{p:m}_{11}[\tilde{k}] = \hat{M}^{p:(m-1)}_{11}[\tilde{k}] + \frac{\left(\hat{M}^{p:(m-1)}_{21}[\tilde{k}]\right)^2}{\hat{M}^{p:(m-1)}_{22}[\tilde{k}] - \hat{M}^m_{11}[\tilde{k}]} \quad (136)$$

$$\hat{M}^{p:m}_{12}[\tilde{k}] = -\hat{M}^{p:m}_{21}[\tilde{k}] \quad (137)$$

$$\hat{M}^{p:m}_{21}[\tilde{k}] = -\frac{\hat{M}^{p:(m-1)}_{21}[\tilde{k}]\hat{M}^m_{21}[\tilde{k}]}{\hat{M}^{p:(m-1)}_{22}[\tilde{k}] - \hat{M}^m_{11}[\tilde{k}]} \quad (138)$$

$$\hat{M}^{p:m}_{22}[\tilde{k}] = \hat{M}^m_{22}[\tilde{k}] - \frac{\left(\hat{M}^m_{21}[\tilde{k}]\right)^2}{\hat{M}^{p:(m-1)}_{22}[\tilde{k}] - \hat{M}^m_{11}[\tilde{k}]} \quad (139)$$

In handling the outer bounding regions of the structure being modeled, it will be useful to have these relations for the iterative combination of layers progressing in the opposite direction. In this case a single relation for a region containing layers p+1 to m is combined with layer index p below. The relation for the region is again described by (135), where the matrix elements now become:

$$\hat{M}^{p:m}_{11}[\tilde{k}] = \hat{M}^p_{11}[\tilde{k}] + \frac{\left(\hat{M}^p_{21}[\tilde{k}]\right)^2}{\hat{M}^p_{22}[\tilde{k}] - \hat{M}^{(p+1):m}_{11}[\tilde{k}]} \quad (140)$$

$$\hat{M}^{p:m}_{21}[\tilde{k}] = -\hat{M}^{p:m}_{21}[\tilde{k}] \quad (141)$$

$$\hat{M}^{p:m}_{21}[\tilde{k}] = -\frac{\hat{M}^p_{21}[\tilde{k}]\hat{M}^{(p+1):m}_{21}[\tilde{k}]}{\hat{M}^p_{22}[\tilde{k}] - \hat{M}^{(p+1):m}_{11}[\tilde{k}]} \quad (142)$$

$$\hat{M}^{p:m}_{22}[\tilde{k}] = \hat{M}^{(p+1):m}_{22}[\tilde{k}] - \frac{\left(\hat{M}^{(p+1):m}_{21}[\tilde{k}]\right)^2}{\hat{M}^p_{22}[k] - \hat{M}^{(p+1):m}_{11}[\tilde{k}]} \quad (143)$$

By repeating this iterative process $(N_L-1)$ time, where $N_L$ is the number of layers in the region, a single transfer relation of the form (135) is obtained where p=0 and m=$(N_L-1)$.

The preceding results can be applied to layered regions separated by sensor conductors located at interfaces on which the current density is described in terms of unknown parameters. However, the outermost regions, which bound the modeled structure on the outside of the first and last of these interfaces, require the use of a modified method to account for the outermost boundary constraints.

It was shown earlier in the development of the MQS and EQS transfer relations for $\tilde{k} \neq 0$ that when the layer thickness became infinite then the electromagnetic quantities on one interface became decoupled from those on the opposite interface. For the EQS case it was also shown that if the potential is constrained to zero at one of the interfaces, then the potential and $\hat{J}^*$ on the other interface are independent of either quantity on the first. Both of these results are useful in the final upper and lower structure layers, which have either an infinite thickness or an imposed zero potential. In either case the relationship between the potential and field quantities on the interface nearer the sensor structure is independent of the interface at infinity or of zero imposed potential. This replaces the full transfer relation of the final layer in the negative x direction with the simplified relation:

$$\hat{Q}_1^-[\tilde{k}] = \hat{M}_{22}^0[\tilde{k}]\hat{P}_1^-[\tilde{k}] \qquad (144)$$

This is the relation for first layer of the region which has index 0. The quantity $\hat{M}_{22}^0[\tilde{k}]$ is taken from the full transfer relation and has superscript denoting the layer, while the quantities $\hat{Q}_1^-[\tilde{k}]$ and $\hat{P}_1^-[\tilde{k}]$ have subscripts indicating the interface index to which they are associated; the sign in the superscript again indicates the sides of the interface to which the quantities belong. The full transfer function can also be replaced for the final layer in the positive x direction with the relation:

$$\hat{Q}_{N_L-1}^+[\tilde{k}] = \hat{M}_{11}^{N_L-1}[\tilde{k}]\hat{P}_{N_L-1}^+[\tilde{k}] \qquad (145)$$

This is the relation of the last layer in the region which has index $(N_L-1)$ where $N_L$ is the number of layers in this bounding region. The interface for which the electromagnetic quantities are being related is on the opposite side of the layer as compared to (144) as reflected in the signs of the superscripts and interface index number relative to the layer number.

When there is only a single layer in the final region bounding the sensor, these relations are sufficient to describe the region. However, when there are additional layers in these bounding regions, it is again desired to reduce the multiple transfer relations of the region to a single relation for the region. The results for combining two adjacent layers developed in the previous section can be utilized here with a slight modification. This will again be accomplished through an iterative approach of combining layers, starting with the combination of the layer described by a simplified relation and the layer adjacent to it. The result of this combination should not be dependent on the electromagnetic quantities for the interface at infinity or alternatively with imposed zero potential, since the presence of first layer has essentially decoupled that interface. The results of this combination can therefore be expressed in a simplified manner similar to (144) and (145). To combine the relations for the bounding region in the negative x direction, (139) is used. This expression for $\hat{M}_{22}^{p:m}[\tilde{k}]$ is only dependent on result of previous iterations $\hat{M}_{22}^{p:(m-1)}[\tilde{k}]$, and the transfer relation elements of the layer with index m being combined. Therefore the element $\hat{M}_{22}^0$ from the first infinite or constrained layer is sufficient to start the iteration process. For this region the iteration process proceeds from layer index 0 to layer index $(N_L-1)$ and therefore the iteration step of (139) can be expressed as:

$$\hat{M}_{22}^{0:m}[\tilde{k}] = \hat{M}_{22}^m[\tilde{k}] - \frac{\left(\hat{M}_{21}^m[\tilde{k}]\right)^2}{\hat{M}_{22}^{0:(m-1)}[\tilde{k}] - \hat{M}_{11}^m[\tilde{k}]} \qquad (146)$$

where $\hat{M}_{22}^{0:0} = \hat{M}_{22}^0$. A similar expression can be generated for use on the region bounding the structure in the positive x direction. The iteration process again proceeds from the layer of infinite thickness or imposed potential toward the remaining modeled structure; however the layer indexing is now reversed. The reversed direction of layer combinations utilizes (140) which after adjustment for the starting iteration layer index becomes:

$$\hat{M}_{11}^{m:(N_L-1)}[\tilde{k}] = \hat{M}_{11}^m[\tilde{k}] + \frac{\left(\hat{M}_{21}^m[\tilde{k}]\right)^2}{\hat{M}_{22}^m[\tilde{k}] - \hat{M}_{11}^{(m+1):(N_L-1)}[\tilde{k}]} \qquad (147)$$

where $\hat{M}_{11}^{(N_L-1):(N_L-1)} = \hat{M}_{11}^{N_L-1}$. With these results in addition to the results of the previous section, the behavior of each of the multilayered regions between interfaces containing conductors can be expressed by a single relation for each region for spatial modes $\tilde{k} \neq 0$.

Up to this point it has been possible to handle the combining of layer relations for the EQS and MQS system using identical relations forms. However, the layer relations for the $\tilde{k}=0$ mode do not have the same form between the MQS and EQS systems when the layer of the MQS system has a non-zero conductivity. Therefore the methodology for combining layers and arriving at a single relation for the region must be developed separately; although regions of the MQS system that are void of conducting layers could use an analogous method to that of the EQS system. For the EQS system, when $\tilde{k}=0$ (the electromagnetic quantities have no y dependence) the forms of the solutions changed as compared to $\tilde{k}\neq 0$ and it was no longer necessary to use a matrix formulation to describe the relationship between the scalar potential $\Phi$ and the current density $\hat{J}^*$. When the layer thickness is finite the relationship has the form:

$$\hat{Q}_m^+[\tilde{k}=0] = \hat{Q}_{m+1}^-[\tilde{k}=0] = \hat{M}_0^m[\tilde{k}=0](\hat{P}_m^+[\tilde{k}=0] - \hat{P}_{m+1}^-[\tilde{k}=0]) \qquad (148)$$

where the subscripts and superscripts retain the same meanings as in preceding analysis. The boundary conditions at interfaces which do not contain sensor conductors require that $\hat{J}^*$ be continuous or in generic notation $\hat{Q}_m^-[\tilde{k}]=\hat{Q}_m^+[\tilde{k}]$ Since the quantity $\hat{Q}[\tilde{k}=0]$ is also identical at both interfaces of a layer, $\hat{Q}[\tilde{k}=0]$ is the same at each layer interface of the region between sensor conductors. Therefore the potential for each layer is related to $\hat{Q}=[\tilde{k}=0]$ at the interfaces bounding the region by:

$$\hat{P}_m^+[\tilde{k}=0] - \hat{P}_{m+1}^-[\tilde{k}=0] = \frac{\hat{Q}_0^+[\tilde{k}=0]}{\hat{M}_0^m[\tilde{k}=0]} = \frac{\hat{Q}_{N_L}^-[\tilde{k}=0]}{\hat{M}_0^m[\tilde{k}=0]} \qquad (149)$$

To obtain a relation of the form (148) for the complete region, the difference of the potential at the boundaries of this region is needed in terms of $\hat{Q}[\tilde{k}=0]$ at either boundary. This is simply the sum of (149) over each layer of the region. After taking this sum and rearranging the expression to match the form of (148), the following relation containing the effects of each layer is obtained for the region:

$$\hat{Q}_0^+[\tilde{k}=0] = \hat{Q}_{N_L}^-[\tilde{k}=0] = \hat{M}_0^{0:(N_L-1)}[\tilde{k}=0](\hat{P}_0^+[\tilde{k}=0] - \hat{P}_{N_L}^-[\tilde{k}=0]) \qquad (150)$$

$$\hat{M}_0^{0:(N_L-1)}[\tilde{k}=0] = \frac{1}{\sum_{m=0}^{(N_L-1)} \frac{1}{\tilde{M}_0^m[\tilde{k}=0]}} \qquad (151)$$

In the EQS system the bounding regions of the structure will either contain an infinitely thick layer or have an interface with the potential constrained to zero. When a layer of infinite thickness is present $\hat{J}^*$ for the region is independent of the bounding potentials and equal to zero. This is a result of the requirement that there is no current density or charge at infinity or equivalently that the net charge of the finite system must remain zero. In the case when there is an imposed bounding potential of zero, (150) is further simplified. The relation for the final region in the negative x direction bounded by an imposed zero potential becomes:

$$\hat{Q}_{N_L}^-[\tilde{k}=0] = -\hat{M}_0^{0:(N_L-1)}[\tilde{k}=0]\hat{P}_{N_L}^-[\tilde{k}=0] \quad (152)$$

while the relation for the final region in the positive x direction bounded by an imposed zero potential becomes:

$$\hat{Q}_0^+[\tilde{k}=0] = \hat{M}_0^{0:(N_L-1)}[\tilde{k}=0]\hat{P}_0^+[\tilde{k}=0] \quad (153)$$

In both cases the relation for the region becomes independent of the electromagnetic quantities at the interface with imposed potential and assumes a form similar to that encountered for $\tilde{k} \neq 0$ in regions with an infinitely thick layer or regions with an interface having an imposed potential of zero. As mentioned previously, the differing forms of the solutions to the governing equations of layers for MQS and EQS systems require a differing treatments in developing combining relations in the case when $\tilde{k}=0$. Solutions for conducting layers in the MQS system allow for three undetermined coefficients, one of which is associated with a constant term. In the development of the boundary conditions for the MQS system, issues associated with this additional constant term were discussed.

Based on the discussion, the layers located between the winding interfaces can be divided into groups of adjacent layers within which inter-layer conduction is expected as a result of appropriate conduction paths. Each of these groups is expected to contain no net current and therefore Ampere's law requires that the tangential magnetic field is identical between each bounding interface of each group of layers. Since the additional layers separating these regions must each contain no net current, the tangential magnetic field has the same value on the bounding interfaces of the region between winding interfaces, on the bounding interfaces of groups of inter-conducting layers, and on the interfaces of all other layers. It will therefore be possible to represent the behavior of the region with a linear relation between the difference in the potential at region interfaces and the tangential magnetic field which is the same at these interfaces; this relation will have the same form as in the EQS case. In order to reach this final relation, each group of layers which allow inter-layer conduction is first analyzed separately. The results from these groups are then combined with the results from the other layers. In order to simplify the description of this method, the layers which compose the groups must be either conducting, or nonconducting and bounded by other conducting layers of the group. Single conducting layers which do not allow inter-layer conduction with neighboring layers are each individually considered as a group, while the layers which are not contained in any group must be nonconducting.

Based on the discussion in developing the MQS boundary conditions, the vector potential solution in each conducting layer is chosen to have a zero constant term. The transfer relation of (18) is then valid and the continuity of the vector potential at interfaces between conducting layers guarantees the continuity of the tangential electric field. At the interface of a conducting layer and a nonconducting layer, the electric field is not uniquely defined in the nonconducting layer and the associated boundary condition cannot be applied at the interface. However, in the discussion Faraday's integral law was applied to a nonconducting layer separating two conducting layers which included conduction paths to one another. The result was that Faraday's law was self-consistent as long as the vector potential was continuous in the nonconducting layer. Therefore, for each interface within the inter-conducting layer group, the boundary conditions require continuity of the tangential magnetic field and the continuity of the vector potential. By using the transfer relation form of (25) rather than the linear form of (26) for the nonconducting layers, the methods of combining layers for $\tilde{k} \neq 0$ can be applied to the group. This results in a single relation for the group of layers with the form:

$$\begin{bmatrix} \hat{Q}_p^+[\tilde{k}] \\ \hat{Q}_{m+1}^-[\tilde{k}] \end{bmatrix} = \begin{bmatrix} \hat{M}_{11}^{p:m}[\tilde{k}] & \hat{M}_{12}^{p:m}[\tilde{k}] \\ \hat{M}_{21}^{p:m}[\tilde{k}] & \hat{M}_{22}^{p:m}[\tilde{k}] \end{bmatrix} \begin{bmatrix} \hat{P}_p^+[\tilde{k}] \\ \hat{P}_{m+1}^-[\tilde{k}] \end{bmatrix} \quad (154)$$

where p is the index of the first layer in the group and m is the index of the last layer in the group. The inverse of this matrix can be taken to produce reverse relationship between the potential and the tangential magnetic field:

$$\begin{bmatrix} \hat{P}_p^+[\tilde{k}] \\ \hat{P}_{m+1}^-[\tilde{k}] \end{bmatrix} = \frac{1}{\hat{M}_{11}^{p:m}[\tilde{k}]\hat{M}_{22}^{p:m}[\tilde{k}] - \hat{M}_{21}^{p:m}[\tilde{k}]\hat{M}_{12}^{p:m}[\tilde{k}]} \begin{bmatrix} \hat{M}_{22}^{p:m}[\tilde{k}] & -\hat{M}_{12}^{p:m}[\tilde{k}] \\ -\hat{M}_{12}^{p:m}[\tilde{k}] & \hat{M}_{11}^{p:m}[\tilde{k}] \end{bmatrix} \begin{bmatrix} \hat{Q}_p^+[\tilde{k}] \\ \hat{Q}_{m+1}^-[\tilde{k}] \end{bmatrix} \quad (155)$$

As stated earlier, the tangential magnetic field is identical on the two bounding interfaces of this group of layers such that $\hat{Q}_p^+[\tilde{k}] = \hat{Q}_{m+1}^-[\tilde{k}]$. The preceding result can therefore be put in terms of the linear relation:

$$\hat{Q}_p^+[\tilde{k}=0] = \hat{Q}_{m+1}^-[\tilde{k}=0] = \hat{M}_0^{p:m}[\tilde{k}=0](\hat{P}_p^+[\tilde{k}=0] - \hat{P}_m^-[\tilde{k}=0]) \quad (156)$$

$$\hat{M}_0^{p:m}[\tilde{k}=0] = \frac{\hat{M}_{11}^{p:m}[\tilde{k}]\hat{M}_{22}^{p:m}[\tilde{k}] - \hat{M}_{21}^{p:m}[\tilde{k}]\hat{M}_{12}^{p:m}[\tilde{k}]}{-\hat{M}_{11}^{p:m}[\tilde{k}] - \hat{M}_{21}^{p:m}[\tilde{k}] + \hat{M}_{12}^{p:m}[\tilde{k}] + \hat{M}_{22}^{p:m}[\tilde{k}]} \quad (157)$$

This method can be applied to each inter-conducting group to produce an associated coefficient $\hat{M}_0^{p:m}[\tilde{k}=0]$. The layers that are not part of any groups are each described by the linear relation between the potential difference and tangential field of (26). The tangential magnetic field in (156) for each group and the tangential magnetic field in (26) for each layer not in an inter-conducting group are identical and therefore a relationship in the form of (150) for the region can be developed where:

$$\hat{M}^{0:(N_L-1)}[\tilde{k}=0] = \frac{1}{\sum_{m \in M} \frac{1}{\hat{M}_0^m[\tilde{k}=0]} + \sum_{g \in G} \frac{1}{\hat{M}_0^{p_g:m_g}[\tilde{k}=0]}} \quad (158)$$

where M is the set of layer indices which are not contained in inter-conducting groups, G is the set of groups of inter-conducting layers, and where $p_g$ and $m_g$ are the starting and ending layer indices of the inter-conducting group g.

In the case when no conducting layers are present in the region and therefore the set G is empty, the calculation of (158) is identical to (151) for the EQS system. This is due to the absence of issues associated with inter-layer conduction and the similarity of the solution forms for nonconducting layers of the MQS system and layers of the EQS system.

The expression of (158) can be applied to each region of the modeled structure, except for the bounding region which presents a special case. For the MQS problem it is required that these bounding regions have a thickness which is approximated to be infinite. If no current is returned at infinity for the bounding region then, as a result of the requirement that there be no net current in the material layers, the tangential field at the finite boundary of the region is zero. However, if the current returned at infinity is nonzero then for the bounding region in the negative x direction the following expression for the tangential field holds:

$$\hat{Q}_{N_1}^-[\tilde{k}=0] = \hat{K}_{-\infty} = \frac{\hat{i}_{-\infty}}{\lambda} \qquad (159)$$

where $\hat{K}_{-\infty}$ is the average current and $\hat{i}_{-\infty}$ is the net current. A similar expression for the bounding region in the positive x direction also holds:

$$\hat{Q}_0^+[\tilde{k}=0] = -\hat{K}_{+\infty} = -\frac{\hat{i}_{+\infty}}{\lambda} \qquad (160)$$

Since these regions are assumed to have infinite extent, the change in vector potential across either bounding region will be infinite unless the corresponding current at infinity is exactly zero. Therefore no relation between the change in vector potential and the tangential magnetic field is developed. Rather the two preceding relations are used whenever the tangential magnetic field is required at the associated boundaries. Now, the potential can be related to the surface current density, using the information above for combining layers within regions separated by interfaces containing the sensor's conductors to arrive at simplified expressions relating region boundary quantities. Each interface within these regions was required to have no net surface current density such that $\hat{Q}(y)$ was continuous. At the interfaces containing the sensor conductors, this is no longer required due to the nonzero surface current density and so the boundary condition for the EQS system of (84) and the boundary condition for the MQS system of (56) can be generically expressed as:

$$\hat{Q}_{(i)}^+(y) - \hat{Q}_{(i)}^-(y) = \hat{K}_{(i)}(y) \qquad (161)$$

Figure 21:
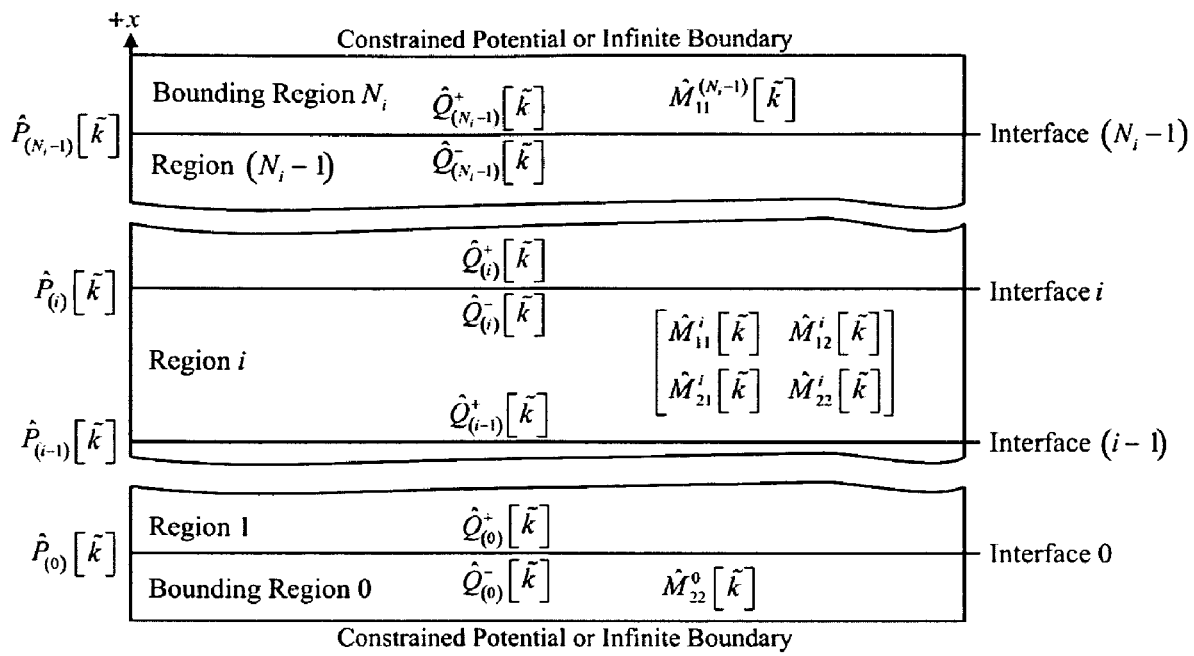
FIG. 21 shows layered regions and interfaces on which boundary conditions related to the surface current density are applied.

The use of parenthesis on the subscripts signifies that the subscript is no longer an index for interfaces within a region, but rather an index for interfaces separating regions as shown in FIG. 21. The simplified relations for each region between interfaces containing conductors are used with the boundary conditions to relate the surface current density at each interface to the potential at each interface. The orthogonality of the modes for the Fourier expression of the boundary quantities in (161) requires:

$$\hat{Q}_{(i)}^+[\tilde{k}] - \hat{Q}_{(i)}^-[\tilde{k}] = \hat{K}_{(i)}[\tilde{k}] \qquad (162)$$

The boundary condition requiring continuity on the vector potential for the MQS system and the scalar potential of the EQS system remains the same for the interfaces separating regions such that:

$$\hat{P}_{(i)}[\tilde{k}] = \hat{P}_{(i)}^+[\tilde{k}] = \hat{P}_{(i)}^-[\tilde{k}] \qquad (163)$$

The superscript indicating the side of the boundary therefore becomes unnecessary.

The coefficients of the simplified relations describing each region between interfaces are also shown in FIG. 21. Applying the boundary conditions of (162) and (163) to the first interface and substituting for $\hat{Q}_{(1)}^+[\tilde{k}]$ and $\hat{Q}_{(1)}^-[\tilde{k}]$ using the simplified region relations in terms of the potential on region interfaces yields:

$$(\hat{M}_{11}^1[\tilde{k}] - \hat{M}_{22}^0[\tilde{k}])\hat{P}_{(0)}[\tilde{k}] + \hat{M}_{12}^1[\tilde{k}]\hat{P}_{(1)}[\tilde{k}] = \hat{K}_{(0)}[\tilde{k}] \text{ for } i=0, N_i \neq 1 \qquad (164)$$

where i is the index of the interface, $N_i$ is the total number of interfaces, and the superscript of $\hat{M}$ indicates the region, such that $\hat{M}$ is equal to the appropriate element $\hat{M}^{0:(N_i-1)}$ corresponding to the region. The same procedure can be applied to the intermediate interfaces $1 \leq i \leq (N_i-2)$ and the final interface to produce:

$$-\hat{M}_{21}^i[\tilde{k}]\hat{P}_{(i-1)}[\tilde{k}] + (\hat{M}_{11}^{i+1}[\tilde{k}] - \hat{M}_{22}^i[\tilde{k}])\hat{P}_{(i)}(k) + \hat{M}_{12}^{i+1}[\tilde{k}]\hat{P}_{(i+1)}(k) = \hat{K}_{(i)}[\tilde{k}] \text{ for } 1 \leq i \leq (N_i-2), N_i \neq 1 \qquad (165)$$

$$-\hat{M}_{21}^{N_i-1}[\tilde{k}]\hat{P}_{(N_i-2)}[\tilde{k}] + (\hat{M}_{11}^{N_i}[\tilde{k}] - \hat{M}_{22}^{N_i-1}[\tilde{k}])\hat{P}_{(N_i-1)}[\tilde{k}] = \hat{K}_{(N_i-1)}[\tilde{k}] \text{ for } i=N_i-1, N_i \neq 1 \qquad (166)$$

In the special case when only a single interface containing conductors is present the boundary conditions result in:

$$(\hat{M}_{11}^1[\tilde{k}] - \hat{M}_{22}^0[\tilde{k}])\hat{P}_{(0)}[\tilde{k}] = \hat{K}_{(0)}[\tilde{k}] \text{ for } i=0, N_i=1 \qquad (167)$$

Since the layer properties are specified numerically in the forward problem the values of $\hat{M}$ are known. These equations can therefore be arranged into the following matrix equation:

$$T[\tilde{k}] \begin{bmatrix} \hat{P}_{(0)}[\tilde{k}] \\ \vdots \\ \hat{P}_{(N_i-1)}[\tilde{k}] \end{bmatrix} = \begin{bmatrix} \hat{K}_{(0)}[\tilde{k}] \\ \vdots \\ \hat{K}_{(N_i-1)}[\tilde{k}] \end{bmatrix} \qquad (168)$$

The Fourier modes of the surface current density have been previously expressed in terms of the surface current function parameters. The Fourier modes of the potential can now be expressed in terms the Fourier modes of the surface current density by calculating the inverse $T^{-1}[\tilde{k}]$ such that:

$$\begin{bmatrix} \hat{P}_{(0)}[\tilde{k}] \\ \vdots \\ \hat{P}_{(N_i-1)}[\tilde{k}] \end{bmatrix} = T^{-1}[\tilde{k}] \begin{bmatrix} \hat{K}_{(0)}[\tilde{k}] \\ \vdots \\ \hat{K}_{(N_i-1)}[\tilde{k}] \end{bmatrix} \qquad (169)$$

In the cases where $N_i=1$ and $T[\tilde{k}]$ is a 1×1 matrix the inverse is easily calculated. However, a closer look at the structure of $T[\tilde{k}]$ for $N_i>2$ reveals that the system is tridiagonal and therefore can be calculated more efficiently than a full matrix). In developing transfer relations for the bounding regions of the modeled structure in which the final layers were approximated as infinite the decoupling behavior of the transfer relations was used to remove any dependence on the boundaries at infinity. The decoupling behavior results from the off-diagonal terms in the transfer relations approaching zero in the limit as $\Delta \to \infty$. However, $\tilde{k}$ appears in such a way that the same behavior also exists as $\tilde{k} \to \infty$. This result can be put to practical use in several ways for improving computational speed.

The first application extends this behavior beyond a single layer to the single relation which encapsulates the layer relations for a given region. If the coupling between the interfaces of any layer within the region becomes negligible then it is reasonable to expect that there will be no coupling between the interfaces bounding the region and this will be reflected in the off-diagonal terms of the simplified region relation. A closer look at (165) and the effect of $\hat{M}_{12}$ and $\hat{M}_{21}$ approaching zero on the internal structure of matrix $T[\tilde{k}]$ reveals that smaller uncoupled tri-diagonal block matrixes are formed when two interfaces become decoupled. Since the value of $\tilde{k}$ for which pairs of interfaces will become decoupled will generally be difference for each region, the matrix $T[\tilde{k}]$ will progressively break into smaller and smaller blocks until the blocks themselves are only 1×1 matrixes and $T[\tilde{k}]$ becomes diagonal. This has great value in that all $T[\tilde{k}]$ matrixes for k greater than the point where $T[\tilde{k}]$ is approximated as diagonal can be very simply inverted. Additionally, the computation of $T^{-1}[\tilde{k}]$, for values of $\tilde{k}$ where $T[\tilde{k}]$ is composed of uncoupled block matrixes, can be done by computing the inverses of the smaller individual blocks which requires less computational time.

The second application of the decoupling of layer interfaces as $\tilde{k} \to \infty$ is in the reduction of unnecessary re-computations. Generally the layers nearest the interfaces containing the sensor's conductors represent air gap or materials of which the sensor is composed and therefore have constant properties as simulations performed over many MUT configurations. For some finite value of k the interfaces of these layers can be approximated as decoupled. This allows for the layers to be treated as infinitely thick for $\tilde{k}$ values greater than this finite value (using the results applied for infinite layers of the bounding regions) and therefore changes in the MUT will not effect the simplified relations. This also allows the inverse matrix $T^{-1}[\tilde{k}]$ to be unaffected by changes in the MUT for $\tilde{k}$ values greater than this finite value and therefore it need not be recomputed. This fact can also allow other repeated matrix operations which occur in forming the final system matrix equation and associated with changes in $T^{-1}[\tilde{k}]$ to be avoided.

The preceding techniques can be taken one step further by allowing only layers which influence $T^{-1}[\tilde{k}]$ for certain ranges of $\tilde{k}$ to be included in calculating simplified region relations. It has been mentioned previously that once the interfaces of any one layer of a region become decoupled that the interface of the region will also be decoupled and the off-diagonal terms of the simplified relation will approach zero. It is therefore a waste of computation to combine layers of this region using the methods which produce all four elements of the simplified transfer relations. Either a pre-analysis or an evaluation of calculations resulting from the computation of simplified region relations for successive $\tilde{k}$ can be used to determine which layers in a region are not contributing for the current value of $\tilde{k}$. As $\tilde{k}$ increases, layers closer and closer to region boundaries can be approximated as infinitely thick such that only the elements $\hat{M}_{11}$ and/or $\hat{M}_{22}$ are calculated using the minimum number of layers.

For the case when $\tilde{k} \neq 0$, it was possible to relate the Fourier series coefficients of the potential to the coefficients of the surface current using the simplified relations for the regions of the modeled structure. This was done without specific regard to whether the system was EQS or MQS or as to the specific boundary conditions for the bounding regions. However, for the $\tilde{k}=0$ mode these boundary conditions have a significant influence on how the relationships are formed in addition to the final form of the relation. Although for each type of boundary condition there is a dual boundary condition for MQS and EQS systems, only those typically required in practice are addressed here. The boundary conditions in this subset apply either to the EQS system or the MQS system and therefore, to promote clarity, each is analyzed in the context of one specific system type even though the analysis would apply equally for the dual condition.

Figure 22:
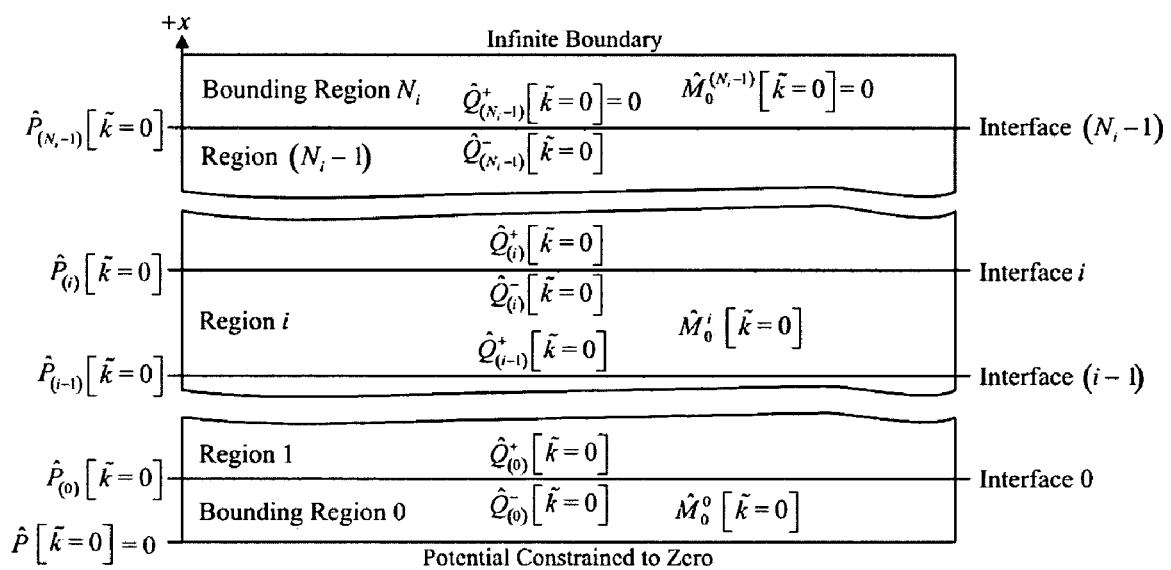
FIG. 22 shows layered regions and interfaces for developing relations between the potential and the surface current density at each interface in the EQS system for $\bar{k}=0$.

For the EQS system, where at least one of the bounding regions of the modeled structure has an interface constrained to zero potential, the analysis is very similar to that of the $\tilde{k} \neq 0$ modes and has the most straightforward form. FIG. 22 indicates the specifics of this configuration including the parameters $\hat{M}_0$ of the simplified relation for each region. The potential on one bounding region interface is constrained to zero and therefore the region is described by a single nonzero parameter. The opposing bounding region is approximated as being infinitely thick and therefore has zero current density at the region boundary. In the case shown, one of the bounding regions has an infinite extent resulting in the current density $\hat{Q}_{(N_i-1)}^-$ being zero. In order for the relation being developed to be applicable to the case of one or both boundaries constrained to zero potential, the term $\hat{M}_0$ is set to zero for bounding regions of infinite extent.

The boundary condition relating the jump in current density to the surface current density must still hold for $\tilde{k}=0$ and therefore:

$$\hat{Q}_{(i)}^+[\tilde{k}=0] - \hat{Q}_{(i)}^-[\tilde{k}=0] = \tilde{K}_{(i)}[\tilde{k}=0] \quad (170)$$

where subscripts are again placed in parentheses to indicate that the index refers to the index of a region interface. The region relations relate the surface current density at either region interface to the potential as:

$$\hat{Q}_{(i)}^-[\tilde{k}=0]\hat{Q}_{(i-1)}^+[\tilde{k}=0] = \hat{M}_0^i[\tilde{k}=0]\hat{P}_{(i-1)}[\tilde{k}=0] - \hat{M}_0^i[\tilde{k}=0]\hat{P}_{(i)}[\tilde{k}=0] \quad (171)$$

except in the special case of the lower and upper bounding regions where $\hat{P}_{(i-1)}$ or $\hat{P}_{(i)}$ are zero respectively. Applying (170) and (171) to the first interface, any intermediate interface, and the last interface results in the following expressions relating the potential to the surface current density:

$$(\hat{M}_0^0[\tilde{k}]+\hat{M}_0^1[\tilde{k}])\hat{P}_{(0)}[\tilde{k}] - \hat{M}_0^1[\tilde{k}]\hat{P}_{(1)}[\tilde{k}] = \hat{K}_{(0)}[\tilde{k}] \text{ for } i=0, N_i \neq 1, \tilde{k}=0 \quad (172)$$

$$-\hat{M}_0^i[\tilde{k}]\hat{P}_{(i-1)}[\tilde{k}]+(\hat{M}_0^i[\tilde{k}]+\hat{M}_0^{i+1}[\tilde{k}])\hat{P}_{(i)}[\tilde{k}] - \hat{M}_0^{i+1}[\tilde{k}]\hat{P}_{(i+1)}[\tilde{k}] = \hat{K}_{(i)}[\tilde{k}] \text{ for } 1 \leq i \leq (N_i-2), N_i \neq 1, \tilde{k}=0 \quad (173)$$

$$-\hat{M}_0^{N_i-1}[\tilde{k}]\hat{P}_{(N_i-2)}[\tilde{k}]+(\hat{M}_0^{N_i}[\tilde{k}]+\hat{M}_0^{N_i}[\tilde{k}])\hat{P}_{(N_i-1)}[\tilde{k}] = \hat{K}_{(N_i-1)}[\tilde{k}] \text{ for } i=N_i-1, N_i \neq 1, \tilde{k}=0 \quad (174)$$

For the special case where there is only a single interface:

$$(\hat{M}_0^0[\tilde{k}]+\hat{M}_0^1[\tilde{k}])\hat{P}_{(0)}[\tilde{k}] = \hat{K}_{(0)}[\tilde{k}] \text{ for } i=0, N_i=1, \tilde{k}=0 \quad (175)$$

The preceding relations can be put into a matrix form similar to the way that the $\tilde{k} \neq 0$ modes were handled to produce a matrix $T[\tilde{k}=0]$ such that:

$$T[\tilde{k}=0] \begin{bmatrix} \hat{P}_{(0)}[\tilde{k}=0] \\ \vdots \\ \hat{P}_{(N_i-1)}[\tilde{k}=0] \end{bmatrix} = \begin{bmatrix} \hat{K}_{(0)}[\tilde{k}=0] \\ \vdots \\ \hat{K}_{(N_i-1)}[\tilde{k}=0] \end{bmatrix} \quad (176)$$

Since at least one of the bounding interfaces had its potential constrained to zero the potentials at the other interfaces are well define since the constant is no longer arbitrary and the matrix $T[\tilde{k}=0]$ has an inverse $T^{-1}[\tilde{k}=0]$. Thus again a simple and straight forward relation between the Fourier coefficients of the potential at region interfaces and the Fourier coefficients of the surface current density at region interfaces exist. The handling of the other boundary conditions, although not difficult, will result in a slightly more complicated relation.

In the case where the lowermost region of FIG. 22 is made to have infinite extent as the uppermost region some additional analysis is required over the previous case. The matrix $T[\tilde{k}=0]$ can again be formed using (172) through (175) with both $\hat{M}_0^0$ and $\hat{M}_0^{N_i}$ now equal to zero due to the infinite extent of the bounding regions. The absence of an absolute reference for the potential now causes the inverse $T^{-1}[\tilde{k}=0]$ to no longer exist due to the lack of uniqueness in the potential which produces the surface current density in (176) (any constant may be added to the potential with no change in the surface current density). It should be noted that this does not mean that there is not a unique solution for the potential in the system; the required terminal constraints on potential will not allow this degree of freedom in the constant term of the Fourier series expansion of the potential. However, at this stage in the overall analysis of the system, these constraints have not been introduced. Therefore a relation between the potential and surface current density at interfaces is needed with an absolute reference for the potential defined in terms of a yet unknown quantity.

The absolute reference for the system will be set in terms of the potential on the first interface and therefore the potential on other interface will be found relative to this potential. Since the potential on the interfaces will be relative to $\hat{P}_{(0)}$, the potential on this interface can be initially set to zero. After a relationship is established for the potential on the other interfaces, expressed in terms of the current density on interfaces, the reference potential $\hat{P}_{(0)}$ can be added back to the interface potentials. By setting $\hat{P}_{(0)}$ to zero the relationship in (176) can be reduced by removing the first column of $T[\tilde{k}=0]$ and removing $\hat{P}_{(0)}$ form the column vector multiplying it. The resulting system of equations is no longer square, however a unique and exact solution is now expected and upon closer inspection the first row can be shown to be redundant due to the initial tridiagonal structure of $T[\tilde{k}=0]$. By removing this row an inverse is now possible such that:

$$\begin{bmatrix} \hat{P}_{(1)}[\tilde{k}=0] \\ \vdots \\ \hat{P}_{(N_i-1)}[\tilde{k}=0] \end{bmatrix} = t^{-1}[\tilde{k}=0] \begin{bmatrix} \hat{K}_{(1)}[\tilde{k}=0] \\ \vdots \\ \hat{K}_{(N_i-1)}[\tilde{k}=0] \end{bmatrix} + \hat{P}_{(0)}[\tilde{k}=0] \quad (177)$$

$$t[\tilde{k}=0] = \begin{bmatrix} T_{22}[\tilde{k}=0] & \cdots & T_{2p}[\tilde{k}=0] \\ \vdots & \vdots & \vdots \\ T_{p2}[\tilde{k}=0] & \cdots & T_{pp}[\tilde{k}=0] \end{bmatrix} \quad (178)$$

and where the subscripts of T indicate the indices of the matrix elements and p is the dimensionality of the square matrix T. Notice that the reference potential $\hat{P}_{(0)}$ has been included in (177) such that the potentials on the other interfaces are absolute. This produces the desired relation between the interface potential and the surface current density at interfaces. However, a problem becomes apparent by realizing that the interface potentials of (177) are independent of the current density of the first interface (i=0).

The earlier statement that the first row of T was redundant should have been prefaced with the requirement that the system have a solution which puts additional requirements on the allowed column vector of surface current densities. This additional requirement comes about through the conservation of charge, which was built into the umnodified matrix T. Since both bounding regions have infinite extent in the current case, the current density for the $\tilde{k}=0$ mode was required to be zero in these regions. For the system to remain charge neutral, this requires that the sum of the surface currents over all interfaces is zero. Since the only surface current on the interfaces is located in the sensor conductors, this is equivalently expressed as:

$$\sum_n^{Conductors} \hat{i}_n = 0 \quad (179)$$

Therefore the current density on the first surface is tied in to the other surface currents through this additional equation which must be appended to the total system equation (the calculation of net conductor currents will be carried out in a latter section) and which balances the additional unknown $\hat{P}_{(0)}$.

One special situation left to discuss is the case of only a single interface, where removing the column and row from T results in a matrix t with no elements. However, this does not create a problem since there is no need to use (177) since the potential on the only interface is equivalent to the new unknown $\hat{P}_{(0)}$.

Figures 23, 24:
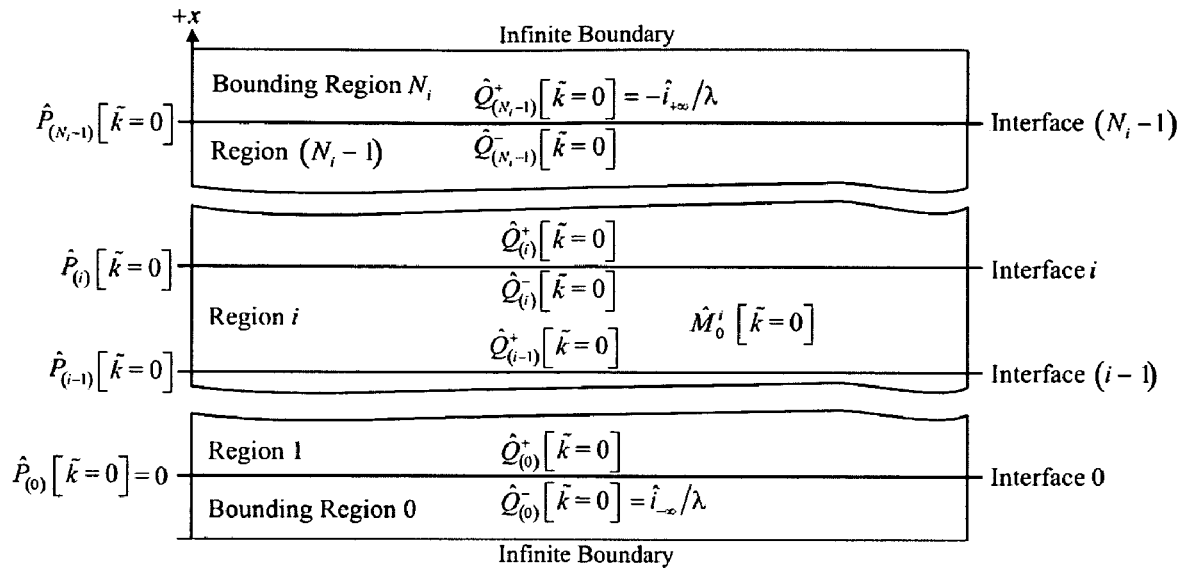
FIG. 23 shows layered regions and interfaces for developing relations between the potential and the surface current density at each interface in the MQS system for $\bar{k}=0$.
FIG. 24 shows the structure of the final system matrix equation for the EQS system.

Unlike the EQS system, only structures with outer bounding regions of infinite extent are addressed for the MQS system. In the EQS system, the regions of infinite extent were restricted to have zero current density and the parameter $\hat{M}_0$ was set to zero for the region. However, return currents are allowed at infinity for the MQS system, which results in a constant tangential magnetic field at the near interfaces of the infinite regions as shown in FIG. 23. Both upper and lower bounding regions of the modeled structure have infinite extent. The tangential field at the near interface of these regions is determined by the return current at positive or negative infinity. Since there is no absolute reference for the vector potential in the system, the first interface is used as the zero reference. The relationship between the return current and the tangential magnetic field was demonstrated in (159) and (160). This change from the EQS system requires that the boundary condition of (170) be reapplied to the first and last interfaces resulting in the new relations:

$$\hat{M}_0^1[\tilde{k}]\hat{P}_{(0)}[\tilde{k}] - \hat{M}_0^1[\tilde{k}]\hat{P}_{(1)}[\tilde{k}] = \hat{K}_{(0)}[\tilde{k}] + \frac{\hat{i}_{-\infty}}{\lambda} \text{ for } i=0, \quad (180)$$
$$N_i \neq 1, \tilde{k}=0$$

$$-\hat{M}_0^{N_i-1}[\tilde{k}]\hat{P}_{(N_i-2)}[\tilde{k}] + \hat{M}_0^{N_i-1}[\tilde{k}]\hat{P}_{(N_i-1)}[\tilde{k}] = \quad (181)$$
$$\hat{K}_{(N_i-1)}[\tilde{k}] - + \frac{\hat{i}_{+\infty}}{\lambda} \text{ for } i=N_i-1, N_i \neq 1, \tilde{k}=0$$

Using (173), (180), and (181) a matrix relation can again be formed between the potential and the surface current density, with the inclusion of the constant terms due to the return current at infinity:

$$T[\tilde{k}=0] \begin{bmatrix} \hat{P}_{(0)}[\tilde{k}=0] \\ \vdots \\ \hat{P}_{(N_i-1)}[\tilde{k}=0] \end{bmatrix} = \begin{bmatrix} \hat{K}_{(0)}[\tilde{k}=0] \\ \vdots \\ \hat{K}_{(N_i-1)}[\tilde{k}=0] \end{bmatrix} + \begin{bmatrix} \frac{\hat{i}_{-\infty}}{\lambda} \\ \vdots \\ -\frac{\hat{i}_{+\infty}}{\lambda} \end{bmatrix} \quad (182)$$

The inverse $T^{-1}$ is again desired, but T is not invertible in its current state due to the non-uniqueness of the potentials caused by the common arbitrary constant term which may be added to each. Since for the MQS system, the conductors will be constrained with current sources and all conductor voltages will be referenced to other conductor voltages, the choice of the reference for the potential is arbitrary. Therefore the potential of the first interface is chosen as the zero reference such that:

$$\hat{P}_{(0)}[\tilde{k}=0]=0 \quad (183)$$

Unlike the EQS system it was not necessary to introduce an unknown since the vector potential is not restricted to an exact value by any system constraint. Following a similar reasoning to that in the previous EQS case, the first row and first column of T can be removed to form a new square matrix t which is invertible. The potential is now related to the surface current density and the current returned at positive infinity as:

$$\begin{bmatrix} \hat{P}_{(1)}[\tilde{k}=0] \\ \vdots \\ \hat{P}_{(N_i-1)}[\tilde{k}=0] \end{bmatrix} = t^{-1}[\tilde{k}=0] \begin{bmatrix} \hat{K}_{(1)}[\tilde{k}=0] \\ \vdots \\ \hat{K}_{(N_i-1)}[\tilde{k}=0] \end{bmatrix} - \frac{\hat{i}_{+\infty}}{\lambda} t_p^{-1}[\tilde{k}=0] \quad (184)$$

where $t_p^{-1}$ is the pth column of the p×p inverse $t^{-1}$. No additional constraints on the sum conductor currents is required as in the EQS case because the net imposed current on conductors, including those at infinity, is required to be zero in the system definition.

The distribution of the surface current density in each conductor of the sensor is defined in terms of the parameters consisting of the density at various positions along the conductor. However, an expression for the total current on each conductor is also necessary for imposing the system excitation, maintaining charge neutrality, and making post-computations.

For the EQS system the total current is required for both creating constraints and for post-computations. In the case when both bounding regions have infinite extent, the net current on each conductor is required such that a system constraint, which forces the sum of the currents over all conductors to be zero, can be created as required in (179). In all cases of the EQS system, the net current on conductors is required for the post-computation of terminal characteristics of self-admittance and/or mutual admittance. For the MQS system the total conductor current is required in order to create the constraints used to impose the excitation currents. The net current will need to be expressed in terms of the surface current density parameters for each conductor and set equal to the numerical value of the excitation current for that conductor. Therefore a new equation is added to the system for each additional conductor.

The net current could be obtained from the Fourier series representation of the current density, but integrating the piecewise representation of the current density over the conductor is more accurate and efficient. The total conductor current is therefore determined by the following integral:

$$\hat{i}_p = \int_{y_0}^{y_N} \hat{K}(y)\,dy = \sum_{n=0}^{N-1} \int_{y_n}^{y_{n+1}} \hat{K}_n(y)\,dy \quad (185)$$

where $\hat{i}_p$ is the current on the pth conductor, $\hat{K}_n(y)$ is the nth interpolation function on the pth conductor, and $y_n$ are the endpoints of the interpolation functions as defined in FIG. 18. This integral is almost identical to that for calculating the Fourier series coefficient of the $\tilde{k}=0$ mode in (107) except for the absence of the factor of $1/\lambda$. Again it is desired to express the result in terms of a sum over the current density parameters of the conductor such that:

$$\hat{i}_p = \sum_{n=0}^{N} \lambda \hat{F}_n^{even}[\tilde{k}=0]\hat{K}(\tilde{y}_n) \quad (186)$$

The results of (116) and (127), corresponding to linear and cubic interpolation methods, can therefore be used to determine the conductor current since the $1/\lambda$ factor has been accounted for in (186).

Next consider the final constraints on the potential. The parameterized surface current density along each conductor has been used to produce the Fourier series coefficients of the surface current density for each interface. These coefficients have then been used with the continuity conditions on either the tangential magnetic field (MQS) or the normal complex current density (EQS) along with the simplified region relations to relate the coefficients of the interface potential back to the current density. Constraints on the potential are now needed in order to produce a sufficient system of equations to uniquely define the current density parameters as the system solution. For the EQS system the potential along each conductor is both constant and defined numerically by the system specifications. The requirement for each conductor of (85), put into generic notation is simply:

$$\hat{P}_{(i)}(\tilde{y}) = \hat{v}_p \text{ for } y_0 \leq y \leq y_N \quad (187)$$

where $\hat{v}_p$ is voltage of the pth conductor, i is the interface on which the conductor is located and $y_0$, $y_N$ are the bounding coordinates of the conductor.

For the MQS system the conductor constraint results from Faraday's law as developed in (58). However, unlike the EQS counterpart, the relation not only involves the conductor potential, but is also directly related to the surface current density. The requirement for each conductor in generic notation is:

$$j\omega \hat{P}_{(i)}(\tilde{y}) + \frac{\hat{K}_{(i)}(\tilde{y})}{\sigma_p} - \hat{v}_p = 0 \text{ for } y_0 \leq y \leq y_N \quad (188)$$

where $\sigma_p$ is the surface conductivity of the pth conductor. Unlike the EQS system, the voltage $\hat{v}_p$ on each conductor is not defined numerically. Therefore a new unknown $\hat{v}_p$ must be introduced for each conductor. These new unknowns are already balanced by the equation constraining each conductor's current which excites the system.

In an exact modeling method in which purely analytic solutions for the electromagnetic quantities were obtainable, (187) and (188) would hold exactly. In evaluating solutions for specific numerical cases, errors would typically result from the ability to numerically evaluate the analytic functions. However, the modeling technique being utilized represents the solution for the surface current density in a piecewise fashion with a finite number of parameters. In the earlier discussion on the details of this piecewise description, the importance of it being able to match the true solution closely was emphasized. It was also realized that as close as this representation may get to the actual solution, the solution will not actually be in the space of functions which are representable by the piecewise description. In other words, except for possibly a few special cases, there will always be some amount of error between the true current density and the piecewise representation (although this error can generally be made sufficiently small by increasing the number of pieces).

Up to this point in the analysis, the boundary conditions at layer interfaces were applied exactly in terms of each Fourier coefficient with no allowance for error. The error due to the representation of the surface current density must now manifest itself in an inconsistency (although small) in these last constraints to be imposed. This becomes more obvious if the uniqueness of the solution is considered. If two solutions could be found the satisfied all surface and volume equations for the system being modeled then uniqueness would be lost. Therefore by definition the true solution fits all the equations of the system exactly while the close approximation must have some error which has been forced into (187) or (188).

With the realization that the error in these equations cannot be made exactly zero, at every point in the continuous range of y specified for each conductor, the closest solution of the surface current density is sought. However, unlike something which is truly exact, close is a matter of the metric by which it is measured. Since the true surface current density will never be known in the general case, building a metric directly from the surface current density is not possible. The metric must therefore be build from (187) or (188). The methods of building these metrics by which the close solution will be found are a central topic of many numerical techniques. A few basic approaches will be discussed before proceeding with the chosen method. The first possibility is to find the closest in the norm sense. For continuous functions this amounts to squaring the error function followed by integrating the error over the dimensions of the functions. In the present case, the error as a function of position is represented by the homogenous form of (187) or (188) for each conductor. The sum of the integral over each conductor of the error squared represents the total squared error in the system. The desired solution is then the one that minimizes this quantity. To get a better understanding of the practical issues associated with this technique, some further explanation is in order.

The makeup of the quantities to be squared will be important in evaluating the computational demands of setting up the expressions which then must be minimized. Since (188) contains the most terms, it will be focused on as (187) will require less computation. The Fourier series coefficients of the potential $\hat{P}$ can be determined in terms of the surface current density. In order to calculate the potential for a given interface as a function of y, the Fourier series expansion of $\hat{P}$ is required, which involves the summation of terms over all modes. Equation (187) also involves the surface current density directly, which is expresses as a sum of the linear or cubic interpolation functions. Due to the summation over modes for the potential and the summation over interpolation functions for the surface current density, the operation of squaring (187), when the quantities involved are expressed in terms of only the surface current density parameters and unknown constants $\hat{v}_p$, produces many cross-terms. The result of the squaring will contain products of sines, cosines, and polynomials which must then be integrated over each conductor. Although these integrations can be carried out analytically, the number of cross-terms involved makes this operation unappealing. Nonetheless, the results of the squaring and integration lead to a system of equations that have the following form:

$$\frac{1}{2}k^T Ak - Bk + C = (\text{error})^2 \tag{189}$$

where k is a column vector of surface current density parameters and where A, B, and C are coefficient matrices. The minimum of the error can then be found by finding k for which the derivative of the preceding is zero or equivalently the solution to:

$$Ak = B \tag{190}$$

It should be noted that a rigorous treatment should verify that certain properties of (189) exist such that a minimum will be present, however the construction of this expression from the square of the error would suggest a minimum exists at the solution of (190).

The rest of the methods for finding a close solution can actually be viewed as a single method with a parameter; however the parameter choice can force this more general method to degenerate into other specific methods. Here the parameter is the choice of the function set used, each of which generally has its number of functions equal to the number of unknown surface current density parameters. The method proceeds by integrating the product of each one of these functions with the error of (187) or (188) and setting the result to zero. This general technique is typically referred to a Galerkin's method or the method of weighted residuals. With the function set chosen to be delta functions at different locations, the method becomes collocation. The error is then forced to be exactly zero at a number of points equal to the number of unknown parameters. However, this method leaves the error in (187) or (188) unchecked over much of the conductor interval on which it is expected to be zero. However, the error behavior between collocation points is indirectly limited by the limited function space of the surface current density representation and its associated smoothness. Other useful choices of function sets exist which involve the value of the error at every location on the conductor.

The choice of a function set, composed of nonzero constants over subintervals of the conductors, results in the inclusion of the error at every location. As compared to the minimization of the error squared, this method has the disadvantage in that the integral of the error over these subintervals may be zero, while the error at each location could have large positive and negative components. However, the limitation in the represented function space of the surface current density and the smoothness which has been imposed on it again provides some relief for this issue.

Additional options for the function set include a choice which forces the error to be orthogonal to the trial functions of which the surface current density is composed. Each trial function can be created by setting one of the surface current density parameters to one and all others to zero. The resulting trial functions then resemble the hat function for the linear interpolation, while the functions have a piecewise cubic description with numeric coefficients for the cubic spline interpolation method. Since the integral of the product of these functions is really the inner product, forcing this quantity to zero guarantees that the error is orthogonal to the basis formed by the trial functions. This produces the weak solution as it is often referred to in mathematics and is typically used in FEM. In comparison to the exact solution, this weak solution uses the definition of the zero function as any function that is orthogonal to the basis, which again does not require the error to be zero in a point-wise fashion. Computationally this choice of function set results in integrals of quadratics and integrals of products of Fourier series and linear terms in the linear interpolation case. In the cubic spline interpolations case, this produces integrals of products of Fourier series and piecewise cubic functions and integrals of sixth degree polynomials. Therefore more computation is required as compared the choice of collocation methods or constants over subintervals, but less than that of determining the minimum in the norm sense.

All of the preceding options have some merit, whether it is purely computational speed or strong mathematical backings, and further investigation into each, including practical comparisons, could be valuable. However, a single option, which utilizes the integrals of the error with constants over subintervals of each conductor for generating the system of equations, was pursued here. This choice has the benefit in reducing additional computations, while still involving the continuous interval on which the error would ideally be zero.

In preceding descriptions of this method, the number of subintervals and therefore the number of equations generated was originally considered to be equal to the number of unknown parameters. However, there is no restriction on increasing the number of intervals to be greater than the number of the unknowns by making each interval smaller. Since the functions interpolating the surface current density have a limited degree of freedom, smaller subintervals will result in a more constant error over each subinterval. If the error is sufficiently constant, it becomes less necessary to perform operations such as squaring the error in order to avoid the net cancellations of large positive and negative errors within these subintervals. This approach trades the complexity resulting from the products of Fourier series which existed in the minimum norm method for an over-defined set of system equations which produces a least squares problem.

The chosen method can now be applied to (187) and (188), which defines the error for each system. The integral of each is taken over a single subinterval of the pth conductor and results in:

$$\frac{1}{(\tilde{Y}_{a+1} - \tilde{Y}_a)} \int_{\tilde{Y}_a}^{\tilde{Y}_{a+1}} \hat{P}_{(i)}(\tilde{y}) d\tilde{y} = \frac{1}{(\tilde{Y}_{a+1} - \tilde{Y}_a)} \int_{\tilde{Y}_a}^{\tilde{Y}_{a+1}} \hat{v}_p d\tilde{y} \quad (191)$$

for the EQS system and:

$$\frac{1}{(\tilde{Y}_{a+1} - \tilde{Y}_a)} \int_{\tilde{Y}_a}^{\tilde{Y}_{a+1}} \left( j\omega \hat{P}_{(i)}(\tilde{y}) + \frac{\hat{K}_{(i)}(\tilde{y})}{\sigma_s} - \hat{v}_p \right) d\tilde{y} = 0 \quad (192)$$

for the MQS system, where the conductor lies on the ith interface between regions and the subinterval is defined by the normalized endpoints $\tilde{Y}_a$ and $\tilde{Y}_{f+1}$ such that:

$$y_0 \leq \tilde{Y}_a < \tilde{Y}_{a+1} \leq y_N \quad (193)$$

The additional factor of $1/(\tilde{Y}_{a+1} - \tilde{Y}_a)$ has been added such than when (191) or (192) are used to form the equations of an over-defined system, the error density is minimized rather than the absolute error in dissimilarly sized subintervals. In either case the potential is expressed in terms of its Fourier series representation:

$$\hat{P}_{(i)}(\tilde{y}) = \hat{P}_{(i)}[\tilde{k} = 0] + \sum_{\tilde{k}=1}^{\infty} \hat{P}_{(i)}^{even}[\tilde{k}]\cos(\tilde{k}\tilde{y}) + \hat{P}_{(i)}^{odd}[\tilde{k}]\sin(\tilde{k}\tilde{y}) \quad (194)$$

The integrals of (191) and (192) can then be expressed as:

$$\hat{\theta} + \hat{P}_{(i)}[\tilde{k}=0] = \hat{v}_p \quad (195)$$

for the EQS system and:

$$j\omega(\hat{\theta} + \hat{P}_{(i)}[\tilde{k}=0]) + \hat{\Omega} - \hat{v}_p = 0 \quad (196)$$

for the MQS system, where:

$$\hat{\theta} = \sum_{\tilde{k}=1}^{\infty} \left[ \hat{P}_{(i)}^{even}[\tilde{k}] \frac{\sin(\tilde{k}\tilde{Y}_{a+1}) - \sin(\tilde{k}\tilde{Y}_a)}{\tilde{k}(\tilde{Y}_{a+1} - \tilde{Y}_a)} + \hat{P}_{(i)}^{odd}[\tilde{k}] \frac{-\cos(\tilde{k}\tilde{Y}_{a+1}) + \cos(\tilde{k}\tilde{Y}_a)}{\tilde{k}(\tilde{Y}_{a+1} - \tilde{Y}_a)} \right] \quad (197)$$

$$\hat{\Omega} = \frac{1}{\sigma_p(\tilde{Y}_{a+1} - \tilde{Y}_a)} \quad (198)$$

$$\begin{cases} \int_{\tilde{Y}_a}^{\tilde{Y}_{a+1}} \hat{K}_n(\tilde{y}) d\tilde{y} & \text{for } y_n \leq \tilde{Y}_a < \tilde{Y}_{a+1} \leq y_{n+1} \\ \int_{\tilde{Y}_a}^{y_{n+1}} \hat{K}_n(\tilde{y}) d\tilde{y} + \int_{y_{n+1}}^{\tilde{Y}_{a+1}} \hat{K}_{n+1}(\tilde{y}) d\tilde{y} & \text{for } y_n \leq \tilde{Y}_a < y_{n+1} < \tilde{Y}_{a+1} \leq y_{n+2} \end{cases}$$

Since the representation of the surface current density inside the integrals contained in the expression for $\hat{\Omega}$ is dependent on the interpolation method, $\hat{\Omega}$ must be calculated for each method. However, in the formulation of the final matrix equations it will be useful for $\hat{\Omega}$ to be expressed as a sum over the surface current density parameters, for the conductor on which the constraint is being applied, as:

$$\hat{\Omega} = \sum_{n=0}^{N} \hat{\Omega}_n \hat{K}(\tilde{y}_n) \quad (199)$$

The coefficients $\hat{\Omega}_n$ in the case of linear interpolation are:

$$\hat{\Omega}_n = \frac{1}{\sigma_p(\tilde{Y}_{a+1} - \tilde{Y}_a)} \begin{cases} & \text{for } y_d \leq \tilde{Y}_a < \tilde{Y}_{a+1} \leq y_{d+1} \text{ and} \\ & 0 \text{ for } n \neq d, n \neq d+1 \\ \tilde{Y}_{a+1} - \tilde{Y}_a - \frac{(\tilde{Y}_{a+1} - \tilde{y}_n)^2 - (\tilde{Y}_a - \tilde{y}_n)^2}{2\tilde{h}_n} & \text{for } n = d \\ \frac{(\tilde{Y}_{a+1} - \tilde{y}_n)^2 - (\tilde{Y}_a - \tilde{y}_n)^2}{2\tilde{h}_n} & \text{for } n = d+1 \end{cases} \quad (200)$$

$$\hat{\Omega}_n = \frac{1}{\sigma_p(\tilde{Y}_{a+1} - \tilde{Y}_a)} \quad (201)$$

$$\begin{cases} & \text{for } y_d \leq \tilde{Y}_a < y_{d+1} < \tilde{Y}_{a+1} \leq y_{d+2} \text{ and} \\ & 0 \text{ for } n \neq d, n \neq d+1, n \neq d+2 \\ \tilde{y}_{n+1} - \tilde{Y}_a - \frac{\tilde{h}_n}{2} + \frac{(\tilde{Y}_a - \tilde{y}_n)^2}{2\tilde{h}_n} & \text{for } n = d \\ \frac{\tilde{h}_n}{2} - \frac{(\tilde{Y}_a - \tilde{y}_n)^2}{2\tilde{h}_n} + \tilde{Y}_{a+1} - \tilde{y}_{n+1} - \frac{(\tilde{Y}_{a+1} - \tilde{y}_{n+1})^2}{2\tilde{h}_{n+1}} & \text{for } n = d+1 \\ \frac{(\tilde{Y}_{a+1} - \tilde{y}_{n+1})^2}{2\tilde{h}_{n+1}} & \text{for } n = d+2 \end{cases}$$

In the case of cubic interpolation method, the surface current density functions within the integrals of (198) are expressed in terms of the cubic coefficients and there for $\hat{\Omega}$ is expressed in terms of these coefficients:

$$\hat{\Omega} = \frac{1}{\sigma_p(\tilde{Y}_{a+1} - \tilde{Y}_a)} \begin{cases} \begin{pmatrix} \frac{(\tilde{Y}_{a+1} - \tilde{y}_n)^4 - (\tilde{Y}_a - \tilde{y}_n)^4}{4}\breve{A}_n + \\ \frac{(\tilde{Y}_{a+1} - \tilde{y}_n)^3 - (\tilde{Y}_a - \tilde{y}_n)^3}{3}\breve{B}_n + \\ \frac{(\tilde{Y}_{a+1} - \tilde{y}_n)^2 - (\tilde{Y}_a - \tilde{y}_n)^2}{2}\breve{C}_n + \\ (\tilde{Y}_{a+1} - \tilde{Y}_a)\breve{D}_n \end{pmatrix} \text{ for } y_n \leq \tilde{Y}_a < \tilde{Y}_{a+1} \leq y_{n+1} \\ \begin{matrix} \frac{\tilde{h}_n^4 - (\tilde{Y}_a - \tilde{y}_n)^4}{4}\breve{A}_n + \\ \frac{\tilde{h}_n^3 - (\tilde{Y}_a - \tilde{y}_n)^3}{3}\breve{B}_n + \\ \frac{\tilde{h}_n^2 - (\tilde{Y}_a - \tilde{y}_n)^2}{2}\breve{C}_n + \\ (\tilde{y}_{n+1} - \tilde{Y}_a)\breve{D}_n + \\ \frac{(\tilde{Y}_{a+1} - \tilde{y}_{n+1})^4}{4}\breve{A}_{n+1} + \\ \frac{(\tilde{Y}_{a+1} - \tilde{y}_{n+1})^3}{3}\breve{B}_{n+1} + \\ \frac{(\tilde{Y}_{a+1} - \tilde{y}_{n+1})^2}{2}\breve{C}_{n+1} + \\ (\tilde{Y}_{a+1} - \tilde{y}_{n+1})\breve{D}_{n+1} \end{matrix} \text{ for } y_n \leq \tilde{Y}_a < y_{n+1} < \tilde{Y}_{a+1} \leq y_{n+2} \end{cases} \quad (202)$$

In order to determine $\hat{\Omega}$ in the form of the sum of (199), the relation between the cubic coefficients and the current density parameters of (103) is used. The coefficients for the summation in the case of cubic interpolation are then determined by:

$$\hat{\Omega}_n = \frac{1}{\sigma_p(\tilde{Y}_{a+1} - \tilde{Y}_a)} \begin{cases} \text{for } y_d \le \tilde{Y}_a < \tilde{Y}_{a+1} \le y_{d+1} \\ \frac{(\tilde{Y}_{a+1} - \tilde{y}_d)^4 - (\tilde{Y}_a - \tilde{y}_d)^4}{4} U_{4d+1,n+1} + \\ \frac{(\tilde{Y}_{a+1} - \tilde{y}_d)^3 - (\tilde{Y}_a - \tilde{y}_d)^3}{3} U_{4d+2,n+1} + \\ \frac{(\tilde{Y}_{a+1} - \tilde{y}_d)^2 - (\tilde{Y}_a - \tilde{y}_d)^2}{2} U_{4d+3,n+1} + \\ (\tilde{Y}_{a+1} - \tilde{Y}_a) U_{4d+4,n+1} \end{cases} \quad (203)$$

$$\hat{\Omega}_n = \frac{1}{\sigma_p(\tilde{Y}_{a+1} - \tilde{Y}_a)} \begin{cases} \text{for } y_d \le \tilde{Y}_a < y_{d+1} < \tilde{Y}_{a+1} \le y_{d+2} \\ \frac{\tilde{h}_d^4 - (\tilde{Y}_a - \tilde{y}_d)^4}{4} U_{4d+1,n+1} + \\ \frac{\tilde{h}_d^3 - (\tilde{Y}_a - \tilde{y}_d)^3}{3} U_{4d+21,n+1} + \\ \frac{\tilde{h}_d^2 - (\tilde{Y}_a - \tilde{y}_d)^2}{2} U_{4d+3,n+1} + \\ (\tilde{y}_{d+1} - \tilde{Y}_a) U_{4d+5,n+1} + \\ \frac{(\tilde{Y}_{a+1} - \tilde{y}_{d+1})^4}{4} U_{4d+5,n+1} + \\ \frac{(\tilde{Y}_{a+1} - \tilde{y}_{d+1})^3}{3} U_{4d+6,n+1} + \\ \frac{(\tilde{Y}_{a+1} - \tilde{y}_{d+1})^2}{2} U_{4d+7,n+1} + \\ (\tilde{Y}_{a+1} - \tilde{y}_{d+1})^2 U_{4d+8,n+1} \end{cases} \quad (204)$$

where the subscript of the matrix U indicates the row and column of the matrix element.

The division of the conductor into subintervals, which define the bounding points $\tilde{Y}_a$ and $\tilde{Y}_{a+1}$, can now be discussed. Again there are many possibilities; however two basic methods were utilized here. The first method is well suited for the case when it is desired to create an equivalent number of subintervals on each conductor as the number of current density parameters, with the final goal of producing a square matrix equation. In order to prevent the allowed freedom of the interpolation functions from producing an integrated zero error as the byproduct of large positive and negative excursions it is desired to cover each interval with as many subintervals as possible. Starting with one subinterval, for each interpolation function interval, results in one less equation than desired. In order to incorporate one additional subinterval, the subintervals are moved to straddle the interpolation interval endpoints and one half-sized subinterval is included on each side. As compared to simply dividing the conductor up evenly into the desired number of subintervals, this method provides a more consistent coverage relative to the interpolation functions intervals.

In the case when more subintervals are to be included than the number of current density parameters, the number of subintervals is generally chosen to be some factor greater than the number of parameters. This is due to the waste in computation efficiently that would be incurred by converting a square matrix problem into an overly defined problem without affecting the results significantly. The previous method of dividing the conductor can be adapted by simply dividing each of the subintervals into smaller, equally sized subintervals such that each original subinterval now contains the same number of smaller intervals. The number of equations is then increased by a factor equal to the number of new intervals inside each of the original intervals. However, when there are approximately twice as many intervals as surface current density parameters, it becomes possible to use a uniform division of the interpolation function intervals. The subintervals are then created by dividing each interpolation function interval into equal subintervals. The number of equations is then increased by a factor equal to the number of subintervals into which each interpolation interval was divided.

The preceding modeling discussion developed the various relationships necessary to form the final system equation. The connections between these relationships have been suggested along the way to motivate the analysis; this section now makes explicit use of the results to develop the expressions which can be directly used to construct the system matrix. However, in order to keep these final expressions from becoming confusing and unreadable, the symbols used to represent terms and coefficients of previously developed relations will continue to be utilized. The complexity of the notation for these relations will still be increased by the addition of many indices which are required to indicate a specific interface, a specific conductor, a specific surface current density parameter, and/or a specific constraint subinterval. Explicit substitution of expressions is also avoided in order to allow both linear and cubic methods to be generically described here.

Due to the generality of the modeled structure (i.e., any number of conductor interfaces, any number of conductors, any number of current density parameters, and a variety of boundary conditions on the modeled structure) no single expression for directly calculating matrix element values bases on matrix indices will be developed. This is due to the awkward, almost inverse-like problem that exists in relating the row or column index of the final matrix back to the interface, conductor, current density parameter, and/or subinterval to which the matrix coefficient corresponds and therefore this type of expression does not represent the method that would typically be used to construct the matrix in practice. Rather the matrix is built by successively appending each system equation generated for each subinterval and represented by a row vector. Since this row vector generally includes contributions from each conductor interface, each conductor of the interface, and each current density parameter of the conductor, it will be created in a similar way by progressing through each contributor and appending its contribution. This technique of building the matrix has more of a forward problem feel and is more efficient. Since a closed form for the matrix elements is not developed, several figures will provide an annotated matrix layout for the MQS and EQS system equations for clarity.

As a starting point for this analysis it will be assumed that the regions, possibly composed of many layers and separating interfaces containing sensor conductors, have been simplified to single transfer relations. These relations are then used in (169), which relates the Fourier coefficients of the potential on interfaces to Fourier coefficients of the surface current density on interfaces through the matrix $T^{-1}[\tilde{K}]$. The development of the system equation begins by connecting the Fourier coefficients of the surface current density to the surface current density parameters. Expressions (114) and (115) describe the contributions of the current density parameters of a single conductor to the Fourier coefficients of the surface current density along the interface on which it is contained. Since the contributions of multiple conductors can be superimposed and since the surface current density parameters associated with conductors on a given interface only contribute to the Fourier coefficients of that interface, these expressions can modified to:

$$\hat{K}_{(i)}^{even}[\tilde{k}] = \sum_{c=0}^{C_i-1} \sum_{n=0}^{N_{i,c}} \hat{F}_{(i),c,n}^{even}[\tilde{k}] \hat{K}_{(i),c}(\tilde{y}_{(i),c,n}) \quad (205)$$

$$\hat{K}_{(i)}^{odd}[\tilde{k}] = \sum_{c=0}^{C_i-1} \sum_{n=0}^{N_{i,c}} \hat{F}_{(i),c,n}^{even}[\tilde{k}] \hat{K}_{(i),c}(\tilde{y}_{(i),c,n}) \quad (206)$$

where i is the index of the interface, $C_i$ is the number of conductors on ith interface, $N_{i,c}$ is the number of interpolation intervals on the cth conductor of the ith interface, and $\hat{K}_{(i),c}(\tilde{y}_{(i),c,n})$ is surface current density parameter at $\tilde{y}_{(i),c,n}$. The quantities $$\hat{F}_{(i),c,n}^{even}[\tilde{k}] \text{ and } \hat{F}_{(i),c,n}^{odd}[\tilde{k}]$$

correspond to the expressions $\hat{F}_n^{even}[\tilde{k}]$ and $\hat{F}_n^{odd}[\tilde{k}]$ developed earlier for a single conductor using both linear and cubic interpolation methods. The addition subscript components (i) and c simply identify the conductor and its associated properties used in calculating $\hat{F}_n^{even}[\tilde{k}]$ and $\hat{F}_n^{odd}[\tilde{k}]$.

The relationship between the Fourier coefficients of the potential on interfaces and the surface current density on interfaces is described by (169). The matrix equation can be rewritten for the potential on a single interface as:

$$\hat{P}_{(i)}[\tilde{k}] = \sum_{g=0}^{N_I-1} T_{i+1,g+1}^{-1}[\tilde{k}] \hat{K}_{(g)}[\tilde{k}] \text{ for } \tilde{k} \neq 0 \quad (207)$$

where the subscript of the inverse matrix $T^{-1}$ indicates the matrix element, and $N_I$ is the number of interfaces containing conductors. The Fourier series coefficients of the potential on a specific interface are required in the $\hat{\theta}$ term of the final constraint equations for the conductors found in (195) (EQS) and (196) (MQS). From (197), the $\hat{\theta}$ term has the form:

$$\hat{\theta}_{(i),\chi,a} = \sum_{\tilde{k}=1}^{\infty} \left( \theta_{(i),\chi,a}^{even}[\tilde{k}] \hat{P}_{(i)}^{even}[\tilde{k}] + \theta_{(i),\chi,a}^{odd}[\tilde{k}] \hat{P}_{(i)}^{odd}[\tilde{k}] \right) \quad (208)$$

where i indicates the interface, $\chi$ indicates the conductor, and $\alpha$ specifies the subinterval of the constraint.

The relations of (205) and (206) for the Fourier coefficients of the surface current density on an interface can now be substituted individually into (207) to produce expressions for the even and odd coefficients of the potential in terms of current density parameters. These results can be further substituted into (208), which after the reordering of summations results in:

$$\hat{\theta}_{(i),\chi,a} = \sum_{g=0}^{N_I-1} \sum_{c=0}^{C_g-1} \sum_{n=0}^{N_{g,c}} \zeta \hat{K}_{(g),c}(\tilde{y}_{(g),c,n}) \quad (209)$$

$$\zeta = \sum_{\tilde{k}=1}^{\infty} \left( \left( \theta_{(i),\chi,a}^{even}[\tilde{k}] T_{i+1,g+1}^{-1}[\tilde{k}] \right) \hat{F}_{(g),c,n}^{even}[\tilde{k}] + \right.$$
$$\left. \left( \theta_{(i),\chi,a}^{odd}[\tilde{k}] T_{i+1,g+1}^{-1}[\tilde{k}] \right) \hat{F}_{(g),c,n}^{odd}[\tilde{k}] \right) \quad (210)$$

The term has not been factored and has been included in parenthesis $$T_{i+1,g+1}^{-1}[\tilde{k}]$$

with the even or odd $\theta_{(i),\chi,a}[\tilde{k}]$ terms to indicate the preferred order of operations for numerical computation. This order is preferred due to the summation over n which changes the even and odd $\hat{F}_{(g),c,n}[\tilde{k}]$ terms, but leaves the product of $T_{i+1,g+1}^{-1}[\tilde{k}]$ and $\theta_{(i),\chi,a}[\tilde{k}]$ unchanged.

The earlier discussion on the behavior of the matrix $T[\tilde{k}]$ as $\tilde{k} \to \infty$ can now be put to use. Recall that $T[\tilde{k}]$ is typically a full matrix at low mode numbers and at some larger mode number all of the interfaces of the modeled structure become essentially decoupled leaving both $T[\tilde{k}]$ and $T^{-1}[\tilde{k}]$ approximately diagonal. At even larger mode numbers the diagonal elements of $T[\tilde{k}]$ are approximately equal to those that would occur if the layers immediately adjacent to the conductor interfaces had infinite thickness. For these larger mode numbers, each diagonal element of $T^{-1}[\tilde{k}]$ is therefore only dependent on the adjacent layers of the corresponding conductor interface. The mode number at which this approximation becomes valid is defined as $\tilde{k}_{Inf}$. In the case when the off diagonal elements of $T^{-1}[\tilde{k}]$ are considered to be zero, the summation over g can be simplified to a single term. The summation of (209) can then be expressed as:

$$\hat{\theta}_{(i),\chi,a} = \sum_{g=0}^{N_I-1} \sum_{c=0}^{C_g-1} \sum_{n=0}^{N_{g,c}} \hat{K}_{(g),c}(\tilde{y}_{(g),c,n}) \begin{cases} (\zeta_1 + \zeta_2) & \text{for } g = i \\ \zeta_2 & \text{for } g \neq i \end{cases} \quad (211)$$

$$\zeta_1 = \sum_{\tilde{k}=1}^{\infty} \left( \left( \theta_{(i),\chi,a}^{even}[\tilde{k}] \hat{G}_{(i)}[\tilde{k}] \right) \hat{F}_{(i),c,n}^{even}[\tilde{k}] + \right.$$
$$\left. \left( \theta_{(i),\chi,a}^{odd}[\tilde{k}] \hat{G}_{(i)}[\tilde{k}] \right) \hat{F}_{(i),c,n}^{odd}[\tilde{k}] \right) \quad (212)$$

$$\zeta_2 = \sum_{\tilde{k}=1}^{\tilde{k}_{inf}} \left( \left( \theta_{(i),\chi,a}^{even}[\tilde{k}] V_{i+1,g+1}[\tilde{k}] \right) \hat{F}_{(g),c,n}^{even}[\tilde{k}] + \right.$$
$$\left. \left( \theta_{(i),\chi,a}^{odd}[\tilde{k}] V_{i+1,g+1}[\tilde{k}] \right) \hat{F}_{(g),c,n}^{odd}[\tilde{k}] \right) \quad (213)$$

$$V_{i+1,g+1}[\tilde{k}] = \begin{cases} T_{i+1,g+1}^{-1}[\tilde{k}] & \text{for } i \neq g \\ T_{i+1,i+1}^{-1}[\tilde{k}] - \hat{G}_{(i)}[\tilde{k}] & \text{for } i \neq g \end{cases} \quad (214)$$

and where $\hat{G}_{(i)}[\tilde{k}]$ represents the matrix element $T_{i+1,i+1}^{-1}[\tilde{k}]$ calculated by assuming that the layers adjacent to the conductor interfaces have infinite thickness. Under this assumption each interface can be treated as independent of the others and (167), relating the potential to the surface current density for a single interface, can be rearranged to produce:

$$\hat{G}_{(i)}[\hat{k}] = \frac{1}{(\hat{M}_{11}^{i+1}[\hat{k}] - \hat{M}_{22}^{i}[\hat{k}])} \quad (215)$$

Although the summations over $\hat{k}$ in $\zeta_1$ and $\zeta_2$ could have been divided such that there was no overlap and therefore V would have been equal to $T^{-1}$, the partitioning used has practical computational value.

In most simulations, the geometry of the conductors and the electrical properties of the material in layers adjacent to the conductor interfaces are remain unchanged and therefore the result of the summation within $\zeta_1$ is unchanged as other layer properties are altered. Since changes in the thickness of layers adjacent to conductor interfaces may change $\hat{k}_{Inf}$, the chosen division of the summations forces only the summation in $\zeta_2$ to be effected. This is preferred since the summation in $\zeta_2$ is over a finite range of $\hat{k}$, which should be faster to compute than the summation range of $\hat{k}$ in $\zeta_1$ which is currently unbounded. This division of the summation is also useful in the cases were the electrical properties of layers adjacent to the conductors is not constant. For these cases a factor dependent on the electrical properties of the adjacent layers can be removed from the summation in $\zeta_1$. Therefore, it is again unnecessary to compute the summation more than once for a fixed geometry of the conductors.

A similar division has been used previously, for example in "Parameter Estimation Using Microdielectrometry with Applications to Transformer Monitoring," by M. C. Zaretsky, M.I.T. Ph.D. thesis, November 1987, and "Uncalibrated, Absolute Property Estimation and Measurement Optimization for Conducting and Magnetic Media Using Imposed ω-k Magnetometry," by N. J. Goldfine, M.I.T. Ph.D. thesis, Sept. 1990, which utilized linear interpolation methods for conductors located on a single interface. However, the infinite summation similar to that in $\zeta_1$, which involve the transfer relations for layers that are approximated as infinitely thick, were evaluated using a rapidly converging series. The use of cubic interpolation functions results in additional powers of $1/\hat{k}$ in the summation of $\zeta_1$ that are not present when using linear interpolation. Although it is expected that rapid methods for computing the summations of these additional terms exist, they were not pursued here. This is due to the fact that the summations only need to be computed once for a specific geometry and therefore do not represent the bulk of the computational time. Additionally, the choice of parameterizing the surface current density instead of the potential results in a summation, which contains terms that decay significantly faster.

This faster decay comes from the smoothness of the quantity represented by its Fourier series reconstruction in the final conductor constraints. In the case of either linear or cubic interpolation methods, the Fourier coefficients of the parameterized surface current density contain a $1/\hat{k}$ factor, while the parameterized potential would contain a $1/\hat{k}^2$ factor. The Fourier coefficients for the potential enjoy a faster decay due to the continuity of the potential as a function of y as opposed to the jump in the surface current density at conductor edges. However, in reaching the conductor constraint for which $\zeta_1$ is being evaluated, the Fourier coefficients of the surface current density are multiplied by a $1/\hat{k}$ factor from the transfer relations and another $1/\hat{k}$ factor from the integration present in applying the constraint. In comparison, the Fourier coefficients of the potential utilize the transfer relations in a reciprocal fashion, which requires a multiplication by $\hat{k}$. In this alternate formulation the final conductor constraint would integrate the Fourier representation of the surface current density and provide an additional $1/\hat{k}$ factor. The end effect is that the parameterization of the surface current density results in a summation with a $1/\hat{k}^3$ factor as compared to the parameterization of the potential for which the summation contains a slower decaying $1/\hat{k}^2$ factor. However, the actual number of terms required for an accurate estimate of the infinite sum in $\zeta_1$ also depends on the functions of $\hat{k}$ which multiple the $1/\hat{k}^3$ factor.

These functions are differences of products of sines and cosines and originate in the evaluation of the Fourier coefficients of the parameterized surface current density and in the Fourier series reconstruction of the potential. With respect to the behavior of the summation terms, these functions tend to modulate the $1/\hat{k}^3$ factor and contain both high and low frequency components. The summation of the higher frequency modulation components converges more rapidly than the summation of lower frequency modulation components and therefore the lowest frequency components limit the rate of convergence for the summation. The lowest frequency components result from the difference of sines or cosines produced by the integration of the final conductor constraints in (197). The use of trigonometric identities for differences of sines and cosines then allows the argument of the dominant low frequency modulation component to be identified as $\hat{k}(\hat{Y}_{a+1} - \hat{Y}_a)$. The modulation frequency can then be determined as the coefficient of the summation variable $\hat{k}$ and can then be expressed for the smallest subinterval dimension $\Delta_{min}$ using unnormalized dimensions as: $2\pi(\Delta_{min}/\lambda)$. Therefore the rate of convergence for the summation in $\zeta_1$ depends on this quantity. Based on the relation for the modulation frequency, it can be seen that in a modeled structure where the ratios of the conductor subintervals to the wavelength are sufficiently large, the summation will converge rapidly. However, in a problem that is poorly scaled this ratio will be very small and therefore many terms will be required to approximate the summation of $\zeta_1$. In these cases the use of a rapidly converging series or other approximation method may be preferred for evaluating $\zeta_1$. However, if the thicknesses of layers adjacent to the conductor interfaces are also very thin as compared to the wavelength, the number of terms required in the summation of $\zeta_2$ will also be large and result in slower computations. The sensor structures, for which these simulation techniques were applied, were well scaled and allowed reasonable computation of $\zeta_1$ and $\zeta_2$ without the use of other special methods.

In addition to the use of the Fourier series coefficients of the potential in the $\hat{\theta}$ term of (195) (EQS) and (196) (MQS), the coefficient for the $\hat{k}=0$ mode also appears directly in each constraint. The form of the relation between the coefficient of the potential and the coefficients of the surface current density on the other interfaces is dependent on the specific conditions imposed on the bounding layers or bounding interfaces of the modeled structure and also on whether the system is EQS or MQS. These various relations have been developed in previous sections and generally put in the form of a matrix relation between the $\hat{k}=0$ coefficients of interface potentials and the $\hat{k}=0$ coefficients of surface current density on interfaces. Since the $\hat{k}=0$ mode of Fourier series representation of the surface current density along an interface can still be related to the surface current density parameters by (205), the $\hat{k}=0$ coefficient of the potential at an interface can then be related to the surface current density. The relations for the EQS system with various bounding constraints of the modeled structure are summarized as:

$$\hat{P}_{(i)}[\tilde{k}=0] = \qquad (216)$$

$$\begin{cases} \sum_{g=0}^{N_I-1}\sum_{c=0}^{C_g-1}\sum_{n=0}^{N_{g,c}} T^{-1}_{i+1,g+1}[\tilde{k}=0] & \text{for } EQS, ZP \\ \hat{F}^{even}_{(g),c,n}[\tilde{k}=0]\hat{K}_{(g),c}(\tilde{y}_{(g),c,n}) & \\ \hat{\Phi}_0 + \sum_{g=0}^{N_I-1}\sum_{c=0}^{C_g-1}\sum_{n=0}^{N_{g,c}} T^{-1}_{i,g}[\tilde{k}=0] & \text{for } EQS, NZP, i \neq 0 \\ \hat{F}^{even}_{(g),c,n}[\tilde{k}=0]\hat{K}_{(g),c}(\tilde{y}_{(g),c,n}) & \\ \hat{\Phi}_0 & \text{for } EQS, NZP, i=0 \end{cases}$$

where $\hat{\Phi}_0$ is an unknown which must be solved for in the system equation, ZP indicates a system with at least one imposed zero potential bounding interface, and NZP indicates a system with no zero potential bounding interfaces. The MQS system is assumed to have bounding layers of infinite extent, however there may be return currents at positive or negative infinity. The relations for the $\tilde{k}=0$ coefficient of the potential in the MQS system are:

$$\hat{P}_{(i)}[\tilde{k}=0] = \qquad (217)$$

$$\begin{cases} -\frac{\hat{i}_{+\infty}}{\lambda}T^{-1}_{i,N_I-1}[\tilde{k}=0] + \sum_{g=0}^{N_I-1}\sum_{c=0}^{C_g-1}\sum_{n=0}^{N_{g,c}} & \text{for } MQS, i \neq 0 \\ T^{-1}_{i,g}[\tilde{k}=0]\hat{F}^{even}_{(g),c,n}[\tilde{k}=0]\hat{K}_{(g),c}(\tilde{y}_{(g),c,n}) & \\ 0 & \text{for } MQS, i=0 \end{cases}$$

The first term for the $i \neq 0$ interfaces is a constant since the current at infinity must be an imposed quantity and therefore this term must ultimately be moved to the constant side of the matrix equation. The conductor constraint of (196) for the MQS system case has an additional term $\hat{\Omega}$, which is not present in the EQS constraint. This term is expressed as a sum over the surface current density parameters of the conductor, on which the constraint is being applied, in (199). The additional subscripts indicating the interface, conductor, constraint subinterval, and current density parameter can be added to the terms in this summation such that the relation becomes:

$$\hat{\Omega}_{(i),\chi,a} = \sum_{n=0}^{N_{i,\chi}} \hat{\Omega}_{(i),\chi,a,n}\hat{K}_{(i),\chi}(\tilde{y}_{(i),\chi,n}) \qquad (218)$$

This provides the final relation needed to express the terminal constraints of both (195) (EQS) and (196) (MQS) in terms of the current density parameters, constant terms and additional unknowns.

The terminal constraint which must be applied to every subinterval of every conductor in the EQS system has the form:

$$\hat{\theta}_{(i),\chi,a} + \hat{P}_{(i)}[\tilde{k}=0] = \hat{v}_{(i),\chi} \qquad (219)$$

where $v_{(i),\chi}$ represents the imposed voltage on the $\chi$th conductor of the ith interface. The quantities on the LHS of this equation have been related to the surface current density parameters and possibly an additional unknown potential by (211) and (216). Substituting these quantities into (219) and rearranging the summation terms produces the following expressions:

$$\sum_{g=0}^{N_I-1}\sum_{c=0}^{C_g-1}\sum_{n=0}^{N_{g,c}} \hat{K}_{(g),c}(\tilde{y}_{(g),c,n})\begin{cases}(\zeta_1+\zeta_2+\zeta_3) & \text{for } g=i \\ \zeta_2+\zeta_3 & \text{for } g \neq i\end{cases} = \qquad (220)$$

$$\hat{v}_{(i),\chi} \text{ for } EQS, ZP$$

$$\sum_{g=0}^{N_I-1}\sum_{c=0}^{C_g-1}\sum_{n=0}^{N_{g,c}} \hat{K}_{(g),c}(\tilde{y}_{(g),c,n})\begin{cases}(\zeta_1+\zeta_2) & \text{for } g=i=0 \\ \zeta_2 & \text{for } g\neq i, i=0 \\ (\zeta_1+\zeta_2+\zeta_4) & \text{for } g=i \neq 0 \\ (\zeta_2+\zeta_4) & \text{for } g\neq i, i\neq 0\end{cases} +$$

$$\hat{\Phi}_0 = \hat{v}_{(i),\chi} \text{ for } EQS, NZP$$

$$\zeta_3 = T^{-1}_{i+1,g+1}[\tilde{k}=0]\hat{F}^{even}_{(i),c,n}[\tilde{k}=0] \qquad (221)$$

$$\zeta_4 = T^{-1}_{i,g}[\tilde{k}=0]\hat{F}^{even}_{(i),c,n}[\tilde{k}=0] \qquad (222)$$

By repeatedly applying (220) to each subinterval of every conductor on every conductor interface, a system of equations having the form:

$$Sk = E \qquad (223)$$

can be constructed, where k is a column vector containing the unknown surface current density parameters, and E contains the imposed conductor voltages.

In the case of a system with no imposed zero potential bounding interfaces (NZP), (220) contains an additional unknown $\hat{\Phi}_0$ which must be appended to k. The introduction of this additional unknown requires the inclusion of an equation restricting the net current into all conductors to be zero. By substituting the expression of (186), for the current into a single conductor, into the net current equation of (179) and adopting the notation of this section, the following equation is produced:

$$\sum_{g=0}^{N_I-1}\sum_{c=0}^{C_g-1}\sum_{n=0}^{N_{g,c}} \lambda \hat{F}^{even}_{(g),c,n}[\tilde{k}=0]\hat{K}_{(i),c}(\tilde{y}_{(g),c,n}) = 0 \qquad (224)$$

which should be appended to the system matrix S. The structure of the resulting matrix and column vectors for both the ZP and NZP cases is shown in FIG. 24. The matrix S contains the coefficients of the unknown surface current density parameters contained in the column vector k. These coefficients are present in the equations resulting from the constraints placed on each subinterval of each conductor. The column vector E then contains the imposed excitation voltage for each conductor. In the case of when no bounding interfaces have an imposed zero potential (NZP), the matrix and each column vector contains an additional component.

The terminal constraint which must be applied to each subinterval of a conductor in the MQS system has additional terms compared to that for the EQS system. In addition, voltage of each conductor in not imposed and therefore becomes an additional unknown. The expression for the constraint on a specific conductor subinterval is:

$$j\omega(\hat{\theta}_{(i),\chi,a} + \hat{P}_{(i)}[\tilde{k}=0]) + \hat{\Omega}_{(i),\chi,a} - \hat{v}_{(i),\chi} = 0 \qquad (225)$$

As in the EQS case, the terms on the LHS of this equation have been expressed in terms of the surface current density parameters and imposed return currents at positive infinity, except for the unknown conductor voltages $v_{(i),\chi}$, by (211), (217), and (218). Substitution of these expressions into (225), followed by rearranging the summations, produces the following expression for the constraint on the ith interface, $\chi$th conductor of the interface and ath subinterval of the conductor:

$$\sum_{g=0}^{N_I-1} \sum_{c=0}^{C_g-1} \sum_{n=0}^{N_{g,c}} \hat{K}_{(g),c}(\bar{y}_{(g),c,n}) \quad (226)$$

$$\begin{cases} (j\omega(\zeta_1 + \zeta_2) + \hat{\Omega}_{(i),\chi,a,n}) & \text{for } g = i = 0 \\ j\omega\zeta_2 & \text{for } g \neq i, i = 0 \\ (j\omega(\zeta_1 + \zeta_2 + \zeta_4) + \hat{\Omega}_{(i),\chi,a,n}) & \text{for } g = i \neq 0 \\ j\omega(\zeta_2 + \zeta_4) & \text{for } g \neq i, i \neq 0 \end{cases} -$$

$$\hat{v}_{(i),\chi} = \begin{cases} \hat{i}_{+\infty}\zeta_5 & \text{for } i \neq 0 \\ 0 & \text{for } i = 0 \end{cases}$$

$$\zeta_5 = \frac{j\omega}{\lambda} t_{i,N_I-1}^{-1}[\tilde{k} = 0] \quad (227)$$

and where $\zeta_4$ has been previously defined in (222). Unlike the EQS system, in which the imposed system excitation is present in each of the constraint equations, the MQS system requires additional equations to constrain the net current for each conductor to the imposed value. The total current for a specific conductor is expressed in terms of its surface current density parameters in (186). The additional equations required to enforce the conductor current have the following form:

$$\sum_{n=0}^{N_{i,\chi}} \lambda \hat{F}_{(i),\chi,n}^{even}[\tilde{k} = 0] \hat{K}(\bar{y}_n) = \hat{i}_{(i),\chi} \quad (228)$$

Figures 25, 26:
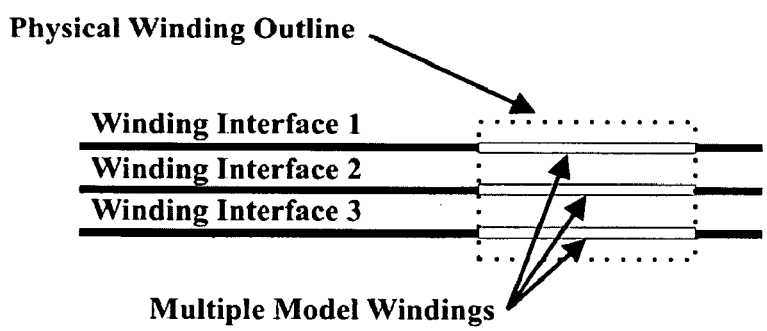
FIG. 25 shows the structure of the final system matrix equation for the MQS system.
FIG. 26 shows an approximation of finite thickness windings using multiple infinitely thin windings.

By applying (226) to each subinterval of each conductor and by applying (228) to each conductor the final system of equations can be built for the MQS system and put in the matrix form of (223). The structure of the resulting matrix equation is shown in FIG. 25. The matrix S contains the coefficients of the unknown surface current density parameters and unknown conductor voltages contained in the column vector k. These coefficients result from the equations produced by the constraints placed on each subinterval of each conductor and each conductor's net current. The column vector E then contains the constants related to either the return current at infinity or the imposed current in each conductor.

The development of the model has made no assumptions about the existence of any symmetry within the modeled structure, allowing it to be applied to the most general problems. Any symmetry present could simply be ignored and all conductors for the complete period of the structure would then be included in reaching the final system equation and solution. However, ignoring the symmetry will generally result in a waste of computational effort in three primary areas. First, the expressions for relating the surface current density parameters to the Fourier coefficients may be calculated for conductors with identical coefficients to other conductors and therefore resulting in redundant calculations. Secondly, the even coefficients, the odd coefficients, and/or the even modes of the coefficients may be exactly zero, in which case their determination by calculation represents wasted computational effort. Furthermore, any computations which utilize these zero or redundant coefficients provide yet another waste in computational effort. Thirdly, the number of unknowns may be increased due to the inclusion of conductors on which the surface current density distributions are directly related to those on other conductors, resulting in a larger final matrix equation which must be inverted. The existence of any useful symmetry should therefore be included in the definition of the modeled structure. The types of symmetry which can easily be included for efficiency are odd, even, and half-wave symmetry; combinations of even or odd and half-wave symmetry may also be included. The result of an even or odd symmetry simply forces the corresponding opposite coefficients to zero. In addition, only one-half period of the structure needs to be defined in either case, and the nonzero coefficients are then simply doubled. The half-wave symmetry forces the coefficients for even mode numbers to zero including the even $\tilde{k}=0$ mode. Again only one-half of the period must be defined and the nonzero coefficients are doubled. In the case when both half-wave symmetry and either even or odd symmetry are present many coefficients will be zero. It is then only necessary to define one-quarter of the period, while nonzero coefficients are quadrupled. Table 2 summarizes the mathematical description of the symmetry types, while Table 3 summarizes the affect on coefficients, and the portion of the period that must be defined. For each type of symmetry, more efficient computational methods result by defining the modeled structure over only the listed portion of the period. The modified coefficients are indicated with a double dot and specified in terms of those calculated using only the indicated portion of the period. Coefficients indicated as zero do not need to be computed or carried through to further computations. Any further calculations based on coefficients which are zero should be omitted.

TABLE 2

Summary of symmetry types which may be imposed on a modeled structure.

| Symmetry Type | Description |
|---|---|
| Periodic | $K(y) = K(y + \lambda)$ |
| Even | $K(y) = K(-y)$ |
| Odd | $K(y) = -K(-y)$ |
| Half-wave | $K(y) = -K(y + \lambda/2)$ |

TABLE 3

Summary describing how symmetry is incorporated into the models.

| Symmetry Type | Adjustment to Coefficients | Part of Period Defined |
|---|---|---|
| Periodic | none | $\lambda$ |
| Even | $\ddot{F}_n^{even}[\tilde{k}] = 2\hat{F}_n^{even}[\tilde{k}]$ $\ddot{F}_n^{odd}[\tilde{k}] = 0$ | $\lambda/2$ |

TABLE 3-continued

Summary describing how symmetry is incorporated into the models.

| Symmetry Type | Adjustment to Coefficients | Part of Period Defined |
|---|---|---|
| Odd | $\hat{f}_n^{odd}[\tilde{k}] = 2\hat{F}_n^{odd}[\tilde{k}]$ | $\lambda/2$ |
| | $\hat{f}_n^{even}[\tilde{k}] = 0$ | |
| Half-wave | $\hat{f}_n^{even}[\tilde{k}] = 2\hat{F}_n^{even}[\tilde{k}]$ for $\tilde{k} = 1, 3, 5, \ldots$ | $\lambda/2$ |
| | $\hat{f}_n^{odd}[\tilde{k}] = 2\hat{F}_n^{odd}[\tilde{k}]$ for $\tilde{k} = 1, 3, 5, \ldots$ | |
| | $\hat{f}_n^{even}[\tilde{k}] = 0$ for $\tilde{k} = 0, 2, 4, \ldots$ | |
| | $\hat{f}_n^{odd}[\tilde{k}] = 0$ for $\tilde{k} = 2, 4, 6 \ldots$ | |
| Even, Half-wave | $\hat{f}_n^{even}[\tilde{k}] = 4\hat{F}_n^{even}[\tilde{k}]$ for $\tilde{k} = 1, 3, 5, \ldots$ | $\lambda/4$ |
| | $\hat{f}_n^{even}[\tilde{k}] = 0$ for $\tilde{k} = 0, 2, 4, \ldots$ | |
| | $\hat{f}_n^{odd}[\tilde{k}] = 0$ | |
| Odd, Half-wave | $\hat{f}_n^{odd}[\tilde{k}] = 4\hat{F}_n^{odd}[\tilde{k}]$ for $\tilde{k} = 1, 3, 5, \ldots$ | $\lambda/4$ |
| | $\hat{f}_n^{odd}[\tilde{k}] = 0$ for $\tilde{k} = 2, 4, 6 \ldots$ | |
| | $\hat{f}_n^{even}[\tilde{k}] = 0$ | |

One of the primary goals of modeling the sensor is to predict its terminal characteristics for use in estimating the sensor's performance or for use in inversion methods which attempt to predict the best set of physical properties responsible for producing a measured terminal response. The preferred characterization of this terminal response is dependent on whether the modeled structure is MQS or EQS.

In the MQS system the impedance matrix is preferred and relates the winding voltages to the winding currents as:

$$\begin{bmatrix} \tilde{v}_1 \\ \vdots \\ \tilde{v}_N \end{bmatrix} = \begin{bmatrix} \tilde{Z}_{11} & \cdots & \tilde{Z}_{1N} \\ \vdots & \cdot & \vdots \\ \tilde{Z}_{N1} & \cdots & \tilde{Z}_{NN} \end{bmatrix} \begin{bmatrix} \tilde{i}_1 \\ \vdots \\ \tilde{i}_N \end{bmatrix} \quad (229)$$

where the system is composed of N windings. The diagonal elements represent the self-impedance of each corresponding winding while the off-diagonal elements represent the transimpedance between windings. One method of determining the impedance matrix is to simulate the modeled structure by selectively exciting one winding at a time. By forcing the current in one winding to be a unit value, while forcing the current in all other windings to be zero, the resulting vector of winding voltages is equivalent to the column of the impedance matrix corresponding to the excited winding. By repeating this process for each winding, the full impedance matrix can be obtained if necessary.

If the voltages on the LHS are equivalent to the voltages used in formulating the system equation, the winding is composed of a single conductor with infinite extent in the z direction. This implied that each of these winding loops consisted of a single conductor in the finite structure and an infinitely conducting path which stretched out to infinity. In most structures, the winding loops of interest are typically formed from the interconnection of these single conductors such that the winding path remains in the finite structure. The form of the relation in (229) can still be used, but the voltages are then calculated as the sum of the individual conductor voltages with the sign of each term determined by whether the path is aligned or anti-aligned with the +z orientation of each individual conductor forming the loop. Each current in the column vector on the RHS of (229) is associated with a winding loop formed by interconnected conductors. The currents in each conductor segment forming a particular loop must then be equal and in the direction dictated by the loop path in order for the terminal response to be described in the form of (229). Although the impedance matrix which relates the voltages of individual conductors to the current in individual conductors can be used to calculate the impedance matrix for the interconnected conductors, this is generally not the most efficient method. Each individual conductor of an interconnected winding can be excited by a unit current with a sign corresponding to the winding path direction, while all other conductors are imposed with no net current. After solving for the individual conductor voltages, the interconnection of the individual winding segments for each winding loop are used to evaluate the voltage of each interconnected winding. The vector of these voltages represents a column of the desired impedance matrix and sequentially exciting each interconnected loop produces the full matrix.

In the case when symmetry within the structure is imposed, the voltages on single conductors which would be interconnected to form the physical winding loops may not be calculated. The voltages of these conductors must be determined by the symmetry which was imposed. For example, if odd symmetry is imposed, the inclusion of a conductor in defining the half-period of the structure implies the existence of an additional conductor in the other half-period. Due to the odd symmetry, the voltage on this implied conductor will be the negative of that calculated for the one included in the structure definition. In considering the sign of each term associated with a winding path, the voltage of the implied conductor is still based on a +z directed path and must be accounted for accordingly. In the case of a pseudo-periodic structure with interconnected windings which involve the interconnection of implied conductors within other periods a method similar the preceding can be employed.

Due to the assumed infinite extent of the conductors in the z direction, the winding voltages involved in the formulation of the system equations have been normalized on a per unit length basis. The impedance matrix quantities determined from these voltages are therefore also on a per unit length basis. The absolute impedance values can be determined by denormalizing the voltages based on the actual winding loop path lengths to which they correspond by multiplying by the physical conductor lengths.

In the EQS system the preferred representation of the terminal response is in terms of the admittance matrix which relates the electrode current to the electrode voltage as:

$$\begin{bmatrix} \hat{i}_1 \\ \vdots \\ \hat{i}_N \end{bmatrix} = \begin{bmatrix} \tilde{Y}_{11} & \cdots & \tilde{Y}_{1N} \\ \vdots & \cdot & \vdots \\ \tilde{Y}_{N1} & \cdots & \tilde{Y}_{NN} \end{bmatrix} \begin{bmatrix} \hat{v}_1 \\ \vdots \\ \hat{v}_N \end{bmatrix} \quad (230)$$

where N is the number of electrodes. As with the MQS system the elements of the matrix can be evaluated by selectively exciting the electrodes. However, in the EQS case the selective excitation is done by imposing the voltage of one electrode to unit a voltage, while forcing the other electrodes to zero voltage. The vector of electrode currents then represent one column of the admittance matrix corresponding to the excited electrode; repeating the method for each electrode produces the fall matrix.

Multiple single conductors included in the structure can also be connected to form larger electrodes. In this case the voltage on each must be identical and the current into the electrode is the sum of the current for each conductor. Since there is no loop path associated with the interconnection of electrodes, the terms of this sum retain their original sign unlike the MQS system. The interconnection of implied electrodes due to symmetry can be handled similarly to the MQS system, again with the requirement that the interconnected electrodes are of the same voltage. In the EQS system, the infinite extent of the electrodes resulted in the electrode current to be expressed on a per length basis; denormalization is accomplished as in the MQS system. In addition to the terminal characteristics of the sensor structure modeled, many other quantities of interest can be evaluated once the surface current density parameters have been solved. These include electromagnetic fields and currents at both interfaces and in the volume of the material of the structure. The fields and currents have value in validating the self consistency of the model, improved understanding of the interaction with the material, and for further use in other models.

The surface current density parameters describe the surface current at discrete points along each conductor and can be used to determine the full distribution in one of two ways. In developing the general model equations, the value of the surface current density at discrete points was related to the current density between the points using interpolation functions. In the case of linear interpolation coefficients of the linear functions are described directly in terms of the surface current density values at discrete points using (90). In the case of the cubic spline interpolation method, the interpolated value is based on the cubic function of (91) and the coefficients this function must be determined from the surface current density values at all discrete points of the conductor using (103). A second method of evaluating the surface current density along an interface containing conductors is to utilize the Fourier series representation. The Fourier coefficients needed for the series representation are related to the surface current density parameters of each conductor on an interface through (205) and (206). The surface current density as a function of the position along the interface is then determined by:

$$\hat{K}_{(i)}(\tilde{y}) = \hat{K}_{(i)}^{even}[\tilde{k}=0] + \sum_{\tilde{k}=1}^{\infty} \hat{K}_{(i)}^{even}[\tilde{k}]\cos(\tilde{k}\tilde{y}) + \hat{K}_{(i)}^{odd}[\tilde{k}]\sin(\tilde{k}\tilde{y}) \quad (231)$$

where i is the index of the interface.

The potential at interfaces containing windings was required in the development of the models and is described by its Fourier series. The coefficients of the series can be evaluated from the surfaces current density parameters using (207), (216), and (217) and used in the Fourier series representation of (194).

The Fourier coefficients of the potential at the interfaces void of conductors are needed for both evaluating the potential at the interface and for calculating the distribution of fields and currents within layers adjacent to the interface. The methods utilized in developing the modeling equations avoided these intermediate calculations by combining the relations for individual layers into a single relation for the region composed of multiple layers. Relations between the coefficients of the potential at these interfaces and any other quantity which can be related to the surface current density parameters by existing equations have not been developed. There are at least a few possible methods of relating the Fourier coefficients at these interfaces to other known quantities. However, a method which utilizes the iterative techniques of combining layer relations was chosen.

As a starting point the interface void of conductors on which the Fourier coefficients are desired is assumed to lie somewhere in the region between two interfaces containing conductors. The expressions for the Fourier coefficients on these interfaces can be evaluated from previous results. The region between these interfaces may contain many layers and interfaces other than the one of interest. For the coefficients associated with $\tilde{k}\neq 0$, the previously developed methods of combining transfer relations from each layer can be applied to the layers between the interface of interest and interface with index zero and again to the layers between the interface of interest and the interface of index $N_I$. This results in one relation for the group of layers below the interface of interest and one relation for the layers above:

$$\begin{bmatrix} \hat{Q}_0^+[\tilde{k}] \\ \hat{Q}_m^-[\tilde{k}] \end{bmatrix} = \begin{bmatrix} \hat{M}_{11}^{0:(m-1)}[\tilde{k}] & \hat{M}_{12}^{0:(m-1)}[\tilde{k}] \\ \hat{M}_{21}^{0:(m-1)}[\tilde{k}] & \hat{M}_{22}^{0:(m-1)}[\tilde{k}] \end{bmatrix} \begin{bmatrix} \hat{P}_0[\tilde{k}] \\ \hat{P}_m[\tilde{k}] \end{bmatrix} \quad (232)$$

$$\begin{bmatrix} \hat{Q}_m^+[\tilde{k}] \\ \hat{Q}_{N_I}^-[\tilde{k}] \end{bmatrix} = \begin{bmatrix} \hat{M}_{11}^{m:(N_I-1)}[\tilde{k}] & \hat{M}_{12}^{m:(N_I-1)}[\tilde{k}] \\ \hat{M}_{21}^{m:(N_I-1)}[\tilde{k}] & \hat{M}_{22}^{m:(N_I-1)}[\tilde{k}] \end{bmatrix} \begin{bmatrix} \hat{P}_m[\tilde{k}] \\ \hat{P}_{N_I}[\tilde{k}] \end{bmatrix} \quad (233)$$

where m is the index of the interface for which the coefficients of the potential are sought.

The usual boundary condition for both the MQS and EQS systems require that $\hat{Q}_m^+[\tilde{k}] = \hat{Q}_m^-[\tilde{k}]$ at the interface with void of conductors. By setting these quantities equal, the coefficients of the potential on the mth interface can be related to the coefficients on the interfaces which bound the region:

$$\hat{P}_m[\tilde{k}] = \frac{\hat{M}_{21}^{0:(m-1)}[\tilde{k}]}{\hat{M}_{11}^{m:(N_I-1)}[\tilde{k}] - \hat{M}_{22}^{0:(m-1)}[\tilde{k}]} \hat{P}_0[\tilde{k}] + \quad (234)$$

-continued $$\frac{\hat{M}_{21}^{m:(N_l-1)}[\tilde{k}]}{\hat{M}_{11}^{m:(N_l-1)}[\tilde{k}] - \hat{M}_{22}^{0:(m-1)}[\tilde{k}]} \hat{P}_{N_1}[\tilde{k}] \text{ for } \tilde{k} \neq 0$$

In the case when the interface of interest is in a bounding region of the structure, one of the region interfaces will either be constrained with zero potential or located at infinity. The methods of combining layers for the bounding regions must then be applied to the layers which lie between the mth interface and this bounding interface. Depending on which side of the mth interface this bounding interface is located, one of the relations (232) or (233) is then replaced by a linear relation. This results in the absence of the term in (234) that is associated with the potential on the corresponding bounding interface.

Evaluation of the $\tilde{k}=0$ coefficient of the potential on an interface void of conductors requires a somewhat specialized handling due to the possibility of conducting layers in the MQS system. Therefore the calculation of the coefficients is only described for the EQS system and for regions of the MQS system composed of nonconducting layers. Note that for the MQS system, the $\tilde{k}=0$ coefficients are often zero due to symmetry or imposed conductor currents, in which case the $\tilde{k}=0$ coefficients can be taken as zero and the issues associated with calculating the coefficients for interfaces in regions with conducting layers are avoided. Under the specified conditions, the quantity $\hat{Q}[\tilde{k}]$ within a region is identical at each interface void of conductors and on the inside of the bounding interfaces. Methods of combining relations for $\tilde{k}=0$ in these regions produced a linear relation between the jump in potential between region interfaces and the quantity $\hat{Q}[\tilde{k}]$. Since the $\tilde{k}=0$ coefficients of the potential at the boundary can be determined from previous methods $\hat{Q}[\tilde{k}]$ can be determined by:

$$\hat{Q}[\tilde{k}=0] = \hat{M}_0^{0:(N_L-1)}[\tilde{k}=0](\hat{P}_0[\tilde{k}=0] - \hat{P}_{N_L}[\tilde{k}=0]) \quad (235)$$

In the special case of the bounding regions, $\hat{Q}[\tilde{k}]$ is zero for the EQS system when an interface is located at infinity while for the MQS system $\hat{Q}[\tilde{k}]$ is dependent on the current returned at infinity as described by (159) or (160). The relation of (235) is valid in the bounding regions of the EQS system in the case of a constrained interface and the potential at the corresponding interface will be zero. The potential at an interface within the region can then be determined by:

$$\hat{P}_m[\tilde{k}] = \hat{P}_0[\tilde{k}] - \frac{\hat{Q}[\tilde{k}=0]}{\hat{M}_0^{0:(m-1)}[\tilde{k}=0]} \quad (236)$$

or:

$$\hat{P}_m[\tilde{k}] = \hat{P}_{N_L}[\tilde{k}] + \frac{\hat{Q}[\tilde{k}=0]}{\hat{M}_0^{m:(N_L-1)}[\tilde{k}=0]} \quad (237)$$

Either relation can generally be used, although in the bounding regions of the structure only one may be useful.

In both the EQS and the MQS systems the distribution of the potential and fields inside each layer is the result of the superposition of multiple solutions corresponding to different values of k. The portion of the solution associated with a specific value of k is described in term of the Fourier coefficients of the potential at the layer's interfaces for the same value of k. Therefore once the coefficients of the potential have been determined at a layer's interfaces, the field and potential in the layer can be evaluated as the sum the solutions over all values of k.

In order to model aperiodic sensors, a long wavelength periodic (Fourier series) approximation or a Fourier transform approach can be used. A closed form for the Fourier transform of the parameterized surface current density can be derived; however the inverse Fourier transform of the resulting surface vector potential requires numerical integration techniques for evaluation. As a result the long wavelength periodic approach is "loosely" one method of carrying out this numerical integration.

In addition to modeling multi-layered sensors, the ability of the model to include multiple winding interfaces can be exploited for approximating the finite winding thickness. In the preceding model description, the finite thickness of the windings was introduced only in terms of its effect on the winding surface conductivity. The actual currents were assumed to be confined to a single plane. The validity of this assumption will depend on the relative geometric dimensions of the sensor. However, in cases were this assumption is in question or violated, additional winding interfaces can be introduced to provide a discrete approximation to the currents distributed over the winding thickness as shown in FIG. 26. For this approximation, each additional winding interface contains a winding of equivalent length positioned directly above or below the other discrete windings and is constrained to be at equal electrical potential as other discrete windings. Since each discrete winding represents a portion of the thickness for the single physical winding, their surface conductivity is adjusted accordingly. Although the introduction of these windings introduces additional unknowns and computation, it is typically more efficient than resorting to finite element or boundary element methods.

The ability to model structures with multiple electrode interfaces not only provides a means for modeling a larger variety of sensors, but also has utility in approximating the finite thickness of the electrodes in these structures. This is accomplished by discretizing the finite thickness of the electrode into two or more of the infinitely thin electrodes provided by the model. Although this is very similar to the technique applied for the MQS model, it differs in the placement of the discrete electrodes. Physically the injected current in the EQS case occurs at electrode surfaces (the electrodes are well approximated as perfectly conducting), therefore the upper and lower most infinitely thin electrodes of the approximation should be placed in the locations of the physical electrodes corresponding upper and lower surfaces. Additional approximating electrodes should be distributed between these two electrodes. This differs from the MQS case where the volume current is being approximated by the infinitely thin windings. Since the distribution of the volume current within the physical winding can vary depending on the skin effect, the ideal location of the discretizing windings will depend on the actual distribution. Most often this will involve the approximating winding taking on a mean position of the volume currents that it represents, only in the case of very thin skin current distributions will the position lie on the upper or lower electrode surfaces.

The ultimate goal of utilizing these MQS and EQS sensors is to obtain physical MUT properties. The modeling techniques described for predicting the sensor response as a function of the MUT properties rarely produce expressions for which the direct inverse can be obtained. The result is the classical inverse problem in which dependent function parameters are known and the independent parameters are sought.

More specifically the measurements consist of transimpedance (or transadmittance) values, in complex form, at one or more frequencies and from one or more sensing elements. The goal is then to find the unknown MUT properties, which are the most likely for the given set of measurements. In order for a unique solution to possibly be found it is necessary that there are at least as many measurements as unknown properties. A single transimpedance measurement generally counts as two measurements since it is a complex value, although certain sensor/MUT configurations may produce completely real or imaginary impedance data in which case only a single measurement is counted. In order for each measurement to be counted it should also be independent of the other measurements, which in the strictest sense is not often an issue. However, in the presence of measurement noise, the degree of independence will directly influence estimation error; this is discussed in the following section.

In order to find the most likely set of properties, inversion problems such as this are typically formulated in one of two ways: as a non-linear root searching problem or as an optimization problem. The root searching approach is comprised of a system of M functions, one corresponding to each measurement. Each of these functions has N independent parameters, one for each MUT property. The problem is then to find the best solution to the set of equations:

$$F_m(x_1, \ldots, x_n) - Z_m = 0, \text{ for } m \in M \tag{238}$$

where $Z_m$ is the mth measurement. In contrast to the non-linear root searching approach, the optimization formulation differs by focusing on a single equation known as the metric. The metric is commonly formed as:

$$\sum_{m \in M} (F_m(x_1, \ldots, x_n) - Z_m)^2 \tag{239}$$

The solution is then sought by finding parameters which minimize this metric equation.

Numerical techniques for root solving of non-linear systems of equations and for optimization are widely available. Popular root searching methods include: Newton-Raphson and Broyden's method, while popular minimization methods include: conjugate-gradient, downhill simplex, and Powell's method. Each of these methods involves iteration in order to converge to a result of sufficient accuracy and in doing so requires repetitive evaluation of the functions: $F_m(x_1, \ldots, x_n)$. Evaluation of these functions is equivalent to evaluating forward sensor models, which is relatively computationally expensive. This can become a limiting factor for the near real-time inversion of large amounts of data.

In order to avoid the time associated with the model computation, it is often possible to pre-compute the sensor response for a sufficiently large number of cases, especially when the number of independent parameters and associated parameter ranges are sufficiently constrained. Typically a set of monotonic parameter values would be chosen for each independent parameter, and all parameter combinations would be simulated. This allows intermediate sensor response values to be efficiently interpolated from the pre-computed values as needed by using linear or higher order interpolation schemes. These are the measurement grids shown in FIGS. 6 and 7.

In the measurement of physical parameters by any type of sensor the question often arises as to whether a property can be measured and with what degree of accuracy and/or precision. Often the answer is determined experimentally by comparison with alternate, though often less convenient, forms of measuring the same property. However, this is not always practical when alternate means of property measurement are of insufficient accuracy or are nonexistent. The prediction of measurement capability without a physical implementation of the complete measurement system and MUT is often useful for optimization of the sensor design (i.e., electrode and winding configuration) and measurement techniques (i.e., excitation frequency) and as a check of the practicality of any measurement.

In order for a theoretical quantification of measurement capability for an EQS or an MQS sensor to be performed there are several required pieces, which will have varying degrees of difficulty in being obtained. First, a sufficient description of the MUT is required. This description should include all material properties, in addition to their variability, to which the sensor may be sensitive including the properties of interest. Since the sensors will respond only directly to geometric and electrical properties, a relation between the known non-electrical properties and electrical properties must be established. This may prove to be challenging since these relations are often complex, material dependent (i.e., alloy composition, heat treat) and not well established in general literature. Therefore additional work of theoretical modeling or empirical characterization of sufficient accuracy may be required if reasonable approximations cannot be made.

Next a method of relating the sensor response to variations in the MUT must be determined. In many MUT configurations the preceding modeling methods can be utilized to provide accurate estimates of the sensor response. However, these models demonstrate increased deviation in the predicted response as the actual MUT deviates from theoretical representation. In other cases different methods must be utilized which are appropriate for the MUT including analytical and numerical modeling techniques such as FEM. In some cases it may be possible to develop relations empirically; however, this generally requires the use of a rather complete physical system and therefore quickly digresses to an empirical estimate of measurement capability.

The last required piece is a description of the noise induced in the process of converting the sensor's terminal response to a numerical representation, which is the function of the instrumentation and associated electronics. In this conversion there are an abundant number of possible noise sources, which can introduce both errors between the expected value of the measurement and that of an individual measurement along with bias error between the expected value and the true value. Some examples of these types of noise sources are: thermal noise, ambient noise, non-linearity, drift, calibration error, parasitics, quantization, and jitter. Although a complete theoretical noise model of the instrumentation and the electronics could be attempted, one would often run into difficulties accounting for all noise sources in the complex system. Fortunately the more complex instrumentation blocks often remain constant, while other simpler blocks such as amplification stages are adapted to a specific sensor. This allows for empirical characterizing of the complex blocks to be carried out once, while more simple noise models can be created for the highly variable blocks. Empirical characterization of the probability distribution for these complex blocks is rather straight forward since many measurements can easily be made automatically. However, determining the error between the expected value and the true value of a measurement can present a challenge, due to the uncertainty of the true value and dependence of this error on operating conditions.

Once a sufficient representation for each of the previously discussed pieces has been achieved a study of the measurement capability for the problem at hand can begin. One approach utilizes the information about the measurement noise and sensor response to simulate synthetic data about a set of MUT properties of interest. The inversion methods, as previously discussed, can then be used to estimate MUT properties for this synthetic data along with the associated error distribution from the expected MUT properties. This type of analysis of simulating experimental data for use in evaluating parameter distributions is known as Monte Carlo simulation.

An alternate approach is to linearize the non-linear relations between MUT properties and sensor response about the MUT properties of interest. This allows linear algebra techniques to be applied in the analysis. One such method was utilized in U.S. Pat. No. 5,453,689, which used singular value decomposition of the Jacobian matrix which contains partial first derivatives of the sensor response with respect to MUT properties. This allowed a method for evaluating the relative performance of different sensor and excitation configurations and some of the underlying physics of the sensor response, but does not utilize measurement noise in determining errors in MUT properties. However, these errors can be evaluated by using matrix inversion and analysis techniques such as least squares to relate measurement errors to property errors.

The preceding techniques were concerned with how measurement noise translates to errors in estimated MUT properties. A second area of interest is how MUT properties which may be assumed constant in the simplification of a problem can translate into errors in the properties of interest. The procedure for evaluating these errors first utilizes the relations for the sensor-MUT response to determine the equivalent error in the measurement induced by a change in the property which was initially held constant. If probability distributions for this property are known, equivalent measurement error distributions can also be obtained. This measurement error can then be included in any of the preceding analysis methods, allowing the effect on the errors in the properties of interest to be resolved.

The noise sources previously described tend to produce incremental though possibly significant errors in the ultimate inversion of measurement data into MUT properties. However, issues associated with global measurement uniqueness can lead to completely incorrect property estimates. This can occur because in general there is no guarantee that a given set of measurements will correspond to a unique set of properties, even when there is a greater number of measurements than unknowns. When this happens locally, for a given set of MUT properties, this corresponds to a lack of independence and results in a minimal change in sensor response for certain coordinated changes in material properties as demonstrated in U.S. Pat. No. 5,453,689; this generally results in a significant variability associated with the estimated MUT properties lacking independence. When this happens globally, the MUT properties may be very locally independent, but there will exist a completely different set of MUT properties, which is equally probable in the absence of any a priori knowledge (such as allowable MUT property ranges). The resulting estimates of MUT properties may exhibit little variability, but be erroneous. It would therefore be useful to apply an appropriate method in the search for these areas of non-uniqueness in order to avoid possible pitfalls during measurement inversion.

With the various possible methods of characterizing the errors associated with the MUT properties being sought, it is possible to perform optimizations which can bring these error quantities closer to prescribed values. This can be accomplished by varying sensor geometry, excitation frequency, and/or sensor location until the requirements have been met or it has been determined that the requirements are too severe for existing measurement noise levels.

The measurement noise levels depend upon the impedance measurement instrumentation for each element of either the EQS or MQS sensor arrays. In order to more efficiently utilize an instrument designed for analyzing a single two-port device, the concept of electrically multiplexing the multiple sensing elements into a single instrument channel can be used. Although, the sensing elements must still be measured sequentially in time, the process can be more efficient and more convenient since it can be controlled via instrument or computer. While the multiplexer (MUX) is functional, it has limitations. The use of the MUX increased measurement noise and resulted in some element to element cross-talk. The significance of the noise induced by the MUX is dependent on the amount of signal conditioning which is done before the element signals enter the multiplexer stage. Placing more signal conditioning before the MUX stage, of the sensing element signal path, results in the MUX switching larger, buffered signals and thereby reducing the significance of the noise induced at the MUX, while increasing the amount of electronics required. Placing less signal conditioning before the MUX stage requires less electronics, but increases the noise since most devices used in MUX designs are less optimized for noise and input loading than the devices used in signal conditioning stages. The relevance of the channel-to-channel cross-talk is dependent on the measurement application, but can still be qualified as worse than a non-MUXed method.

Most impedance instrumentation provides some type of setting corresponding to the duration used for making a single impedance measurement. There is a general tradeoff between speed and measurement noise, such that a shorter measurement will contain more uncertainty in the measured impedance value than a longer measurement. Since the element measurements are made sequentially when a MUX is utilized, the noise/speed performance is increasingly degraded with the number of elements MUXed, even in the absence of MUX induced noise. If the same measurement rate per channel is to be maintained, the individual measurement duration needs to be inversely related to the number of MUXed elements. Most often this will not be possible with larger element counts, due to either ultimate instrument limitations, or the presence of an intolerable amount of noise. The inability to trade acquisition rate for reduced noise is most commonly an issue for scan mode operation of sensor arrays, where the scan speed is directly related to the rate at which data can be taken for a certain level of noise. If the scan speed is too large compared with the measurement rate, the data will be too sparse and/or the individual measurements will be averaged over the area traversed by the array during the scan movement, in which case material property details may be missed. Compensating for this effect by reducing the measurement time will produce more uncertainty in measured values, which will again increase the chance of important material property details being missed.

In order to obtain the best noise/speed performance, it is desired to utilize as much time as possible on each element for making measurements. In a MUXed configuration, only a fraction of the total time is spent on a given element, so the solution to providing ultimate performance is to utilize a parallel measurement approach in which case all elements are measured simultaneously. Also of importance in the area of noise performance are bias type noise sources, which cannot be reduced by increased measurement duration and therefore must be reduced by design or calibrated out of the measurement; these bias errors are introduced by parasitics found in system components such as sensor-instrument cabling and interconnections. The following sections focus on parallel impedance instrumentation for improved noise/speed performance, sensor probes for reduced parasitics, and calibration methods for providing measurement accuracy.

In order to provide parallel multi-channel acquisition capability, one can consider utilizing multiple two-port type impedance instruments, ideally one per sensor element. However, one would find this to be prohibitive due to cost, size, and compatibility. Alternatively, a dedicated instrument providing simultaneous impedance measurement on each channel in such a way as to provide maximum filtering of undesired noise and minimum uncertainty in measured values suitable for accurate impedance data for use with both EQS and MQS sensors can be used. This type of instrument is described in U.S. patent application Ser. No. 10/155,887, filed May 23, 2002, the entire teachings of which are incorporated herein by reference. The main function of the instrument is to provide a sinusoidal excitation of appropriate amplitude, frequency, and type (current or voltage) and characterize the ratio of the complex representation of each sinusoidal channel signal to the complex representation of the excitation (usually measured directly), for each channel. Therefore the instrument must be capable of analyzing each channel and the excitation signal, and then determine its complex representation in terms of magnitude and phase or in-phase and quadrature components relative to some absolute reference.

Since channel multiplexing was to be avoided in order to achieve the best speed/noise performance, each channel would be identical and integrated together with some common support systems. This means that the bulk of the instrument would be determined by the obtainable size and complexity of each channel. Channel complexity within the main instrument was partially reduced by placing the element conditioning (amplification and bandwidth characteristics) for each channel external to the unit. This was also useful as a result of EQS sensors and MQS sensors utilizing sufficiently different conditioning electronics, different sensors being more optimal with certain conditioning parameters, and certain parasitic affects being minimized by element conditioning placed local to the sensor rather than the instrument. By moving the conditioning external, the complexity of the conditioning electronics was also reduced since it is easy to select from a variety of interfaces with "hard" conditioning settings, which reduces the degree of reconfigurability that would otherwise be required if placed within the instrument. Therefore, each channel of the instrument needs only to deal with voltage signals in a single range.

One approach to analyzing the voltage input signals to determine their complex representation for such a multichannel system is to immediately digitize each signal upon entry into the instrument. This would traditionally be followed by some type of digital signal processing (DSP) such as: correlation with in-phase and quadrature signals, or performing an FFT. However, for MQS applications such as measuring thin coatings, it is desired to measure at frequencies exceeding 20 MHz in order to limit the skin depth of the fields in the MUT. The analog-to-digital (A/D) converters available for sampling at these frequencies are generally contained in larger packages, expensive, and of lower bit resolution.

A second approach is to utilize a down-conversion method, such that the input signal is mixed down in frequency to a range where more common, high resolution A/D converters are acceptable. Again DSP processing techniques would be applied to the sampled signal in order to determine the complex representation. However, these DSP operations require multiply-accumulate operations (MACs) to be performed at the speed of the incoming A/D conversions. Alternatively one could try to postpone the data analysis, however the quantity of individual A/D measurements is generally several orders of magnitude larger than the quantity of processed impedance measurements and would require excessively increased intermediate local storage and/or data paths, while resulting in a delay in the availability of impedance data. The type of MAC performance required to handle only a few channels, in real time, is traditionally found in high throughput digital signal processors, which can be somewhat costly (although cost/performance ratios continually decrease). These digital signal processors are also larger type devices requiring significant space and power.

The approach utilized here is a direct to DC down-conversion, such that the input signal is mixed all the way down to DC, while other mix products are removed using analog filtering. Again correlation is required, but since the correlation will be carried out with a constant (essentially taking the average of A/D values), no multiplies are required, only additions. This opens the accumulation task to very compact, low power, and less expensive microcontrollers, with one dedicated to each channel.

Figure 27:
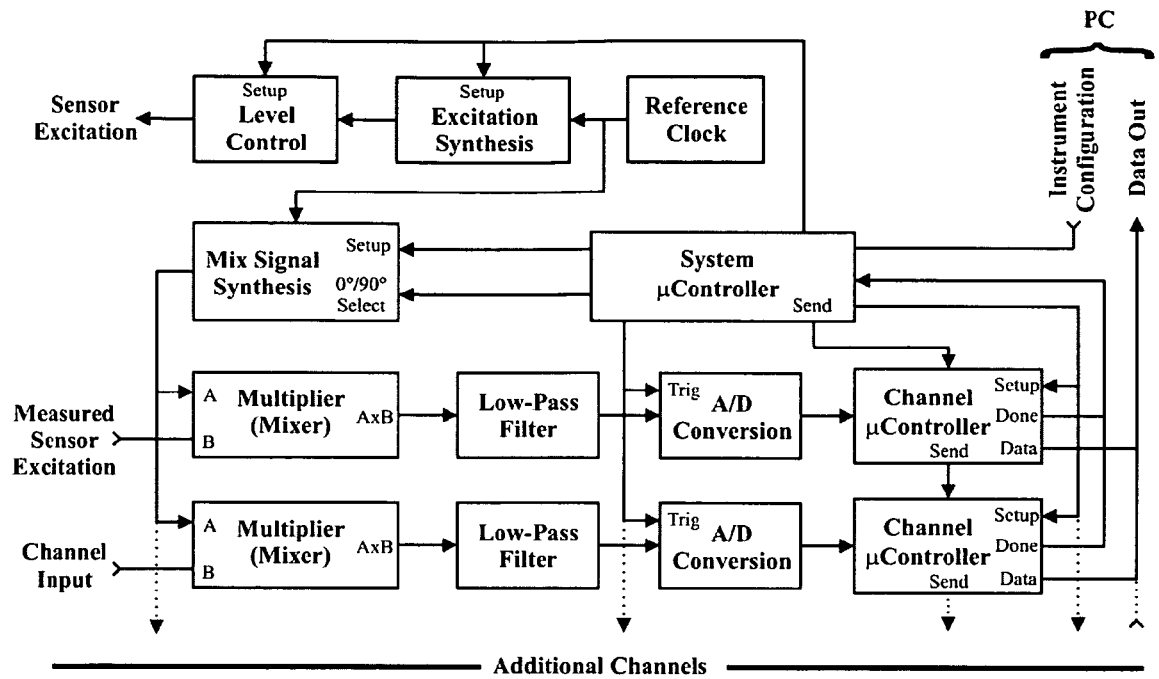
FIG. 27 shows a block diagram of the instrumentation developed for the simultaneous impedance measurement of a many element sensor.

A block diagram of the complete system including the mixer, filtering, A/D conversion, channel microcontrollers, excitation synthesis, mix signal synthesis and system microcontroller blocks is shown in FIG. 27. The instrument is designed to be used with a PC which is used for configuring impedance measurement parameters such as swept frequencies and measurement durations in addition to controlling the start and stop of acquisition. The PC is also used to store the acquired data, since it is the platform on which further impedance data processing such as calibration and inversion to material properties will be performed, and on which the results will be displayed.

In preparation for measurement, the configuration information is transmitted from the PC to the system microcontroller, including: a list of frequencies to sweep, corresponding measurement durations in terms of the number of A/D samples, and sensor excitation levels. The system microcontroller extracts necessary information and immediately passes it on to the channel microcontroller to avoid future measurement delays. The acquisition of one or more impedance measurements is then initiated by the PC through communication with the system microcontroller. The system microcontroller responds by placing the channel microcontrollers in an appropriate acquisition mode. The system microcontroller then configures the frequency of the excitation synthesizer, which generates the sinusoidal waveform for driving the sensor, and the level control, to provide the proper magnitude of excitation. The mix signal synthesizer is simultaneously configured with the identical frequency of excitation. The excitation and mix sinusoidal signals are highly synchronized in frequency and relative phase due to the use of direct digital synthesis (DDS) driven from a common reference clock. The use of a DDS technique also allows the phase of the mix signal relative to the excitation signal to be accurately and instantaneously shifted by 90 degrees. With additional circuitry, both the in-phase and quadrature phase signals can be measured simultaneously if the improvement in data acquisition rate warrants the additional circuit complexity.

Once the connected sensor has been excited, the measured excitation and the conditioned sensing element signals will appear at the channel inputs. The magnitude and phase of these signals will be altered from those exciting the sensor and can be represented in terms of their in-phase and quadrature parts relative to a common reference as:

$$v_{ch}(t) = V_I \cos(\omega t) + V_Q \sin(\omega t) \quad (240)$$

In the first stage of each channel the inputs are multiplied by the synthesized mix signal which in its un-shifted state will be defined as the common reference with an absolute phase of zero and therefore be represented as: $\cos(\omega t)$. The resulting output of the multiplier is:

$$v_{mult}(t) = V_I \cos^2(\omega t) + V_Q \sin(\omega t)\cos(\omega t) \quad (241)$$
$$= \frac{V_I}{2} + \frac{V_I}{2}\cos(2\omega t) + \frac{V_Q}{2}\sin(2\omega t)$$

By filtering the non-DC component of this signal, the in-phase coefficient $V_I$ can be obtained. As mentioned previously, it is possible to instantaneously shift the phase of the mix signal by 90 degrees (leading) relative to its current phase, which has been defined as the absolute zero reference, without affecting the absolute phase of the excitation and therefore the phase of the input signals. Under this condition the mix signal is represented as: $\sin(\omega t)$ and the output of the multiplier is:

$$v_{mult}(t) = V_I \cos(\omega t)\sin(\omega t) + V_Q \sin^2(\omega t) \quad (242)$$
$$= \frac{V_I}{2}\sin(2\omega t) + \frac{V_Q}{2} - \frac{V_Q}{2}\cos(2\omega t)$$

The quadrature coefficient $V_Q$ can be obtained by filtering the non-DC output of the multiplier. Although, for improved speed, each channel could have utilized two multipliers (and following stages), while a 0 and 90 degree mix signal were produced simultaneously, this results in essentially doubling the size of the required hardware for each channel. Using a single signal path for both in-phase and quadrature measurements also simplifies calibration since it is not necessary to account for gain and phase errors between signal paths.

The choice of filter characteristics for removing the non-DC components of the signal is important, as they can affect the frequency range of the instrument and the maximum acquisition speed. The lowest excitation frequency which can be utilized in the currently described mode of operation is determined by the cut-off frequency of the filter used. At excitation frequencies lower than twice this cutoff frequency (assuming an idealized low-pass characteristic), the non-DC components of the multiplied signal will start to pass through the filter, and require additional filtering. However, using too low of a cut-off frequency also will degrade the performance. Since making a complete measurement requires a two-step process of measuring in-phase followed by quadrature components, the output of the filter will first contain the DC component equal to $V_I$, followed by the DC component equal to $V_Q$. Since $V_I$ and $V_Q$ will not be equal, in general, the output will contain a step. A filter with too low of a cut-off will have poor settling characteristics and will result in an excessive delay before useful measurements can be acquired by the A/D converter. The net effect would be to reduce the rate at which impedance values could be taken. A $5^{th}$ order elliptical filter with a cutoff frequency of 10 kHz was used because of its sharp cutoff and reasonable settling characteristic. This allows a lower frequency bound of 5 kHz, however, below these frequencies it is possible for the A/D converter to acquire data fast enough to do additional digital filtering of the non-DC components and push the usable low frequency range significantly lower. The choice of cutoff frequency also provides a settling time on the order of 1 mS, which allows for rapid acquisition of in-phase and quadrature parts of the input signals.

Based on the previous discussion, the measurement cycle is carried out by the system microcontroller first configuring the excitation frequency and level, along with the mix signal for measuring the in-phase component of the input signals. After the settling time required by the filter has elapsed, the system microcontroller can coordinate A/D conversions across all signal channels. If only a DC component was present, a single measurement would theoretically be sufficient on each channel. Since the filter removes the extraneous mix components, what is left are noise sources in the 10 kHz band of the filter. Some of this noise has been mixed down from the excitation frequency along with the desired DC component and is due to thermal noise sources within electronic components and ambient noise possibly picked up by the sensor. Additional noise may be inherently present in the filtering stage or may be induced from digital signals. Therefore multiple A/D conversions of the in-phase component may be averaged to further filter the noise from the measurement. More measurements will result in lower noise, but at the expense of longer measurement duration. Since the number of A/D conversions utilized in a single impedance measurement can easily be configured, this provides a means for the user to reach an acceptable compromise between noise and speed.

Once the desired number of A/D conversions has been made for the in-phase portion of the signals, the system microcontroller can set the mix signal for a 90 degree leading phase and the same procedure described previously can be performed to obtain the quadrature component of each channel signal. The dedication of a single microcontroller to each channel allows digital data to be simultaneously extracted from each A/D converter and accumulated for averaging. When both the in-phase and quadrature signal values have been obtained the system microcontroller can initiate the transmission of the measurement back to the PC. Each channel microcontroller has direct access to the data stream to the PC such that the system controller does not need to keep up with the throughput of data. Since, only one channel transmits its data on a given data stream at a time, each channel has the ability to signal its neighboring channel as to when it has completed its transmission of data. This ability allows the channels utilizing the same data stream to sequentially send their data without direct coordination by the system microcontroller. In an acquisition mode of multiple frequencies and/or multiple measurements, this allows new data to be simultaneously acquired while the previous data is transmitted, with minimal interruption of the system microcontroller.

The measurement of the in-phase components of all channels are measured simultaneously followed by the simultaneous measurement of the quadrature components of all channels at a specific frequency. If the instrument has been configured for multiple frequencies, these will be acquired sequentially. The complete cycle of in-phase and quadrature measurements at multiple frequencies is then repeated for each complete set of measurements until the required number is obtained or the PC terminates the acquisition of data.

The system architecture utilized here, in terms of parallel acquisition and processing on each channel, nearest neighbor signaling, and common data, setup, and system controller signaling lines, lends itself to the modular expandability to many channel systems without redesign. This is due to the fact that unique interconnections do not exist between each channel and any common system component. All channel connections are made to a common signal bus or are made to the two nearest neighbors. Also, each additional channel contains all of the resources that it utilizes highly, and therefore minimal additional load (processing/acquisition) is placed on common system components.

As previously discussed, the data sent back to the PC represents the in-phase and quadrature components of the excitation measurement and of each sensing element signal. In the case of an MQS sensor, the measured excitation is related to the current through the sensor's primary winding, while the sensing element signals are related to the sensor's secondary voltages and the complex transimpedance between the sensor drive and each channel is desired. For EQS sensors, the measured excitation is related to the voltage on the drive electrode, while the sensing element signals are related to the currents flowing to the sensing electrodes, and the transadmittance is desired. Since the complex amplitude representation of the input signals is simply related to the measured in-phase and quadrature components as:

$$v_{ch}(t) = V_I \cos(\omega t) + V_Q \sin(\omega t) = \Re\{(V_I - jV_Q)e^{j\omega t}\} \quad (243)$$

The transimpedance for the MQS connection and the transadmittance for the EQS connection between the sensor drive and the Nth sense element are related to the measured signals as:

$$\hat{Z}_{DN}, \hat{Y}_{DN} = \hat{K}_{cal} \frac{(V_I^N - jV_Q^N)}{(V_I^D - jV_Q^D)} \quad (244)$$

where $\hat{K}_{cal}$ is a constant complex scale factor (discussed later in more detail), which is unique for each frequency and required to calibrate the instrument for gain and phase shifts created by the various stages within the instrument and in the external sensor element conditioning electronics. A typical freqequency ranges is approximately 100 Hz to 40 MHz with sub-Hertz resolution. The measurement duration can be configured from approximately 3 ms to over one second for all channels at a single frequency.

The impedance instrument performs the task of providing excitation for the sensor and measuring the ratio of the complex representation of the sensing element signal to the complex representation of the excitation. However, the sensing element signals are often relatively small and may be in the incorrect form (e.g., current instead of voltage) or have an output impedance that is not directly compatible with the instrument inputs. The excitation signal applied to the sensor terminals may also be altered from that at the instrument terminals due to cabling effects, or the desired excitation quantity may be of the incorrect form (e.g., current instead of voltage) compared to the instrument inputs.

The probe and the signal conditioning electronics provide several important functions including making the instrument terminal requirements compatible with the sensor terminal characteristics. The probe provides signal conditioning for the sensing elements, which includes amplification, buffering, and filtering of the signals. This is important because the low level signals found at the sensor terminals can easily be contaminated by loading and parasitic coupling within the cabling to the instrument. The amplification minimizes the relative coupling by increasing the signal to noise ratio within the cable, while the buffering function provides sufficient cable driving capability which will not be affected by changes in MUT properties (the element signals are still dependent on MUT properties); the filtering function removes noise signals that are out of the frequency band of interest. Additionally, the probe provides an accurate measurement of the sensor excitation at a location local to the sensor, while decoupling this measurement from adversely affecting the sensor excitation. This local signal conditioning of the sensing elements and measured excitation allows the electronics to be optimized for various sensor configurations without requiring excessive adaptability of the main impedance instrument. The buffering that the probe provides also allows much longer cables to be utilized with a smaller degradation in performance than would otherwise result. The probe also provides mechanical support for gripping sensors, a place for the sensor interconnect, and provides strain relief between sensors and instrument cables.

Measurement of MQS sensors is usually accomplished by exciting the primary winding, while measuring the excitation current and simultaneously measuring the voltages developed across the sensing elements composed of secondary windings. Since the controlled excitation of the instrument is in terms of a differential voltage across the primary winding, the probe is necessary for providing an accurate measurement of the current, which is converted to a voltage signal that is compatible with the impedance instrument's inputs. The voltage developed across the secondary windings should ideally be measured under open-circuit conditions. The electronics within the probe provides high impedance inputs for the secondary windings, amplification and the capability to drive the impedance instrument inputs. For the arrays, the probes have identical channel modules which simplify the design, fabrication, and testing complexity of the probe. The modularity also simplifies repair, as individual modules can be simply replaced immediately and debugged later. The use of vertically mounted modules on a common backplane improves packing efficiency, resulting in a smaller probe package, while providing flow paths for forced air cooling. The design also minimizes the distance between the sensor interconnection and signal conditioning resulting in reduced parasitic effects.

Measurement of EQS sensors is accomplished by the excitation of a drive electrode, while measuring the voltage level of the excitation and simultaneously measuring the short-circuit current of the sensing electrodes. In this configuration, the probe provides an accurate voltage signal to the instrument for measurement, which is related to the excitation voltage at the drive electrode. The signal conditioning electronics provides virtually grounded inputs for the sensing electrodes, which emulates a short circuit terminal condition. The conditioning electronics also converts the short circuit current to an amplified voltage signal which is supplied to the impedance instrument.

In order to ultimately arrive at the correct MUT properties, the transimpedance (transadmittance) data produced by the instrument must be a precise measurement of the sensors terminal response. However, the measurement instrumentation is composed of many electrical components, each of which has some finite tolerance on their specifications. Therefore, although one could utilize these components' values to relate measurements to actual sensor terminal values, one would expect some error. In addition, there are opportunities for non-expected parasitic affects to enter the measured value, further degrading the measurement accuracy. To compensate for all of these possible effects, some form of calibration based on measurements of a known value is necessary.

Figure 28:
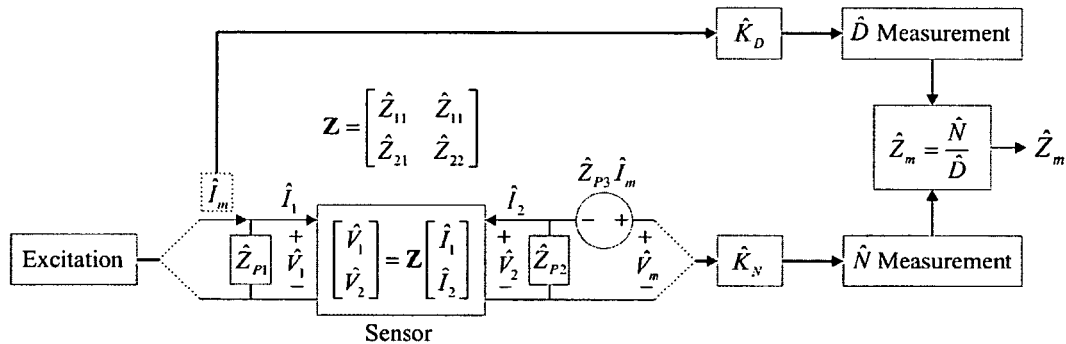
FIG. 28 shows a schematic diagram of possible sources of measurement error for MQS sensors.

In order to provide a calibration method which is robust over a wide measurement range without requiring an excessive number of different calibration measurements, a model which sufficiently describes the sources of corruption is required. FIG. 28 shows one such model that includes various sources of measurement error. The need for a large scale calibration stems from tolerance limitations on the electrical devices composing the measurement system. In order to arrive at the correct measured value $\hat{D}$ for the actual current $\hat{I}_m$, a complex scale factor $\hat{K}_D$ is introduced, which is in general a function of frequency. Here it is assumed that the transfer relation between the measured current and the actual current is simply a linear relation and the errors are manifested in a deviation in the scale factor from the one which would be calculated using expected component values. In a similar manner, a complex frequency dependent scale factor $\hat{K}_N$ is introduced to arrive at the correct measured value $\hat{N}$ for the voltage $\hat{V}_m$. In addition to the errors introduced by component uncertainty, additional electrical parasitics may be of significance. Some system parasitics will be compensated for by the previously mentioned scale factors while others, which produce offsets or influence the measurement in a way that is dependent on MUT properties, must be handled separately.

Three possible sources of parasitic effects are shown FIG. 28. Impedances $\hat{Z}_{P1}$ and $\hat{Z}_{P2}$ represent parasitics which affect the measured sensor response in a way that is dependent on the MUT. This is due to the fact that their "loading" effects are located in close proximity to the sensor, before active electrical buffering is provided, and therefore they interact with the MUT dependent input and output impedances of the sensor. Parasitic transimpedance $\hat{Z}_{P3}$ represents a coupling between the excitation current and measured signal not included in the ideal model of the sensor. This occurs in the vicinity of the sensor before measured signals have been sufficiently amplified, where achieving perfect isolation can be difficult, and is due to physical limitations of making electrical connections to sensor windings. Although some portion of this type of parasitic may actually be MUT dependent, it is assumed as a constant here.

To compensate for these corrupting affects, the circuit represented in FIG. 28 can be analyzed. Since the self-impedance of the primary and secondary winding is MUT dependent, it is only possible to directly undo the effects of $\hat{Z}_{P1}$ and $\hat{Z}_{P2}$ to arrive at $\hat{Z}_{12}=\hat{Z}_{21}$, with knowledge of the MUT properties. However, the MUT properties are in general unknown at this point, since the calibrated measurement data will be used for the purpose of obtaining MUT properties. Therefore the following new MUT dependent quantity is defined, which utilizes parasitic quantities and sensor transimpedance matrix values.

$$\hat{Z}_S \equiv \frac{\hat{V}_2}{\hat{I}_m} = \frac{\hat{Z}_{12}\hat{Z}_{P1}\hat{Z}_{P2}}{(\hat{Z}_{11}+\hat{Z}_{P1})(\hat{Z}_{22}+\hat{Z}_{P2})-\hat{Z}_{12}^2} \quad (245)$$

The parasitic quantities may be obtained empirically, based on electrical component specifications, and/or calculated with additional simulations. For a well designed system the effects of these parasitics should be "second order", and therefore not require extreme accuracy in their determination.

The quantity $\hat{Z}_S$ can be calculated for any set of MUT properties and therefore if a value of $\hat{Z}_S$ is known from measurement, proper application of inversion techniques can produce an estimate for the MUT properties. Therefore all that remains is to obtain a precise value of $\hat{Z}_S$ from the measured value $\hat{Z}_m$. The value $\hat{Z}_m$ is altered from $\hat{Z}_S$ by the remaining corrupting effects as:

$$\hat{Z}_m = \frac{\hat{N}}{\hat{D}} = \frac{\hat{K}_N}{\hat{K}_D}(\hat{Z}_S+\hat{Z}_{P3}) \quad (246)$$

By lumping together the scale factors, the following relation for recovering $\hat{Z}_S$ from the measurement is obtained:

$$\hat{Z}_S = \hat{K}_{cal}\hat{Z}_m - \hat{Z}_{P3} \quad (247)$$

For this calibration to be applied, it is still necessary to determine $\hat{K}_{cal}$ and $\hat{Z}_{P3}$. If two or more measurements are made for which the corresponding values of $\hat{Z}_S$ are known, then a best fit estimate of $\hat{K}_{cal}$ and $\hat{Z}_{P3}$ can be obtained by solving the following linear system:

$$\begin{bmatrix} \hat{Z}_m^{(1)} & -1 \\ \hat{Z}_m^{(2)} & -1 \\ \vdots & \vdots \end{bmatrix} \begin{bmatrix} \hat{K}_{cal} \\ \hat{Z}_{P3} \end{bmatrix} = \begin{bmatrix} \hat{Z}_S^{(1)} \\ \hat{Z}_S^{(2)} \\ \vdots \end{bmatrix} \quad (248)$$

Where similar parenthesized superscripts indicate the correspondence between a measured value ($\hat{Z}_m$) and a known value ($\hat{Z}_S$).

The model for possible measurement error sources focused on a MQS sensor represented by a two-port system, which would be equivalent to a single element sensor. Although many of the sensors are arrays, which are described by many port networks, an exact analysis which includes the effects of $\hat{Z}_{P1}$ and $\hat{Z}_{P2}$ would be cumbersome in this framework since the MUT properties for each sensor would need to be simultaneously estimated in a much larger inversion problem. However, for sensors with homogenous sensing elements, a reasonable approximation can often be made by independently analyzing each element with the assumption that all other elements are observing an identical MUT. The loading effects are then simply analyzed by multiplying the term $\hat{Z}_{12}$ in equation (245) by the total number of elements and dividing the total equation by the number of total elements. A set of calibration parameters $\hat{K}_{cal}$ and $\hat{Z}_{P3}$ are then determined independently for each sensing element.

For non-homogenous sensors with only a few element types, similar assumptions can be made, although it is necessary to utilize a sensor representation in FIG. 28, which contains an additional port for each element type. However, as mentioned previously, the effect of $\hat{Z}_{P1}$ and $\hat{Z}_{P2}$ should be "second order" in nature for a well designed system and therefore an overly complex analysis to produce higher order corrections to this "second order" error will generally not produce improvements due to other "second order" errors in the measurement system.

Obtaining measurements for which known values of $\hat{Z}_S$ exist is an issue that remains for the final calibration. One possible method would involve the use of electrical references, which can simulate the terminal response of a sensor and which have known values with sufficient accuracy. Though this is a method which is used for the calibration of some measurement equipment, it has some disadvantages. References with compatible terminal response values would be necessary for each probe configuration due to various sensor terminal response value ranges, which would require many references. Additional work is also required to maintain the integrity of the electrical references, further requiring sufficiently accurate methods for characterizing the references to be available. When references are scarce due to cost or availability, calibrations which can easily be performed regularly before measurement, are more likely to be skipped during practical use, lowering measurement performance.

The use of independent electrical references can be avoided by utilizing the sensor as the electrical reference. If the agreement between the response predicted by numerical simulation, and the actual response is sufficient, the requirement of a separate method for characterizing electrical calibration references is avoided. Furthermore, by using the sensor, which will ultimately be used in the measurement, during the calibration process, some degree of self-compensation for possible manufacturing variability and unmodeled effects is achieved. This self-compensation can assist in avoiding the need for exact characterization and calibration of every sensor used for measurement.

In order to determine the values for $\hat{K}_{cal}$ and $\hat{Z}_{P3}$, at least two measurements with two corresponding known responses with sufficient independence are required. One possible choice is referred to as an "Air/Shunt" calibration. In this case, one of the measurements is carried out in air, for which the predicted response depends on sensor geometry, sensor fabrication materials, and the MUT. Since the MUT is composed of air, it has electrical properties that are established with good precision and therefore introduces minimal error in the calibration. The shunt part of the calibration is accomplished with a modified or specially fabricated variation of the sensor. The shunt is designed to maintain an excitation that is consistent with the actual sensor, while the sensing windings are decoupled from the measurement system resulting in the known value $\hat{Z}_S$ being zero.

Although this type of calibration is often the most convenient and repeatable, it may not always provide a sufficient amount of calibration precision over the desired frequency range for which sensor use is desired. This is a shortcoming of the simplicity of the model used to represent possible sources of systematic measurement error. Several errors sources are not exactly compensated for by the linear scaling corrections, or the constant assumption of the parasitic $\hat{Z}_{P3}$. These sources include additional sensing element to excitation coupling which is not modeled exactly and non-linearity within the measurement system. Unfortunately, obtaining the correct model for some of these error sources is difficult. Also, constructing a very complex model with too many parameters is undesired, since the number of calibration measurements required would make the calibration operation cumbersome.

An approach to dealing with these types of errors is to utilize a calibration which contains measurements that are local to the desired region of operation for the specific measurements that require the additional precision. The same mathematics for the calibration is applied, although the assumption is that some of the non-linear errors can be locally corrected by the estimated parameters $\hat{K}_{cal}$ and $\hat{Z}_{P3}$. For the calibration measurements to be local to the ultimate measurements, they will need to be performed with a reference MUT that has properties known to a sufficient accuracy and similar to the MUT under investigation. This type of calibration is referred to as a "reference calibration", due to the use of MUTs with known properties. Since at least two measurements are still required, either MUTs with different properties are required, or a property such as the distance from the sensor to the MUT can be altered in a known way.

The disadvantage of this type of calibration technique is the introduction of errors due to uncertainties in MUT properties. For example, the electrical properties of most metals have a temperature dependence. Even if sufficiently precise values of a metal's electrical properties are known, a lack of compensation information for temperature can introduce error. Additionally references may have spatially varying properties, which may also be anisotropic and therefore the sensor response will be dependent on sensor's location and rotation. There is also generally some uncertainty in the liftoff (exact distance from the sensor to the MUT), which may be dependent on contact pressure. However, many of the repeatability errors introduced can be overcome by repetitive measurement or by careful control of the calibration measurement. Errors due to uncertainty in absolute values of the references are often of less importance since many times the goal of a measurement may be to characterize one MUT with respect to another of approximate known value.

Figure 29:
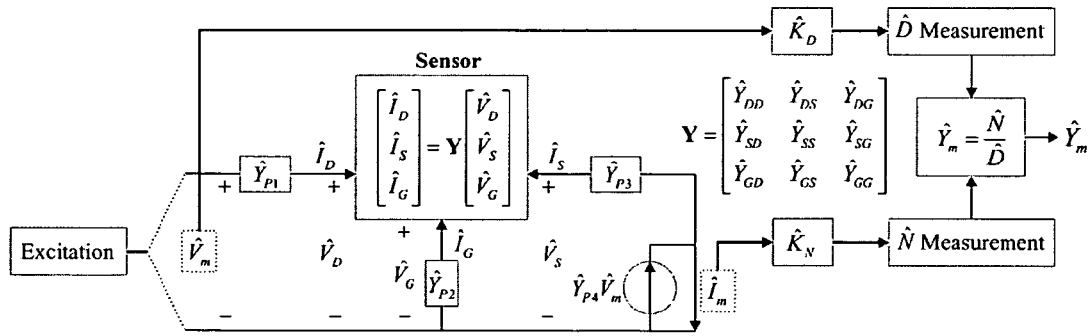
FIG. 29 shows a schematic diagram of possible sources of measurement error for EQS sensors.

A model, which is analogous to the MQS model for sources of measurement error, is presented for the EQS system in FIG. 29. The possible measurement error sources include parasitic excitation admittance $\hat{Y}_{p1}$, parasitic ground plane admittance $\hat{Y}_{p2}$, parasitic sense electrode admittance $\hat{Y}_{p3}$, parasitic coupling $\hat{Y}_{p4}$, errors in excitation measurement gain $\hat{K}_D$, and errors in sensing element signal measurement gain $\hat{K}_N$. The complex scale factors which contain the effects of uncertainties in electrical component specifications are again introduced in the measurement of excitation and sensing signals. The single sensing element sensor is characterized by its complete three-port representation to allow for the possibility of non-ideal terminal constraints. The admittances of several possible series parasitics are shown and represented by $\hat{Y}_{p1}$, $\hat{Y}_{p2}$, and $\hat{Y}_{p3}$, while parasitic coupling between the excitation signal and measured sense electrode currents are represented by $\hat{Y}_{p4}$.

Many of the parasitics shown can often be ignored, due to both the typical frequency of operation and the sensor/MUT configurations encountered. Since the sensor is usually not placed in direct electrical contact with the MUT, in addition to the MUT usually being significantly more insulating than the materials from which the sensor's electrodes and interconnections are fabricated, series parasitics $\hat{Y}_{p1}$, $\hat{Y}_{p2}$ and $\hat{Y}_{p3}$ can generally be ignored. This is due to the essentially infinite admittance of the parasitics as compared to the sensor admittances which include series capacitance in the coupling between electrodes. Although, at high frequencies the admittances of the sensor continue to increase, while inductive effects in electrical connections can cause these parasitic admittances to decrease; this is not the typical mode of operation. The parasitic quantity $\hat{Y}_{p3}$ is also ignored due to the virtual ground provided by the active electronics in the measurement of $\hat{I}_m$, which results in a high admittance to the ground reference.

When these parasitics are ignored, only $\hat{K}_N$, $\hat{K}_D$, and $\hat{Y}_{p4}$ affect the measurement of the sensor's response. The relationship between the sensors excitation $\hat{V}_D$ and sense electrode current $\hat{I}_S$ is also simplified by the resulting terminal constraints. The measured transadmittance can then be related to the sensor's response as:

$$\hat{Y}_m = \frac{\hat{N}}{\hat{D}} = \frac{\hat{K}_N}{\hat{K}_D}(\hat{Y}_{DS} + \hat{Y}_{P4}) \qquad (249)$$

By lumping together complex scale factors, the sensor response can be determined from the measurement as:

$$\hat{Y}_{DS} = \hat{K}_{cal}\hat{Y}_m - \hat{Y}_{P4} \qquad (250)$$

where $\hat{K}_{cal}$ and $\hat{Y}_{P4}$ can be determined from calibration measurements and solving the following linear system:

$$\begin{bmatrix} \hat{Y}_m^{(1)} & -1 \\ \hat{Y}_m^{(2)} & -1 \\ \vdots & \vdots \end{bmatrix} \begin{bmatrix} \hat{K}_{cal} \\ \hat{Y}_{P4} \end{bmatrix} = \begin{bmatrix} \hat{Y}_{DS}^{(1)} \\ \hat{Y}_{DS}^{(2)} \\ \vdots \end{bmatrix} \quad (251)$$

The similar parenthesized superscripts indicate the correspondence between measured responses $\hat{Y}_m$ and known responses $\hat{Y}_{DS}$. Methods of obtaining these known values are similar to those previously described for MQS sensors. Calibration models for multiple sensing electrode sensors follows in a manner similar to those described for multiple sensing element MQS sensors. However, when the parasitics $\hat{Y}_{p1}$, $\hat{Y}_{p2}$ and $\hat{Y}_{p3}$ are ignored, this is simply handled by determining unique values of $\hat{K}_{cal}$ and $\hat{Y}_{P4}$ for each sensing element.

An understanding of the errors in the impedance measurement and their dependency on instrument settings and other factors is important for both predicting measurement capability and intelligently optimizing measurement parameters (e.g., frequency, sensor configuration, measurement duration). These impedance errors can be lumped into two primary groups: uncertainty error and bias error. This bias error can also be called a systematic error. Uncertainty errors are manifested in the deviation of a single measurement from the expected value which would be obtained as the mean of an infinite number of measurements, while bias errors represent the deviation of this expected value from the true value.

The concept of uncertainty error is similar to that of measurement precision or repeatability. In quantifying this type of error it is important to consider the time scale over which the quantification applies. For example, one may consider only the deviations from the expected value, which are observed within several hours. This however may not be representative of the deviations that may be observed over several days or months. Any type of error which is not truly constant may be considered a contributor to uncertainty error.

Since the calibration techniques utilized (discussed elsewhere) are generally of sufficiently short duration that they can be repeated on the order of each hour, between measurements, this interval defines at least one time scale of interest for evaluating uncertainty errors. In this case it would generally be assumed that the calibration process would compensate for the larger uncertainty errors that may be observed over larger time scales. However, other factors, such as calibration repeatability due to setup error and errors in determining the expected value of the measurement for calibration, would result in some bias error variability. Nonetheless, uncertainty errors will generally be considered here over time scales on the order of an hour.

There are many causes of uncertainty error on this time scale which include sources such as: thermal noise in electronics, jitter in oscillators, and ambient electromagnetic fields (EMF). Although some of the errors induced by these sources could theoretically be accounted for if their instantaneous exact values were known, this is generally not possible since their values are time-varying in a nondeterministic way and cannot be independently measured. However, the cumulative structure of the uncertainty error resulting from these sources is easy to evaluate by taking a sufficiently large sample of measurements, while keeping the expected value of the measurement constant.

Bias error is comparatively more difficult to evaluate than the uncertainty error since the true value is often not exactly known. Also, no number of repeated measurements (under constant conditions) will give any better estimate of the true value, such that the bias error can be better evaluated (although the estimate of the expected value is improved). Bias errors also tend to be more dependent on the true value of the measurement, than uncertainty error, which can often be described by a constant distribution under certain conditions. This is due to the fact that they are often caused by non-linear effects (it is assumed that linear bias errors are dealt with during calibration), such as: non-linear electronic device transfer functions, unmodeled parasitics, and manufacturing errors in sensor parameters. Since bias errors can only be quantified against an assumed true value, they are not focused on in this analysis, though they are the ultimate measurement limitation, when measurement duration is not limited.

The uncertainty error in the measured impedance (for the following discussion, impedance will be used generically in place of transimpedance and transadmittance) is due to the uncertainty error in the variables used in its calculation, which are found in (244). Since the impedance is complex, it represents two functions of random variables, one corresponding to the real part and one corresponding to the imaginary part. Each of the random variables involved in the expression for the impedance can be broken up into an expected value plus a noise component as:

$$\hat{X}_{DN} = \hat{K}_{cal} \frac{(\overline{N}_r + \tilde{N}_r) + j(\overline{N}_i + \tilde{N}_i)}{(\overline{D}_r + \tilde{D}_r) + j(\overline{D}_i + \tilde{D}_i)} \quad (252)$$

Where $\hat{X}_{DN}$ represents either the complex transimpedance or transadmittance between drive and sensing element, $N_r$ and $N_i$ are the real and imaginary parts of the complex amplitude representation of the measured signal from any channel, $D_r$ and $D_i$ are the real and imaginary parts of the complex amplitude representation of the measured excitation, the over-bar indicates the expected value, and the tilde indicates a noise component.

The noise is assumed to result in an incremental change in the measured value $\hat{X}_{DN}$ from its expected value such that equation (252) can be linearized with respect to the noise quantities as:

$$\hat{X}_{DN} = \hat{K}_{cal} \left[ \frac{\overline{N}_r + j\overline{N}_i}{\overline{D}_r + j\overline{D}_i} + \left( \frac{\overline{D}_r}{\overline{D}_r^2 + \overline{D}_i^2} \right) \tilde{N}_r + \right.$$
$$\left( \frac{\overline{D}_i}{\overline{D}_r^2 + \overline{D}_i^2} \right) \tilde{N}_i + \left( \frac{(-\overline{D}_r^2 + \overline{D}_i^2)\overline{N}_r - 2\overline{N}_i\overline{D}_r\overline{D}_i}{(\overline{D}_r^2 + \overline{D}_i^2)^2} \right) \tilde{D}_r +$$
$$\left( \frac{(\overline{D}_r^2 - \overline{D}_i^2)\overline{N}_i - 2\overline{N}_r\overline{D}_r\overline{D}_i}{(\overline{D}_r^2 + \overline{D}_i^2)^2} \right) \tilde{D}_i + j \left( \left( \frac{-\overline{D}_i}{\overline{D}_r^2 + \overline{D}_i^2} \right) \tilde{N}_r + \right.$$
$$\left( \frac{\overline{D}_r}{\overline{D}_r^2 + \overline{D}_i^2} \right) \tilde{N}_i + \left( \frac{(-\overline{D}_r^2 + \overline{D}_i^2)\overline{N}_i + 2\overline{N}_r\overline{D}_r\overline{D}_i}{(\overline{D}_r^2 + \overline{D}_i^2)^2} \right) \tilde{D}_r +$$
$$\left. \left. \left( \frac{(-\overline{D}_r^2 + \overline{D}_i^2)\overline{N}_r - 2\overline{N}_i\overline{D}_r\overline{D}_i}{(\overline{D}_r^2 + \overline{D}_i^2)^2} \right) \tilde{D}_i \right) \right] \quad (253)$$

If the noise sources are assumed to be independent random variables and the standard deviation of the real and imaginary parts of the noise component of the signal are assumed equal with a value $\sigma_N$ and the standard deviation of the real and imaginary noise components of the measured excitation are assumed equal with a value $\sigma_D$, then the variance for both the real and imaginary components of $\hat{X}_{DN}$ can be expressed as:

$$\sigma_X^2 = |\hat{K}_{cal}|^2 \left[ \frac{1}{|\hat{D}|^2} \sigma_N^2 + \frac{|\hat{N}|^2}{|\hat{D}|^4} \sigma_D^2 \right] \quad (254)$$

The assumption of independence for the random variables is reasonable for noise sources such as thermal noise since the random variables are either from different signal paths or measured at an independent time, in which case one would not expect any correlation. Other noise sources such as ambient EMF may create instantaneous noise components in the random variables which may be correlated, however in practice it is expected that these noise sources would only be significant in the random variables representing the sensing element signal measurement. Assuming this ambient EMF is not greatly structured (e.g., synchronized with the sensor excitation) no significant correlation should be observed. Other correlation, which may be present in the random variables, such as an increase in the magnitude of the excitation signal, resulting in an increase in the magnitude of the measured signal are automatically cancelled in the calculation of impedance. The assumption of equal variance between real and imaginary components for the signal and for the measured excitation is based on the fact that identical signal paths are utilized in their measurement.

In order to test the assumptions used in arriving at (254) and validate the relation, experimental instrument data was taken. Although the obvious approach to this task may seem to proceed by directly measuring $\hat{D}$ and $\hat{N}$ in order to obtain the standard deviation quantities $\sigma_D$ and $\sigma_N$ under various conditions, this is not the approach taken. This is due to the fact that some of the variability in the components of $\hat{D}$ and $\hat{N}$ is due to changes that tend to cancel in the calculation of $\hat{X}_{DN}$. For example, a slight change in the excitation level, over the time interval during which the standard deviation characterization is made, may result in an increase in the standard deviation of $\hat{D}$ and $\hat{N}$ but may not change the standard deviation of $\hat{X}_{DN}$ due to the canceling changes in $\hat{D}$ and $\hat{N}$. To avoid the additional complexities of trying to separate out correlated changes, which do not induce noise in the impedance, direct calculations of $\sigma_D$ and $\sigma_N$ from $\hat{D}$ and $\hat{N}$ are avoided.

Figure 30:
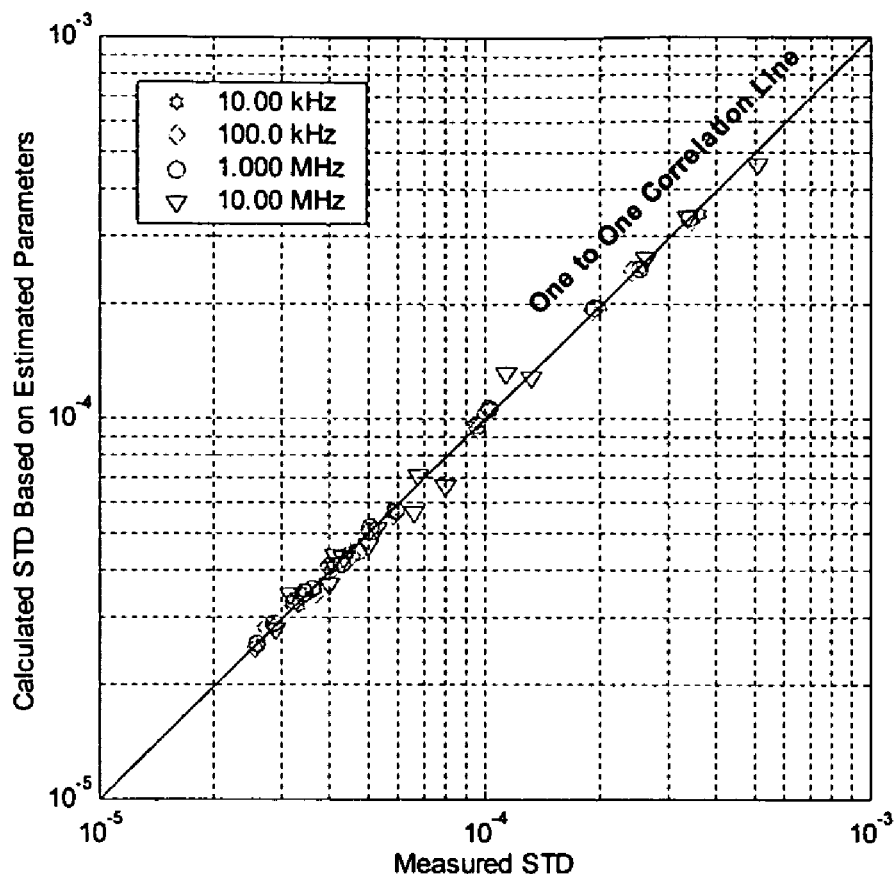
FIG. 30 shows a correlation plot between the actual measured impedance standard deviation and the calculated standard deviation.

The approach utilized, evaluated $\sigma_X$ (based on 1000 data points) at various operating points consisting of different values of $|D|$ and $|N|$ for which a best fit $\sigma_D$ and $\sigma_N$ were calculated for the set of data, when used in (254). The success can then be judged by the correlation between the measured $\sigma_X$ and that calculated using the best fit parameters $\sigma_D$ and $\sigma_N$. The measurements were conducted with the instrument excitation directly connected to the input ports for the measurement of $\hat{D}$ and $\hat{N}$, such that the instrument noise levels could be established in the absence of noise sources present in the sensor and probe. Since the absolute value of $\sigma_X$ will ultimately depend on the impedance to which the instrument is calibrated, presented values are effectively normalized by setting $\hat{K}_{cal}=1$. The noise sources may have nonuniform spectral energy distributions and therefore measurements were made at four frequencies, covering three decades in frequency, for which unique values of $\sigma_D$ and $\sigma_N$ were estimated as shown in Table 4. The standard deviations at each frequency were determined as the best fit for data taken under several operating conditions with the instrument excitation directly connected to input channels, such that no probe or sensor noise was introduced. From this table it is useful to note that $\sigma_D$ and $\sigma_N$ are relatively close, which is expected since the measurement paths for the signals represented by $\hat{D}$ and $\hat{N}$ are equivalent in structure for the instrumentation configuration used in this experiment. FIG. 30 shows the quality of the correlation between actual standard deviation and calculated standard deviations. The results appear to be sufficiently accurate for approximating the noise behavior over a wide range of operating conditions.

TABLE 4

Estimated standard deviation of instrument input measurement noise at four frequencies.

| | 10.00 kHz | 100.0 kHz | 1.000 MHz | 10.00 MHz |
|---|---|---|---|---|
| $\sigma_N$ | 2.12E−03 | 2.09E−03 | 2.12E−03 | 1.99E−03 |
| $\sigma_D$ | 2.22E−03 | 2.13E−03 | 2.14E−03 | 2.66E−03 |

With parameters estimated for a system composed of the instrument only, it is desired to now include the noise sources found in the probe and the sensor. Measurements were conducted for one possible probe and sensor configuration under various operating conditions in order to characterize the impedance noise and estimate best fit parameters. The operating conditions were varied by changing both the MUT and the excitation level of the sensor, so that measurements over a wide range of operating conditions were obtained. The resulting best fit parameters are found in Table 5. The standard deviations at each frequency were determined as the best fit for data taken with an instrument connected to a probe and sensor under various operating conditions imposed by changing MUT properties and sensor excitation. The standard deviations $\sigma_D$ and $\sigma_N$ are no longer comparable due to the different signal paths associated with excitation measurement as compared to sensing element signal measurement. Comparison of the fitted parameters with those obtained for the instrument only, demonstrates the increase in noise resulting from the probe and sensor. It can also be seen that the increase was dominantly in the element signal measurement as opposed to the excitation measurement. This is somewhat expected due to the lower signal levels present on the sensing elements, which require greater amplification, as compared to the excitation signals for which measurement requires less amplification. Similar to FIG. 30, the agreement between the actual standard deviations of the measurements and those calculated from (254) is again sufficient to justify the assumptions made and allow a method of estimating noise levels under different operating conditions.

TABLE 5

Estimated standard deviation of input measurement noise at two frequencies with one possible MQS probe and sensor combination.

| | 1.000 MHz | 10.00 MHz |
|---|---|---|
| $\sigma_N$ | 5.43E−02 | 1.45E−02 |
| $\sigma_D$ | 5.78E−03 | 4.28E−03 |

The techniques described, up to this point, can be repeated for different probe and sensor combinations to build a library of parameters $\sigma_D$ and $\sigma_N$ over a range of frequencies. However, it seems reasonable that the noise sources for electronically similar probes, which differ simply by gain settings, may be constant, if corrected for the gain differences. This would allow the characterization of a single implementation of a probe type to be used for other probes of the same type with different gain configurations. In practice this would reduce the work associated with characterizing each probe type and act as a model for estimating noise for performance simulations.

Figure 31:
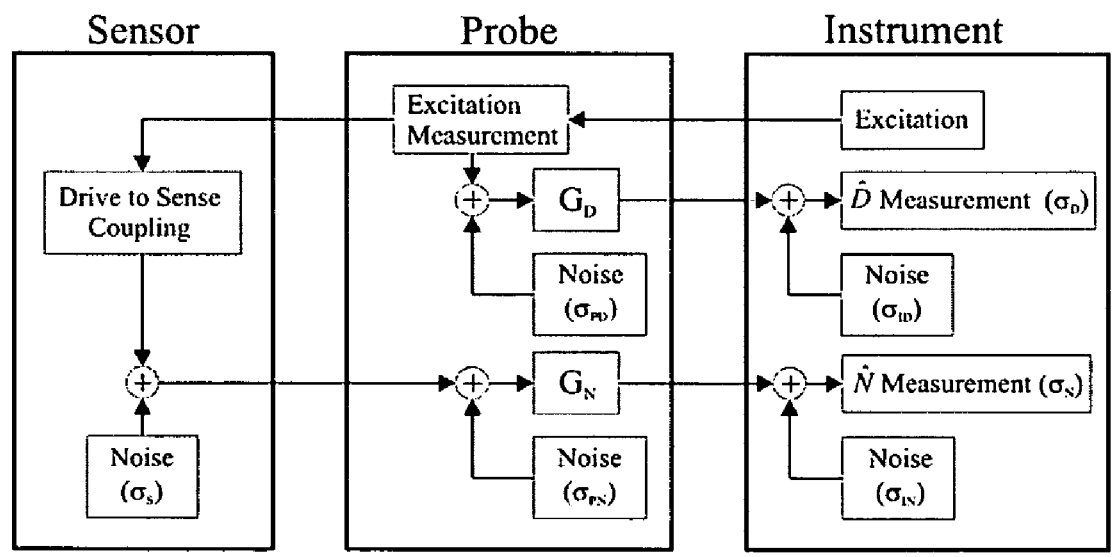
FIG. 31 shows a simplified schematic of noise sources within the measurement system composed of an instrument, probe, and sensor.

The schematic of FIG. 31 represents a simplistic representation of possible noise sources within the system composed of the instrument, probe, and sensor. Although the noise sources are distributed throughout the various internal stages of the instrument and probe, they have been lumped at the inputs of each. Each noise source is characterized by its standard deviation and is assumed to have a mean value of zero. Since the instrument configuration is generally not altered, the exact distribution of noise sources is not important here. However, for the probe, alteration of the gain will generally require alteration of the distribution of gain among the distributed noise sources within the probe. To be exact, this would require a model more closely matching the implementation of the probe. Although, as an approximation, most of the noise can be attributed to the input stage, for which the simplified model can be applied. Based on the simplified model for the noise sources, equations for the standard deviation of the noise in the measured excitation and sensing element signal can be determined as follows:

$$\sigma_D^2 = G_D^2 \sigma_{PD}^2 + \sigma_{ID}^2 \quad (255)$$

$$\sigma_N^2 = G_N^2 (\sigma_S^2 + \sigma_{PN}^2) + \sigma_{IN}^2 \quad (256)$$

where $\sigma_{ID}$ and $\sigma_{IN}$ are the standard deviations of the internal instrument noise sources, $\sigma_{PD}$ and $\sigma_{PN}$ are the standard deviations of the internal probe noise sources, $\sigma_S$ is the standard deviation of noise pickup up at the sensor sensing element, and $G_D$, $G_N$ are probe gain settings.

The quantities $\sigma_{ID}$ and $\sigma_{IN}$ are equivalent to $\sigma_D$ and $\sigma_N$ which were obtained with the instrument configured without a probe and sensor as described previously, since the other noise sources are removed and therefore equal to zero. If it is assumed that the noise introduced by the sensor is negligible or at least constant for the sensors of interest, then it is not necessary to determine $\sigma_S$ and $\sigma_{PN}$ independently, instead they can remain lumped together; otherwise additional measurements would be necessary. Based on knowledge of the gain settings utilized, $\sigma_D$ and $\sigma_N$ which were obtained with the probe type of interest, the unknowns $\sigma_{PD}$ and $\sqrt{\sigma_{PN}^2 + \sigma_S^2}$ are easily obtained. The gain configurations used in the measurements, along with calculated parameters are summarized in Table 6, along with the gain configurations utilized in the measurements from which these parameters were obtained.

TABLE 6

Summary of parameters for estimating the noise in similar probes with different gain configurations.

|  | 1.000 MHz | 10.00 MHz |
| --- | --- | --- |
| $G_N$ | 1500 | 1500 |
| $G_D$ | 2.3 | 5.1 |
| $\sigma_{IN}$ | 2.12E-03 | 1.99E-03 |
| $\sigma_{ID}$ | 2.14E-03 | 2.66E-03 |
| $(\sigma_S + \sigma_{PN})^{1/2}$ | 3.62E-05 | 9.56E-06 |
| $\sigma_{PD}$ | 2.33E-03 | 6.59E-04 |

In addition to the standard deviation of the error in the measured impedance, the structure of the error is also of interest. This structure is best described by a probability distribution function (PDF) which contains information about the likelihood of obtaining a certain amount of error in the measurement. An understanding of the distributions produced by the measurement instrumentation can serve as both an indicator of anomalous instrument behavior and also be used to motivate the choice of properties of inversion methods utilized.

Although the exact PDF is difficult to obtain, since it would require extensive knowledge of the underlying PDFs found throughout the instrument, a reasonable approximation can be obtained empirically due to the speed and simplicity with which a large number of measurements can be made. The effect of varying instrument settings, including frequency and measurement duration, on the PDFs is also of interest. Measurements were performed with the instrument only (excitation directly connected to measured excitation and channel signal inputs), at four frequencies including 10.00 kHz, 100.0 kHz, 1.000 MHz, and 10.00 MHz and over a wide range of measurement durations. One thousand data points were included in the approximation of the PDF for each frequency and measurement duration. Additional measurements were performed at a single frequency of 1.000 MHz with both a probe and sensor attached over a range of measurement durations.

Figure 32:
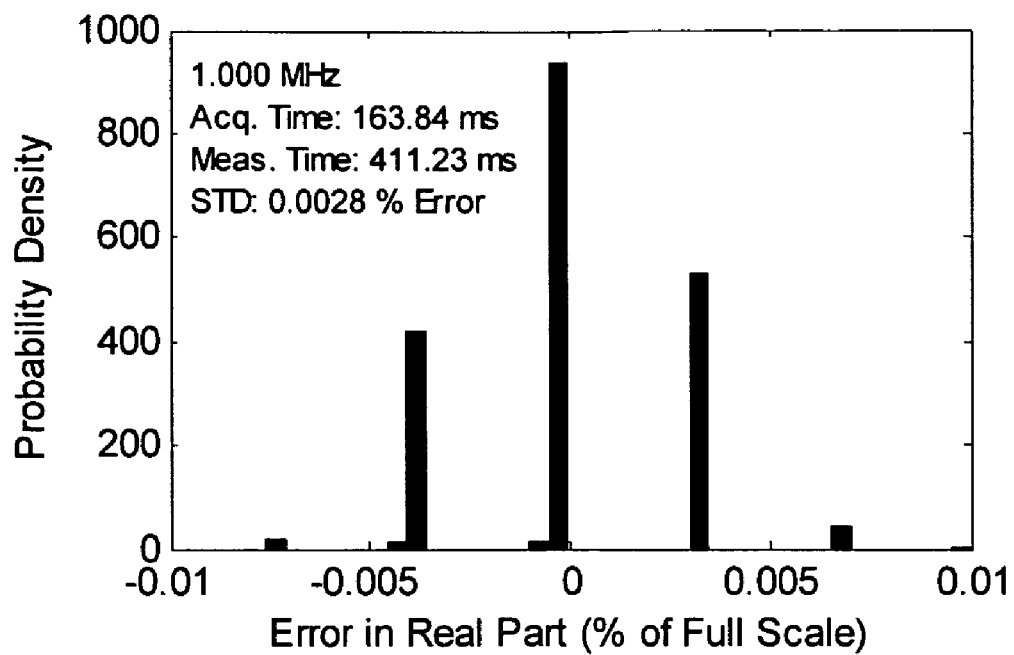
FIG. 32 shows a probability density of measurement error at 1.00 MHz with impedance analyzer configured for direct measurement of its excitation output.

A representative measurement result for the instrument only is presented in FIG. 32. The PDFs for both the real and imaginary part of the impedance measurement are similar. The distributions have an envelope which can be considered similar to that of a normal distribution for all frequencies and measurement durations. As the measurement duration time is reduced the distributions also tend to "fill in." The distributions appear increasingly discrete at larger measurement durations, due to the reduction of noise to the point where quantization effects of the digitization process are pronounced.

Figure 33:
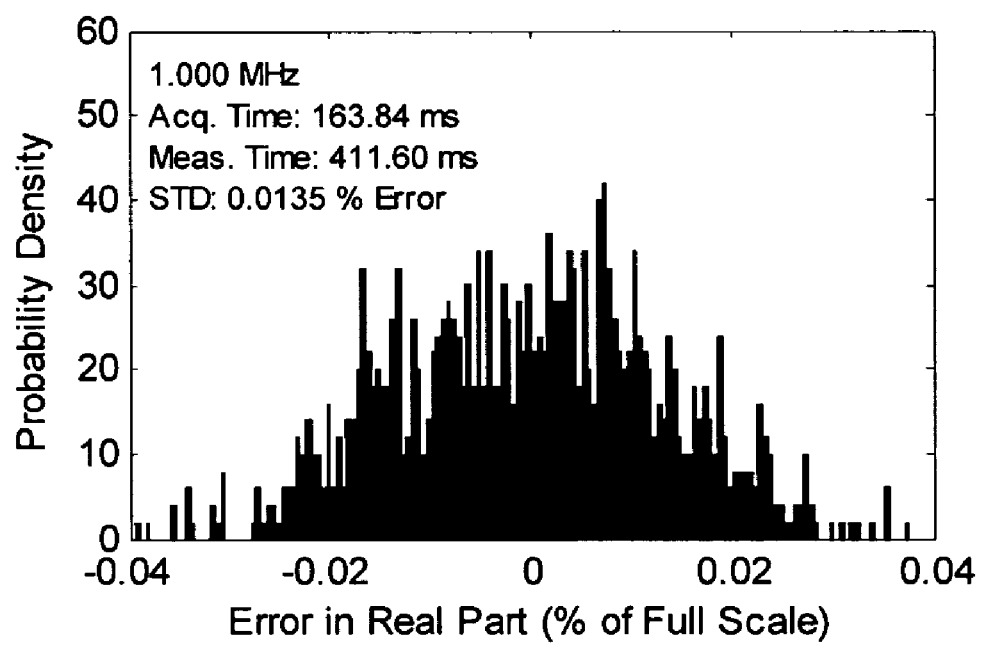
FIG. 33 shows a probability density of measurement error at 1.00 MHz with impedance analyzer connected to one possible MQS probe and sensor configuration.

The characterization of the PDF with the inclusion of a probe and sensor is presented in FIG. 33. Again, the distribution appears to match that of a normal distribution. The quantization effects that were apparent with the instrument only configuration are no longer observable at the scale used, due to the increase in the standard deviation, although there are some vertical quantization artifacts due to the choice of binning intervals used for the histogram approximating the PDF (more measurements or wider bins would tend to smooth the envelope without changing the general shape).

Figure 34:
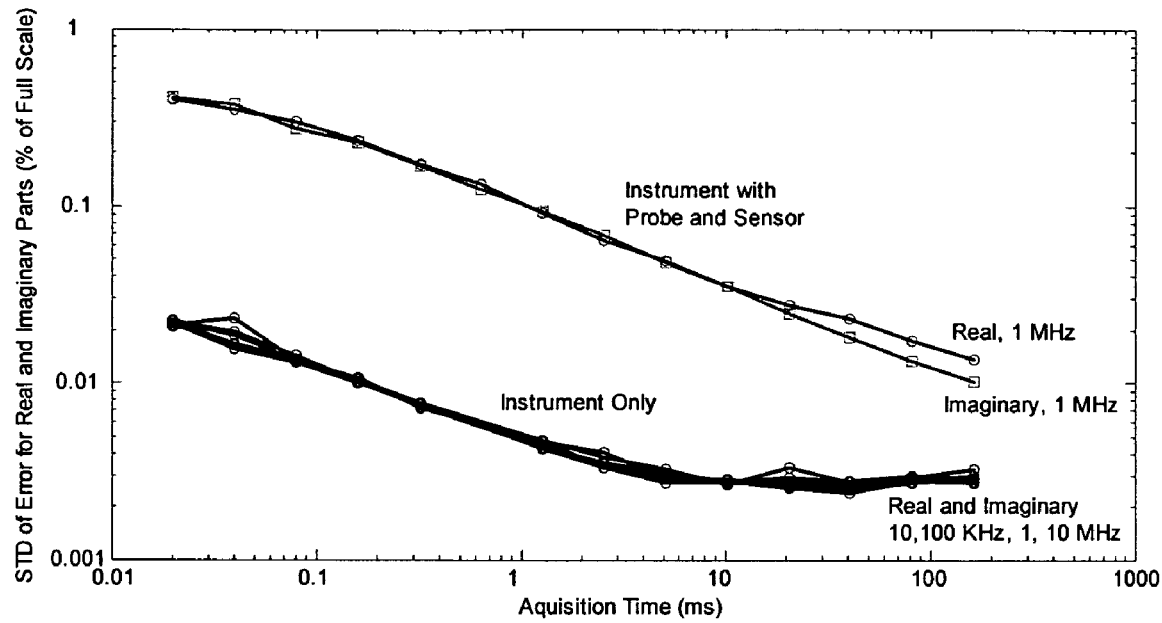
FIG. 34 shows a plot of the standard deviation of error against data acquisition time.
Figure 35:
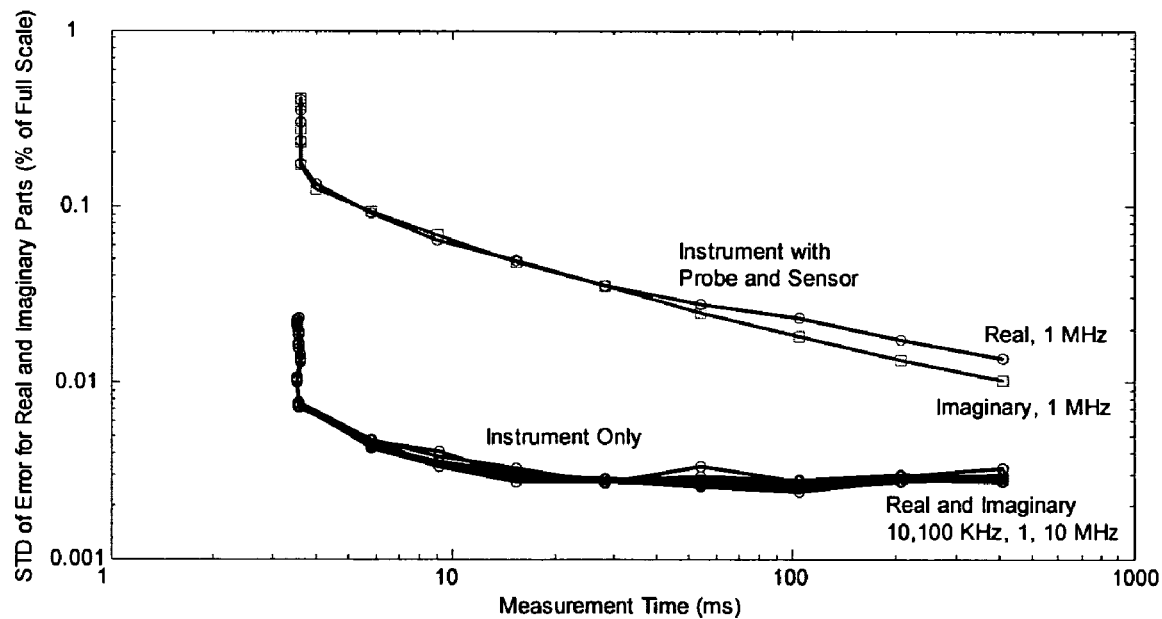
FIG. 35 shows a plot of the standard deviation of error against the measurement acquisition time.

The width of the PDF tends to decrease with measurement duration, as would be expected due to the narrower pass band which results in the frequency domain, thereby limiting the noise energy in the measurement. Since the width of the distribution can be characterized by the standard deviation of the measurements, a comparison of the standard deviation of the impedance as a function of both the actual acquisition duration and of the total measurement duration is presented in FIGS. 34 and 35. The total measurement time is always greater than the acquisition time for a specific duration setting, due to other "overhead" which exists in the measurement cycle. This becomes very apparent at the shorter duration settings, where the measurement time appears to reach a lower limit, although the standard deviation continues to increase. Also significant is the similarity of the curves for the instrument only configuration over the wide frequency range. The inclusion of the probe and sensor chosen for this analysis can be seen to introduce almost an order of magnitude increase in noise over the best performance expected by the instrument. Additionally, in the case of the instrument only, a diminishing reduction in the standard deviation with increased duration setting is observed at larger measurement durations. These curves can be used to judge the relative tradeoff between measurement uncertainty and measurement duration for use in measurement optimization.

This type of instrument noise or error can influence the resulting error in the estimates of the material properties. The following discussion concerns a method for predicting the influence of both impedance bias errors and impedance noise errors on estimated material properties. The determination of impedance noise errors based on a combination of empirical measurements and noise models is discussed later, while methods of approximating bounds for the impedance bias errors are investigated herein. The use of these impedance errors to predict errors in estimated material properties is useful in optimizing the sensor geometry for specific material configurations. It is also useful in gauging the errors that may be expected in the measurement of material properties before proceeding with physical measurements.

Two possible approaches for predicting the material property errors are apparent. The first follows from the inversion operation which must eventually be performed in order to convert measured impedance data into the desired material properties by utilizing the ability to simulate the sensor's terminal response. The inversion may be performed by using inverse interpolation methods based on a database of simulated responses for two unknown problems, or one of many optimization or root searching algorithms for problems with greater numbers of unknowns. For the material configuration of interest the measured impedance, absent of any measurement errors, can be determined using the sensor models. If this impedance were supplied to a robust inversion algorithm the estimated material properties should be nearly identical to those used in the forward simulation. If the bias error in the impedance measurement is known then this error can be added to the simulated impedance, which is absent of any measurement errors. Inversion of this new impedance produces estimated material properties which contain some amount of error relative to those used in the forward simulation. Therefore in the case of a bias error which is exactly known, the material property error is estimated.

However, impedance bias errors are unlikely to be known exactly since this would allow measured impedance values to be corrected for the bias error and perfect measurement accuracy to be achieved. More likely some bounds will be available for the impedance bias errors. A single impedance measurement consists of two components while a measurement utilizing multiple impedance measurements will contain many components, each which may have a value falling within specified error bounds about the true value. Due to the relation between the material properties and the impedance, the bounds on estimated material property errors will not necessarily occur when the individual component errors are at bounding values. In order to then find the error bounds on material properties, the space containing the bounded impedance values must be searched. This is not desired since it will usually require many inversions, which may be computationally time consuming. This is especially true if the material errors are to be evaluated for a range of sensor parameters and material configurations in which this process must be repeated for each variation.

Determination of the noise errors in the estimated properties can also be accomplished using this approach of inverting impedance values with errors introduced. Noise type impedance errors are characterized by a statistical measure describing the distribution of the measurements about the expected value such as its standard deviation. The distribution of the estimated material properties due to this impedance distribution is desired. This can be accomplished by creating an artificial data set of impedance values with a distribution matching the impedance noise specification. Inversion of this data set produces a set of material property estimates for which the distribution of each provides an approximation of the noise due to the impedance noise. For this approximation to be useful a sufficiently sized data set must be used, which again requires computational effort.

The second method for predicting the errors in the estimated material properties arises by making the simplifying assumption that the dependence of the impedance on material properties can be approximated as locally linear for impedance variations on the scale of the impedance errors. Since a closed form expression is not available for the relation between the sensor's impedance and the material properties, calculation of the approximation accuracy for a given sensor with a given material configuration requires direct comparison between the approximated values and exact values. In practice this would require additional simulations to be performed and require additional computational time. No direct investigation of this approximation accuracy is made here; instead the general usefulness of the technique is relied on as an indicator.

By making the assumption of linearity, the material property errors can generally be evaluated more efficiently. Rather than requiring a database of simulations or repetitive inversions, which may be iterative and require many simulations, only enough sensor simulations are required to determine the partial derivatives of the impedance with respect to material properties. These partial derivatives can be calculated with two simulations per material property for each frequency. The partial derivatives are then placed in a matrix to form the Jacobian. The inverse of this matrix can be found using linear algebra techniques and contains all of the information needed to evaluate both bias and noise errors from the impedance errors. This approach to evaluating the material property errors is used here.

The linear approximation for the relationship between the real and imaginary components of the sensor impedance and the measured material properties can be written as:

$$\begin{bmatrix} \Delta Z_1^r \\ \Delta Z_1^i \\ \vdots \\ \Delta Z_M^r \\ \Delta Z_M^i \end{bmatrix} = J \begin{bmatrix} \Delta P_1 \\ \vdots \\ \Delta P_N \end{bmatrix} \quad (257)$$

where J is the Jacobian which is defined as:

$$J \equiv \begin{bmatrix} \frac{\partial Z_1^r(P_1, \ldots, P_N)}{\partial P_1} & \cdots & \frac{\partial Z_1^r(P_1, \ldots, P_N)}{\partial P_N} \\ \frac{\partial Z_1^i(P_1, \ldots, P_N)}{\partial P_1} & \cdots & \frac{\partial Z_1^i(P_1, \ldots, P_N)}{\partial P_N} \\ \vdots & \vdots & \vdots \\ \frac{\partial Z_M^r(P_1, \ldots, P_N)}{\partial P_1} & \cdots & \frac{\partial Z_M^r(P_1, \ldots, P_N)}{\partial P_N} \\ \frac{\partial Z_M^i(P_1, \ldots, P_N)}{\partial P_1} & \cdots & \frac{\partial Z_M^i(P_1, \ldots, P_N)}{\partial P_N} \end{bmatrix} \quad (258)$$

and where $P_n$ is the value of the nth material property, $\Delta P_n$ is a change in the nth material property, and $\Delta Z_m^r$ and $\Delta Z_m^i$ are the changes in the real and imaginary parts of the mth impedance measurement due to the changes in the material properties, respectively.

The partial derivatives in (258) are approximated numerically by simulating the sensor response with all properties at their nominal values except for the property for which the particular partial derivative is with respect to. This property is perturbed about its nominal value by a small amount $\delta/2$ from which the resulting impedance is used to calculate the partial derivatives for the real and imaginary components by:

$$\frac{\partial Z_m^r(P_1, \ldots, P_N)}{\partial P_1} = \mathcal{R}\left\{\frac{Z_m(P_1, \ldots, P_n + \delta_n/2, \ldots, P_N) - Z_m(P_1, \ldots, P_n - \delta_n/2, \ldots, P_N)}{\delta_n}\right\} \quad (259)$$

$$\frac{\partial Z_m^i(P_1, \ldots, P_N)}{\partial P_1} = \mathcal{I}\left\{\frac{Z_m(P_1, \ldots, P_n + \delta_n/2, \ldots, P_N) - Z_m(P_1, \ldots, P_n - \delta_n/2, \ldots, P_N)}{\delta_n}\right\}$$

The quantity $\delta/2$ must be chosen with some care such that it is small enough that the resulting partial derivative is a good approximation of that at the nominal property values and also sufficiently large that numerical errors in the simulation do not dominate the result.

The multiple impedance measurements which may be present in (257) and (258) have several possible sources. Most often for MQS sensors these measurements are produced by a fixed set of material properties at different excitation frequencies. However, these multiple measurements may also result from sensors in which multiple sensing elements are utilized to provide additional material property information rather than surface image resolution. Also possible is the inclusion of multiple impedance measurements resulting from altering the material configuration. The material configuration is generally altered by changing either a measured material property or by changing a material property for which the value is specified. In the case of a specified value, the partial derivatives which correspond to a given impedance measurement must utilize the correct specified properties during their numberical evaluation. In the case of a changed measured property, a new measured property $P_{N+1}$ must be introduced in (257) to represent this property value in the alternate material configuration. Strictly speaking, this requires that the partial derivatives be evaluated about a set of N+1 properties. However, since two of the measured properties correspond to the same physical property, but during different measurements at different times, only the value of the measured property associated with the impedance measurement is utilized in the partial derivative calculation. Also, since the value of a measured property during a different measurement at a different time does not affect the current measurement, the partial derivatives with respect to measured properties that represent values during alternate configurations are equal to zero. Many combinations of the aforementioned sources for multiple impedance measurements are possible in the estimation of material properties and can be included in the error analysis by their incorporation into the linearized relation as described.

The next step in evaluating the material property errors requires that the inverse of the matrix J be found. It is worth noting that J will often be rectangular such that the system is overly defined or at least appears to be, based on the size of the matrix. The situation in which the matrix size represents an underfined solution is avoided since it is does not correspond to a useful inversion problem when ultilmately estimating material properties from real data. The fact that the matrix is rectangular in the overly defined system requires that the standard inverse for a square matrix be replaced by the pseudo inverse. In either case the inverse or the pseudo inverse will be denoted as such that:

$$\begin{bmatrix} \Delta P_1 \\ \vdots \\ \Delta P_N \end{bmatrix} = J^{-1} \begin{bmatrix} \Delta Z_1^r \\ \Delta Z_1^i \\ \vdots \\ \Delta Z_M^r \\ \Delta Z_M^i \end{bmatrix} \quad (260)$$

In the case when J is overly defined, the solution vector containing the changes in material properties which results from the vector of impedance changes using (260) does not necessarily solve (257) exactly. Rather the least squares solution is determined such that the sum of the squares of the errors in each component of the impedance vector which results by substituting the solution vector of material properties into (257) is minimized. Therefore the relative magnitude of the impedance for each impedance measurement included plays a role in determining the amount of emphasis that the material property solution puts on minimizing the error in that particular impedance measurement. Since the magnitude of the impedance produced by the sensor simulation does not correspond to the relative importance of the measurement, additional weighting is typically applied in the final inversion techniques used and is therefore mimicked here for error predictions. The weighting is applied to (257) such that:

$$W \begin{bmatrix} \Delta Z_1^r \\ \Delta Z_1^i \\ \vdots \\ \Delta Z_M^r \\ \Delta Z_M^i \end{bmatrix} = WJ \begin{bmatrix} \Delta P_1 \\ \vdots \\ \Delta P_N \end{bmatrix} \quad (261)$$

where:

$$W = \begin{bmatrix} w_1 & 0 & 0 & \cdots & 0 \\ 0 & w_1 & 0 & \vdots & \vdots \\ 0 & 0 & \vdots & 0 & 0 \\ \vdots & \vdots & 0 & w_M & 0 \\ 0 & \cdots & 0 & 0 & w_M \end{bmatrix} \quad (262)$$

The weights $w_1 \ldots w_M$ in (262) are duplicated to correspond with the real and imaginary components of each impedance measurement. Typically if the error in each impedance measurement is sufficiently characterized, the weights are inversely proportional to the corresponding errors. These errors may be described by the standard deviation of the measured impedance in the case that the noise errors are dominant or in terms of absolute error bounds if the bias errors are dominant.

In the case when the errors are not well known, the full scale impedance range of the measurement instrument can be utilized. As a starting point it may be assumed that the instrument will exhibit errors that are constant when expressed in terms of the full scale measurement range. A more optimal emphasis on each measurement is then accomplished by setting each weight equal to the reciprocal of the full scale impedance range of the instrument which is associated with the specific measurement. Since the impedance measurement instrumentation described later is capable of dynamically adjusting its full scale range to the sensor at each frequency and since the maximum sensor impedance for an MQS sensor is often determined by its impedance in air, the determination of the weights can often be simplified. The impedance of the sensor in air is essentially inductive and therefore this impedance is proportional to the excitation frequency. The weights can then be set equal to the reciprocal of the excitation frequency. When the weight matrix is included, the inverse $J^{-1}$ in (260) is calculated in terms of the Jacoabian of (258) and the weight matrix as:

$$J^{-1} = (WJ)^{-1} W \qquad (263)$$

As mentioned earlier the inverse or pseudo inverse can be evaluated using standard linear algebra techniques.

In order to calculate material property error bounds resulting form bias errors in the impedance the method in which the impedance error bounds are specified must now be decided. Two possible candidates are: specifying error bounds on each individual component of each impedance measurement or specifying error bounds on the magnitude of the error for each complex impedance measurement. Since the actual structures of the bias errors have not been investigated in depth and since both methods are relatively easy to apply, both are presented.

The method that will be used for determining bounds on material property errors is based on the case when the specified bias error bounds produce the largest material property error. In the case when impedance bounds are specified individually for each component, the material property errors are calculated by:

$$\begin{bmatrix} P_1^e \\ \vdots \\ P_N^e \end{bmatrix} = \mathrm{abs}(J^{-1}) \begin{bmatrix} Z_1^{er} \\ Z_1^{ei} \\ \vdots \\ Z_M^{er} \\ Z_M^{ei} \end{bmatrix} \qquad (264)$$

where the superscript e indicates that a quantity is a bound and the abs( ) function is the element-wise absolute value of the matrix argument. It should be noted that the error bounds represent the bounding deviations from the actual value and are required to be positive values such that the possible deviations about the true value are symmetric.

In the case when the impedance bounds are specified in terms of the magnitude of the error in each complex measurement quantity some additional computation is necessary. In this case the error results in possible impedance values that lie in a circular region which is centered about the true value within the complex impedance plane. The bias error in the nth property due to the error in the impedance of the mth measurement is described by:

$$P_n^e = z^e (J_{n,2m-1}^{-1} \cos\theta + J_{n,2m}^{-1} \sin\theta) \text{ for } z^e \leq Z_m^e, \\ 0 \leq \theta < 2\pi \qquad (265)$$

where $Z_m^e$ is the magnitude error bound and $P_n^e$ is the property error at a radius $z^e$ and angle $\theta$ within the circular region. The location of the largest property error is desired since this is the criteria being utilized for evaluation property bounds. Since the error $P_n^e$ is directly proportional to the radius, the maximum error occurs on the circumference of the error circle in the impedance plane when $z^e = Z_m^e$. The angle that maximizes the property error can be determined and when substituted into (265) results in:

$$P_n^e = Z_m^e \sqrt{(J_{n,2m-1}^{-1})^2 + (J_{n,2m}^{-1})^2} \qquad (266)$$

The error bounds for each property due to the impedance error bounds of all measurements described in terms of magnitude bounds on the complex error are determined by:

$$P_n^e = \sum_{m=1}^{M} Z_m^e \sqrt{(J_{n,2m-1}^{-1})^2 + (J_{n,2m}^{-1})^2} \qquad (267)$$

Impedance measurement noise analysis demonstrates several important characteristics that simplify the prediction of the resulting material property errors. The probability distribution functions found from the measurement of both the real and imaginary components of the impedance were shown to be very similar to normal distributions. The standard deviation of these distributions then provides a rather complete characterization of the noise. It was also shown that under fixed conditions (e.g., excitation frequency, material configuration, and instrument gain settings), the standard deviations of the real and imaginary components are nearly the same. Reasonable results in predicting impedance noise levels under varied conditions also demonstrated that the noise in the real and imaginary components of the impedance could be treated as uncorrelated in the instrumentation being utilized. Due to the previously described results, the noise in estimated material properties can be predicted from the standard deviation of the components for each impedance measurement by:

$$P_n^\sigma = \sqrt{\sum_{m=1}^{M} \sigma_m^2 ((J_{n,2m-1}^{-1})^2 + (J_{n,2m}^{-1})^2)} \qquad (268)$$

where $P_n^\sigma$ is the standard deviation of the predicted noise in the nth property and $\sigma_m$ is the standard deviation of the noise in the real and imaginary parts of the mth impedance measurement.

Often in attempting to measure properties of multi-layered material structures the number of material properties can become too large for each to be independently estimated. In these cases it becomes necessary to specify as many of the known properties as possible. The value of these specified properties is only known to a finite level of accuracy due to variations in the material or due to accuracy of the method in which they are measured. Therefore it is desirable to predict the extent to which these errors will influence the unknown properties which are estimated from sensor measurements.

Although the direct simulation and inversion technique discussed earlier as a possible method for error analyis could be used in incorporating these types of error sources, the method resulting from linearization is continued. The determination of the estimated property errors due the the specified property errors then requires the Jacobian based on the partial derivatives of the impedance measurements with respect to the specified properties, such that:

$$\begin{bmatrix} \Delta Z_1^r \\ \Delta Z_1^i \\ \vdots \\ \Delta Z_M^r \\ \Delta Z_M^i \end{bmatrix} = S \begin{bmatrix} \Delta p_1 \\ \vdots \\ \Delta p_L \end{bmatrix} \qquad (270)$$

where $\Delta p_l$ is a change in the lth specified material property and the Jacobian is defined as:

$$S \equiv \begin{bmatrix} \frac{\partial Z_1^r(P_1,\ldots,P_N)}{\partial p_1} & \cdots & \frac{\partial Z_1^r(P_1,\ldots,P_N)}{\partial p_L} \\ \frac{\partial Z_1^i(P_1,\ldots,P_N)}{\partial p_1} & \cdots & \frac{\partial Z_1^i(P_1,\ldots,P_N)}{\partial p_L} \\ \vdots & \vdots & \vdots \\ \frac{\partial Z_M^r(P_1,\ldots,P_N)}{\partial p_1} & \cdots & \frac{\partial Z_M^r(P_1,\ldots,P_N)}{\partial p_N} \\ \frac{\partial Z_M^i(P_1,\ldots,P_N)}{\partial p_1} & \cdots & \frac{\partial Z_M^i(P_1,\ldots,P_N)}{\partial p_L} \end{bmatrix} \quad (271)$$

The partial derivatives of this matrix can be approximated numerically using the methods described for evaluating J. The relation between changes in the specifed material properties and the estimated material properties can now be produced by substituting (270) into (260)

$$\begin{bmatrix} \Delta P_1 \\ \vdots \\ \Delta P_N \end{bmatrix} = J^{-1}S \begin{bmatrix} \Delta p_1 \\ \vdots \\ \Delta p_L \end{bmatrix} \quad (272)$$

The bounds for the estimated property bias error are evaluated for the case when the error bounds of the specified material properties produce the larges estimated property errors using:

$$\begin{bmatrix} P_1^e \\ \vdots \\ P_N^e \end{bmatrix} = \text{abs}(J^{-1}S) \begin{bmatrix} p_1^e \\ \vdots \\ p_L^e \end{bmatrix} \quad (273)$$

where $p_l^e$ is the error bound for lth specified material property. The standard deviation of the noise error in the estimated material properties is determined from the standard deviation of the noise in the specified properties using:

$$P_n^\sigma = \sqrt{\sum_{l=1}^{L} (p_l^\sigma)^2 (J^{-1}S)_{n,l}^2} \quad (274)$$

where $p_l^\sigma$ is the standard deviation of the error in the lth specified material property and $P_n^\sigma$ is the predicted standard deviation of the nth estimated material property.

These methods for predicting estimated property errors are now utilized to evaluate the performance of a representative MQS sensor design, although sensor arrays and EQS sensors could also be considered with these methods. A visual analysis of the terminal response, represented in the form of a measurement grid, was previously used to estimate general performance trends of the sensor in the presence of an infinite half-space MUT. The quantitative method discussed in the preceding section allows a more direct comparison of the performance at various frequencies and material configurations. It also avoids the visualization issues that arise when three or more material properties are unknown or when the material properties are determined using multiple impedance measurements.

The performance of the sensor will generally be analyzed for the specific material configuration of interest; the most basic measurement of the conductivity and lift-off of an infinitely thick uniform half-space of material is analyzed. The results will demonstrate the excitation frequency which is most optimal for a specific material configuration, in addition to the increase in error as the measurement frequency is altered from the optimal. The method in which this error analysis can be used to optimize sensor parameters is also demonstrated.

Since the errors associated with impedance measurement noise can often be reduced to a desired level by making either multiple or longer measurements, estimated property errors associated with bias errors in the impedance are investigated. However, these errors have yet to be determined and therefore an assumption of a constant full scale impedance error with respect to varying frequency will be applied. The full scale impedance is based on the sensor response when the MUT is composed of a non-permeable and nonconducting material such as air. This configuration is used to determine the full scale range since calibration of the instrumentation is often based on the sensor response in this configuration. A bounding bias error value of 0.1% of full scale is used in the analysis as a rough order of magnitude estimate. This allows error bounds in material properties to be plotted in terms of absolute quantities. The linearity of the analysis allows the property errors to be proportionally scaled to any other desired full scale error value.

Figure 36:
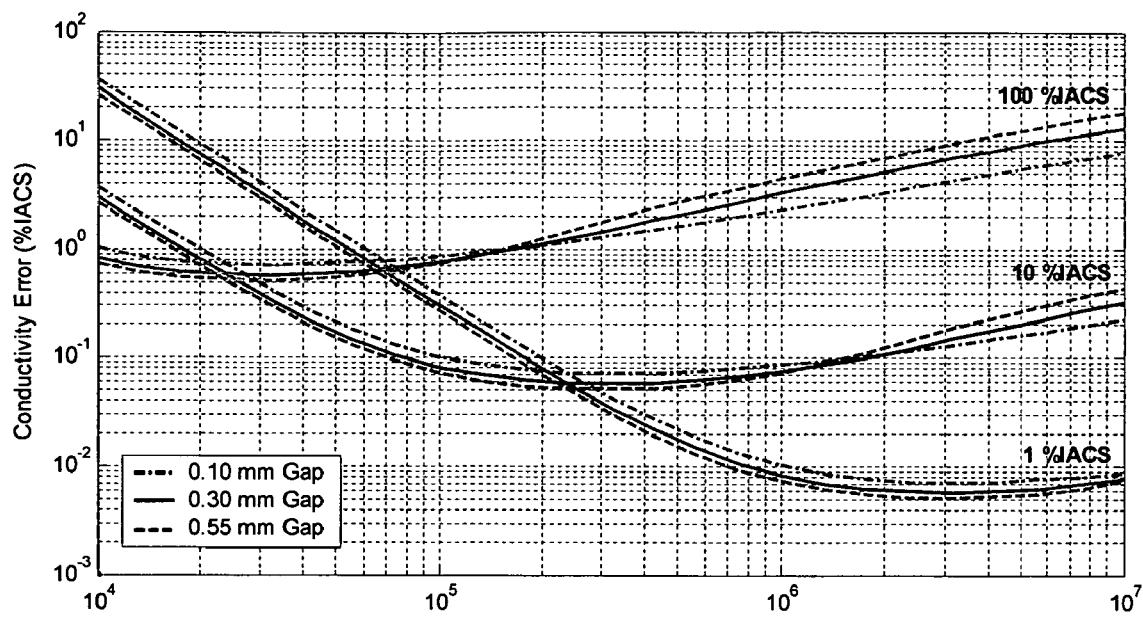
FIG. 36 shows a conductivity error plot of the simulated performance of an MQS sensor on an infinite half-space material at a 0.05 mm lift-off for various material conductivity values.
Figure 37:
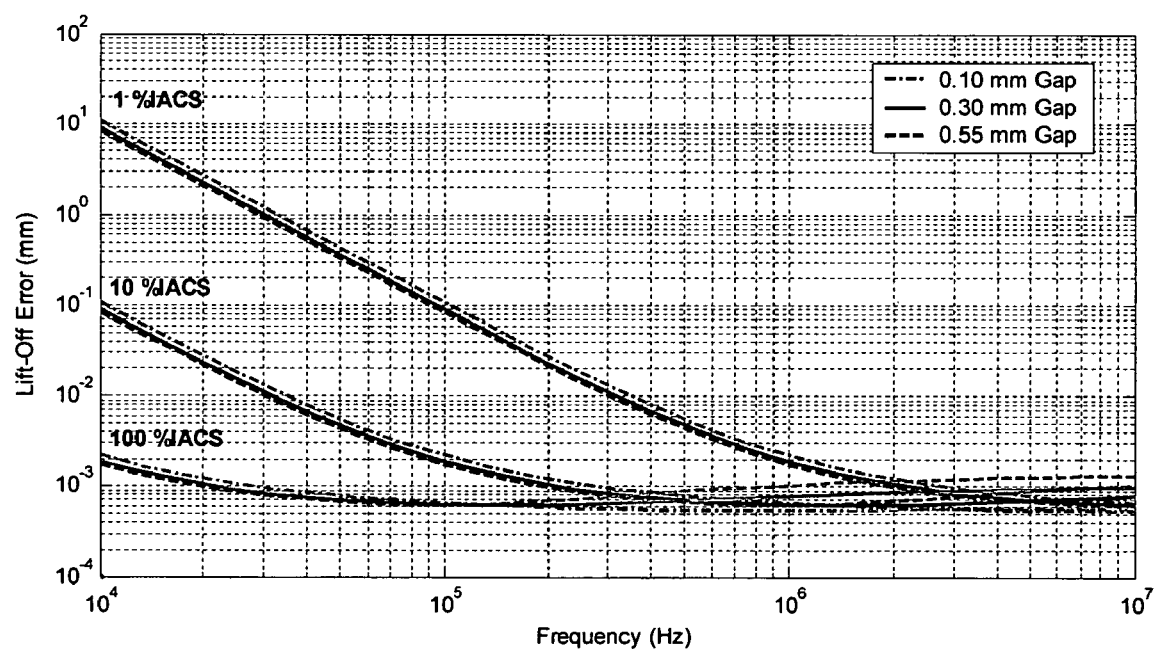
FIG. 37 shows a lift-off error plot of the simulated performance of an MQS sensor on an infinite half-space material at a 0.05 mm lift-off for various material conductivity values.

A representative frequency spectrum of the conductivity error is shown in FIG. 36 and lift-off error is shown in FIG. 37 for material conductivity values of 1% IACS (0.58 MS/m), 10% IACS (5.8 MS/m) and 100% IACS (58.0 MS/m). Error estimates are provided at two different sensor lift-off values of 0.05 mm (~0.002 in.), but similar results are obtained at a lift-off of 0.25 mm (~0.010 in.). The errors were calculated based on an assumed full scale impedance bias error of 0.1% at each frequency. For each material configuration the errors associated with the nominal sensor geometry, which has a 0.3 mm primary to secondary gap are shown in addition to the errors for cases in which this gap is altered to values of 0.10 mm and 0.55 mm. From these plots several conclusions about the performance of the sensor relative to material configuration and frequency can be made:

1. An optimal frequency which produces the minimal conductivity error exists for each conductivity value. The width and depth of the induced currents in the material are roughly related to the frequency and conductivity dependent skin depth. At sufficiently low frequency and conductivity values the superposition of opposing material currents produced by primary windings located a distance of $\lambda/2$ apart results in partial cancellations of net currents. The diminished intensity and diffuseness of the induced currents results in a smaller contribution to the flux linked by the secondary winding as compared to the primary winding, for which impedance errors result in greater estimated property errors. At sufficiently high frequency and conductivity values, the changes in the distribution of induced currents result in a diminished change in the flux linked by the secondary winding due to the relative distance from the induced currents as compared to the size of the current distribution. The optimal frequency exists when the induced current distribution, as perceived by the secondary windings, is both intense and rapidly changing with respect to conductivity changes. If the characteristic dimension of the induced currents is taken as two skin depths, then the frequency at which this quantity becomes comparable to half the spacing of primary windings with opposing currents (λ/4) appears to approximately predict the optimal frequency for each conductivity value.
2. The optimal frequency for each conductivity value is minimally dependent on the sensor lift-off for the lift-off range investigated. For the lift-off ranges investigated, the characteristic dimension of the current distribution is well approximated by the skin depth which is independent of lift-off.
3. Although the absolute conductivity error is different for each material conductivity value at the optimal frequency, the relative error is very similar. The skin depth within the material relative to geometric dimensions is important in determining the sensor performance. When the geometric dimensions of a given sensor are fixed, the absolute skin depth value is an important characteristic. For frequency and conductivity values which produce similar skin depth values, similar absolute changes in the skin depth result from similar relative changes in the conductivity.
4. Both conductivity and lift-off errors increases with increasing lift-off. The magnetic flux produced by the current distribution within the material becomes more diffuse and reduces the change in the flux linked to the secondary winding due to conductivity and lift-off changes. In addition, the intensity of the flux produced by the induced currents composes a smaller part of the total flux linked by the secondary winding as compared to the flux produced by the primary currents which are essentially independent of material properties.
5. As the excitation frequency is increased, lift-off errors become independent of the material conductivity values and approximately constant with frequency. At increased frequencies the induced current distribution has the approximate appearance of a surface current in comparison to other geometric parameters. The changes in this distribution due to increased frequency or conductivity do not significantly change the flux linked to the secondary windings. The lift-off errors then remain similar for further increases in frequency or conductivity.
6. Lift-off errors increase with decreasing frequency. The larger skin depth values associated with lower frequency result in the currents being distributed more deeply into the material. The additional average distance between the secondary windings and the induced currents reduces the contribution of the linked flux from the induced currents in comparison to the linked flux from primary currents.

Changes in the primary to secondary winding gap can be seen to alter the calculated errors from those in the nominal 0.3 mm case. Decreasing the gap tends to increase both the lift-off and conductivity errors except in the case of the higher conductivity and frequency values when the material is at a 0.05 mm lift-off. The most noticeable improvement can be found in the errors corresponding to the 100% IACS conductivity value. In this case the closer proximity of the secondary winding to the induced current distribution allows the changes in the distribution to have a greater impact on the flux linked to the secondary winding. The improvement occurs when the characteristic dimension of the distributions relative to the secondary distance is becoming small. The same behavior is not found at the greater lift-off value of 0.25 mm since the decrease in gap only creates a minor improvement to the secondary windings proximity to the induced currents. Rather, a greater error in produced due to the increase in linkages to the flux produced by the primary current. This increase in flux linkage is also responsible for the the increase in errors for the other frequency and material configurations.

The uniform conductivity half-space material analyzed here is one of the most basic material configurations. Though the analysis determined optimal measurement frequencies for the conductivity of materials with different conductivity values, the situation is somewhat artificial in that rarely is a truly uniform material present. The measurement frequency is then generally used as a control of the depth of interrogation of the material. However, the performance analysis here can easily be adapted to more complex material configurations.

Another important aspect of sensor performance includes the robustness of measurement accuracy with respect to manufacturing tolerances of the sensor. Due to the photolithographic process which is typically used to fabricate the sensors, one parameter of interest is the alignment of the windings which are located on different sensor layers. Manufacturing limitations result in a finite relative shift of the layer containing the primary windings with respect to the layer containing the secondary windings. Although it is possible to characterize these errors to some degree using an optical or other methods, it will be assumed that the misalignment is not accounted for. The scenario is that the misaligned sensor is used for air calibration of the instrument and measurements on the MUT, while sensor simulations for calibration and estimation of material properties utilize the nominal sensor geometry. The analysis to predict the outcome must determine the impedance bias errors by accounting for the calibration and measurement steps. The resulting bias error can then be utilized with the linear error analysis methods to predict the errors in estimated material properties.

The air calibration method was discussed with respect to the instrumentation. For this analysis, the measurement system will be considered ideal and therefore void of any parasitic impedance or transimpedance. The instrumentation is therefore calibrated by determining the complex calibration coefficient $\hat{K}_{cal}$ for each frequency such that the actual impedance is determined from the impedance measurement by the instrument using:

$$\hat{Z}_S = \hat{K}_{cal}\hat{Z}_m \tag{275}$$

A measurement of the shifted sensor with impedance $$\hat{Z}_{shift}^{air}$$

is calibrated to produce the impedance of the nominal sensor with impedance $$\hat{Z}_{nom}^{air}$$

by setting the calibration coefficient as:

$$\hat{K}_{cal} = \frac{\hat{Z}_{nom}^{air}}{\hat{Z}_{shift}^{air}} \tag{276}$$

The value $$\hat{Z}_{shift}^{air}$$

is produced by simulation of the sensor using shifted geometric parameters while the value of $$\hat{Z}_{nom}^{air}$$

is produced by simulation using the nominal parameters.

The impedance bias error for a specific material configuration can then be calculated by:

$$\hat{Z}_{bias} = \frac{\hat{Z}_{nom}^{air}}{\hat{Z}_{shift}^{air}} \hat{Z}_{shift}^{MUT} - \hat{Z}_{nom}^{MUT} \quad (277)$$

where $$\hat{Z}_{shift}^{MUT} \text{ and } \hat{Z}_{nom}^{MUT}$$

are produced by simulation using the corresponding sensor geometry for the specified material configuration. In preceding error analyses the impedance bias errors have been specied in terms of a bound on the error magnitude which constrained the impedance to a circular region in the complex plane about the exact value. In this case the error structure is completely predicted through simulation and therefore the actual complex value of the error is known. Equation (260) is then used to directly determine the errors in the estimated properties from the real and imaginary components of $\hat{Z}_{bias}$. Since the scenario for which the resulting errors are being analyzed utilizes the nominal sensor geometry in the parameter estimation stage of the measurement, the linearization required to produce J⁻ in (260) is completely based on this same nominal geometry.

Figure 38:
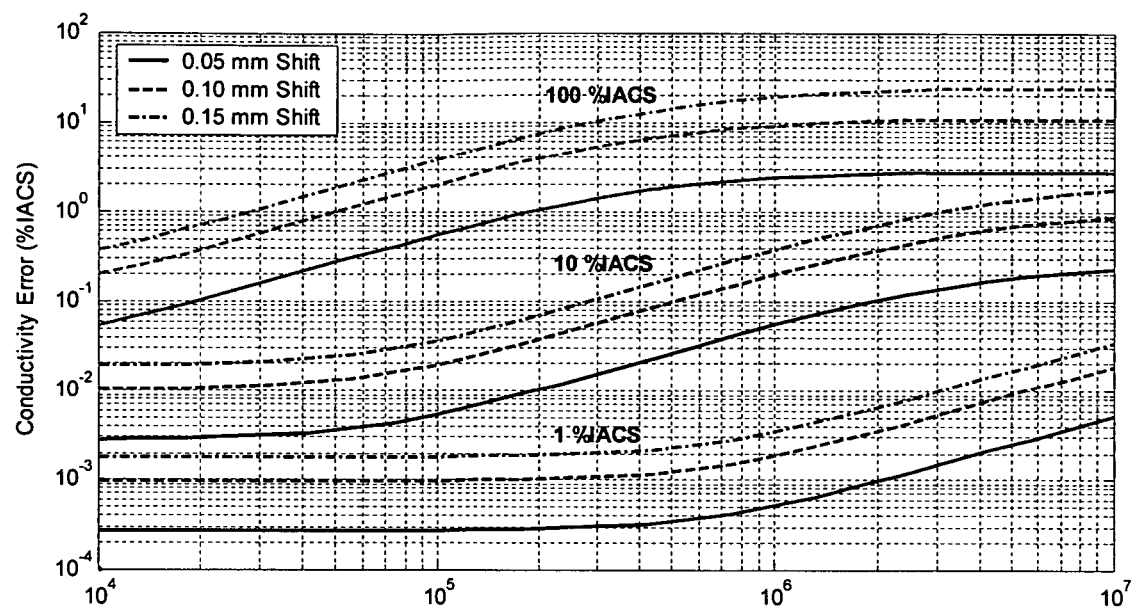
FIG. 38 shows a conductivity error plot of the simulated performance of an MQS sensor on an infinite half-space material at a 0.05 mm lift-off for various winding layer misalignments.
Figure 39:
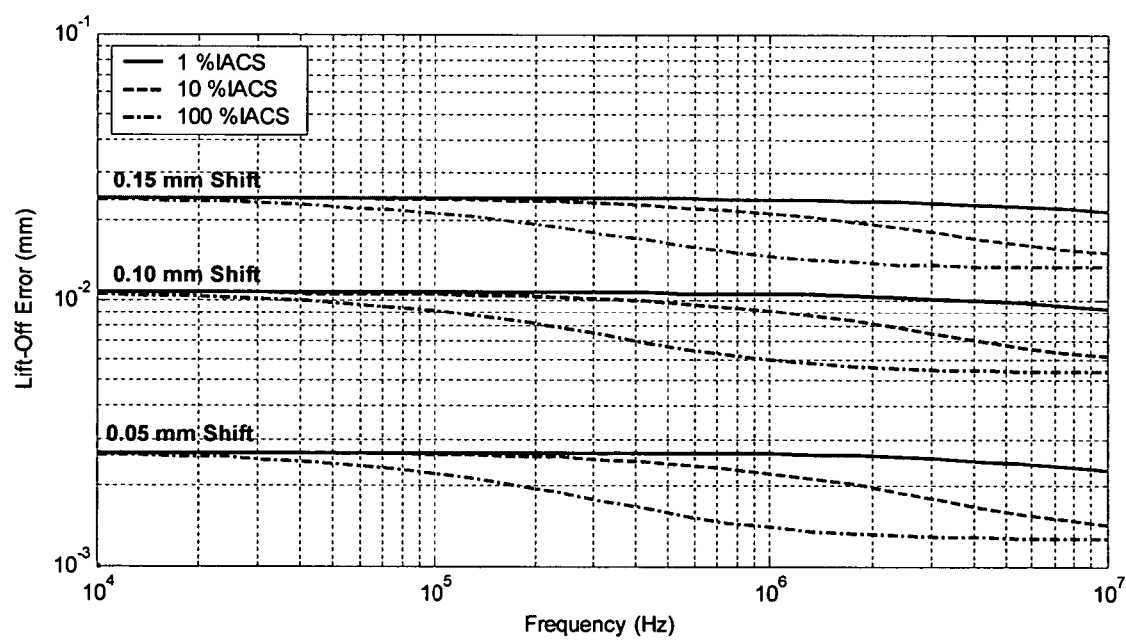
FIG. 39 shows a lift-off error plot of the simulated performance of an MQS sensor on an infinite half-space material at a 0.05 mm lift-off for various winding layer misalignments.

The conductivity and lift-off errors due to misalignment were evaluated for the uniform conductivity half-space at a lift-off of 0.05 mm. FIGS. 38 and 39 show the frequency dependence of these errors for misalignments values of 0.05 mm (~0.002 in.), 0.10 mm (~0.004 in.), and 0.15 mm (~0.006 in.). The errors are calculated assuming the air calibration and measurements are performed with the misaligned sensor, while the simulated impedance values required for calibration and parameter estimation are based on the unshifted sensor geometry. Note that although the impedance error $\hat{Z}_{bias}$ will produce property errors with positive or negative signs using (260), the absolute value has been taken in order to allow the logarithmic plots. These plots demonstrate the general trends of the errors such as apparent low and high frequency asymtotic conductivity error values and a low frequency lift-off error which is independent of frequency.

Although the uniform conductivity half-space can again be considered somewhat artificial, the method described here for analyzing estimated property errors can be applied to more complex configurations. In addition, a similar analysis for variations in other sensor parameters can be accomplished by altering the appropriate parameter(s) of the sensor in simulating $$\hat{Z}_{shift}^{air} \text{ and } \hat{Z}_{shift}^{MUT}.$$

This next discussion utilizes the previously presented results on the MQS models and the instrumentation and calibration methods for a single element sensor to assess measurement errors of material properties. For each of the major configurations material properties are altered to produce many additional configurations. Basic conductivity and lift-off measurements of thick materials which are assumed to have uniform conductivity are presented first. Comparison with typical property ranges found in literature will help to build confidence in the overall measurement system. The use of these measurements in estimating bounds for the impedance bias errors is then investigated. A more complex measurement problem involving three unknown material properties follows. One of the estimated properties of this measurement is a thickness which can easily be verified by a secondary measurement method. The error in measured thickness values are then predicted using the bias error bounds determined by a worst case method and an optimistic method to determine the most appropriate bounds. The final measurement configuration involves four unknown measurement properties and simulates a metal coating on metal substrate measurement problem. First consider conductivity measurements on uniform metals. These measurements focus on solid metal plates which will be modeled as having uniform electrical properties and as infinitely thick. Before proceeding with the measurements details and results it is worth reviewing the skin depth of several materials including those measured. The skin depth is calculated in the usual manner as $$\delta = \sqrt{\frac{2}{\omega\mu\sigma}}.$$

The excitation frequency range which will be used for the measurements spans from 10 kHz to 10 MHz. The materials measured include brass, aluminum (2024 alloy), aluminum (99% pure) and copper. The skin depth associated with these frequencies and materials ranges from 0.021 mm (1 mil=0.001 in.) to 1.296 mm (51 mils). Although the skin depth a is based on a uniform plane wave incident on a planar conductor of uniform conductivity, it provides a useful estimate as to the maximal depth to which the material may be excited. Since one skin depth corresponds to a single exponential decay of the fields and currents within the material, typically the fields and currents at depths greater than 3-5 skin depths can be assumed to have minimal or no influence on the measurement. The properties of the material greater than these depths therefore also can be neglected. As a result, the metal plates measured are not required to be infinitely thick; they are only required to be sufficiently thick such that the "missing" material does not influence the measurement.

Measurements on the metal plates were conducted using an MQS sensor design of FIG. 1. The instrumentation was calibrated using only measurements of the sensor in air and measurements of a shunt version of the sensor in addition to the simulated response for the sensor in air. Impedance data was taken at seven logarithmically spaced frequencies between 10 kHz and 10 MHz on each material. Measurements of each material were also made with the addition of one and two nonconducting shims, each with a nominal thickness of 1 mil (0.0254 mm), in order to vary the sensor lift-off from the surface of the metal plates. The unknown properties to be determined are the left-off and conductivity. These properties were used to create a database of sensor responses covering the expected range of material conductivity and lift-off by utilizing the model simulation methods described earlier. A single conductivity and lift-off value were then estimated from each impedance measurement at each frequency using the database of sensor responses and the measurement grids. Results for the conductivity are listed in Table 7 and the lift-off in Table 8.

TABLE 7

Conductivity measurements of a uniform MUT by a single element MQS sensor.

| Material | Reference Conductivity (% IACS) | Sample Thickness* (mils) | Additional Lift-Off (mils) | 10 kHz | 31.62 kHz | 100 kHz | 316.2 kHz | 1 MHz | 3.162 MHz | 10 MHz |
|---|---|---|---|---|---|---|---|---|---|---|
| | | | | | | Measured Conductivity (% IACS) | | | | |
| Copper | 100 | 187 | 0 | 100.4 | 100.2 | 100.0 | 100.0 | 99.9 | 100.9 | 87.5 |
| | | | 1 | 100.3 | 100.1 | 100.0 | 99.8 | 98.8 | 99.2 | 81.1 |
| | | | 2 | 100.0 | 100.1 | 99.9 | 99.5 | 97.7 | 97.6 | 75.4 |
| Aluminum | 60 | 30.5 | 0 | 57.0 | 59.3 | 59.2 | 59.3 | 59.5 | 60.3 | 54.5 |
| | | | 1 | 56.6 | 59.3 | 59.1 | 59.2 | 59.0 | 59.5 | 51.1 |
| | | | 2 | 56.7 | 59.2 | 59.0 | 59.0 | 58.5 | 58.7 | 48.1 |
| Aluminum (2024 Alloy) | 30 | 250 | 0 | 26.7 | 29.1 | 29.1 | 29.2 | 29.3 | 29.7 | 28.0 |
| | | | 1 | 26.5 | 29.1 | 29.1 | 29.1 | 29.2 | 29.5 | 26.7 |
| | | | 2 | 26.2 | 29.0 | 29.1 | 29.1 | 29.0 | 29.2 | 25.5 |
| Brass | 26 | 31.4 | 0 | 23.5 | 26.2 | 26.5 | 26.4 | 26.4 | 26.6 | 25.0 |
| | | | 1 | 23.0 | 26.2 | 26.4 | 26.4 | 26.3 | 26.4 | 24.0 |
| | | | 2 | 22.8 | 26.1 | 26.4 | 26.3 | 26.1 | 26.3 | 23.1 |

*Obtained by Micrometer Measurement

TABLE 8

Lift-off measurements of a uniform MUT by a single element MQS sensor.

| Material | Reference Conductivity (% IACS) | Sample Thickness* (mils) | Additional Lift-Off (mils) | 10 kHz | 31.62 kHz | 100 kHz | 316.2 kHz | 1 MHz | 3.162 MHz | 10 MHz |
|---|---|---|---|---|---|---|---|---|---|---|
| | | | | | | Measured Lift-Off (mils) | | | | |
| Copper | 100 | 187 | 0 | 1.10 | 1.12 | 1.12 | 1.12 | 1.11 | 1.11 | 1.08 |
| | | | 1 | 2.14 | 2.17 | 2.17 | 2.17 | 2.15 | 2.15 | 2.10 |
| | | | 2 | 3.20 | 3.25 | 3.24 | 3.24 | 3.22 | 3.22 | 3.15 |
| Aluminum | 60 | 30.5 | 0 | 0.59 | 1.03 | 1.05 | 1.05 | 1.05 | 1.06 | 1.03 |
| | | | 1 | 1.55 | 2.05 | 2.07 | 2.07 | 2.06 | 2.07 | 2.02 |
| | | | 2 | 2.62 | 3.10 | 3.12 | 3.13 | 3.11 | 3.12 | 3.04 |
| Aluminum (2024 Alloy) | 30 | 250 | 0 | −0.06 | 0.99 | 1.03 | 1.04 | 1.04 | 1.07 | 1.04 |
| | | | 1 | 0.91 | 2.02 | 2.07 | 2.08 | 2.08 | 2.10 | 2.05 |
| | | | 2 | 1.89 | 3.08 | 3.13 | 3.15 | 3.14 | 3.16 | 3.09 |
| Brass | 26 | 31.4 | 0 | −0.36 | 0.96 | 1.07 | 1.07 | 1.06 | 1.08 | 1.05 |
| | | | 1 | 0.47 | 1.94 | 2.08 | 2.08 | 2.06 | 2.08 | 2.02 |
| | | | 2 | 1.45 | 3.00 | 3.14 | 3.15 | 3.12 | 3.14 | 3.06 |

*Obtained by Micrometer Measurement

Before comparing the estimated conductivity values to the literature values, it is worthwhile to provide a brief description of the various factors that may affect the conductivity of a particular metal. The composition of the metal is a primary factor and includes both the concentration of intentional alloying materials and undesired impurities. Further processing of the material in operations such as annealing, heat-treating, and aging have an effect on the internal structure of the metal and can alter the conductivity. In addition, forming operations which may introduce work hardening and plastic deformation can also contribute to conductivity changes. Furthermore, the conductivity is also temperature dependent. Therefore in comparing reference values to those measured, some deviation is expected.

Examination of the estimated properties reveals several important aspects of the measurements. Comparing estimated conductivity values for each material to those of the same material at other frequencies indicates bands of frequencies with similar conductivity values. Based on the sensor performance evaluated in FIGS. 36 and 37, these bands of frequencies generally coincide with those at which the best sensor performance is expected for a specific material conductivity. It should be noted that increased measurement errors for the aluminum and brass materials at the lowest frequencies may also be attributable to the thinness of these materials. The conductivity values in these bands are also within reasonable agreement with the literature values. The relative independence of the estimated conductivity with respect to changes in lift-off resulting from the addition of nonconducting shims is also important in evaluating the measurement. This independence is best for frequencies near the optimal for a particular material and deteriorates for increasingly distant frequencies. The estimated lift-off can also be used in evaluating the measurement. However, the measured lift-off of the sensor with no shims generally contains some degree of sensor to sensor deviation due to manufacturing tolerances. Instead of the absolute lift-off values, the change in lift-off due to the addition of a shim can be compared to the 1 mil shim thickness. As the performance curves indicated, the most consistent lift-off changes are observed at the higher frequencies. The measured lift-off changes are very reasonable when considering the degree to which dust and gaps from minor wrinkles in the shim material could affect the lift-off.

The estimated conductivity values, relative independence of conductivity with lift-off, and lift-off changes, when compared with the performance expected with a 0.1% full scale error, provide evidence that the various components of the measurement system are functioning with reasonable accuracy. This includes: the numerical accuracy of the sensor models for layered materials, the accuracy of the the instrumentation in providing a numerical representation of the sensor's terminal response, and the ability of the sensor to match the idealized model.

In evaluating the general performance characteristics of the sensor, estimated values for the impedance error bounds, such as 0.1% full scale, can be used in the absence of empirical data. However, better performance characteristics and error bound estimates can be obtained when empirical data is available. It would be a relatively easy task to evaluate the impedance error in each of these measurements if the exact estimated properties were known. Unfortunately neither the exact conductivity values of the plates nor the exact lift-off values are known. The approach taken here is to determine a set of error bounds in the absence of these exact values. Because of the approach that will be used, the calculated error bounds will most likely be an overestimate of the possible error in the measurement; however, this will be a step better than the a rough guess in the absence of empirical information.

Several assumptions will be necessary in order to evaluate the error bounds. First, some assumptions about the structure of the impedance bias error will be necessary. A study of the detailed structure of the impedance bias errors has not been performed nor has a method to do so been presented. A magnitude bound for the impedance error will therefore be used to characterize the maximum deviation of the true impedance value from any measurement of the value for the complete range of possible impedance values of the sensor. Based on the arguments presented elsewhere, this magnitude bound will again be assumed as a constant for each frequency when represented in terms of a percentage of the full scale impedance of the instrument with the exception that the highest and lowest of the seven frequencies used may have a larger error. This exception is made to allow for the larger parasitic affects which tend to be exhibited at frequency extremes.

The next assumption relates to the metal plates which where used in previous measurements. Although the exact conductivity will not be assumed as known due to the many possible ways in which the conductivity can be altered, the plates will be assumed as uniform. In reality the plates may have some non-uniformity due to processing which may add to the overestimation of error bounds. However, this must suffice for the current analysis and future work may utilize plates with improved processing or apply additional processing steps such as annealing before utilizing such plates for the current purpose. In the absence of any impedance bias error, the estimated properties for each uniform metal plate should be identical for each of the seven frequencies at which they are measured. The deviation of the estimated properties for different frequencies will form the basis of the bias error bound determination.

Two similar approaches will be used to evaluate the bias error. The first method will focus on finding the absolute worst-case bounds when the preceding assumptions are true. Since these bounds are expected to overestimate the impedance errors that will be experienced in practice, a second method will be presented which generates more optimistic values. Based on the ability to predict errors in the estimated properties and on the empirical data from the metal plates, the following procedure is used to predict the worst-case full scale error bounds:

1. An identical full scale error is assumed at each frequency and the spectrum of the predicted error for a specific property and material configuration is plotted.
2. The measured property value at the frequency which produces the minimal error is chosen to be the most correct. The error in this measured property value is then assumed to be equal to the frequency's predicted property error.
3. Deviations of the measured property from the property value at the minimal error frequency are then assumed to be due to further increases in the error at these other frequencies. Based on this calculation, the errors for these other frequencies are plotted.
4. The assumed full scale error which produces property errors for all five central frequencies that are less than or equal to the predicted error are then found.
5. Using this full scale error to evaluate the error in the measured property of the highest and lowest frequencies according to step 3, the independent high and low frequency full scale errors which each predict an error equivalent to the corresponding measurement error are then found.
6. Steps 1-5 are repeated for both lift-off and conductivity properties and for different materials to determine the worst-case errors bounds.

Figure 40:
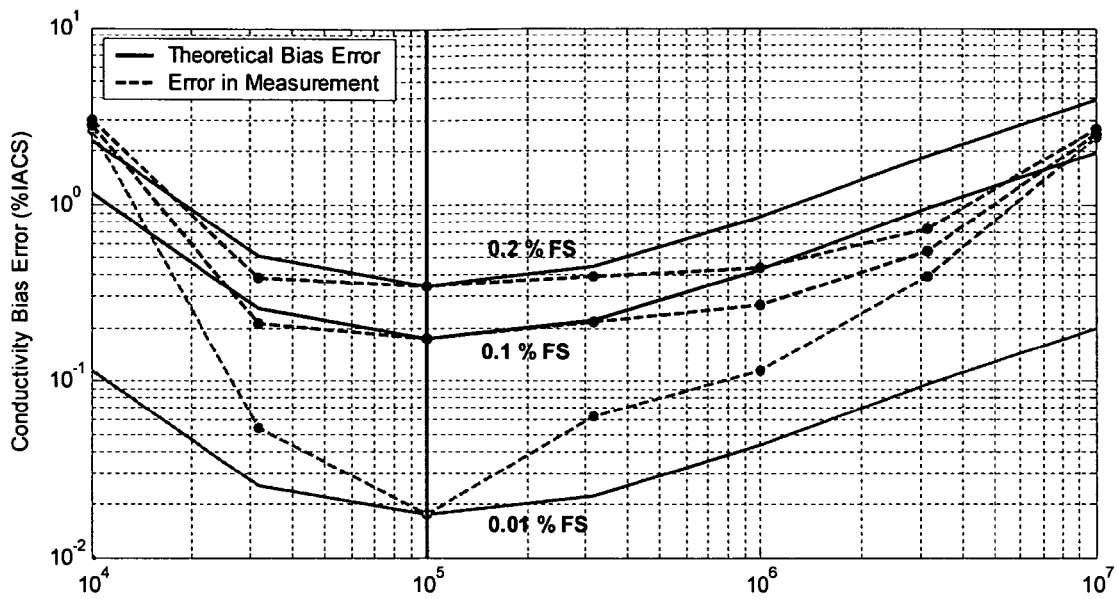
FIG. 40 shows simulated conductivity bias errors and measurement errors determined using the worst-case methodology for an infinite half-space with a nominal sensor lift-off of 2 mils (50.8 µm) and material conductivity values of 30% IACS (17.4 MS/m).
Figure 41:
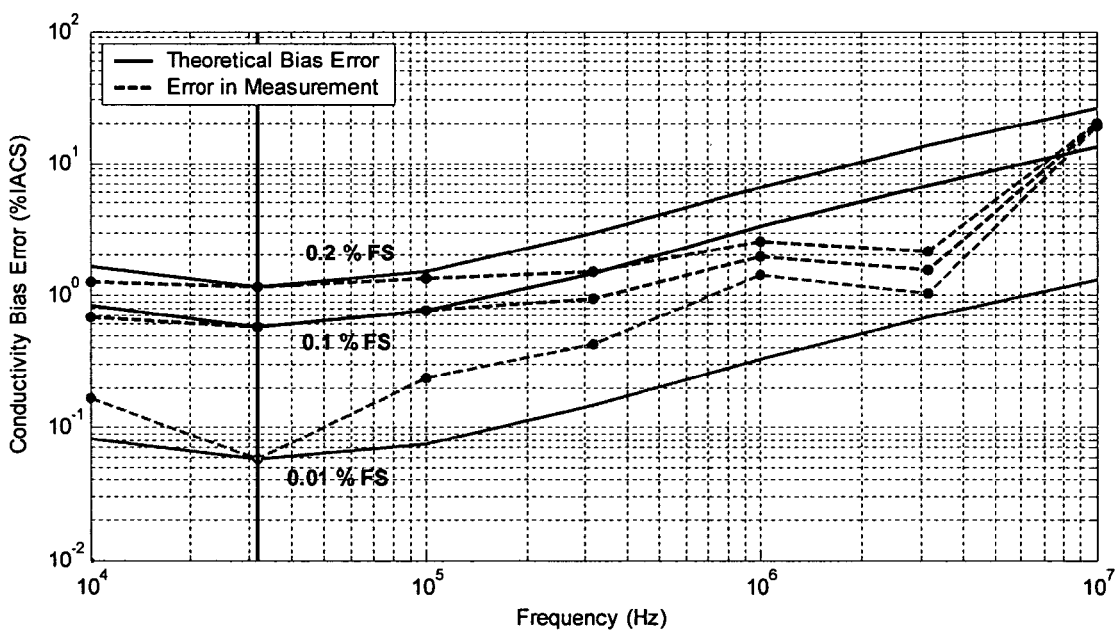
FIG. 41 shows simulated conductivity bias errors and measurement errors determined using the worst-case methodology for an infinite half-space with a nominal sensor lift-off of 2 mils (50.8 µm) and material conductivity values of 100% IACS (58 MS/m).
Figure 42:
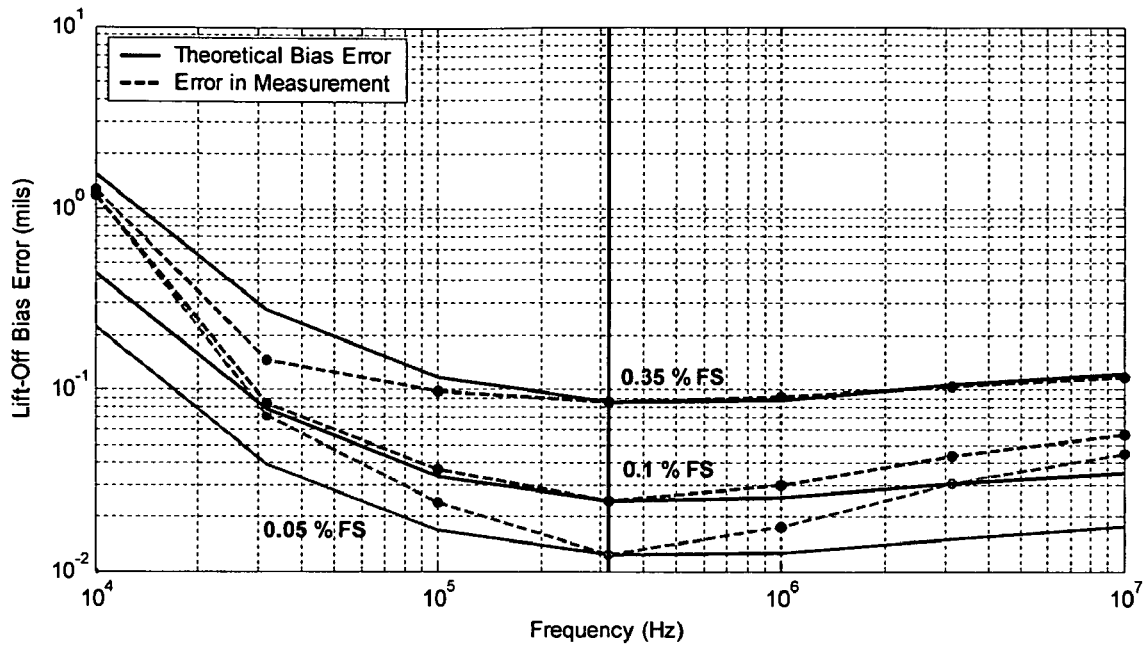
FIG. 42 shows simulated lift-off bias errors and measurement errors determined using the worst-case methodology for an infinite half-space with a nominal sensor lift-off of 2 mils (50.8 µm) and material conductivity values of 30% IACS (17.4 MS/m).

The plots in FIGS. 40-42 demonstrate this procedure on both lift-off and conductivity properties using measurements of the metal plates with the addition of a 1 mil shim. To further explain the procedure, FIG. 40 which is based on the conductivity measurements of the 30% IACS plate is focused on. The predicted conductivity error and associated error for the measurement are plotted for the assumed full scale errors of 0.01%, 0.1% and 0.2%. The measurement error calculated for the 0.01% assumed error is significantly greater than that predicted for each of the five central frequencies. Therefore the worst-case full scale error must be greater than 0.01%. A 0.1% full scale error produces a calculated measurement error in each of these five frequencies that is less than or equal to the predicted error. This is the bounding error for the five central frequencies based on this property and material configuration. The calculated measurement errors based on the 0.1% full scale error at the lowest and highest frequencies are then compared to predicted values from other full scale errors. The lowest and highest frequency errors are determined to be 0.27% and 0.13%, respectively. The results from each material property and plate material are summarized in Table 9. The greatest errors for all of the cases are then used as the error bounds as described in Table 10.

The second approach which provides more optimistic values for the error bounds results from a slight modification of the previously outline method. In step 2, the same frequency is used for the most correct property value; however, the error in the measurement is now optimistically assumed to be zero, rather than the maximum predicted. There is no justification given for this other than to indicate that because of the unknown structure of the bias errors it probably as likely that the error is zero as it is likely that the error is maximal. The results of this method cannot be considered as absolute bounds, but are rather as a method of produce more practically useful values.

Figure 43:
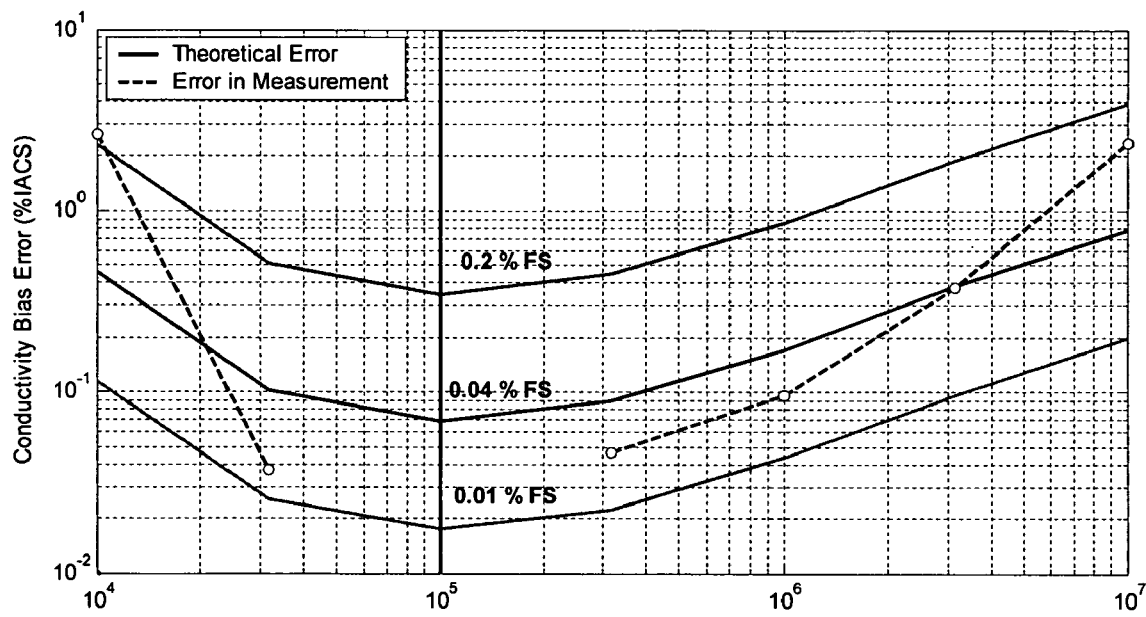
FIG. 43 shows simulated conductivity bias errors and measurement errors determined using the optimistic methodology for an infinite half-space with a nominal sensor lift-off of 2 mils (50.8 µm) and material conductivity values of 100% IACS (58 MS/m).
Figure 44:
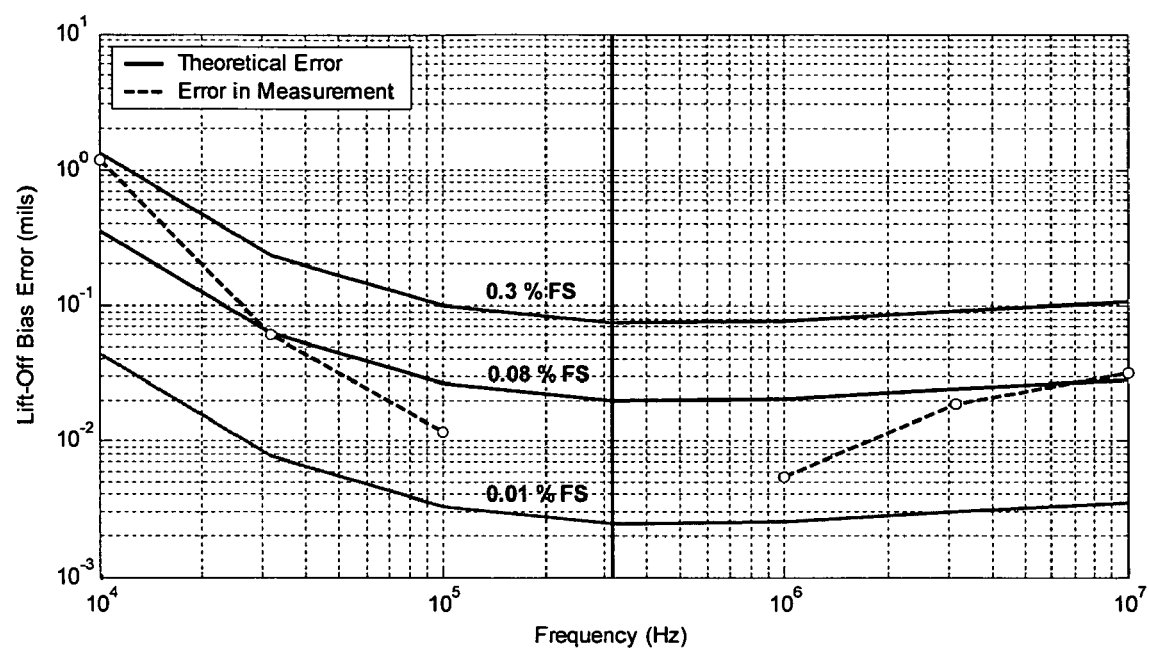
FIG. 44 shows simulated lift-off bias errors and measurement errors determined using the optimistic methodology for an infinite half-space with a nominal sensor lift-off of 2 mils (50.8 µm) and material conductivity values of 30% IACS (17.4 MS/m).

The graphical analysis using the optimistic method is presented in the representative plots of FIGS. 43 and 44. The main difference between these figures and those of the previous method is that the calculated measurement errors are now independent of the assumed full scale error. The error at the optimal frequency does not appear because, as discussed, it is assumed as zero and therefore cannot be plotted on the logarithmic plots. The errors bounds extracted from each property and material are included in Table 9, while the maximum bounds are included in Table 10.

TABLE 9

Summary of error bounds determined using either conductivity or lift-off errors at each material conductivity for both worst-case and optimistic methods.

| Error Evaluation Method | Property on Which Error Bounds are Based | Material Conductivity (% IACS) | Estimated Full Scale Impedance Error Bounds (% FS) | | |
|---|---|---|---|---|---|
| | | | 10 kHz | 31.6 kHz to 3.16 MHz | 10 Mhz |
| Worst-Case | Conductivity | 30 | 0.27 | 0.10 | 0.13 |
| | | 60 | — | 0.07 | 0.15 |
| | | 100 | 0.10 | 0.10 | 0.15 |
| | Lift-Off | 30 | 0.35 | 0.35 | 0.35 |
| | | 60 | — | 0.30 | 0.32 |
| | | 100 | — | 0.30 | 0.42 |
| Optimistic | Conductivity | 30 | 0.23 | 0.04 | 0.11 |
| | | 60 | — | 0.02 | 0.12 |
| | | 100 | 0.05 | 0.05 | 0.15 |
| | Lift-Off | 30 | 0.28 | 0.08 | 0.10 |
| | | 60 | — | 0.05 | 0.14 |
| | | 100 | 0.07 | 0.07 | 0.19 |

TABLE 10

Summary of maximum error bounds determined using either conductivity or lift-off errors at each material conductivity for both worst-case and optimistic methods.

| Error Evaluation Method | Property on Which Errors are Based | Estimated Full Scale Impedance Error Bounds (% FS) | | |
|---|---|---|---|---|
| | | 10 kHz | 31.6 kHz to 3.16 MHz | 10 Mhz |
| Worst-Case | Both | 0.35 | 0.35 | 0.42 |
| | Conductivity | 0.27 | 0.10 | 0.15 |
| | Lift-Off | 0.35 | 0.25 | 0.42 |
| Optimistic | Both | 0.28 | 0.08 | 0.19 |
| | Conductivity | 0.23 | 0.05 | 0.15 |
| | Lift-Off | 0.28 | 0.08 | 0.19 |

These error bounds were also used in the evaluation of measurements of sensor lift-off, thickness, and conductivity for thin plates of various metals. These measurements demonstrate several aspects of the measurement capability, including the use of multiple impedance measurements from different frequencies in estimating the material properties. In addition, the empirically determined error bounds are tested by comparing predicted errors in the thickness values to those of the actual measurements. This is possible since the thickness can be measured using a secondary method (micrometer) and compared to thickness values estimated from the impedance data.

In this measurement, the unknown properties are the sensor lift-off, the metal conductivity, and the metal thickness. The metals chosen are usually considered to be nonmagnetic and therefore the permeability in the models utilized has been set to that of free space. The thin metal is also assumed to be backed with a nonconducting and nonpermeable material. Separating the measured plate by a sufficient distance from any other metals using most common insulators allow this assumption to be valid. The instrumentions was calibrated using the measured sensor response in air, the simulated response in air, and a special shunt sensor as discussed above. Impedance measurements were made at seven logarithmically spaced frequencies from 10 kHz to 10 MHz. For each type of metal, three different material thicknesses were measured with and without the inclusion of a 1 mil nonconducting shim. Using the impedance data from all seven frequencies and the model for predicting the sensor response at each frequency an inversion method was used to estimate the three unknown properties. The results are shown in Table 11.

TABLE 11

Results from measurements of conductivity, thickness, and lift-off on thin metal shims using a single element planar MQS sensor.

| Shim Material | Metal Shim Thickness* (mils) | Additional Lift-Off (mils) | Measured Thickness (mils) | Measured Conductivity (% IACS) | Measured Lift-Off (mils) |
|---|---|---|---|---|---|
| Copper | 6.2 | 0 | 5.96 | 99.1 | 1.06 |
| | | 1 | 6.00 | 98.5 | 2.05 |
| | 9.9 | 0 | 9.84 | 99.5 | 1.05 |
| | | 1 | 9.87 | 99.2 | 2.04 |
| | 15.6 | 0 | 15.44 | 98.5 | 1.04 |
| | | 1 | 15.47 | 98.2 | 2.04 |
| Aluminum | 5.3 | 0 | 5.12 | 58.5 | 1.07 |
| | | 1 | 5.19 | 57.8 | 2.06 |
| | 10.3 | 0 | 10.21 | 59.1 | 1.06 |
| | | 1 | 10.25 | 58.8 | 2.05 |
| | 20.9 | 0 | 20.98 | 57.5 | 1.03 |
| | | 1 | 20.97 | 57.5 | 2.03 |
| Brass | 8.1 | 0 | 7.94 | 26.1 | 1.02 |
| | | 1 | 8.01 | 25.9 | 2.02 |
| | 15.3 | 0 | 15.26 | 25.4 | 1.04 |
| | | 1 | 15.30 | 25.3 | 2.04 |
| | 20.3 | 0 | 20.31 | 26.9 | 1.05 |
| | | 1 | 20.35 | 26.8 | 2.05 |

*Obtained by Micrometer Measurement

The estimated parameters shown in the table agree favorably with expected values. The thickness estimates are almost always within 0.2 mils (0.0051 mm) when compared with those taken with a micrometer. The resolution of the micrometer utilized was 0.05 mils; however, the absolute accuracy was not certified. Factors such as the repeatability of the micrometer related to the pressure applied by the mechanism and variability of the metal thickness within each part also play a part in calculating exact errors at this magnitude. The change in the estimated thickness due to the lift-off change produced by the introduction of a 1 mil shim is generally less than 0.05 mils. The observed change in the sensor lift-off produced by the addition of a 1 mil shim is within 0.01 mils. The conductivity values measured are close to the reference values and exhibit a reasonably small change when the shim is introduced. The conductivity value differences between different thickness pieces of the same type of metal are possibly caused by variations in metallurgical properties; the metals were obtained in the thickness values shown and therefore may have been produced from different metal sources in addition to having processing variations.

The determined impedance bias error bounds of the previous section are next utilized to predict the error bounds on the three estimated properties. Table 12 shows the predicted property error bounds using both the worst-case and optimistic impedance errors bounds. Since the thickness errors were determined using a secondary measurement technique, they are used as the basis for evaluating the success or failure of the predictions. Comparison of the actual thickness errors and those predicted using the worst-case bounds demonstrate that the errors are always within the predicted bounds. However, the actual errors in the measurements are always much smaller than the predicted bounds and therefore the predicted error seems overly restrictive in evaluation the measurement capability. Comparison of the estimated property bounds using the optimistic impedance bounds indicates that they are more useful, since they provide a much tighter bound of the actual errors. Further analysis will therefore utilize the optimistic bounds rather than the worst-case bounds.

three unknowns; to arrive at a unique solution, at least three independent equations are necessary. In predicting the estimated property errors, the linearization that is utilized results in a similiar system.

The goal is now to determine whether fewer measurements can be utilized and the effect it will have on the property errors. Although individual components of each impedance measurement could be included or excluded in estimating material properties, complete impedance measurements are utilized since simulations and measurements produce both real and imaginary components for each frequency. Therefore the minimal requirement of three independent equations or three components is rounded up to two complex impedance measurements. Since the permutations of the seven frequencies, when taken between 2 and 7 at a time, total up to 120 cases, a brute force approach can be applied in which the errors for each case are evaluated. The computation time of the linear analysis is kept to a minimal by computing the partial derivatives corresponding to each of the seven frequencies only once. The main computation for each permutation then involves the calculation of a matrix inverse, which does not pose a problem here because of the relatively small number of unknown material properties and impedance measurements that produce a sufficiently small matrix.

For each material configuration (conductivity and thickness) the frequency selections that produced the minimal error bounds for each property were determined from all possible permutations of the listed frequencies. For each configuration the first three property error bounds correspond to

TABLE 12

Predicted error bounds on the thickness, conductivity, and lift-off for measurements of the thin metal shims and comparisons to actual thickness errors.

| Shim Material | Micrometer Thickness (mils) | Measured Thickness (mils) | Actual Thickness Error (mils) | Estimated Thickness Error Bounds | | Estimated Conductivity Error Bounds | | Estimated Lift-Off Error Bounds | |
|---|---|---|---|---|---|---|---|---|---|
| | | | | Optimistic (mils) | Worst Case (mils) | Optimistic (% IACS) | Worst Case (% IACS) | Optimistic (mils) | Worst Case (mils) |
| Copper | 6.2 | 6.00 | 0.20 | 0.20 | 0.69 | 2.6 | 9.1 | 0.04 | 0.13 |
| | 9.9 | 9.87 | 0.03 | 0.21 | 0.74 | 1.5 | 5.3 | 0.03 | 0.11 |
| | 15.6 | 15.47 | 0.14 | 0.32 | 1.01 | 1.0 | 3.5 | 0.03 | 0.10 |
| Aluminum | 5.3 | 5.19 | 0.11 | 0.20 | 0.70 | 2.0 | 6.7 | 0.04 | 0.14 |
| | 10.3 | 10.25 | 0.05 | 0.21 | 0.76 | 0.8 | 3.0 | 0.03 | 0.11 |
| | 20.9 | 20.97 | 0.07 | 0.48 | 1.50 | 0.5 | 1.7 | 0.03 | 0.10 |
| Brass | 8.1 | 8.01 | 0.09 | 0.20 | 0.71 | 0.5 | 1.7 | 0.04 | 0.12 |
| | 15.3 | 15.30 | 0.00 | 0.28 | 1.00 | 0.2 | 0.9 | 0.03 | 0.10 |
| | 20.3 | 20.35 | 0.05 | 0.41 | 1.44 | 0.2 | 0.7 | 0.03 | 0.10 |

Note:
All measurements and estimates include an additional 1 mil of lift-off such that the nominal sensor lift-off is approximately 2 mils.

The estimated material properties and error analysis have focused on the use of impedance data from seven frequencies to estimate three unknown properties. Since there are two components to each impedance measurement, there are actually 14 measurements used to estimate the three parameters. Since there are significantly more measurements than unknowns, one can conclude that it may not be necessary to utilize all fourteen of these measurements. Although the actual relations between the impedance and material properties are not linear, this can intuitively be understood by comparison to the case of a linear system of 14 equations with optimal frequency selections for thickness, conductivity, and lift-off, respectively. Error bounds using the central five frequencies and all frequencies are also included as the fourth and fifth entry for each material configuration. When all seven frequencies are utilized, the values are identical to those determined in Table 12. In all cases the frequency selection predicted as being optimal for measuring a specific property was composed of either two or three frequencies; however, depending on the metal's conductivity and thickness, the specific frequencies varied. A slight to moderate improvement in the error bounds was generally predicted while at the same time reducing the number of measurements required.

TABLE 13

Actual errors in estimated thickness for measurements of the thin metal shims using frequencies determined as optimal.

| Shim Material | Metal Shim Thickness (mils) | Frequencies Utilized | | | | | | | |
|---|---|---|---|---|---|---|---|---|---|
| | | x | | | | | | | 10.0 kHz |
| | | x | x | | | x | | | 31.6 kHz |
| | | x | x | x | x | x | x | | 100 kHz |
| | | x | x | x | | x | x | x | 316 kHz |
| | | x | x | | x | | x | x | 1.00 MHz |
| | | x | x | | | | | x | 3.16 MHz |
| | | x | | | | | | | 10.0 MHz |
| | | Actual Thickness Error (mils)* | | | | | | | |
| Copper | 6.2 | 0.20 | 0.20 | 0.22 | 0.19 | 0.19 | 0.20 | 0.19 | |
| | 9.9 | 0.03 | 0.03 | 0.07 | 0.00 | 0.05 | 0.03 | 0.02 | |
| | 15.6 | 0.14 | 0.13 | 0.22 | 0.08 | 0.15 | 0.17 | 1.32 | |
| Aluminum | 5.3 | 0.11 | 0.15 | 0.10 | 0.12 | 0.01 | 0.08 | 0.13 | |
| | 10.3 | 0.05 | 0.05 | 0.06 | 0.04 | 0.05 | 0.04 | 0.02 | |
| | 20.9 | 0.07 | 0.13 | 0.22 | 0.14 | 0.21 | 0.21 | 1.05 | |
| Brass | 8.1 | 0.09 | 0.13 | 0.33 | 0.09 | 0.05 | 0.06 | 0.11 | |
| | 15.3 | 0.00 | 0.01 | 0.04 | 0.01 | 0.01 | 0.05 | 0.06 | |
| | 20.3 | 0.05 | 0.05 | 0.04 | 0.12 | 0.00 | 0.11 | 0.19 | |

Of the nine optimal frequency selections related to the thickness property for different metals and thickness values, only five unique frequency combinations are present. The corresponding impedance data was extracted from the seven frequency impedance data utilized earlier for evaluating the unknown properties. The impedance data for each set of frequencies was then inverted to produce estimated properties. The error in the thickness data based on micrometer measurements is shown in Table 13. The errors using all seven frequencies and only the central five frequencies are also shown. For each set of frequencies, the error corresponding to the material configuration for which it was determined as optimal is shown in bold. Though these errors were predicted to be smaller than the errors produced by using all seven frequencies, they are often slightly larger. For a given frequency set, the errors for the material configurations that are not associated with the set may be substantially larger. This indicates that if a measurement problem is sufficiently limited in the range of material properties, the number of impedance measurements required may be reducible without severely increasing the error in the measurement property of interest.

It may also be possible to further reduce the number of impedance measurements by specifying one of the three estimated properties. For example, if the type of metal is known, its actual conductivity could be assumed as equal to the reference value of the metal type. Since there will be difference in the actual conductivity as compared to the reference value, the predicted sensor response will contain some errors with respect to the actual measurement situation. This will ultimately translate into an error in the remaining unknown properties. If the conductivity is specified then the lift-off and thickness can be estimated from a single impedance measurement at a single frequency.

TABLE 14

Comparison of actual thickness errors to predicted errors introduced by assuming the conductivity of the metal shims to be known and allowing a 1% deviation from the known value.

| Shim Material | Shim Thickness (mils) | Actual Thickness Error* (mils) | 10.0 kHz | 31.6 kHz | 100 kHz | 316 kHz | 1.00 MHz | 3.16 MHz | 10.0 Mhz |
|---|---|---|---|---|---|---|---|---|---|
| | | | Predicted Thickness Error Due to a 1% Error in Conductivity (mils) | | | | | | |
| Copper | 6.2 | 0.20 | 0.07 | 0.07 | 0.07 | 0.10 | 0.11 | 4.51 | >>10 |
| | 9.9 | 0.03 | 0.12 | 0.12 | 0.15 | 0.22 | 2.64 | >>10 | >>10 |
| | 15.6 | 0.13 | 0.21 | 0.24 | 13.10 | >10 | >>10 | >>10 | >>10 |
| Aluminum | 5.3 | 0.15 | 0.06 | 0.06 | 0.06 | 0.06 | 0.30 | 0.38 | >>10 |
| | 10.3 | 0.05 | 0.12 | 0.13 | 0.14 | 0.94 | 2.07 | >10 | >>10 |
| | 20.9 | 0.13 | 0.33 | 0.38 | >10 | >10 | >>10 | >>10 | >>10 |
| Brass | 8.1 | 0.13 | 0.09 | 0.09 | 0.09 | 0.10 | 0.29 | 0.52 | >10 |
| | 15.3 | 0.01 | 0.21 | 0.21 | 0.23 | 0.74 | 1.74 | >10 | >>10 |
| | 20.3 | 0.05 | 0.31 | 0.32 | 0.41 | 1.20 | 9.48 | >>10 | >>10 |

*Using five frequencies to estimate the conductivity, thickness, and lift-off

Using the linearization method, Table 14 indicates the predicted error in the thickness due to a 1% error in the assumed conductivity for each frequency. The actual errors resulting from the three unknown estimation when compared to micrometer measurements are also shown for comparison. In the cases of the thinner materials, it appears that the predicted errors resulting from the 1% error in the specified conductivity may be less than the actual errors encountered by estimating all three properties. The lowest frequency also produced the smallest thickness errors for any specific material configuration. The higher frequencies cannot sufficiently penetrate the thin plates and therefore large thickness errors are produced by the conductivity error. This analysis only incorporated errors from the assumed conductivity. Errors in the impedance measurement must also be accounted for and are therefore included in Table 15 based on the optimistic impedance errors.

Inclusion of the impedance errors further increases the total thickness error. The lowest frequency is no longer the best choice and the optimal frequency is dependent on the metal type and thickness. In some cases the predicted error is smaller than the actual error of the three unknown technique, but only for the thinner materials.

thickness, and substrate conductivity. The materials are expected to be nonmagnetic and therefore the permeability is specified as that of free space. The substrate metals utilized are much thicker than the skin depth associated with the lowest excitation frequency and therefore are assumed as infinitely thick in modeling the sensor response.

The M3 sensor design was utilized in the measurements at seven logarithmically spaced frequencies between 10 kHz and 10 MHz. The instrumentation was again calibrated using only the predicted response of the sensor in air, measurements of the sensor in air, and measurements of a special shunt sensor. The impedance measurements were made on metal coating on metal parts with substrates of copper or aluminum

TABLE 15

Comparison of metal shim thickness error bounds due to impedance error bounds for errors predicted by estimating the conductivity, thickness, and lift-off to those predicted by estimating the thickness and lift-off only.

| Shim Material | Shim Thickness (mils) | Predicted Thickness Error* (mils) | 10.0 kHz | 31.6 kHz | 100 kHz | 316 kHz | 1.00 MHz | 3.16 MHz | 10.0 Mhz |
|---|---|---|---|---|---|---|---|---|---|
| | | | \multicolumn{7}{c}{Predicted Thickness Error Bounds Due to a 1% Conductivity Error and Optimistic Impedance Bias Error Bounds (mils)} | | | | | | |
| Copper | 6.2 | 0.15 | 0.67 | 0.10 | 0.09 | 0.18 | 0.51 | >10 | >>10 |
| | 9.9 | 0.16 | 0.64 | 0.15 | 0.20 | 0.55 | 9.44 | >>10 | >>10 |
| | 15.6 | 0.21 | 0.79 | 0.31 | >10 | >>10 | >>10 | >>10 | >>10 |
| Aluminum | 5.3 | 0.15 | 1.83 | 0.12 | 0.07 | 0.08 | 0.85 | 2.01 | >>10 |
| | 10.3 | 0.16 | 1.46 | 0.18 | 0.17 | 1.69 | 6.02 | >>10 | >>10 |
| | 20.9 | 0.31 | 1.95 | 0.52 | >10 | >>10 | >>10 | >>10 | >>10 |
| Brass | 8.1 | 0.15 | 7.51 | 0.32 | 0.13 | 0.12 | 0.55 | 1.81 | >>10 |
| | 15.3 | 0.21 | 6.90 | 0.43 | 0.29 | 1.10 | 3.64 | >>10 | >>10 |
| | 20.3 | 0.30 | 7.76 | 0.59 | 0.55 | 1.93 | >10 | >>10 | >>10 |

*Using five frequencies and the optimistic impedance errors to estimate the conductivity, thickness, and lift-off The same approach can be followed when the MUT are more complex so that the number of unknown material properties from three to four. The material configuration utilized is designed to represent metal coatings which have been applied to a metal substrate. However, unlike the types of coatings that would usually be encountered in practice, these are simulated using thin metal pieces for the coating and placing them in close contact with the thick substrate metal. This allows the thickness of the coating to be directly measured using a micrometer and also allows the substrate and coating metals to be used in various combinations. In this case the unknown properties are the sensor lift-off, coating conductivity, coating (2024 alloy). The simulated metal coatings of these parts were made of brass or aluminum (99% pure) with various thickness values. Measurements with and without a 1 mil nonconducting shim were again made to test the independence of the other estimated properties on changes in the sensor lift-off. The seven impedance measurements and the modeled sensor response for the general material configuration were used with an inversion method to produce estimates of the four unknown parameters. The estimates for the different coating-substrate-shim configurations are shown in Table 16.

TABLE 16

Results from measurements of conductivity, thickness, substrate conductivity, and lift-off on simulated metal on metal coatings using a single element MQS sensor.

| Substrate Material | Coating Material | Metal Coating Thickness* (mils) | Additional Lift-Off (mils) | Measured Thickness (mils) | Coating Conductivity (% IACS) | Substrate Conductivity (% IACS) | Measured Lift-Off (mils) |
|---|---|---|---|---|---|---|---|
| Copper | Aluminum | 5.3 | 0 | 5.82 | 58.6 | 100.3 | 1.07 |
| | | | 1 | 5.77 | 58.2 | 99.9 | 2.06 |
| | | 10.3 | 0 | 11.02 | 59.4 | 99.6 | 1.05 |
| | | | 1 | 11.38 | 59.2 | 99.6 | 2.06 |
| | | 15.6 | 0 | 15.69 | 57.9 | 97.7 | 1.06 |
| | | | 1 | 15.48 | 57.9 | 97.0 | 2.06 |
| | Brass | 8.1 | 0 | 8.49 | 26.1 | 99.8 | 1.03 |
| | | | 1 | 8.42 | 26.0 | 99.5 | 2.02 |
| | | 15.3 | 0 | 15.74 | 25.3 | 98.4 | 1.03 |
| | | | 1 | 15.66 | 25.3 | 97.9 | 2.02 |
| Aluminum (2024 Alloy) | Aluminum | 5.3 | 0 | 4.92 | 58.8 | 29.0 | 1.07 |
| | | | 1 | 5.02 | 58.3 | 28.9 | 2.06 |
| | | 10.3 | 0 | 10.11 | 59.4 | 28.8 | 1.05 |
| | | | 1 | 10.27 | 59.2 | 28.5 | 2.04 |

TABLE 16-continued

Results from measurements of conductivity, thickness, substrate conductivity, and lift-off on simulated metal on metal coatings using a single element MQS sensor.

| Substrate Material | Coating Material | Metal Coating Thickness* (mils) | Additional Lift-Off (mils) | Measured Thickness (mils) | Coating Conductivity (% IACS) | Substrate Conductivity (% IACS) | Measured Lift-Off (mils) |
|---|---|---|---|---|---|---|---|
| | | 15.6 | 0 | 15.93 | 58.1 | 27.7 | 1.06 |
| | | | 1 | 16.19 | 58.0 | 27.1 | 2.05 |

*Obtained by Micrometer Measurement

The results can again be considered favorable when considering that the only calibration made was based on the response of the sensor in air. Due to the addition of an unknown, the accuracy of the thickness values is somewhat worse than in the case of the thin metals in the absence of the conducting substrate. The possibility also exists that increased errors resulted from the coating metals not being in perfect intimate contact with the substrate due to slight curvatures. The substrate and coating conductivity values are comparable to the reference literature values. The substrate conductivity values tend to deviate from the reference value as the coating thickness increases. This is due to a loss of sensitivity to the substrate since the lowest frequcies no longer penetrate as deeply into the substrate; the substrate is essentially becoming shielded from the sensor, thereby making its properties more difficult to measure. The apparent accuraracy of the change in lift-off due to the addition of the 1 mil shim is comparable to that observed in previous less complex measurements. This is due to the shallow penetration achieved by the higher measurement frequencies, which can provide information about the lift-off that is less dependent on other material properties. The use of the other calibration methods, which utilize reference parts of known properties, may improve the accuracy of these measurements. This is most likely if the available reference parts have properties similar to the parts being measured.

Figure 45:
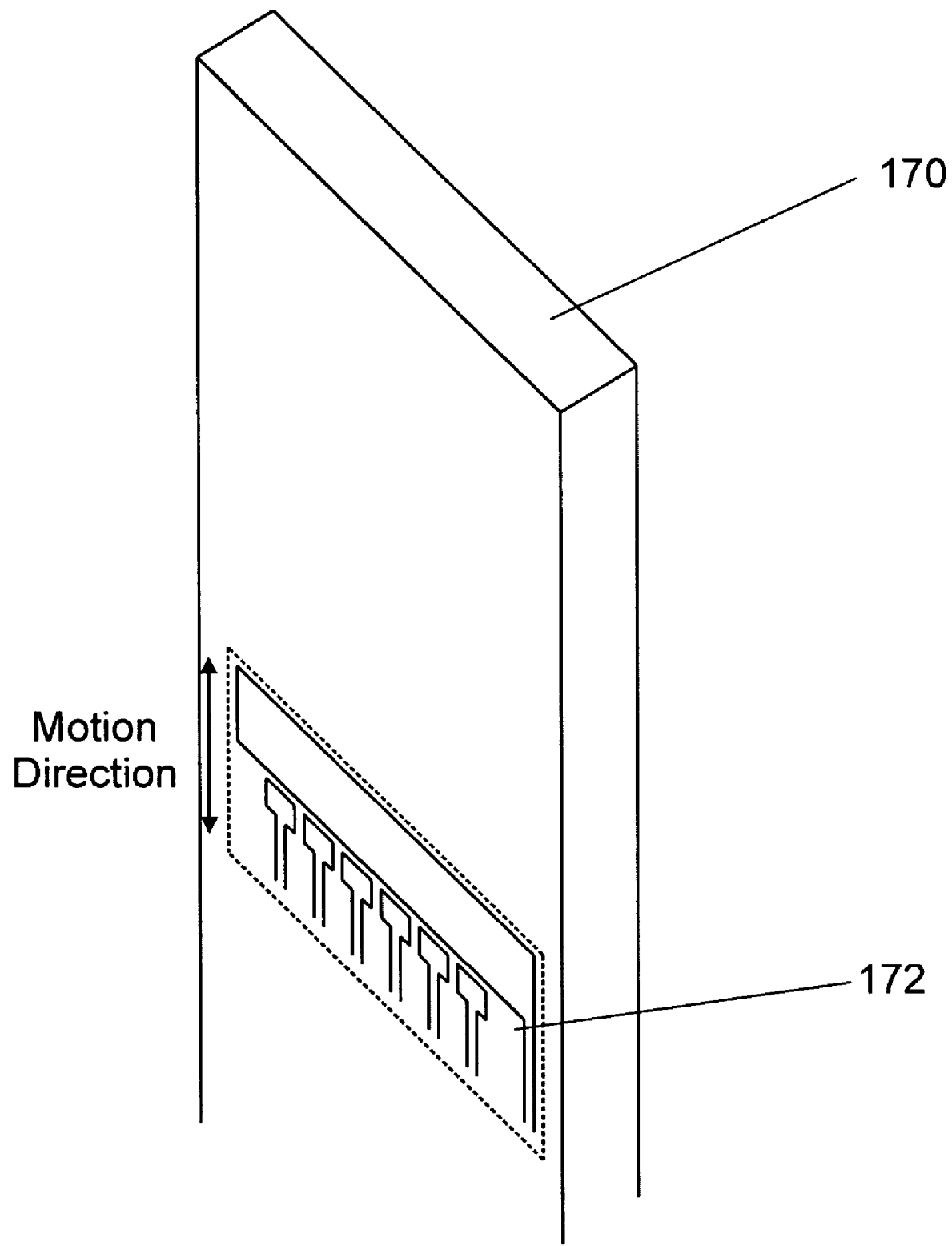
FIG. 45 shows a schematic for sensor calibration where the sensor response is measured at various locations over a reference material surface.

Measurements can also be improved by calibration methods that accommodate local variations in the material properties or "material noise." This noise includes roughness effects, microstructural variations, the presence of defects, and variations in absolute material properties such as the magnetic permeability and electrical conductivity. The conventional method of calibrating on a material is to hold the sensor stationary proximate to a reference material. However, if there are local property variations in, for example, the electrical conductivity or magnetic permeability, then the material properties in the vicinity of the sensor or some elements of a sensor array may be incorrectly accounted for in the calibration. FIG. 45 illustrates a method for accounting for these local property variations whereby the sensor 172 is moved over the reference material 170, either with constant motion or by dithering (moving the sensor or sensor array in a back and forth motion), so that the sensor response provides an average of the material properties as a part of the calibration procedure. The sensor response can even be measured when the sensor is stationary at different locations on the material surface. The reference material may also be a portion of the test material where the properties are known. For situations where a shim is required, the shim can then be inserted or removed and the procedure repeated. This dithering approach can be applied to uncoated as well as coated material systems and, for coated systems, should be performed on representative coated materials.

In another embodiment, the motion of the sensor during calibration is similar to the motion of the sensor during the actual measurement. For example, the motion of the sensor is started and then the calibration measurements are performed, as in an actual measurement on a test material, so that any transient effects caused by the start or stop of motion will not bias the calibration or lead to an error. In another embodiment, which is particularly important to linear arrays of sense elements, the sensor or sensor array is moved in a direction parallel to the linear array of sense elements and calibration measurements are performed when each sense element is over the same local material region. In this fashion, the response of each sense element is measured over the same material so that material property variations across the sensor array at any given instant in time do not perturb the calibration.

Figure 46:
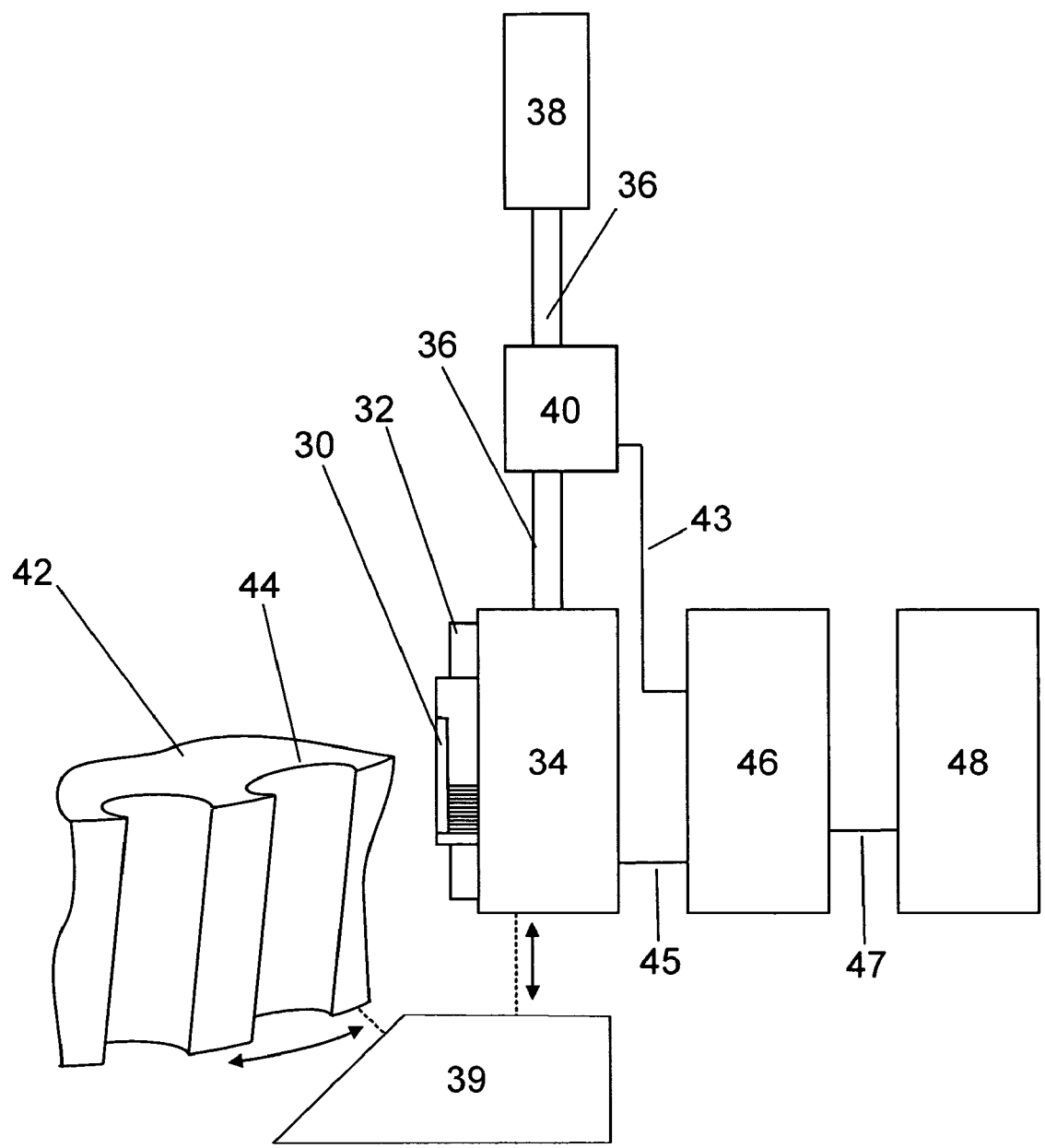
FIG. 46 is a drawing of a probe for inspection of engine disk slots.

Another aspect of this invention involves the automated scanning methods for engine disk slots to inspect for fatigue damage, cracks, fretting damage, and other flaws. FIG. 46 provides an illustration of an MWM-Array probe configured for slot inspection. The flexible MWM-Array 30 is placed in the slot 44 of the disk 42 with a support 32. The support can be rigid or can include conformable components such as an inflatable balloon as described in U.S. patent application Ser. Nos. 10/172,834, filed Jun. 13, 2002 and 10/419,702, filed Apr. 18, 2003, the entire teachings of which are incorporated herein by reference. The inflatable balloon can be filled with water to provide pressure behind the sensor and can improve sensor durability (i.e., by deflating the balloon prior to entry into the slot). The support 32 can be attached to probe electronics 34, which provide amplification of the sense element signals, a shaft 36, which guides the scan direction for the sensor, and a balloon inflation mechanism 38. A position encoder 40 can provide longitudinal registration of the MWM-Array data along the axis of the inspected slot. The sensing elements positions (wit 0.04 in. spacing) provide the position in the transverse direction, resulting in a fully registered two-dimensional image using an single, axial, position encoder. The balloon can span the circumferential distance around the slot so that the entire slot surface can be inspected with a single scan using an MQS sensor array. The scanning of the sensor array in the slot and the rotation of the disk so that slots can be sequentially scanned are controlled by the same scanner unit 39. The electrical signals are monitored with the parallel architecture data acquisition impedance instrumentation 46 through electrical connections from the probe electronics 45 and the position encoder 43. A connection 47 between the impedance instrument and a processor 48, such as a computer, is used to control the data acquisition and process and display the data.

Figure 47:
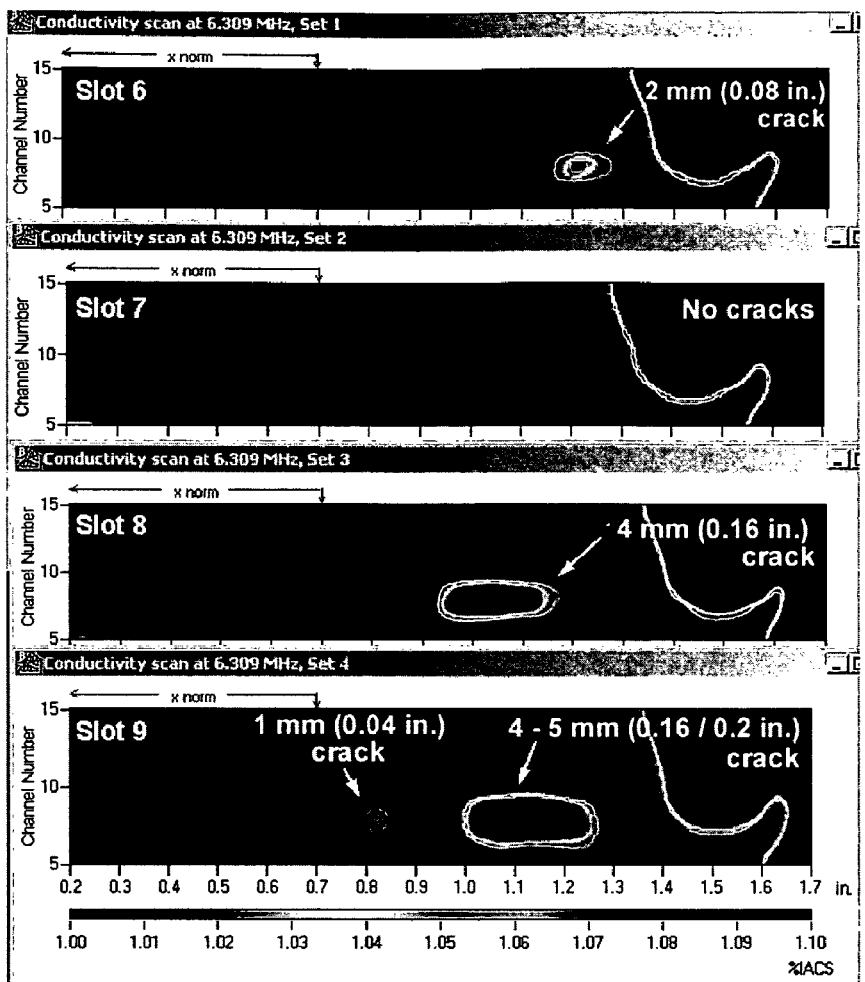
FIG. 47 shows two-dimensional MWM-Array conductivity images for Slots 6 through 9. Note the large crack in Slot 9 is listed with the apparent (4 mm) and total length where the latter includes a tight 1 mm extension barely detectable on the replica in a microscope, even at 10×.
Figure 48:
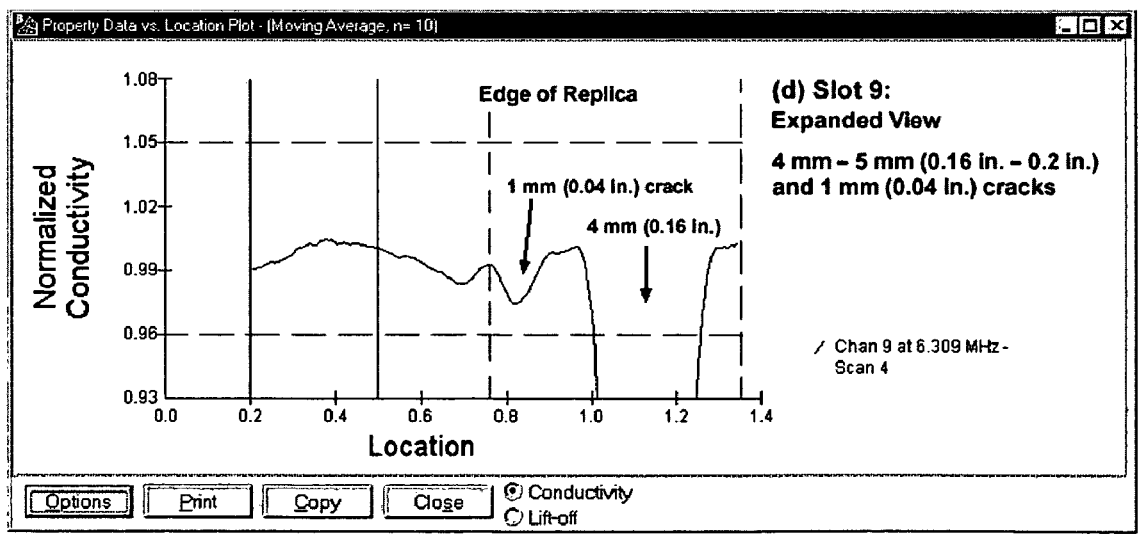
FIG. 48 shows an expanded view of the single-channel (sensing element) conductivity plot for the element crossing the crack for Slot 9 to show the presence of the smaller crack.
Figure 49:
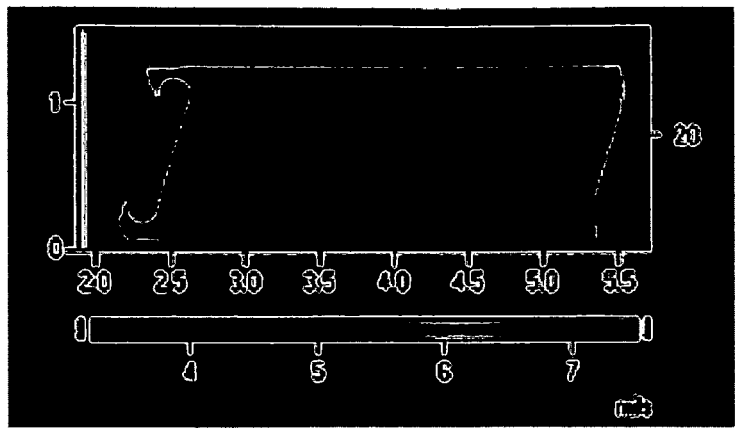
FIG. 49 shows a two-dimensional MWM-Array lift-off image for a slot.

FIG. 47 provides typical conductivity images obtained from engine slots with fretting damage. These slots of this F-110 engine disk were selected because they contain several cracks in the range from 0.38 mm (0.015-in.) to 5.1 mm (0.20-in.), with documented cracks under 2.5 mm (0.1-in.) based on acetate replicas. In this case, the objective was to reliably detect cracks 1.5 mm (0.06-in.) and longer with reasonable false alarm rates. As shown in FIG. 47, cracks 1.25 mm (0.05-in.) and longer provide large indications easily visualized in the two-dimensional images (C-scans) with no background indications even approaching their signal level. The smaller cracks 1.0 mm (0.04-in.) long in slot 9 produce significant signals; however, these are well below the required detection threshold so no attempt was made to enhance their detection. The single frequency measurements shown here may produce false positive indications if the smaller crack images are enhanced. FIG. 48 provides an individual channel (sensing element) responses (B-scans) for slot 9 in one of the disks. Only the response from the channel that passes over the crack is plotted. Repeated measurements within these slots continually produce similar results. Even the background variations appear repeatable. In Slot 9 there are two significant crack indications. FIG. 49 shows a lift-off image. The color scales in the images can be adjusted to indicate the presence of cracks or to show that the sensor is properly conforming to the slot surface and the lift-off is below a predetermined level required to provide acceptable crack detection sensitivity.

Figure 50:
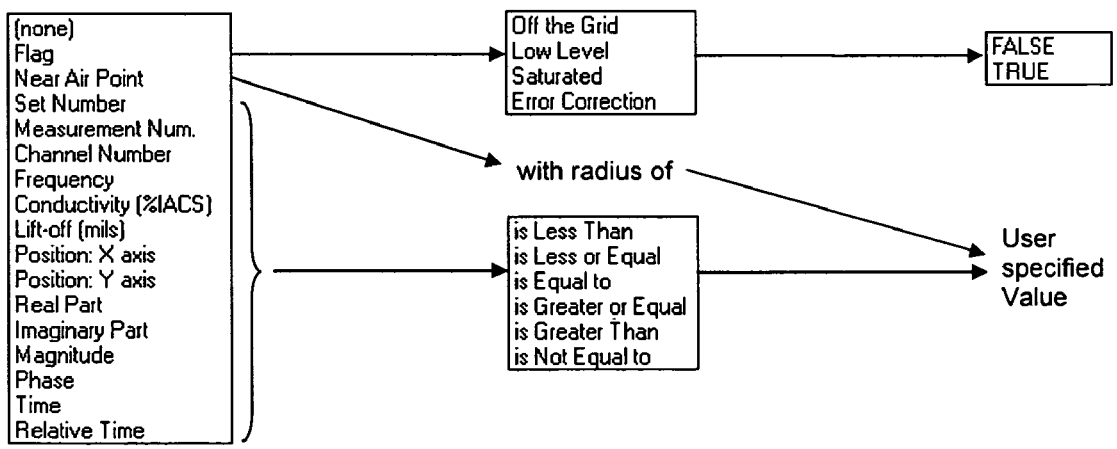
FIG. 50 illustrates a Boolean decision protocol for filtering data.

The measurement data can also be filtered to highlight or exclude specific features of a response. The filtering can be performed on the impedance data or on the property data and can be created to tag data according to a set of conditions. The tagged data may be excluded from a plot or image, or it can be represented differently, e.g., a different color or a differently shaped symbol. The dialog table and tests shown in FIG. 50 illustrates how a user could create such a filter. Each line in the table constitutes a Boolean clause, and if all the tests in any one such clause are satisfied, then the data point is tagged. Individual tests include:

1. A flag indicating a particular condition of the data point is set or unset. FIG. 50 lists four flags (off the measurement grid which is a database of responses that relates the impedance measured with a sensor to electrical and/or geometric properties of the test material, low level or saturated signal levels, and error correction).
2. The data fall inside a circle in real/imaginary complex impedance space, drawn with its center at the air point (response of the sensor in air), and with a radius specified as a fraction of a certain length that is a property of the measurement grid. The radius of the tag circle is typically the distance from the air point to the closest grid point. This method can also be applied to other spaces for displaying the data, such as magnitude/phase representations of the complex impedance, and magnitude-magnitude or phase-phase representations for the response from multiple sensing elements.
3. A numerical equality or comparison applied to a property of the data point. FIG. 50 shows a set of potential properties that can be tested. As indicated, the property could be an electrical or geometric property of the test material, an impedance value, a location, or some other characteristic associated with the particular data point. Note that the "conductivity" and "lift-off" properties illustrated in FIG. 50 are examples from a particular measurement application. Depending upon the type of measurement that is performed, other properties could be displayed, such as magnetic permeability or layer thickness.

Tagged data can then be removed from the images or plots of the sensor response, as desired, or reported in another format.

Figure 51:
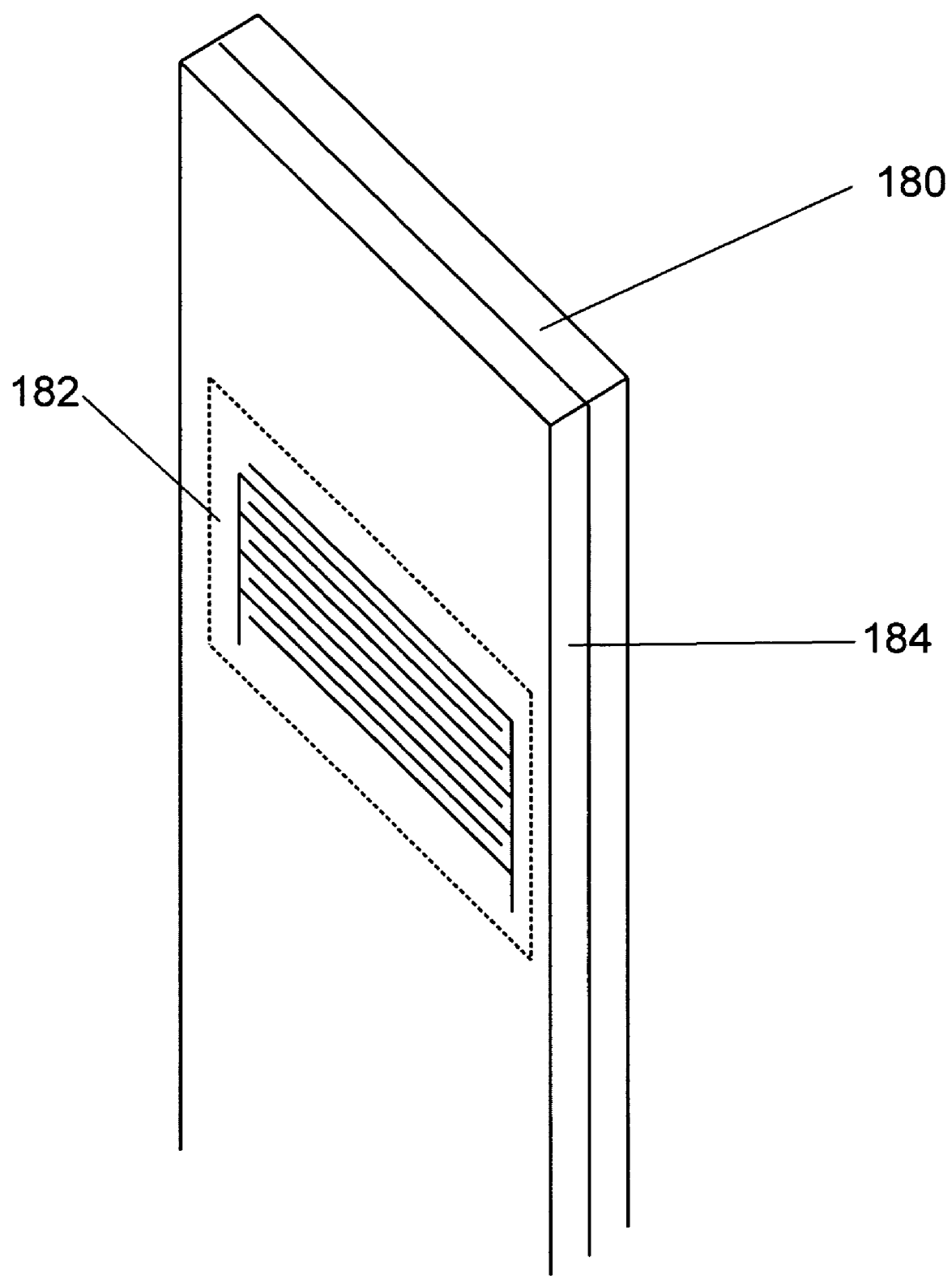
FIG. 51 shows an EQS sensor over a dielectric material for assessing the mechanical condition of the material.

Scanning and embedded EQS sensors also permit the mechanical condition of the dielectric materials to be determined through measurements of their frequency dependent property behavior. This dielectric spectroscopy permit stress and strain measurements in dielectric materials. This includes self-monitoring dielectric materials, such as polymers, adhesives and epoxies, that either inherently have sensitivity to stress and strain or have been fabricated with special materials to enhance their strain, stress, or temperature sensitivity. FIG. 51 shows one such application, where the sensor 182 is mounted or scanned over the surface of the test material 180. A coating 184 may also be applied to the test material to enhance the sensitivity of the dielectric measurement. An example application of this approach uses these sensors and materials to monitor damage from crash testing of automobiles or on human dummies used in automobile crashing. The automobile components or dummies are instrumented with special materials, such as paints, coatings, etc., which can later be scanned with dielectric sensor arrays to determine damage to the human as well as coating. These self-monitoring materials can be applied on the automobile itself, other impact or crash tested articles, fatigue tested or damaged articles, or battle damage tested articles for the purpose of improving forensic observability.

While the inventions have been particularly shown and described with reference to preferred embodiments thereof, it will be understood to those skilled in the art that various changes in form and details may be made therein without departing from the spirit and scope of the invention as defined by the appended claims. All references cited above are incorporated herein by reference in their entirety.

What is claimed is:

1. A method for calibrating a sensor comprising:
   placing a sensor proximate to a reference material;
   measuring the response of the sensor, at different surface locations on the reference material while causing relative movement between the sensor and the surface of the reference material, for one or more operating conditions; and
   using multiple responses from the different surface locations to calibrate the sensor to the reference material for material property measurements while accounting for material noise due to local material property variations.
2. The method as claimed in claim 1 wherein the sensor is a magnetic field sensor.
3. The method as claimed in claim 1 wherein the sensor is an electric field sensor.
4. The method as claimed in claim 1 wherein the motion is constant in one direction.
5. The method as claimed in claim 1 wherein the motion is a back and forth dithering motion.
6. The method as claimed in claim 1 wherein the sensor has a least one linear array of elements.
7. The method as claimed in claim 6 wherein the motion is in a direction parallel to the array of elements.
8. The method as claimed in claim 7 wherein the response for each element is measured over the same test material location.
9. The method as claimed in claim 1 wherein the operating conditions are with and without a shim.
10. The method as claimed in claim 1 wherein the operating conditions are at multiple frequencies.
11. The method as claimed in claim 1 wherein the motion is translation.

12. The method as claimed in claim 1 wherein the motion is rotation.

13. The method as claimed in claim 1 wherein using the response further comprises:
   using an average measurement response to calibrate the sensor.

14. The method as claimed in claim 1 wherein the material property variation is electrical conductivity variation.

15. The method as claimed in claim 1 wherein the material property variation is magnetic permeability variation.

16. The method as claimed in claim 1 wherein the material property variation is microstructural variation.

17. The method as claimed in claim 1 wherein the sensor response is measured when the sensor is stationary at the different surface locations on the reference material.

18. The method as claimed in claim 1 wherein the relative movement is caused by moving the sensor over the surface of the reference material.

* * * * *